(12) United States Patent
Bender et al.

(10) Patent No.: US 8,143,244 B2
(45) Date of Patent: Mar. 27, 2012

(54) CYCLOPROPYL FUSED INDOLOBENZAZEPINE HCV NS5B INHIBITORS

(75) Inventors: John A. Bender, Middletown, CT (US);
Kyle Eastman, Killingworth, CT (US);
John F. Kadow, Wallingford, CT (US);
Zhong Yang, Southington, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

(21) Appl. No.: 12/710,527

(22) Filed: Feb. 23, 2010

(65) Prior Publication Data

US 2010/0216774 A1    Aug. 26, 2010

Related U.S. Application Data

(60) Provisional application No. 61/155,634, filed on Feb. 26, 2009.

(51) Int. Cl.
*A61P 31/00* (2006.01)
*A61K 31/55* (2006.01)
*C07D 223/14* (2006.01)

(52) U.S. Cl. .................... 514/214.01; 540/576

(58) Field of Classification Search ............ 514/214.01; 540/576
See application file for complete search history.

(56) References Cited

U.S. PATENT DOCUMENTS

| | | |
|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,153,848 B2 | 12/2006 | Hudyma et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,232,819 B2 | 6/2007 | Di Francesco et al. |
| 7,273,859 B2 | 9/2007 | Naidu |
| 7,348,425 B2 | 3/2008 | Hudyma et al. |
| 7,399,758 B2 | 7/2008 | Meanwell et al. |
| 7,414,045 B2 | 8/2008 | Crescenzi et al. |
| 7,452,876 B2 | 11/2008 | Yeung et al. |
| 7,456,165 B2 | 11/2008 | Bergstrom et al. |
| 7,456,166 B2 | 11/2008 | Bender et al. |
| 7,456,167 B2 | 11/2008 | Bergstrom |
| 7,473,688 B2 | 1/2009 | Bergstrom et al. |
| 7,485,633 B2 | 2/2009 | Meanwell et al. |
| 7,494,984 B2 | 2/2009 | Banville et al. |
| 7,517,872 B2 | 4/2009 | Nickel et al. |
| 7,521,441 B2 | 4/2009 | Gentles et al. |
| 7,521,442 B2 | 4/2009 | Gentles et al. |
| 7,521,443 B2 | 4/2009 | Bender et al. |
| 7,521,444 B2 | 4/2009 | Bender et al. |
| 7,538,102 B2 | 5/2009 | Yeung et al. |
| 7,538,103 B2 | 5/2009 | Hewawasam et al. |
| 7,893,055 B2 | 2/2011 | Walker et al. |
| 7,897,592 B2 | 3/2011 | Naidu |
| 7,897,593 B2 | 3/2011 | Naidu et al. |
| 7,902,182 B2 | 3/2011 | Naidu et al. |
| 2007/0111984 A1 | 5/2007 | Naidu et al. |
| 2007/0129379 A1 | 6/2007 | Naidu et al. |
| 2008/0171015 A1 | 7/2008 | Bender et al. |
| 2008/0221090 A1 | 9/2008 | Yeung et al. |
| 2008/0226591 A1 | 9/2008 | Gentles et al. |
| 2008/0227769 A1 | 9/2008 | Gentles et al. |
| 2009/0018163 A1 | 1/2009 | Schmitz et al. |
| 2009/0130056 A1 | 5/2009 | Bender et al. |
| 2009/0130057 A1 | 5/2009 | Hewawasam et al. |
| 2009/0253677 A1 | 10/2009 | Beaulieu et al. |

FOREIGN PATENT DOCUMENTS

| | | |
|---|---|---|
| JP | 2004-244320 | 9/2004 |
| WO | WO 03/062211 | 7/2003 |
| WO | WO 2005/061490 | 7/2005 |
| WO | WO 2005/061501 | 7/2005 |
| WO | WO 2005/070901 | 8/2005 |
| WO | WO 2005/080399 | 9/2005 |
| WO | WO 2006/046030 | 5/2006 |
| WO | WO 2006/046039 | 5/2006 |
| WO | WO 2006/103399 | 10/2006 |
| WO | WO 2006/121831 | 11/2006 |
| WO | WO 2007/014352 | 2/2007 |
| WO | WO 2007/029029 | 3/2007 |
| WO | WO 2007/129119 | 11/2007 |
| WO | WO 2009/120745 | 10/2009 |

OTHER PUBLICATIONS

U.S. Appl. No. 61/421,843, filed Dec. 10, 2010, Ueda et al.
U.S. Appl. No. 61/429,919, filed Dec. 10, 2010, Peese et al.
Colarusso, S. et al., "Suzuki Coupling at the 2-Position of Densely Functionalized Pyrimidones", Synthesis, No. 8, pp. 1343-1350 (2006).

(Continued)

*Primary Examiner* — Brenda Coleman
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

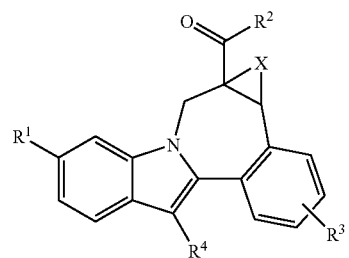

13 Claims, No Drawings

OTHER PUBLICATIONS

Pace, P. et al., "Dihydroxypyrimidine-4-carboxamides as Novel Potent and Selective HIV Integrase Inhibitors", J. Med. Chem., vol. 50, No. 9, pp. 2225-2239 (2007).

Petrocchi, A. et al., "From dihydroxypyrimidine carboxylic acids to carboxamide HIV-1 integrase inhibitors: SAR around the amide moiety", Bioorganic & Medicinal Chemistry Letters, vol. 17, pp. 350-353 (2007).

Summa, V. et al., "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species", J. Med. Chem., vol. 49, No. 23, pp. 6646-6649 (2006).

CYCLOPROPYL FUSED INDOLOBENZAZEPINE HCV NS5B INHIBITORS

CROSS REFERENCE TO RELATED APPLICATIONS

This application claims the benefit of U.S. provisional application Ser. No. 61/155,634 filed Feb. 26, 2009.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities, NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides" (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N. Engl. J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during exteneded dosing of the combination regimens. U.S. Pat. No. 7,265,152 and the corresponding PCT patent application WO2004/041201A2 describe compounds of the HCV-796 class.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

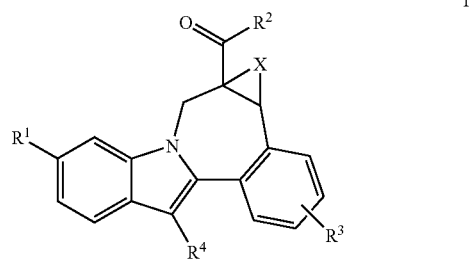

where:
$R^1$ is $CO_2R^5$ or $CONR^6R^7$;
$R^2$ is

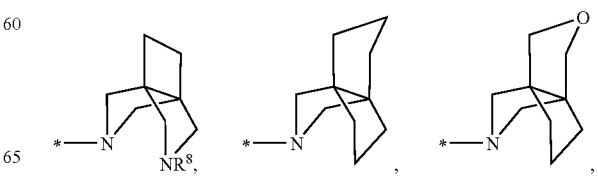

-continued

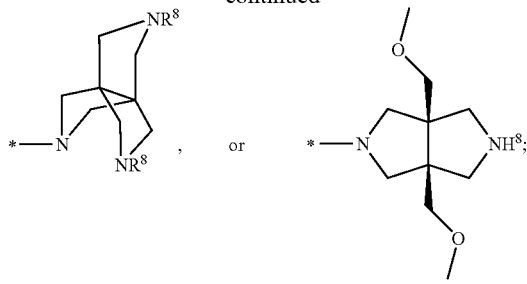

R³ is hydrogen, halo, alkyl, alkenyl, hydroxy, benzyloxy, alkoxy, or haloalkoxy;
R⁴ is cycloalkyl;
R⁵ is hydrogen or alkyl;
R⁶ is hydrogen, alkyl, alkylSO₂, alkenylSO₂, cycloalkylSO₂, haloalkylSO₂, (R⁹)₂NSO₂, or (R¹⁰)SO₂;
R⁷ is hydrogen or alkyl;
R⁸ is hydrogen, alkyl, cycloalkyl, (cycloalkyl)alkyl, haloalkyl, alkoxyalkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, R¹¹CO, benzyl, benzyloxycarbonyl, or pyridinyl;
R⁹ is hydrogen, alkyl, or cycloalkyl;
R¹⁰ is azetidinyl, pyrrolidinyl, piperidinyl, piperazinyl, morpholinyl, thiomorpholinyl, homopiperidinyl, or homomorpholinyl and is substituted with 0-3 alkyl substituents;
R¹¹ is azetidinyl, pyrrolidinyl, piperidinyl, piperazinyl, morpholinyl, thiomorpholinyl, homopiperidinyl, or homomorpholinyl and is substituted with 0-3 alkyl substituents; and
X is absent, a bond, or methylene;
or a pharmaceutically acceptable salt thereof.

Another aspect of the invention is a compound of formula I where
R¹ is CO₂R⁵ or CONR⁶R⁷;
R² is

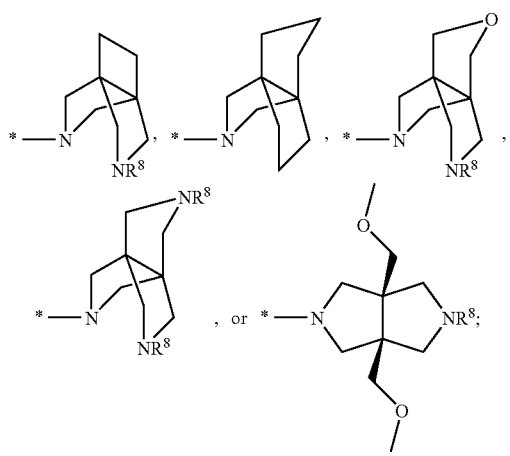

R³ is hydrogen, halo, alkyl, alkenyl, hydroxy, benzyloxy, alkoxy, or haloalkoxy;
R⁴ is cycloalkyl;
R⁵ is hydrogen or alkyl;
R⁶ is hydrogen, alkyl, alkylSO₂, alkenylSO₂, cycloalkylSO₂, haloalkylSO₂, (R⁹)₂NSO₂, or (R¹⁰)SO₂;
R⁷ is hydrogen or alkyl;
R⁸ is hydrogen, alkyl, cycloalkyl, (cycloalkyl)alkyl, haloalkyl, alkoxyalkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, R¹¹CO, benzyl, benzyloxycarbonyl, or pyridinyl;
R⁹ is hydrogen, alkyl, or cycloalkyl;
R¹⁰ is azetidinyl, pyrrolidinyl, piperidinyl, piperazinyl, morpholinyl, thiomorpholinyl, homopiperidinyl, or homomorpholinyl and is substituted with 0-3 alkyl substituents;
R¹¹ is azetidinyl, pyrrolidinyl, piperidinyl, piperazinyl, morpholinyl, thiomorpholinyl, homopiperidinyl, or homomorpholinyl and is substituted with 0-3 alkyl substituents; and
X is absent, a bond, or methylene;
or a pharmaceutically acceptable salt thereof.

Another aspect of the invention is a compound of formula I where
R¹ is CONR⁶R⁷;
R² is

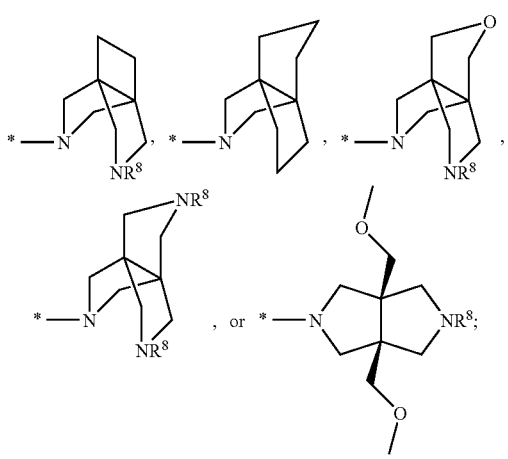

R³ is alkoxy;
R⁴ is cycloalkyl;
R⁶ is alkylSO₂, alkenylSO₂, cycloalkylSO₂, or (R⁹)₂NSO₂;
R⁷ is hydrogen;
R⁸ is hydrogen, alkyl, cycloalkyl, haloalkyl, alkoxyalkyl, alkylcarbonyl, alkoxycarbonyl, alkylSO₂, aminocarbonyl, (alkylamino)carbonyl, (dialkylamino)carbonyl, or (R¹¹)CO;
R⁹ is alkyl; and
X is absent, a bond, or methylene;
or a pharmaceutically acceptable salt thereof.

Another aspect of the invention is a compound of formula I where
R¹ is CONR⁶R⁷;
R² is

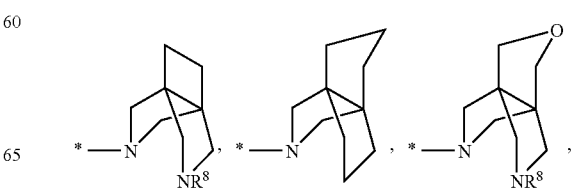

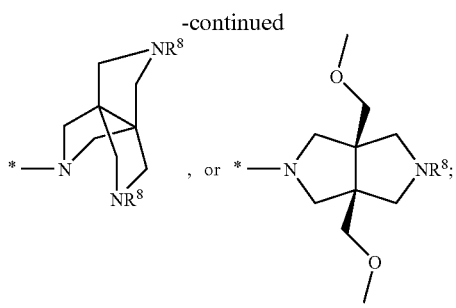

R³ is methoxy;
R⁴ is cyclohexyl;
R⁶ is isopropylSO₂, isobutylSO₂, isopropenylSO₂, cyclopropylSO₂, or (Me)₂NSO₂;
R⁷ is hydrogen; and
R⁸ is hydrogen, methyl, ethyl, cyclopropyl, trifluoroethyl, ethoxyethyl, acetyl, methoxycarbonyl, isopropylSO₂, (methylamino)carbonyl, (dimethylamino)carbonyl, (diisopropylamino)carbonyl, (pyrrolidinyl)CO, and (morpholinyl)CO; and
X is absent, a bond, or methylene;
or a pharmaceutically acceptable salt thereof.

Another aspect of the invention is a compound of formula I where R¹ is CONR⁶R⁷; R⁶ is alkylSO₂, cycloalkylSO₂, haloalkylSO₂, (R⁹)₂NSO₂, or (R¹⁰)SO₂; and R⁷ is hydrogen.

Another aspect of the invention is a compound of formula I where R² is

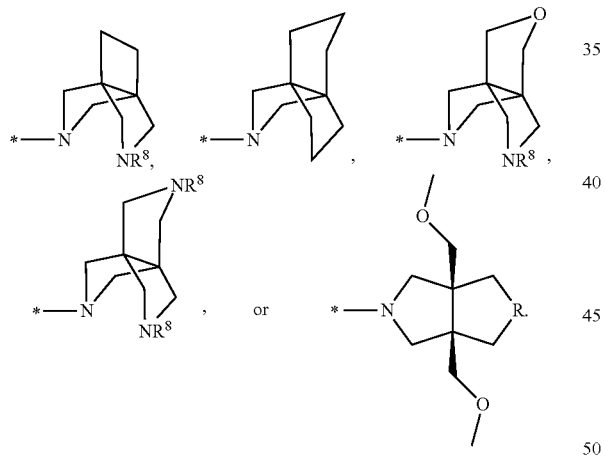

Another aspect of the invention is a compound of formula I where R³ is hydrogen.
Another aspect of the invention is a compound of formula I where R³ is methoxy.
Another aspect of the invention is a compound of formula I where R⁴ is cyclohexyl.
Another aspect of the invention is a compound of formula I where R⁶ is (R⁹)₂NSO₂ or (R¹⁰)SO₂.
Another aspect of the invention is a compound of formula I where R⁶ is (dimethylamino)SO₂.
Another aspect of the invention is a compound of formula I where R⁶ is alkylSO₂.
Another aspect of the invention is a compound of formula I where R⁶ is isopropylSO₂.
Another aspect of the invention is a compound of formula I where R⁸ is hydrogen, alkyl, cycloalkyl, (cycloalkyl)alkyl, haloalkyl, alkoxyalkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, (R¹¹)CO, benzyl, benzyloxycarbonyl, or pyridinyl.

Another aspect of the invention is a compound of formula I where R⁸ is hydrogen, methyl, ethyl, cyclopropyl, trifluoroethyl, ethoxyethyl, acetyl, methoxycarbonyl, isopropylSO₂, (methylamino)carbonyl, (dimethylamino)carbonyl, (diisopropylamino)carbonyl, (pyrrolidinyl)CO, or (morpholinyl)CO.

Another aspect of the invention is a compound of formula I where X is methylene.

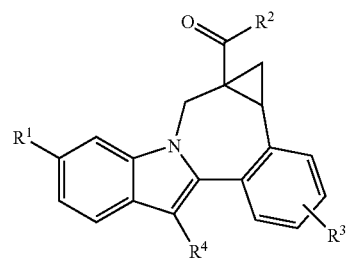

Another aspect of the invention is a compound of formula I where X is a bond.

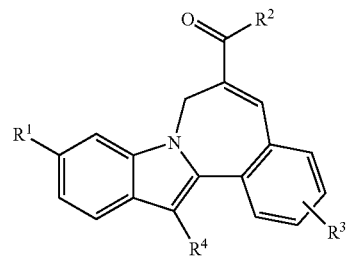

Another aspect of the invention is a compound of formula I where X is absent.

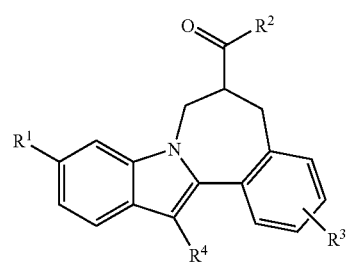

Another aspect of the invention is a compound of formula I according to the following stereochemistry.

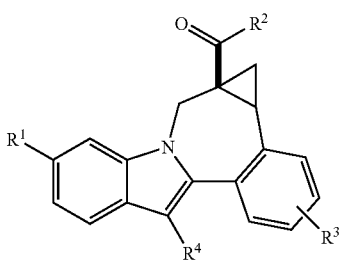

Another aspect of the invention is a compound of formula I according to the following stereochemistry.

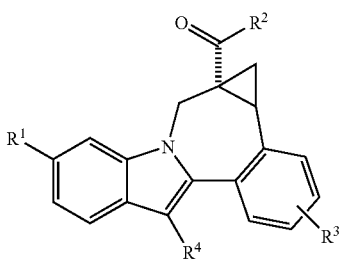

Another aspect of the invention is a compound of formula I according to the following stereochemistry.

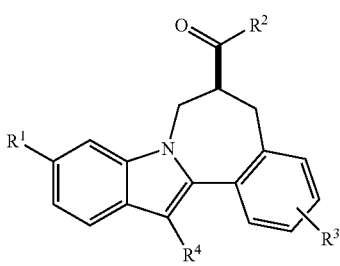

Another aspect of the invention is a compound of formula I according to the following stereochemistry,

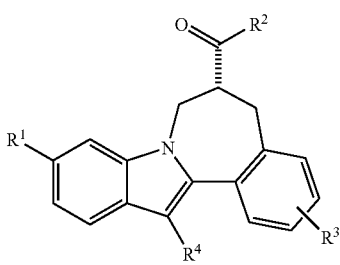

Any scope of any variable, including $R^1$, $R^2$, $R^3$, $R^4$, $R^5$, $R^6$, $R^7$, $R^8$, $R^9$, $R^{10}$, $R^{11}$, or X can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

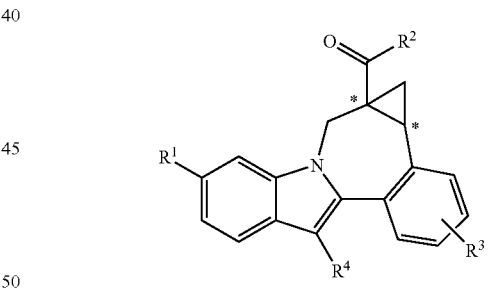

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaH-MDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Methyl 2-bromo-3-cyclohexyl-1H-indole-6-carboxylate can be hydrolyzed to 2-bromo-3-cyclohexyl-1H-indole-6-carboxylic acid (See Scheme 1). This compound can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions with a diversity of 2-formyl boronic acids or esters, using for example, Suzuki coupling conditions, to provide cyclic heraiaminal intermediates of the type depicted. These compounds can be converted to indolobenzazepines derivatives by treatment with methyl 2-(dimethoxyphosphoryl)acrylate under the influence of cesium carbonate in DMF via consecutive Michael and Homer Emmons reactions.

Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a variety of alkyl-bridged piperazines. For example, O-(1H-benzotriazol-1-yl)-N,N, N',N'-tetramethyluronium tetrafluoroborate and diisopropyl ethyl amine in DMSO can give alkyl bridged piperazine carboxamides.

Scheme 1.

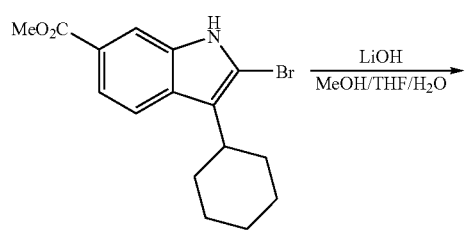

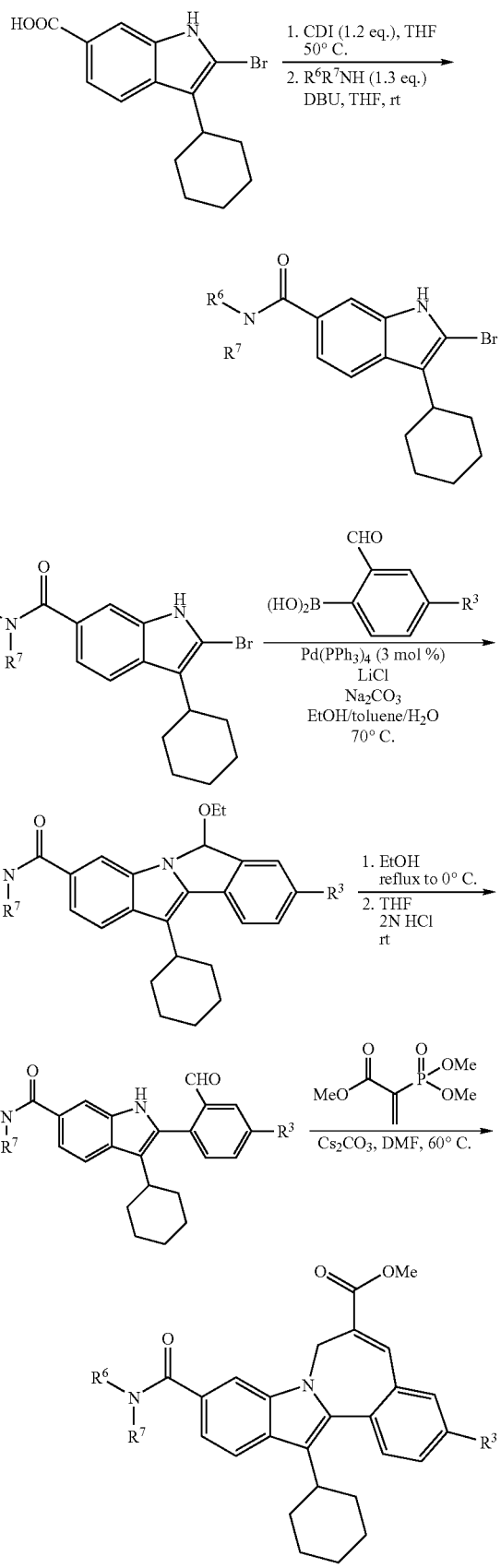

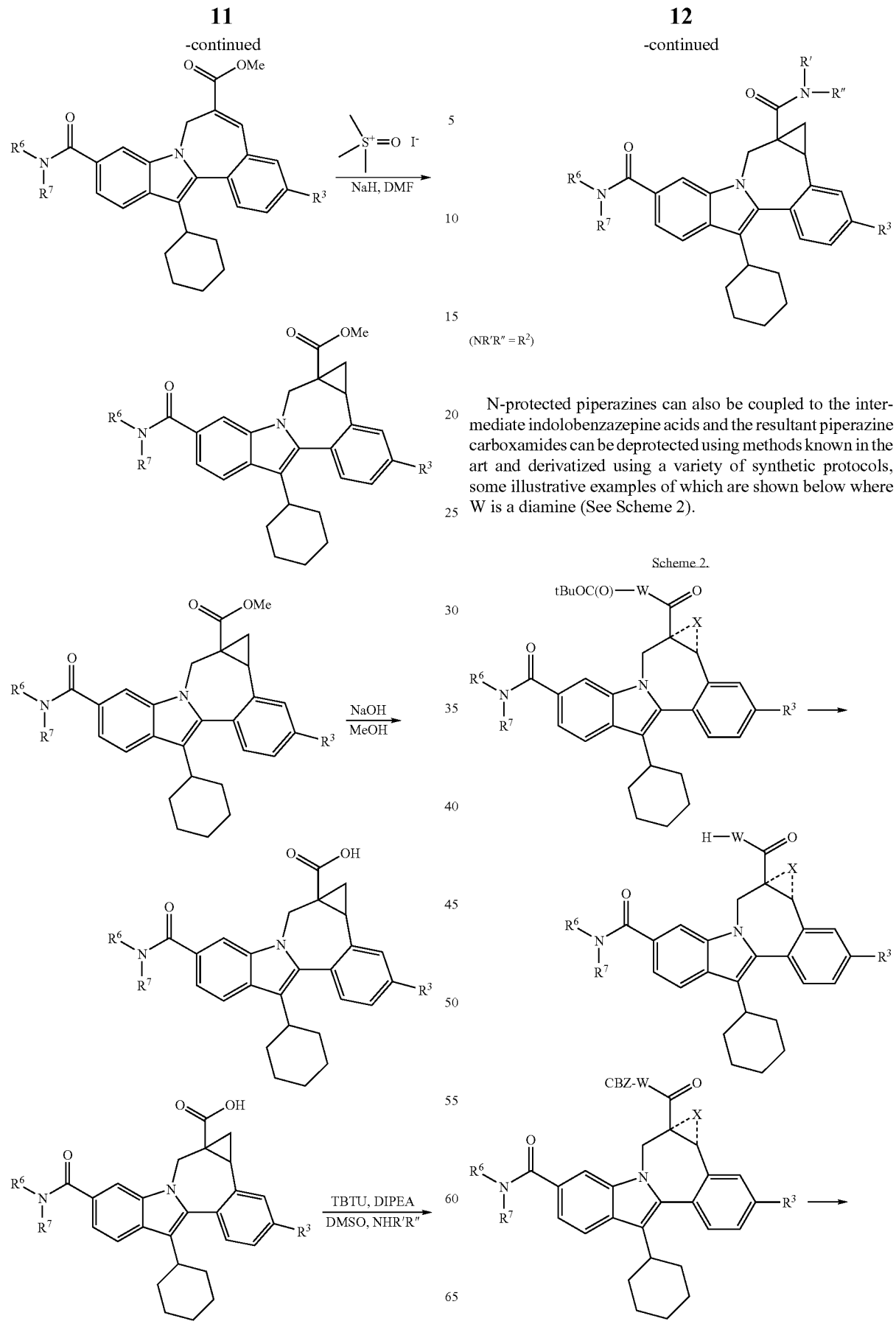
N-protected piperazines can also be coupled to the intermediate indolobenzazepine acids and the resultant piperazine carboxamides can be deprotected using methods known in the art and derivatized using a variety of synthetic protocols, some illustrative examples of which are shown below where W is a diamine (See Scheme 2).

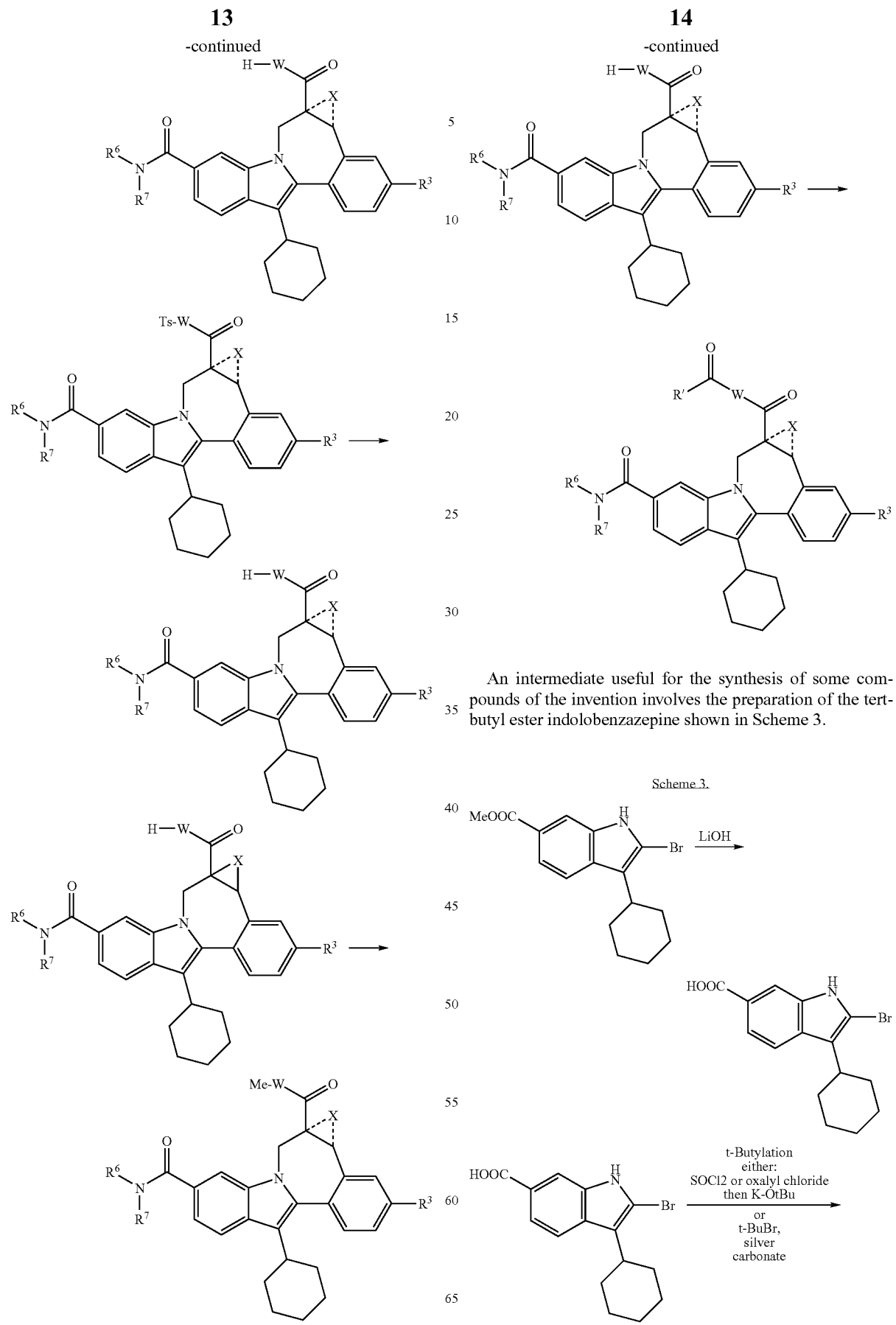
An intermediate useful for the synthesis of some compounds of the invention involves the preparation of the tert-butyl ester indolobenzazepine shown in Scheme 3.

-continued

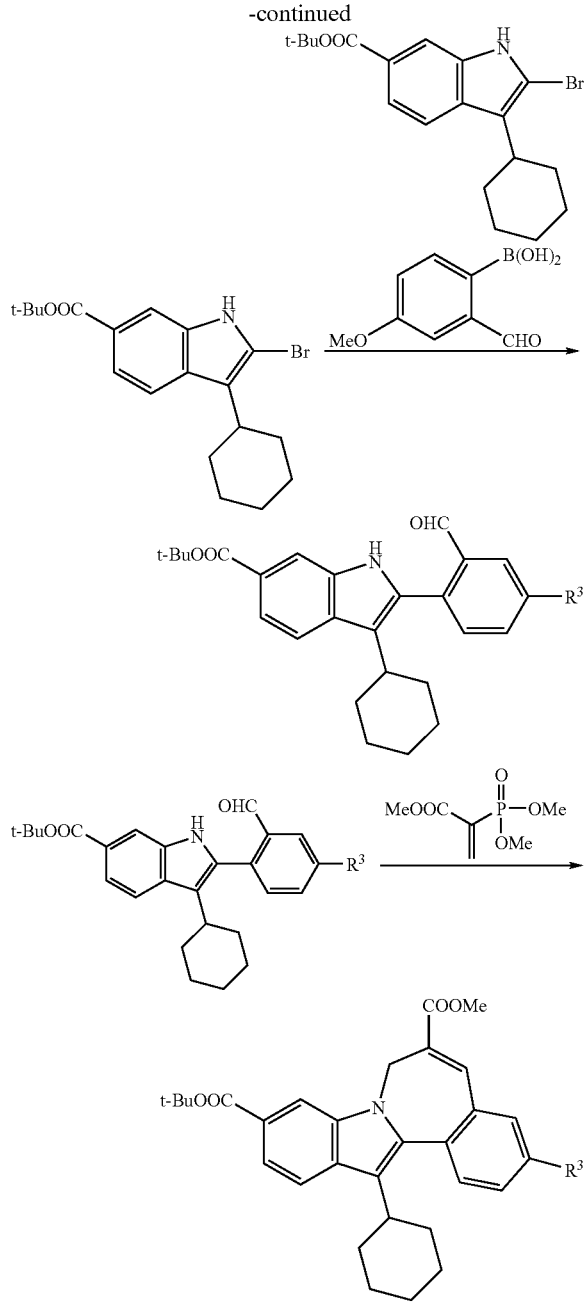

This methodology involves base catalyzed hydrolysis of the indole methyl ester shown, followed by its reaction with either thionyl chloride and potassium tertiary butoxide, or alkylation with silver carbonate and tertiary butyl bromides. The resultant compound can be transformed using chemistry analogous to that outlined previously to provide the mixed ester indolobenzazepines shown above.

These intermediates are useful in an alternative procedure that can be employed for the preparation of acylsulfamide and acylsulfonamide alkyl-bridged piperazines as shown in Scheme 4. Cleavage of the t-butyl ester group can generate the acid which can be coupled to a diversity of sulfonamides and sulfonylureas. Subsequent hydrolysis affords the related aliphatic acid, which can be coupled with a diversity of alkyl-bridged piperazines. For example, O-(1H-benzotriazol-1-yl)-N,N,N',N'-tetramethyluronium tetrafluoroborate and diisopropyl ethyl amine in DMSO can give the alkyl bridged piperazine carboxamides.

Scheme 4.

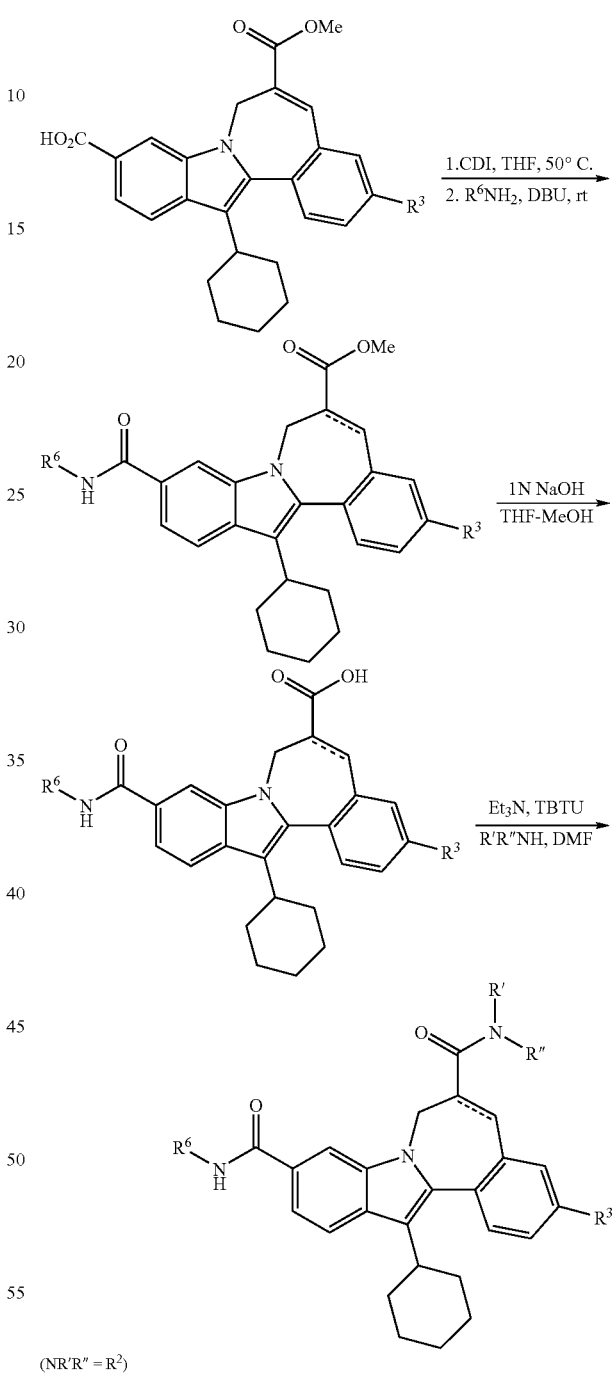

(NR'R'' = R²)

These intermediates are also useful in an alternative procedure that can be employed for the preparation of acylsulfamide and acylsulfonamide alkyl-bridged piperazines in compounds containing a bridged cyclopropane, as shown in Scheme 4. Cyclopropanation of an intermediate t-butyl ester indolobenzazepine and subsequent cleavage of the t-butyl ester group can generate the acid which can be coupled to a diversity of sulfonamides and sulfonylureas. Subsequent hydrolysis affords the related aliphatic acid, which can be coupled with a diversity of alkyl-bridged piperazines. For example, O-(1H-benzotriazol-1-yl)-N,N,N',N'-tetramethyluronium tetrafluoroborate and diisopropyl ethyl amine in DMSO can give the alkyl bridged piperazine carboxamides.

Scheme 5.

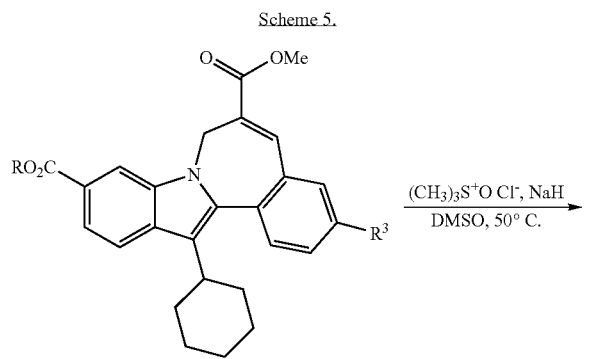

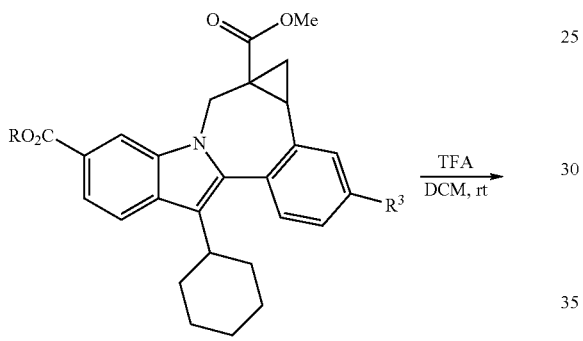

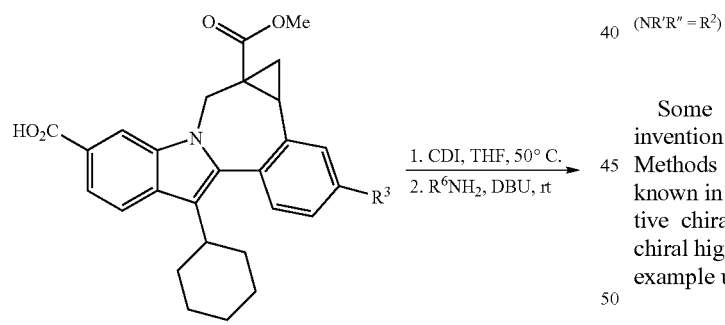

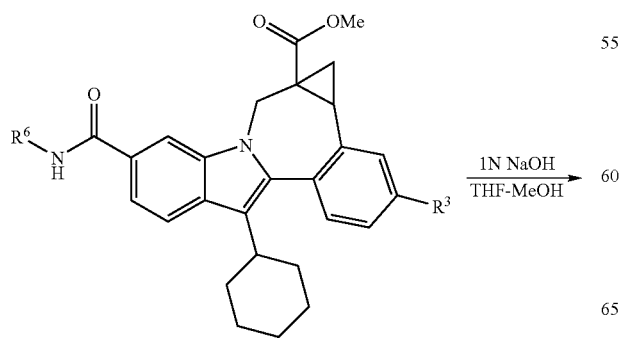

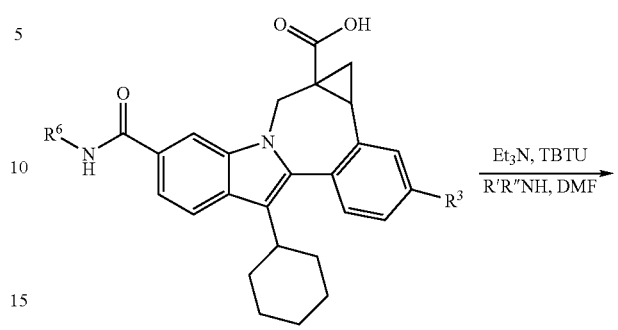

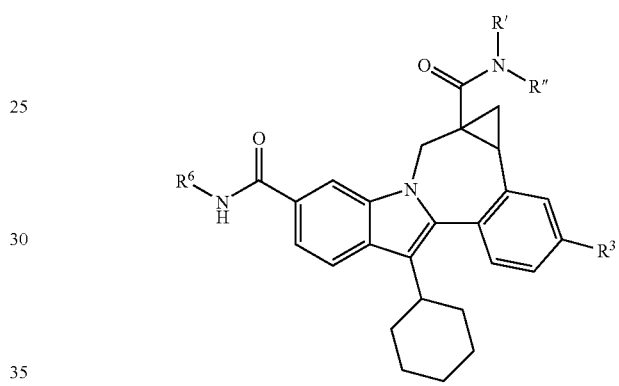

(NR'R" = R²)

Some examples exist as stereoisomeric mixtures. The invention encompasses all stereoisomers of the compounds. Methods of fractionating stereoisomeric mixtures are well known in the art, and include but are not limited to; preparative chiral supercritical fluid chromatography (SFC) and chiral high performance liquid chromatography (HPLC). An example using this approach is shown in scheme 6.

Scheme 6.

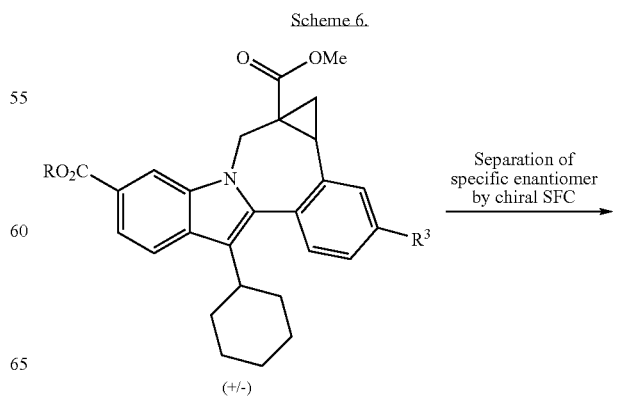

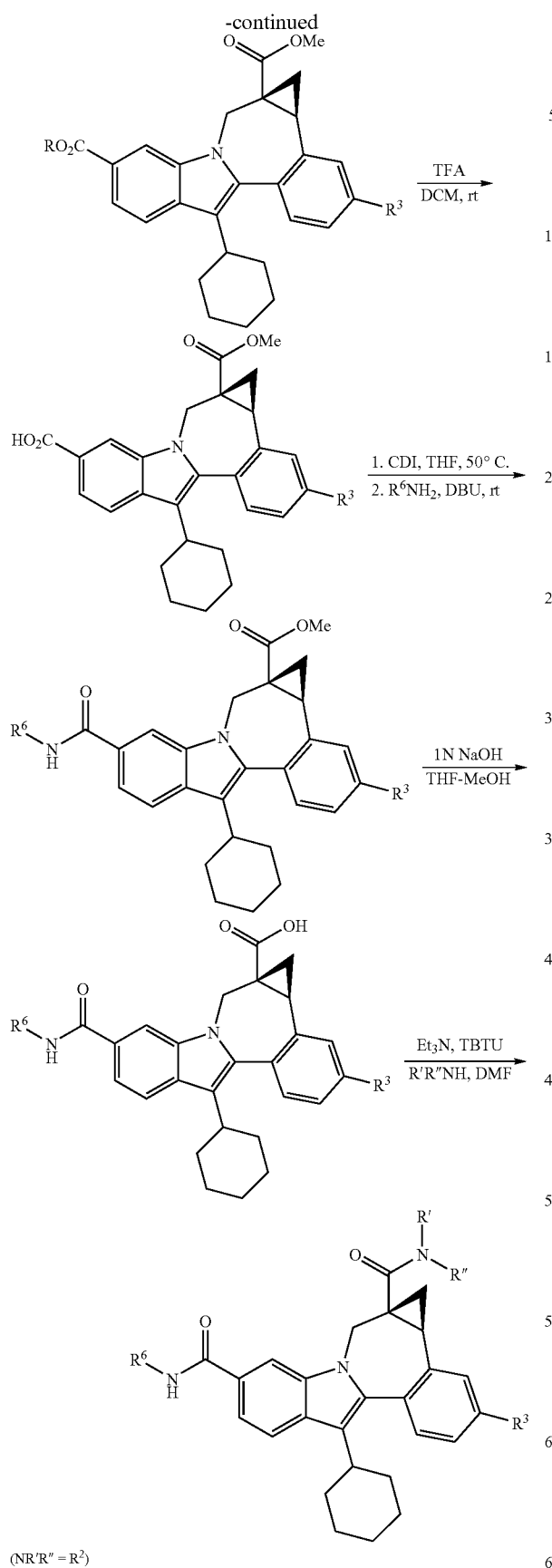

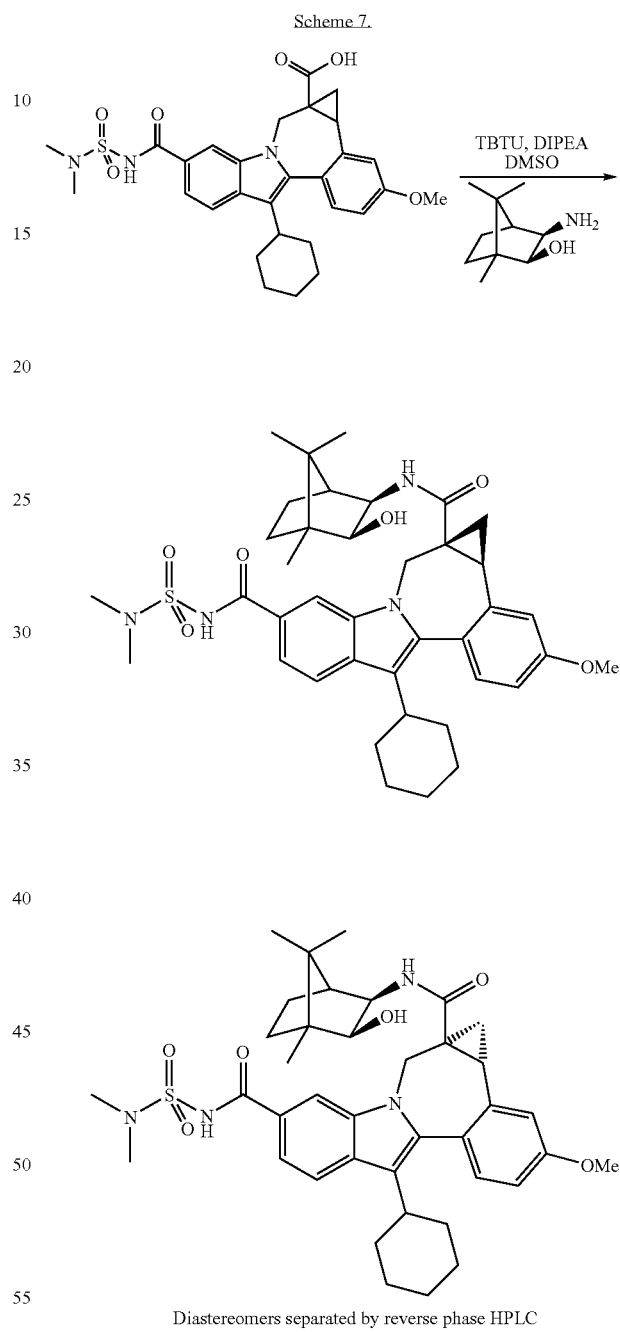

An additional method to achieve such separations involves the preparation of mixtures of diastereomers which can be separated using a variety of methods known in the art. One example of this approach is shown below (Scheme 7).

Diastereomers separated by reverse phase HPLC

Some diastereomeric amides can be separated using reverse phase HPLC. After hydroysis, the resultant optically active acids can be coupled with bridged piperazine derivatives (Scheme 8). For example, O-(1H-benzotriazol-1-yl)-N,N,N',N'-tetramethyluronium tetrafluoroborate and diisopropyl ethyl amine in DMSO can be used to give the alkyl bridged piperazine carboxamides. Other standard acid amine coupling methods can also be used to give optically active carboxamides.

Scheme 8.
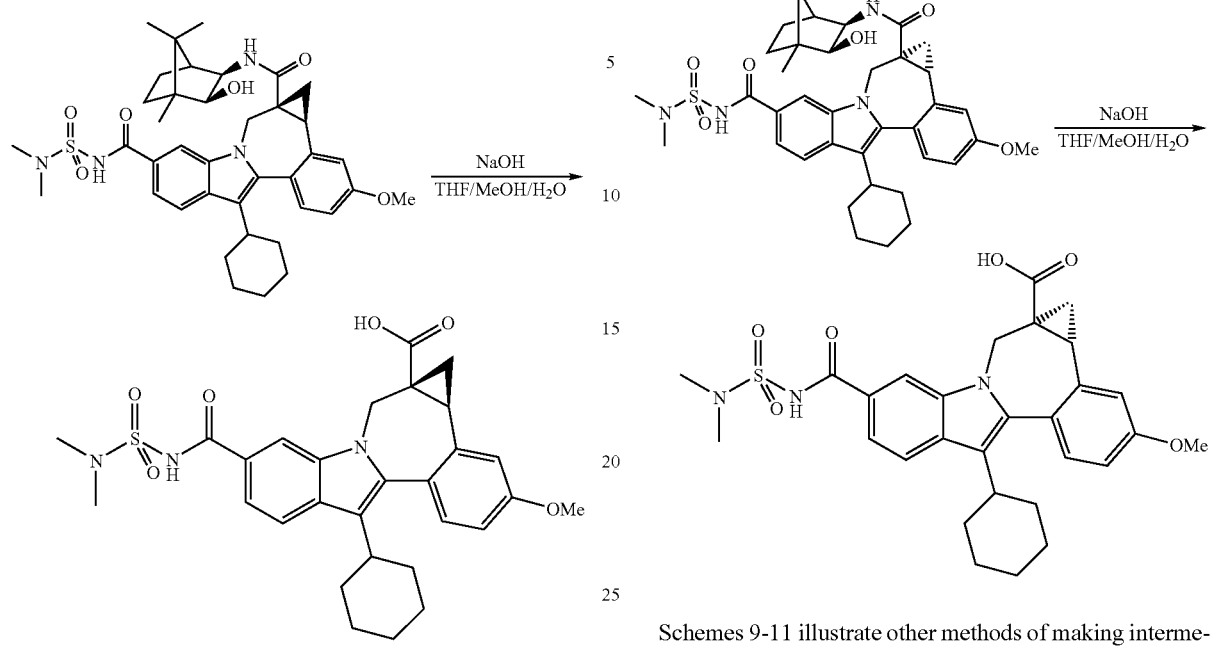
Schemes 9-11 illustrate other methods of making intermediates and compounds.
Scheme 9.
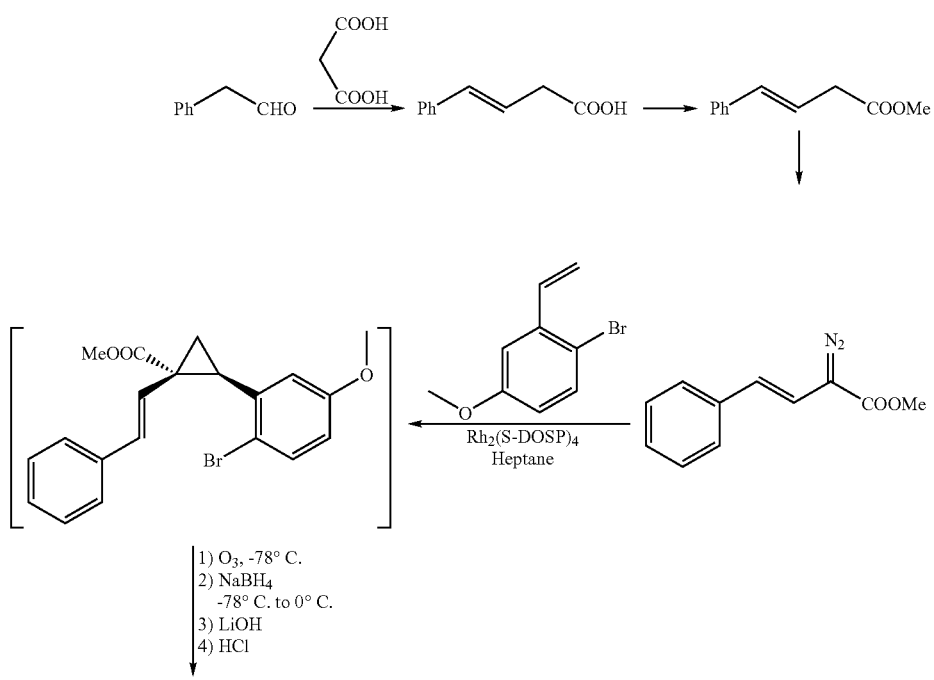
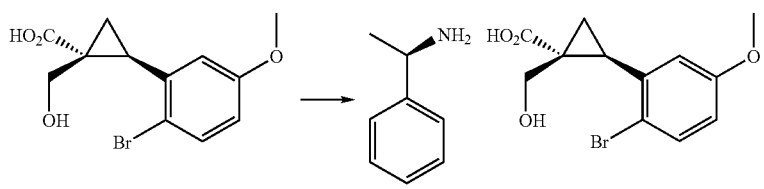

Scheme 10.
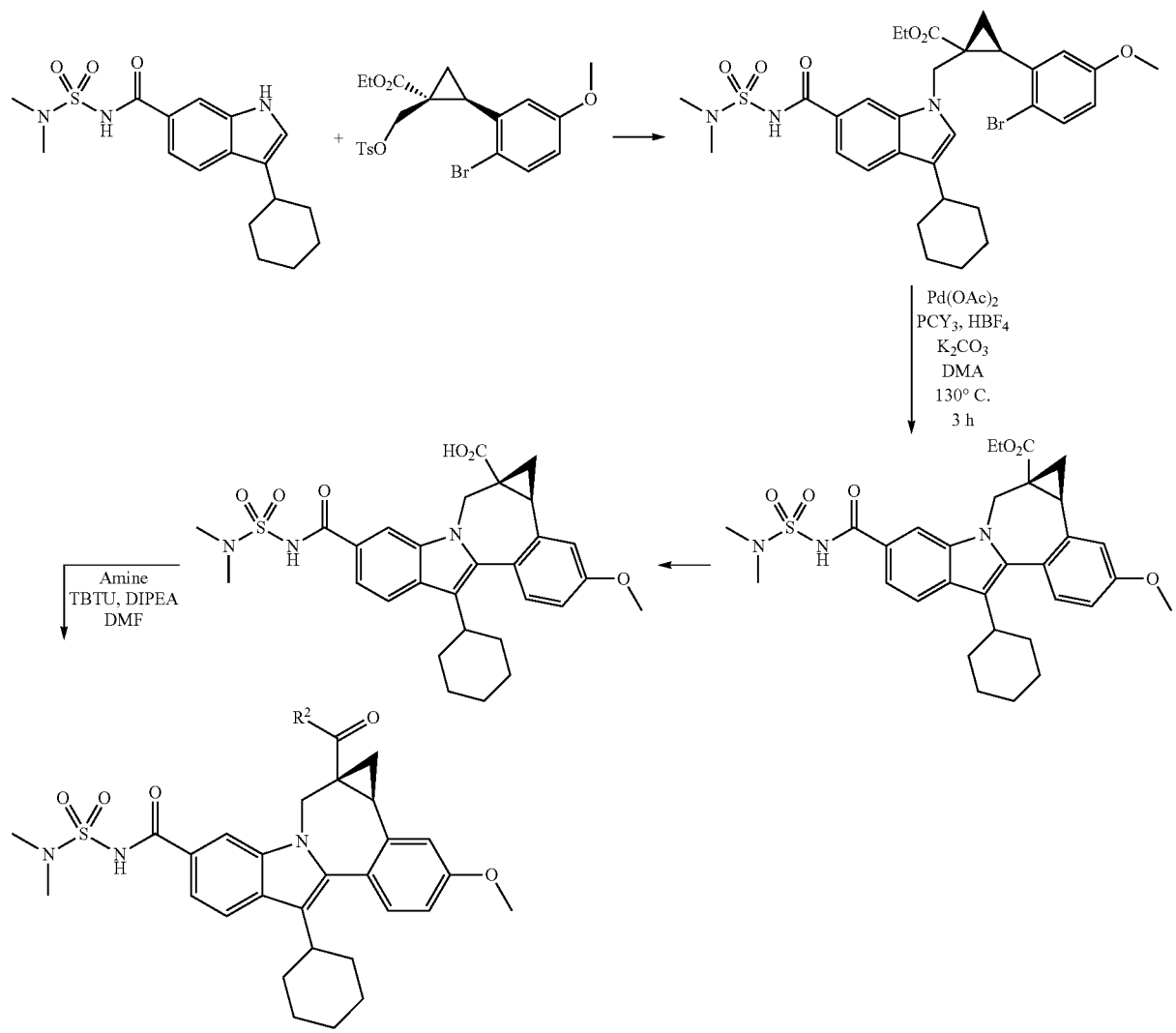
Scheme 11.
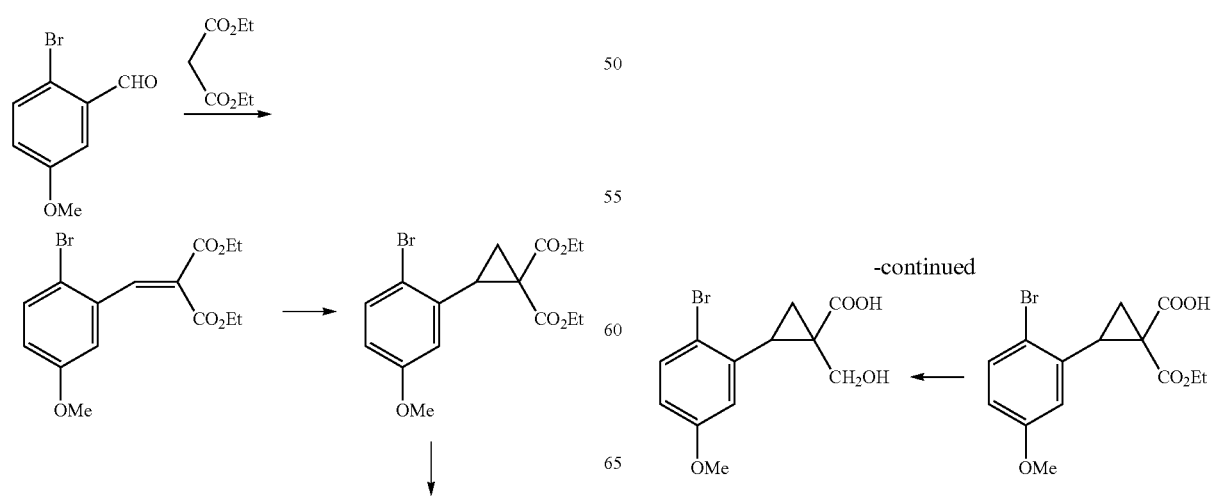

Scheme 12.
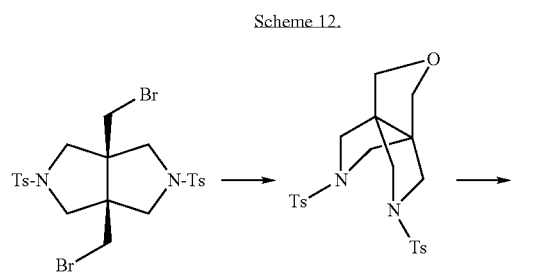
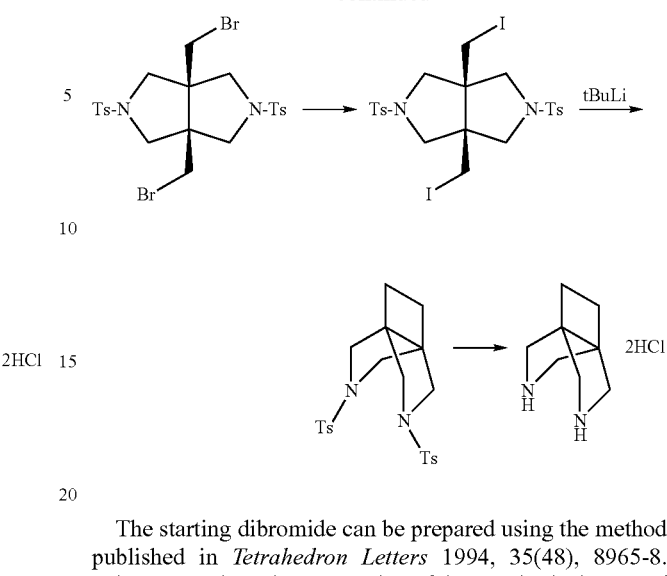
The starting dibromide can be prepared using the method published in *Tetrahedron Letters* 1994, 35(48), 8965-8. Schemes 13 show the preparation of the novel substituents of the compounds of this invention and the specific details and conditions are contained in the experimental section.
Scheme 13.
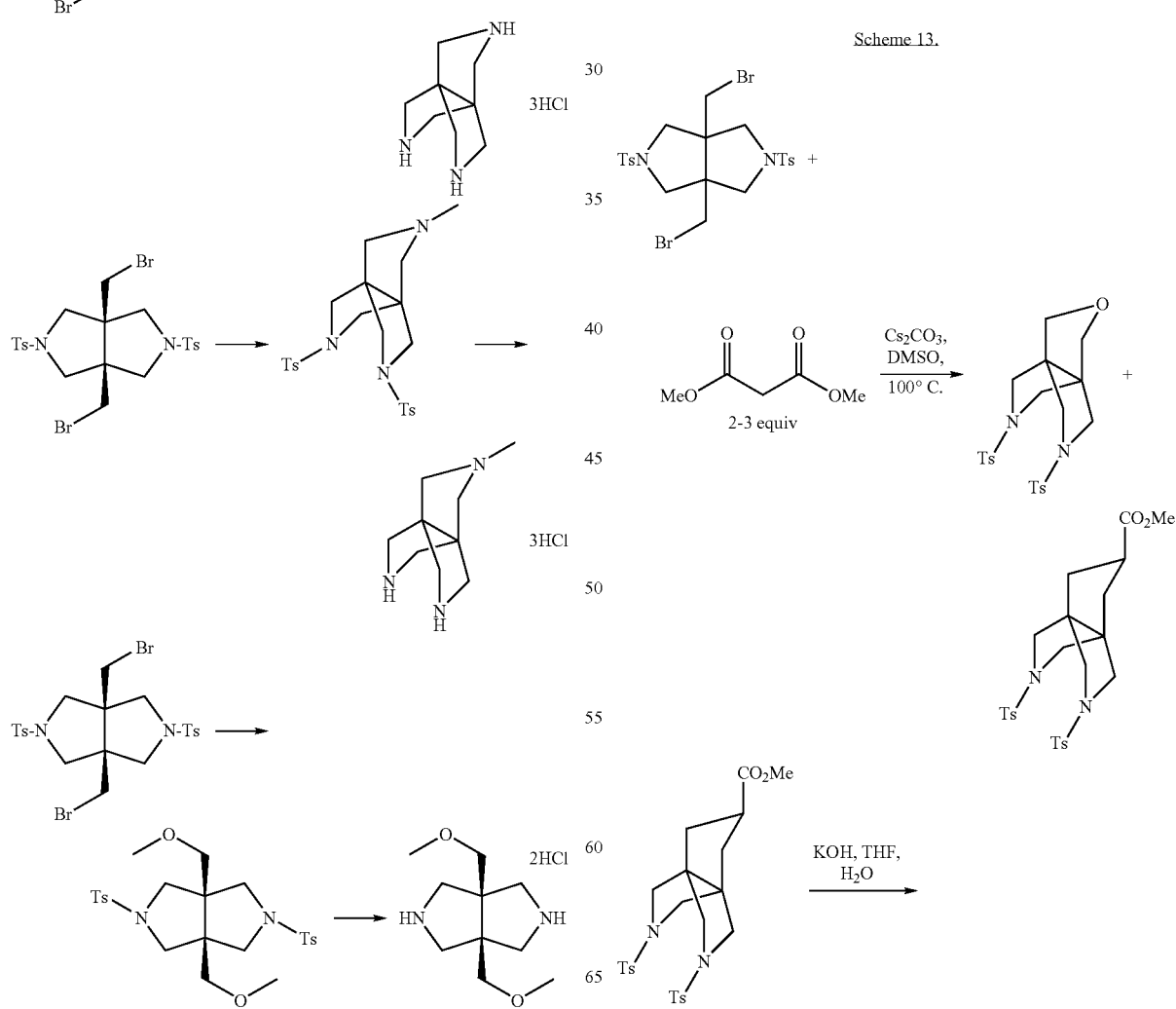

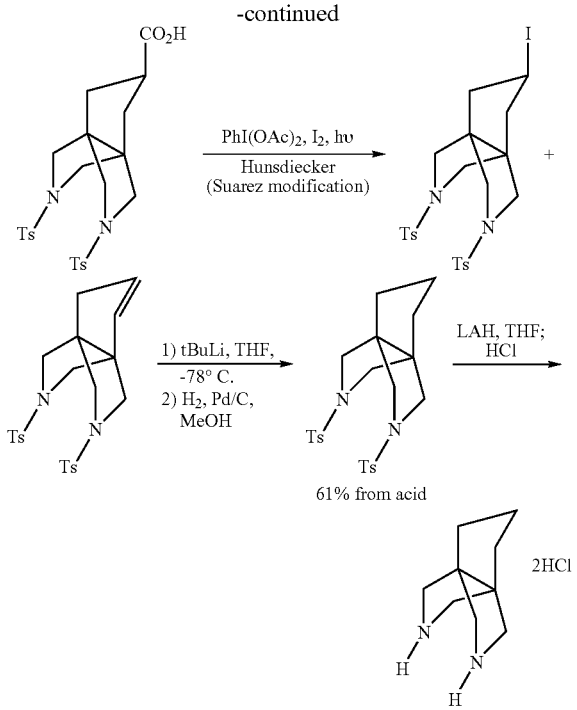

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH2O, NaCl added to 150 mM final, the FRET peptide diluted to 20 µM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System, Compound analysis was deteiniined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

HCV Replicon Luciferase Reporter Assay (LE Assay in Table)

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, J. Virol. 75(10):4614-4624 (2001)). HUH-7 cells, constitutively expressing the HCV replicon, were grown in Dulbeccors Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Coming cat #3571). The plates were then seeded with 50 μl of cells at a density of $3.0 \times 10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). 3 μl of Cell-Titer Blue was added to each well and incubated for 8 hrs at 37° C. The fluorescence signal from each well was read, with an excitation wavelength at 525/10 nm and an emission wavelength of 598/10 nm, using the Viewlux Imager.

Representative data for compounds are reported in Tables 1 and 2.

TABLE 1

| Structure | NeoLuc $EC_{50}$ (μM) | LE NeoLuc $EC_{50}$ (μM) | $IC_{50}$ (μM) |
|---|---|---|---|
| 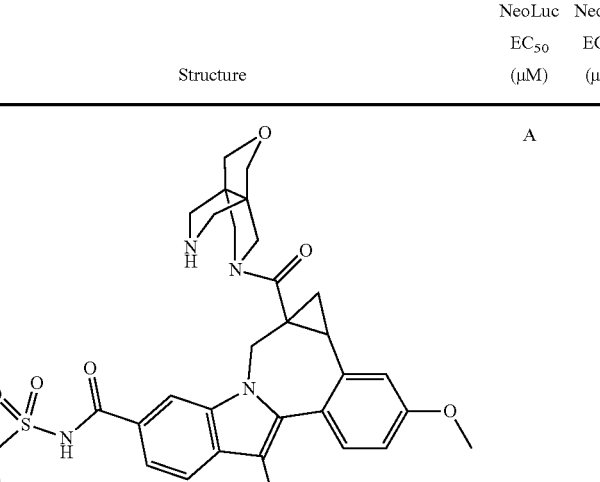 | A | A | |

TABLE 1-continued

| Structure | NeoLuc EC$_{50}$ (μM) | LE NeoLuc EC$_{50}$ (μM) | IC$_{50}$ (μM) |
|---|---|---|---|
| 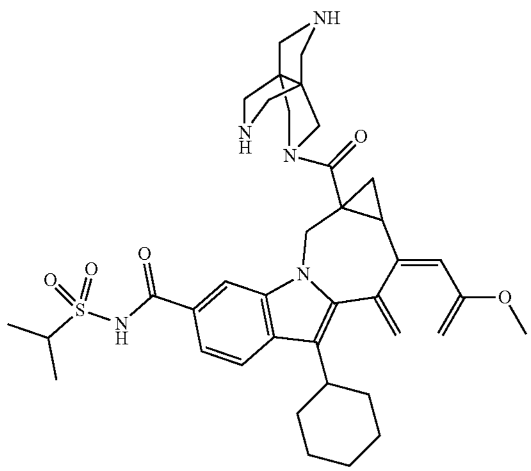 | C | | I |
| | A | | I |
| | A | | I |

TABLE 1-continued
| Structure | NeoLuc EC$_{50}$ (μM) | LE NeoLuc EC$_{50}$, (μM) | IC$_{50}$ (μM) |
|---|---|---|---|
| 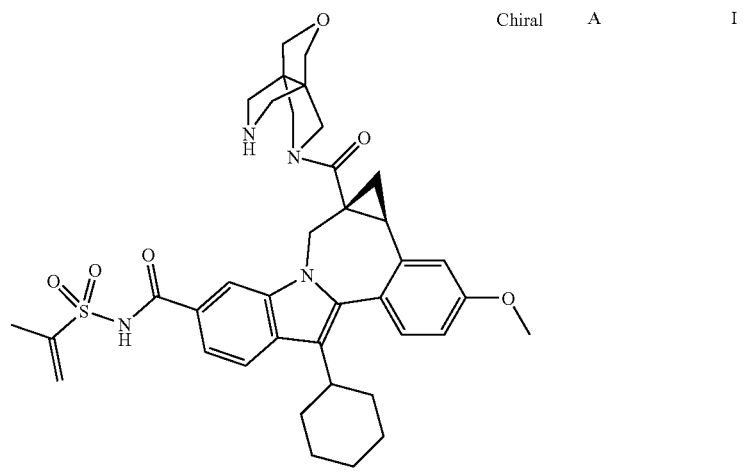 Chiral | A | | I |
| 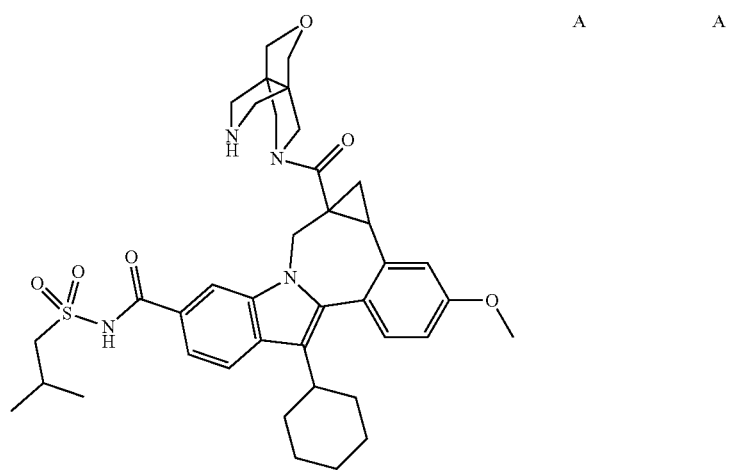 | A | | A |

TABLE 1-continued

| Structure | NeoLuc EC$_{50}$ (μM) | LE NeoLuc EC$_{50}$, (μM) | IC$_{50}$ (μM) |
|---|---|---|---|
| | A | | A |
| | | | |
| (Chiral) | A | A | A |

TABLE 1-continued

| Structure | NeoLuc EC$_{50}$ (μM) | LE NeoLuc EC$_{50}$, (μM) | IC$_{50}$ (μM) |
|---|---|---|---|
| | A | | A |
| | A | | |
| Chiral | B | | H |

TABLE 1-continued

| Structure | NeoLuc EC$_{50}$ (μM) | LE NeoLuc EC$_{50}$, (μM) | IC$_{50}$ (μM) |
|---|---|---|---|
| (structure) | | A | A |
| (structure) Chiral | | A | H |
| (structure) Chiral | A | B | A |

TABLE 1-continued
| Structure | NeoLuc EC$_{50}$ (μM) | LE NeoLuc EC$_{50}$, (μM) | IC$_{50}$ (μM) |
|---|---|---|---|
| 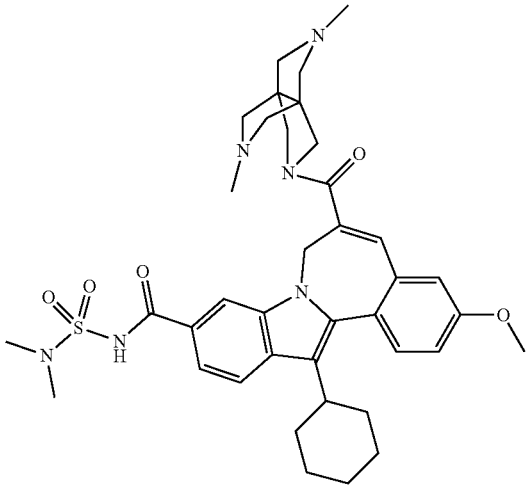 | A | A | A |
| 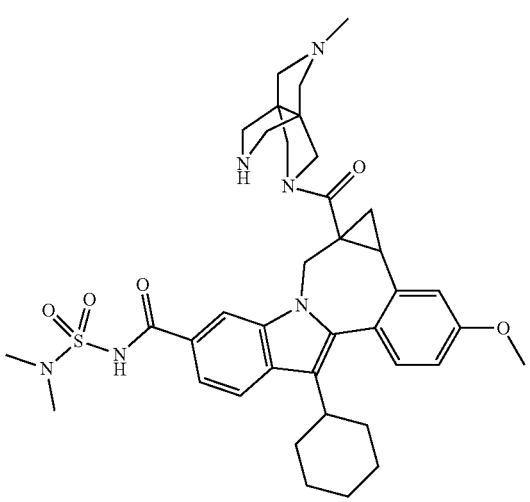 | A | A | A |
| 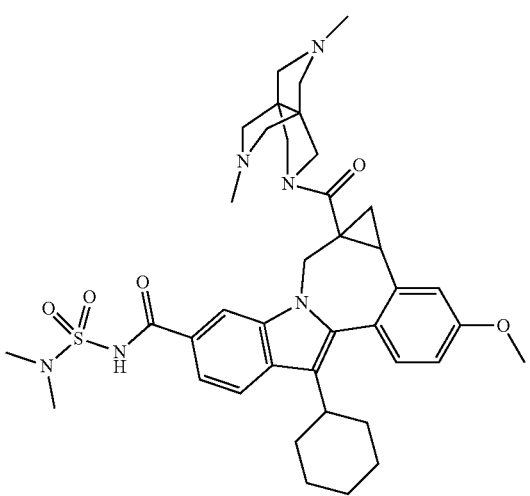 | A | A | A |

TABLE 1-continued
| Structure | | NeoLuc EC$_{50}$ (μM) | LE NeoLuc EC$_{50}$, (μM) | IC$_{50}$ (μM) |
|---|---|---|---|---|
| 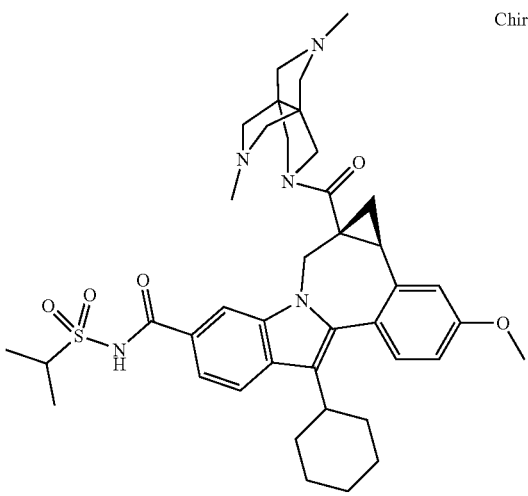 | Chiral | A | A | A |
| 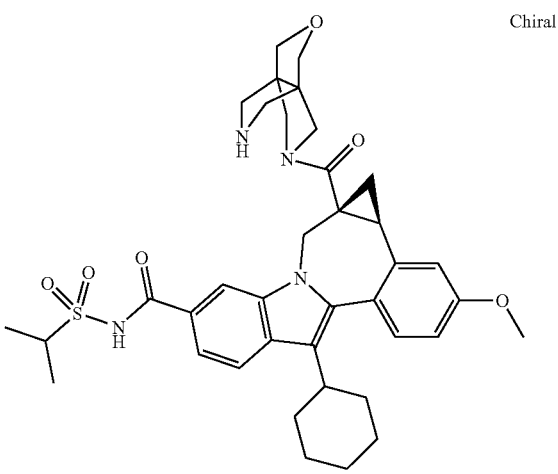 | Chiral | A | A | A |
| 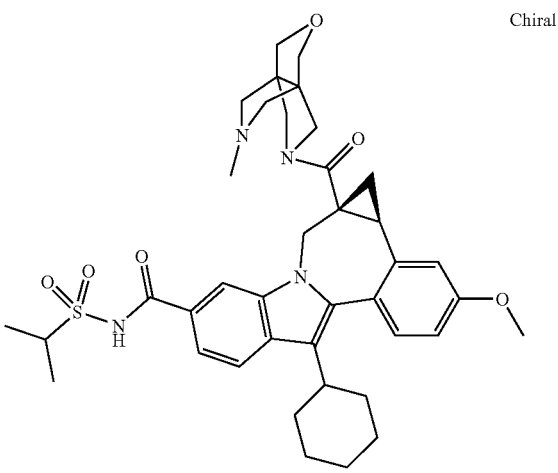 | Chiral | A | A | A |

TABLE 1-continued
| Structure | NeoLuc EC$_{50}$ (μM) | LE NeoLuc EC$_{50}$, (μM) | IC$_{50}$ (μM) |
|---|---|---|---|
| 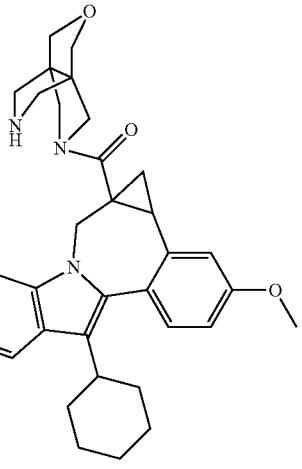 | A | A | A |
| 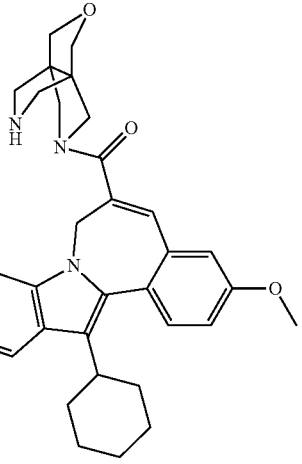 | A | A | A |
| 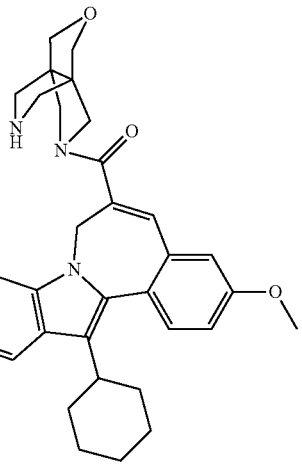 | A | A | A |

TABLE 1-continued

| Structure | NeoLuc EC₅₀ (μM) | LE NeoLuc EC₅₀ (μM) | IC₅₀ (μM) |
|---|---|---|---|
| (structure) | A | A | A |
| (structure) | A | A | A |
| (structure) | A | A | A |

TABLE 1-continued
| Structure | | NeoLuc EC$_{50}$ (μM) | LE NeoLuc EC$_{50}$, (μM) | IC$_{50}$ (μM) |
|---|---|---|---|---|
| 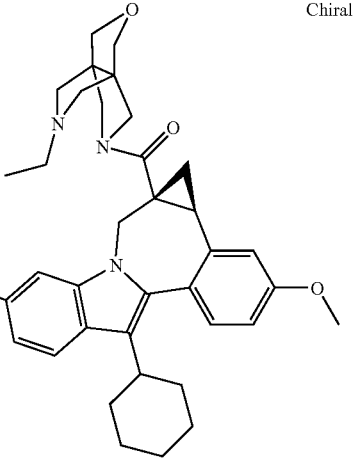 | Chiral | A | A | A |
| 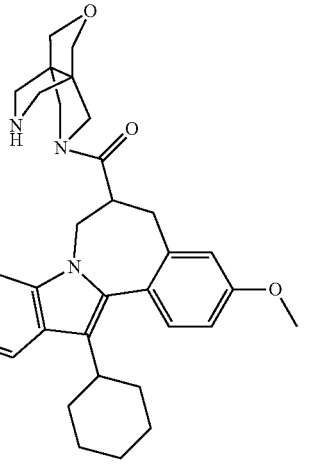 | | C | E | A |
| 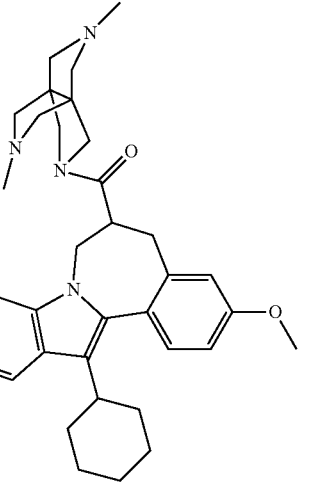 | | A | A | A |

TABLE 1-continued

| Structure | NeoLuc EC$_{50}$ (μM) | LE NeoLuc EC$_{50}$, (μM) | IC$_{50}$ (μM) |
|---|---|---|---|
| | A | B | A |
| 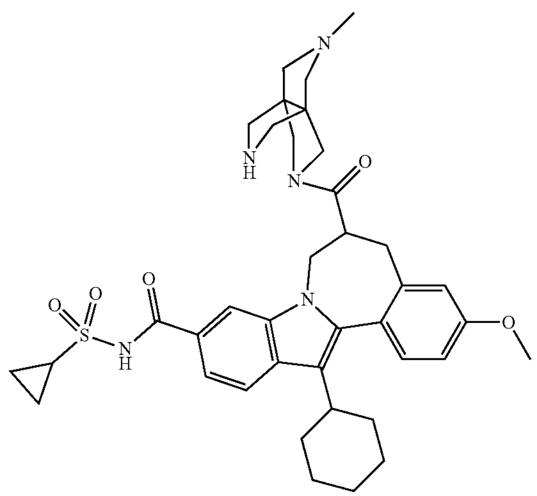 | C | B | A |
| | A | A | A |

TABLE 1-continued
| Structure | NeoLuc EC$_{50}$ (μM) | LE NeoLuc EC$_{50}$, (μM) | IC$_{50}$ (μM) |
|---|---|---|---|
| Chiral 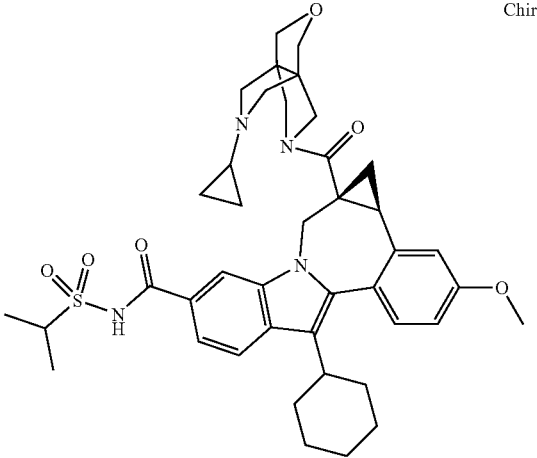 | A | A | F |
| Chiral 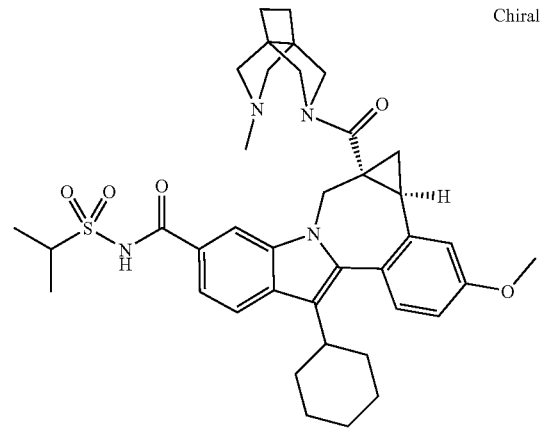 | A | A | |
| Chiral 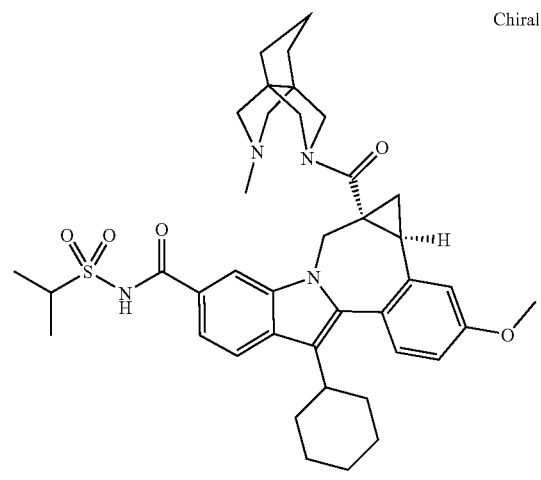 | A | A | |

TABLE 1-continued

| Structure | | NeoLuc EC$_{50}$ (μM) | LE NeoLuc EC$_{50}$, (μM) | IC$_{50}$ (μM) |
|---|---|---|---|---|
| | Chiral | A | A | A |
| | Chiral | A | A | A |
| | | | A | A |

TABLE 1-continued

| Structure | NeoLuc EC$_{50}$ (μM) | LE NeoLuc EC$_{50}$, (μM) | IC$_{50}$ (μM) |
|---|---|---|---|
| 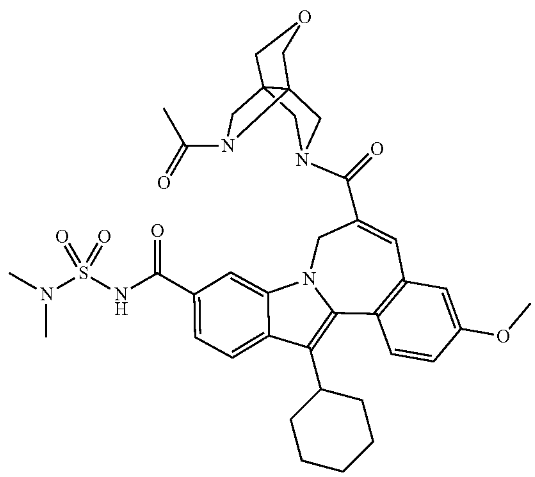 | A | A | A |
| | Chiral | A | A |
| | Chiral | | A |

TABLE 1-continued

| Structure | NeoLuc EC$_{50}$ (μM) | LE NeoLuc EC$_{50}$, (μM) | IC$_{50}$ (μM) |
|---|---|---|---|
| (Chiral structure) | | | C |
| (Chiral structure) | A | | A |
| (Chiral structure) | A | | A |

TABLE 1-continued
| Structure | NeoLuc EC$_{50}$ (μM) | LE NeoLuc EC$_{50}$ (μM) | IC$_{50}$ (μM) |
|---|---|---|---|
| 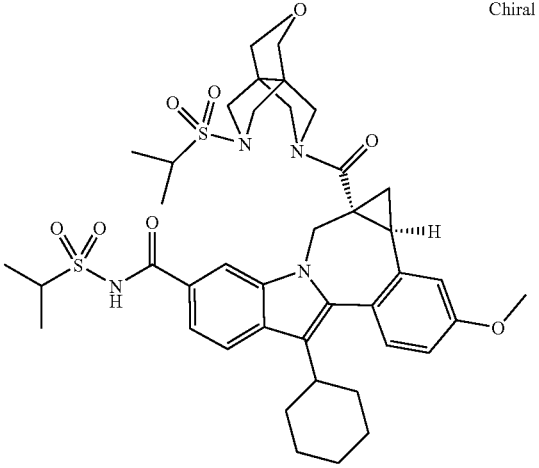 Chiral | A* | A |  |
| 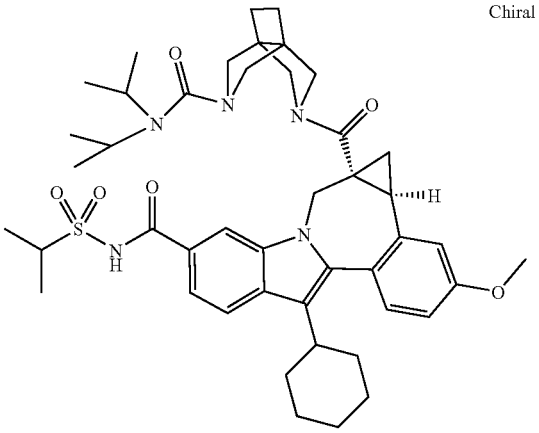 Chiral | A* | A |  |
| 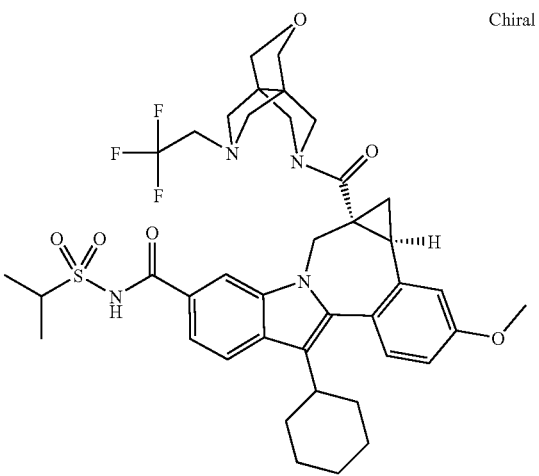 Chiral | A* | A |  |

TABLE 1-continued
| Structure | NeoLuc EC₅₀ (μM) | LE NeoLuc EC₅₀, (μM) | IC₅₀ (μM) |
|---|---|---|---|
| 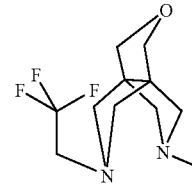 Chiral | | A* | A |
| 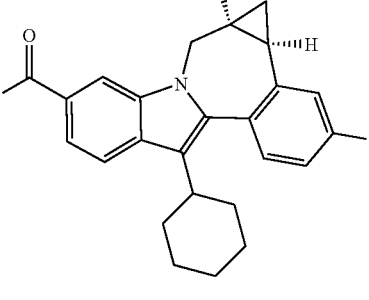 Chiral | | A* | G |
| 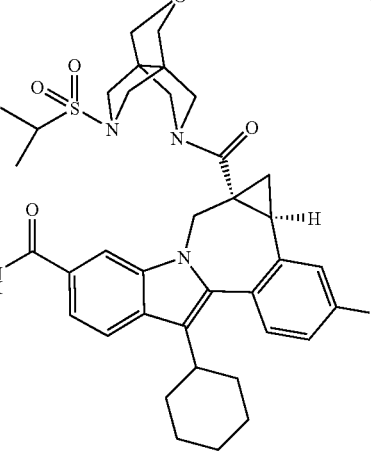 Chiral | | A* | A |

TABLE 1-continued

| Structure | NeoLuc EC$_{50}$ (μM) | LE NeoLuc EC$_{50}$, (μM) | IC$_{50}$ (μM) |
|---|---|---|---|
| Chiral | | A* | A |
| Chiral | | A* | A |
| Chiral | | | |

TABLE 1-continued

| Structure | NeoLuc EC$_{50}$ (μM) | LE NeoLuc EC$_{50}$, (μM) | IC$_{50}$ (μM) |
|---|---|---|---|
| Chiral | | A* | A |
| Chiral | | A* | A |
| Chiral | | A* | A |

TABLE 1-continued
| Structure | NeoLuc EC$_{50}$ (μM) | LE NeoLuc EC$_{50}$, (μM) | IC$_{50}$ (μM) |
|---|---|---|---|
| 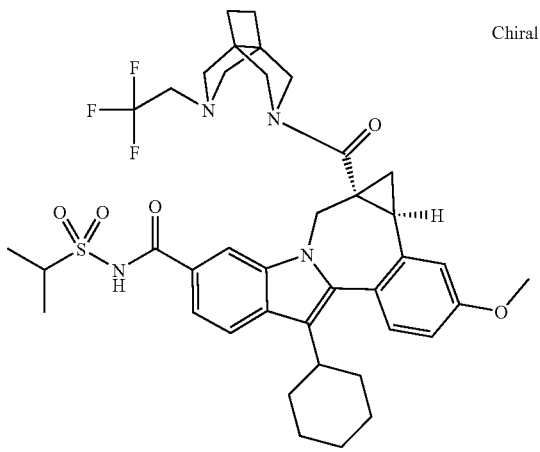 Chiral | A* | A | |
| 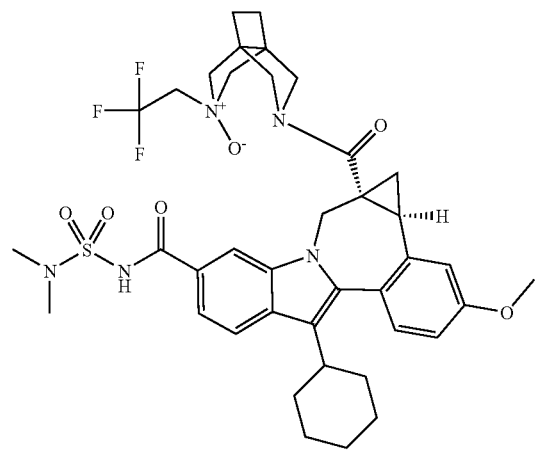 | A* | G | |
| 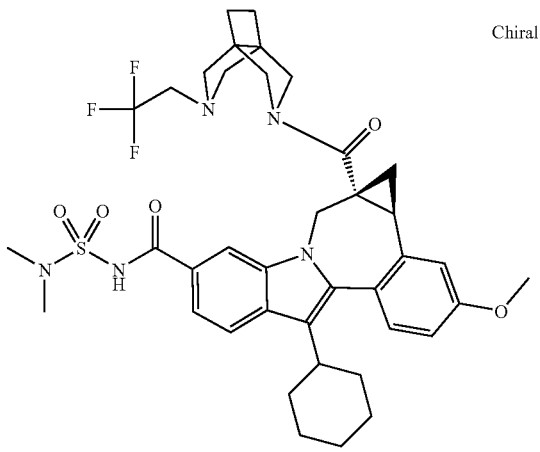 Chiral | A | A | |

TABLE 1-continued

| Structure | NeoLuc EC$_{50}$ (μM) | LE NeoLuc EC$_{50}$, (μM) | IC$_{50}$ (μM) |
|---|---|---|---|
| Chiral | A | A | |
| Chiral | A | A | |
| Chiral | A | G | |

TABLE 1-continued
| Structure | NeoLuc EC$_{50}$ (μM) | LE NeoLuc EC$_{50}$, (μM) | IC$_{50}$ (μM) |
|---|---|---|---|
| 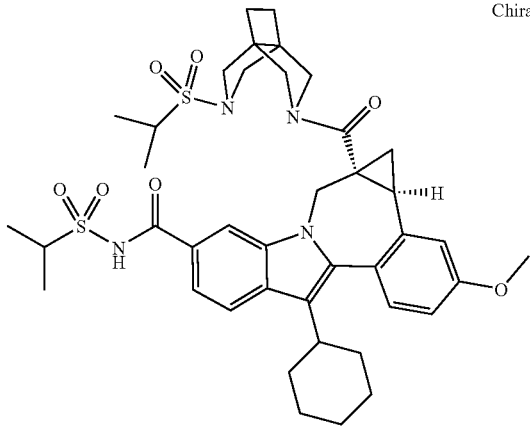 Chiral | | A | A |
| 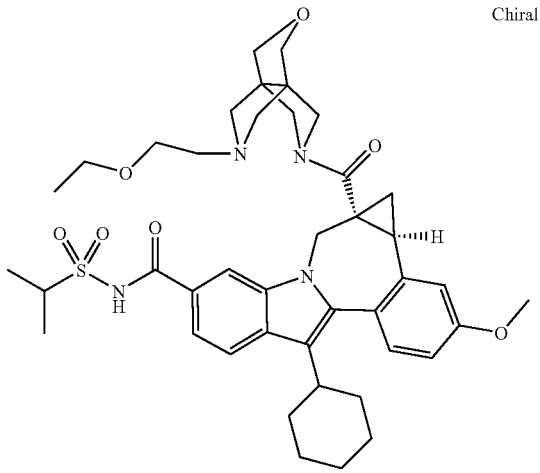 Chiral | A | | A |
| 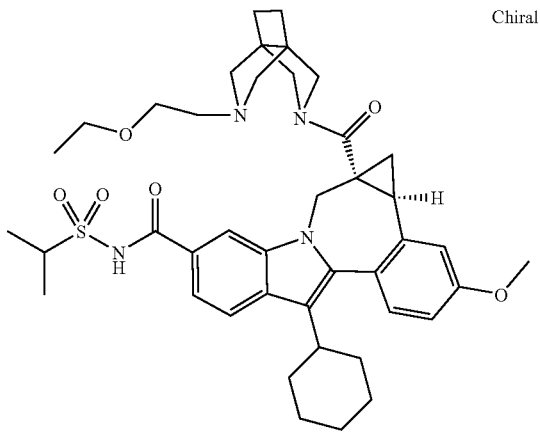 Chiral | | A* | |

TABLE 1-continued

| Structure | NeoLuc EC$_{50}$ (μM) | LE NeoLuc EC$_{50}$, (μM) | IC$_{50}$ (μM) |
|---|---|---|---|
| Chiral | A | | A |
| Chiral | A | | A |
| Chiral | | A* | |

A 0.0019 to 0.5 μM; B >0.5 μM–1.0 μM; C >1.0 μM but an exact value was not determined; D 0.00341 or less to 0.5 μM; E >0.5 μM–5 μM; ; F 0.0025 or less to 0.5 μM; but an exact value was not determined; G <0.0017 μM but an exact value was not determined; H <0.02 μM but an exact value was not determined; I <0.0023 μM but an exact value was not determined, * a gentoptype 1a rather than 1b replicon was used to get this data.

TABLE 2
| Structure | NeoLuc EC50 (μM) | LE NeoLuc EC50, (μM) | IC50 (μM) |
|---|---|---|---|
| 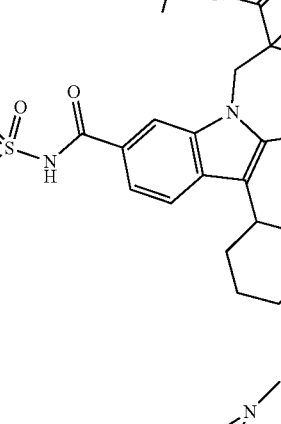 | 0.02 | 0.04 | 0.00879 |
| 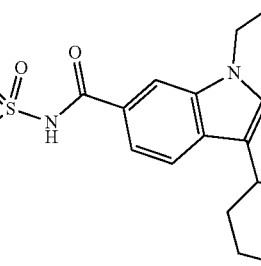 | >1.0 | 2.10 | 0.0078 |
| 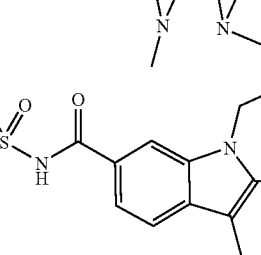 Chiral | | 0.00696 | 0.0035 |

TABLE 2-continued

| Structure | | NeoLuc EC50 (μM) | LE NeoLuc EC50, (μM) | IC50 (μM) |
|---|---|---|---|---|
| | Chiral | 0.13 | 0.09 | 0.0031 |
| | Chiral | 0.01 | 0.03 | 0.0024 |
| | Chiral | | 0.06 | <0.0017 |

TABLE 2-continued

| Structure | NeoLuc EC50 (μM) | LE NeoLuc EC50, (μM) | IC50 (μM) |
|---|---|---|---|
| 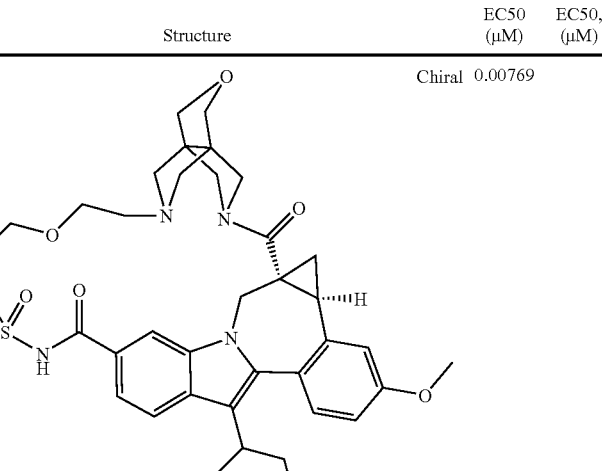 Chiral | 0.00769 | | 0.0019 |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imigimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 3.

TABLE 3

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Pharmaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmaceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | SciClone Corporation, Kenilworth, NJ |
| Zadazim | Immune modulator | SciClone Pharmaceuticals Inc., San Mateo, CA |
| Rebif | IFN-β1a | Serono, Geneva, Switzerland |

TABLE 3-continued

| Brand Name | Type of Inhibitor or Target | Source Company |
|---|---|---|
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Unless otherwise specified, analytical LCMS data on the following intermediates and examples were acquired using the following columns and conditions. Stop time: Gradient time+1 minute; Starting cone: 0% B unless otherwise noted; Eluent A: 5% $CH_3CN$/95% $H_2O$ with 10 mM $NH_4OAc$ (for columns A, D and E); 10% MeOH/90% $H_2O$ with 0.1% TFA (for columns B and C); Eluent B: 95% $CH_3CN$/5% $H_2O$ with 10 mM $NH_4OAc$ (for columns A, D and E); 90% MeOH/10% $H_2O$ with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18.

Intermediate 1

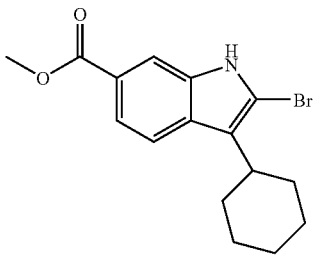

1H-Indole-6-carboxylic acid, 2-bromo-3-cyclohexyl-, methyl ester. Freshly recrystallized pyridinium tribromide (recrystallization from hot AcOH (5 mL per 1 g), rinsed with cold AcOH and dried under high vacuum over KOH) was added in portions (over 10 min.) to a stirring solution of methyl 3-cyclohexyl-1H-indole-6-carboxylate (60 g, 233 mmol) (prepared using procedures describe in WO2004/065367) in $CHCl_3$/THF (1:1, 1.25 L) at 2° C. The reaction solution was stirred at 0-5° C. for 2.5 h, and washed with sat. aq. $NaHSO_3$ (1 L), 1 N HCl (1 L) and brine (1 L). The organic layer was dried ($MgSO_4$) and concentrated. The resulting red oil was diluted with $Et_2O$ and concentrated. The resulting pink solid was dissolved into $Et_2O$ (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%) as a fluffy pink solid, which was used without further purification. 1HNMR (300 MHz, $CDCl_3$) δ 8.47 (br s, 1H), 8.03 (d, J=1.4 Hz, 1H), 7.74 (dd, J=1.4, 8.8 Hz, 1H), 7.69 (d, J=8.8 Hz, 1H), 3.92 (s, 3H), 2.82 (tt, J=3.7, 11.7 Hz, 1H), 1.98-1.72 (m, 7H), 1.50-1.27 (m, 3H). 13CNMR (75 MHz, CDCl3) δ 168.2, 135.6, 130.2, 123.1, 120.8, 120.3, 118.7, 112.8, 110.7, 52.1, 37.0, 32.2(2), 27.0 (2), 26.1. LCMS: m/e 334 (M−H)⁻, ret time 3.34 min, column A, 4 minute gradient.

Intermediate 2

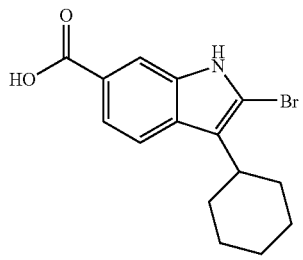

1H-Indole-6-carboxylic acid, 2-bromo-3-cyclohexyl-. A solution of methyl 2-bromo-3-cyclohexyl-1H-indole-6-carboxylate (20 g, 60 mmol) and LiOH (3.8 g, 160 mmol) in MeOH/THF/$H_2O$ (1:1:1, 300 mL) was heated at 90° C. for 2 h. The reaction mixture was cooled in an ice/$H_2O$ bath, neutralized with 1M HCl (~160 mL) diluted with $H_2O$ (250 mL) and stirred for 1 h at rt. The precipitates were collected by filtration rinse with $H_2O$ and dried to yield 1H-indole-6-carboxylic acid, 2-bromo-3-cyclohexyl- (quant.) which was used without further purification.

An alternative procedure that can by used to provide 1H-indole-6-carboxylic acid, 2-bromo-3-cyclohexyl- is described below:

A solution of methyl 2-bromo-3-cyclohexyl-1H-indole-6-carboxylate (117 g, 349 mmol) and LiOH.H₂O (26.4 g, 629 mmol) in MeOH/THF/H2O (1:1:1, 1.8 L) was heated at reflux for 3 h. The reaction mixture was cooled in an ice/H2O bath to ~2° C., neutralized with 1M HCl (~650 mL) (added at such a rate that temperature did not exceed 5° C.), diluted with H₂O (1 L) and stirred while warming to ambient temperature. The precipitates were collected by filtration rinsed with H₂O and dried to yield the mono THF solvate of 1H-indole-6-carboxylic acid, 2-bromo-3-cyclohexyl- (135.5 g, 345 mmol, 99%) as a yellow solid, which was used without further purification. 1HNMR (300 MHz, CDCl₃) δ 11.01 (br s, 1H), 8.77 (s, 1H), 8.07 (d, J=1.5 Hz, 1H), 7.82 (dd, J=1.5, 8.8 Hz, 1H), 7.72 (d, J=8.8 Hz, 1H), 3.84-3.74 (m, 4H), 2.89 (m, 1H), 1.98-1.72 (m, 11H), 1.50-1.24 (m, 3H). 13CNMR (75 MHz, CDCl3) δ 172.7, 135.5, 130.7, 122.3, 120.9(2), 118.8, 113.3, 111.1, 67.9(2), 37.0, 32.2(2), 27.0(2), 26.1, 25.5(2). LCMS: m/e 320 (M–H)⁻, ret time 2.21 min, column A, 4 minute gradient.

Intermediate 3

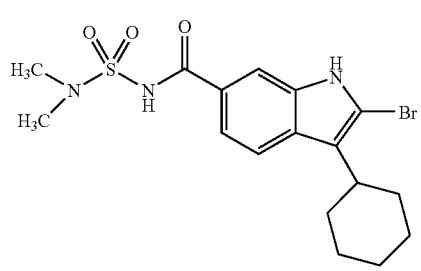

1H-Indole-6-carboxamide, 2-bromo-3-cyclohexyl-N-[(dimethylamino)sulfonyl]-. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO₂ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g ,8.8 mmol) in THF (4 mL). Stirring was continued for 24 hr. The mixture was partitioned between ethyl acetate and dilute HCl. The ethyl acetate layer was washed with water followed by brine and dried over Na₂SO₄. The extract was concentrated to dryness to leave the title product as a pale yellow friable foam, (2.0 g, 74%, >90% purity , estimated from NMR). ¹H NMR (300 MHz, DMSO-D6) δ ppm 1.28-1.49 (m, 3 H) 1.59-2.04 (m, 7 H) 2.74-2.82 (m, 1 H) 2.88 (s, 6 H) 7.57 (dd, J=8.42, 1.46 Hz, 1H) 7.74 (d, J=8.78 Hz, 1 H) 7.91 (s, 1 H) 11.71 (s, 1 H) 12.08 (s, 1 H).

An alternative method for the preparation of 1H-indole-6-carboxamide, 2-bromo-3-cyclobexyl-N-[(dimethylamino)sulfonyl]- is described below.

To a 1 L four necked round bottom flask equipped with a mechanical stirrer, a temperature controller, a N2 inlet , and a condenser, under N2, was added 2-bromo-3-cyclohexyl-1H-indole-6-carboxylic acid (102.0 g, 0.259 mol) and dry THF (300 mL). After stirring for 10 min, CDI (50.3 g, 0.31 mol) was added portion wise. The reaction mixture was then heated to 50° C. for 2 h. After cooling to 30° C., N,N-dimethylaminosulfonamide (41.7 g, 0.336 mol) was added in one portion followed by addition of DBU (54.1 mL, 0.362 mol) drop wise over a period of 1 h. The reaction mixture was then stirred at rt for 20 h. The solvent was removed in vacua and the residue was partitioned between EtOAc and 1 N HCl (1:1, 2 L). The organic layer was separated and the aqueous layer was extracted with EtOAc (500 mL). The combined organic layers were washed with brine (1.5 L) and dried over MgSO4. The solution was filtered and concentrated in vacuo to give the crude product (111.0 g). The crude product was suspended in EtOAc (400 mL) at 60° C. To the suspension was added heptane (2 L) slowly. The resulting suspension was stirred and cooled to 0° C. It was then filtered. The filter cake was rinsed with small amount of heptane and house vacuum air dried for 2 days. The product was collected as a white solid (92.0 g, 83%). ¹H NMR (MeOD, 300 MHz) δ 7.89 (s, H), 7.77 (d, J=8.4 Hz, 1H), 7.55 (dd, J=8.4 and 1.8 Hz, 1H), 3.01 (s, 6H), 2.73-2.95 (m, 1H), 1.81-2.05 (m, 8H), 1.39-1.50 (m, 2H); m/z 429 (M+H)+.

Intermediate 4

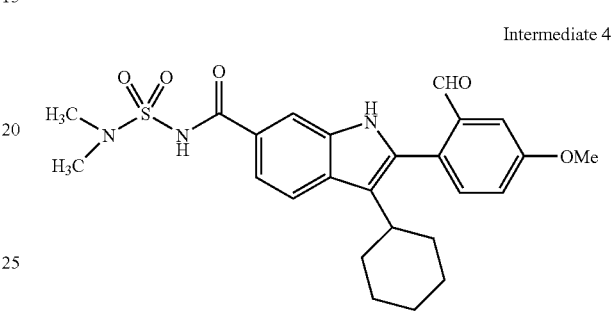

1H-Indole-6-carboxamide, 3-cyclohexyl-N-[(dimethylamino)sulfonyl]-2-(2-formyl-4-methoxyphenyl)-. A mixture of the 2-Bromo-3-cyclohexyl-N-[(dimethylamino)sulfonyl]-1H-indole-6-carboxamide (4.28 g, 0.01 mol), 4-methoxy-2-fonnylphenyl boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

An alternative procedure for the preparation of 1H-indole-6-carboxamide, 3-cyclohexyl-N-[(dimethylamino)sulfonyl]-2-(2-formyl-4-methoxyphenyl)- is provided below:

To a slurried solution of 2-bromo-3-cyclohexyl-N-[(dimethylamino)sulfonyl]-indole-6-carboxamide (54.0 g, 126 mmol), 4-methoxy-2-formylphenylboronic acid (29.5 g, 164 mmol) and LiCl (13.3 g, 315 mmol) in EtOH/toluene (1:1, 1 L) was added a solution of Na₂CO₃ (40.1 g, 379 mmol) in water (380 mL). The reaction mixture was stirred 10 min. and then Pd(PPh3)4 (11.3 g, 10.0 mmol) was added. The reaction solution was flushed with nitrogen and heated at 70° C. (internal monitoring) overnight and then cooled to rt. The reaction was diluted with EtOAc (1 L) and EtOH (100 mL), washed carefully with 1N aqueous HCl (1 L) and brine (500 mL), dried (MgSO4), filtered and concentrated. The residual solids were stirred with Et2O (600 mL) for 1h and collected by filtration to yield 1H-indole-6-carboxamide, 3-cyclohexyl-N-[(dimethylamino)sulfonyl]-2-(2-formyl-4-methoxyphenyl)- (52.8 g, 109 mmol, 87%) as a yellow powder which was used without further purification. 1HNMR (300 MHz, d6-DMSO) δ 11.66 (s, 1H), 8.17 (s, 1H), 7.75 (d, J=8.4 Hz, 1H), 7.74 (d, J=8.4 Hz, 1H), 7.59 (dd, J=1.4, 8.4 Hz, 1H), 7.23-7.16 (m, 2H), 7.08 (dd, J=2.6, 8.4 Hz, 1H), 6.54 (d, J=8.8 Hz, 1H), 3.86 (s, 3H), 3.22-3.08 (m, 1H), 2.91 (s, 6H), 2.00-1.74 (m, 7H), 1.60-1.38 (m, 3H). 13CNMR (75 MHz, CDCl3) δ 165.7, 158.8, 147.2, 139.1, 134.3, 132.0, 123.4, 122.0, 119.2, 118.2, 114.8, 112.3, 110.4, 109.8, 79.6, 45.9, 37.2(2), 34.7, 32.0(2), 25.9(2), 24.9. LCMS: m/e 482 (M−H)−, ret time 2.56 min, column A, 4 minute gradient.

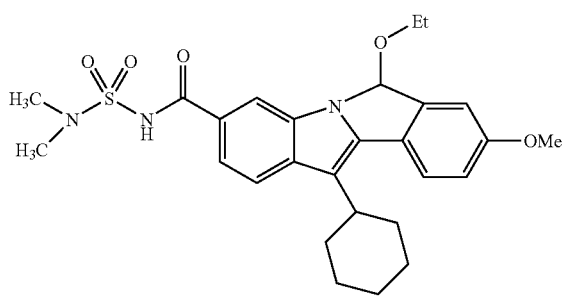

Intermediate 5

6H-Isoindolo[2,1-a]indole-3-carboxamide, 11-cyclohexyl-N-[(dimethylamino)sulfonyl]-6-ethoxy-8-methoxy,
To a 5 L four necked round bottom flask equipped with a temperature controller, a condenser, a N2 inlet and a mechanical stirrer, was charged toluene (900 mL), EtOH (900 mL), 2-brorno-3-cyclohexyl-N-(N,N-dimethylsulfamoyl)-1H-indole-6-carboxamide (90 g, 0.21 mol), 2-formyl-4-methoxyphenylboronic acid (49.2 g, 0.273 mol) and LiCl (22.1 g, 0.525 mol). The resulting solution was bubbled with N2 for 15 mins. A solution of Na2CO3 (66.8 g, 0.63 mol) in H2O (675 mL) was added and the reaction mixture was bubbled with N2 for another (10 mins). Pd(PPh3)4 (7.0 g, 6.3 mmol) was added and the reaction mixture was heated to 70° C. for 20 h. After cooling to 35° C., a solution of 1 N HCl (1.5 L) was added slowly. The resulting mixture was transferred to a 6 L separatory funnel and extracted with EtOAc (2×1.5 L). The combined organic extracts were washed with brine (2 L), dried over MgSO4, filtered and concentrated in vacuo to give a yellow solid, which was triturated with 20% EtOAc in hexane (450 mL, 50° C. to 0° C.) to give 3-cyclohexyl-N-(N,N-dimethylsulfamoyl)-2-(2-formyl-4-methoxyphenyl)-1H-indole-6-carboxamide (65.9 g) as a yellow solid. HPLC purity, 98%.

The mother liquid from the trituration was concentrated in vacua The residue was refluxed with EtOH (50 mL) for 3 h. The solution was then cooled to 0° C. The precipitates were filtered and washed with cooled TBME (5° C.) (20 mL). The filter cake was house vacuum air dried to give a further quantity of the title compound as a white solid (16.0 g). HPLC purity, 99%. 1HNMR (CDCl3, 300 MHz) δ 8.75 (s, 1H), 7.96 (s, 1H), 7.73 (d, J=8.4 Hz, 1H), 7.67 (d, J=8.4 Hz, 1H), 7.45 (dd, J=8.4 and 1.4 Hz, 1H), 7.09 (d, J=2.2 Hz, 1H), 6.98 (dd, J=8.4 and 2.2 Hz, 1H), 6.50 (s, 1H), 3.86 (s, 3H), 3.05 (s, 6H), 2.92-3.13 (m, 3H), 1.85-1.93 (m, 7 H), 1.40-1.42 (m, 3H), 1.05 (t, J=7.1 Hz, 3H). m/z 512 (M+H)+.

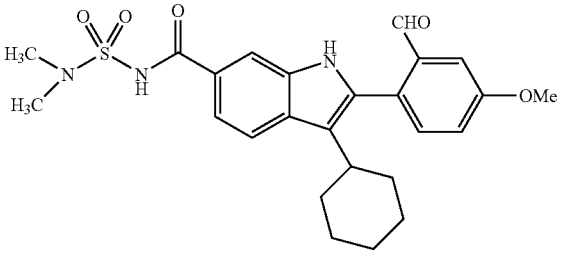

Intermediate 6

1H-indole-6-carboxamide, 3-cyclohexyl-N-[(dimethylamino)sulfonyl]-2-(2-formyl-4-methoxyphenyl)-. 11-cyclohexyl-N-(N,N-dimethylsulfamoyl)-6-ethoxy-8-methoxy-6H-isoindolo[2,1-a]indole-3-carboxamide was dissolved in THF (75 mL). To the solution was added a solution of 2 N HCl (300 mL). The mixture was vigorously stirred under N2 at rt for 16 h. The resulting suspension was filtered and washed with cooled TBME (2×30 mL). the filer cake was vacuum air dried overnight to give the title compound as a yellow solid. HPLC purity, 99% 1H NMR (DMSO-d6, 300 MHz) δ 11.65 (s, 1H), 8.16 (s, 1H), 7.76 (d, J=5.9 Hz, 1H), 7.73 (d, J=5.9 Hz, 1H), 7.58 (dd, J=8.5 and 1.5 Hz, 1H), 7.17-7.20 (m, 2H), 7.08 (dd, J=8.5 and 1.4 Hz, 1H), 6.55 (d, J=8.6 Hz, 1H), 3.86 (s, 3H), 3.14-3.18 (m, 1H), 2.91 (s, 6H), 1.75-1.99 (m, 7H), 1.48-1.60 (m, 3H); m/z 484 (M+H)+.

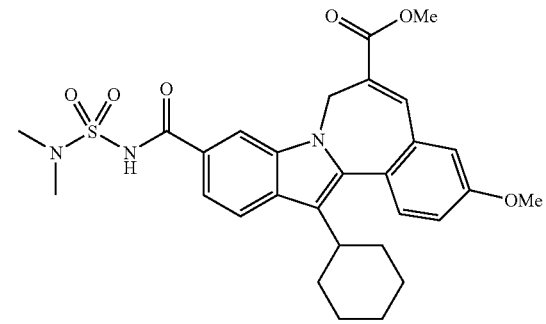

Intermediate 7

7H-Indolo[2,1-a][2]benzazepine-6-carboxylic acid, 13-cyclohexyl-10-[[[(dimethylamino)sulfonyl]amino]carbonyl]-3-methoxy-, methyl ester. A mixture of the 3-cyclohexyl-N-(N,N-dimethylsulfamoyl)-2-(2-formyl-4-methoxyphenyl)-1H-indole-6-carboxamide (4.8 g, 0.01 mol), methyl 2-(dimethoxyphosphoryl)acrylate (9.7 g, 0.02 mol) and cesium carbonate (7.1 g, 0.02 mol) in DMF (28mL) was stirred for 20 hr at an oil bath temperature of 55° C. The mixture was poured into ice-water and acidified with dilute HCl to precipitate the crude product. The solid was collected, dried and flash chromatographed on SiO2 (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

An alternate procedure for the preparation of 7H-indolo[2,1-a][2]benzazepine-6-carboxylic acid, 13-cyclohexyl-10-[[[(dimethylamino)sulfonyl]amino]carbonyl]-3-methoxy-, methyl ester is provided below.

A solution of 11-cyclohexyl-N-[(dimethylamino)sulfonyl]-6-hydroxy-8-methoxy-6H-isoindolo[2,1-a]indole-3- carboxamide (cyclic hemiaminal) (63.0 g, 130 mmol), methyl 2-(dimethoxyphosphoryl)acrylate (60 g, 261 mmol), cesium carbonate (106 g, 326 mmol) in DMF (400 mL) was heated at 60° C. (bath temp) for 4.5 h. Additional methyl 2-(dimethoxyphosphoryl)acrylate (15 g, 65 mmol) and cesium carbonate (21.2 g, 65 mmol) were added and the reaction was heated at 60° C. overnight then and cooled to rt. The stirring reaction mixture was diluted with H₂O (1 L), slowly neutralized with 1N aqueous HCl (800 mL), stirred 3 h, and then the precipitates were collected by filtration. The solids were triturated with Et2O (800 mL) and dried to yield methyl 7H-indolo[2,1-a][2]benzazepine-6-carboxylic acid, 13-cyclohexyl-10-[[[(dimethylamino)sulfonyl]amino]carbonyl]-3-methoxy-, methyl ester (70.2 g, 127 mmol, 98%) as a yellow solid which was used without further purification. 1HNMR (300 MHz, CDCl3) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H), 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)−, ret time 3.21 min, column A, 4 minute gradient.

Intermediate 8

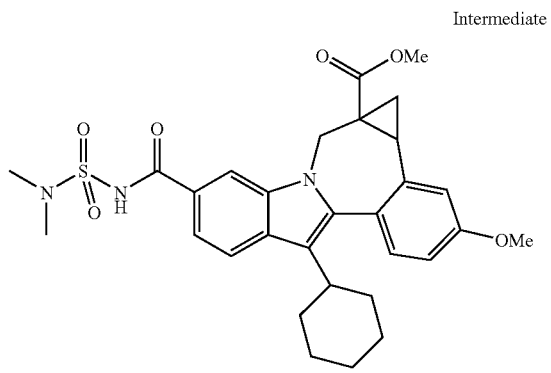

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-, 11-methoxy-, methyl ester, (+/−)−. DMSO (5 mL) was added to a mixture of trimethylsulfoxonium iodide (199 mg, 0.906 mmol) and NaH (38 mg in 60% oil dispersion, 0.953 mmol) in a round-bottomed flask. The reaction mixture was stirred at rt for 0.5 hr. 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was then added and the reaction mixture was stirred at rt. for 3 hr., and then at 50° C. for a further 3 hr. The reaction was then quenched with water and acidified with 1N HCl solution. The crude product then precipitated as a light yellow solid which was collected by filtration and air dried, (106 mg, 83% yield). 6 mg of this material was then purified by Prep. HPLC to afford the title compound as a light yellow solid (1.8 mg). MS m/z 566(MH⁺), Retention time: 3.850 min. 1H NMR (500 MHz, MeOD) δ ppm 0.28 (m, 0.36 H) 1.19-2.20 (m, 11.64 H) 2.70-3.02 (m, 2 H) 3.03 (s, 2.16 H) 3.05 (s, 3.84 H) 3.49 (d, J=15.26 Hz, 0.64 H) 3.54 (s, 1.92 H) 3.83 (s, 1.08 H) 3.91 (s, 3 H) 4.08 (d, J=15.26 Hz, 0.36 H) 5.29 (d, J=15.26 Hz, 0.36 H) 5.50 (d, J=14.95 Hz, 0.64 H) 6.98-7.06 (m, 1 H) 7.16 (d, J=2.44 Hz, 0.36 H) 7.23 (d, J=2.44 Hz, 0.64 H) 7.30 (d, J=8.55 Hz, 0.64 H) 7.34 (d, J=8.55 Hz, 0.36 H) 7.56 (d, J=8.55, 1.53 Hz, 0.64 H) 7.63 (dd, J=8.55, 1.53 Hz, 0.36 H) 7.88 (d, J=8.55 Hz, 0.64 H) 7.91 (d, J=8.55 Hz, 0.36 H) 8.12 (s, 0.36 H) 8.33 (d, J=1.53 Hz, 0.64 H).

An alternative procedure for the preparation of the title compounds is provided below.

To a flame dried, four necked, 1 L round bottom flask equipped with a mechanical stirrer, N2 inlet and a thermometer, under N2, was charged sodium hydride (95%) (3.09 g, 129.2 mmol) and dry DMF (200 mL). With vigorous stirring, trimethylsulfoxonium iodide (32.5 g, 147.3 mmol) portion wise during which time the temperature rose to 30° C. After stirring for 30 mins, a solution of 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (33.8 g, 61.3 mmol) in dry DMF (70 mL) was added quickly. The reaction mixture was stirred below 30° C. for 30 mins and then poured into an ice cold solution of 1 N HCl (130 mL) in H2O (2 L) portion wise. After the resulting suspension was mechanically stirred for 1 h, the precipitates were filtered and the filter cake was washed with H2O (100 mL). The filter cake was partitioned between EtOAc and 0.5 N HCl (1:1, 4 L). The organic phase was separated, washed with H2O (1 L) and brine (1 L), dried over MgSO₄, filtered and concentrated in vacuo. The residue was dissolved in EtOAc (150 mL), and the solution was filtered through a silica gel pad (300 g in hexane) and rinsed with 50% EtOAc in hexane (5 L). The filtrate was concentrated in vacuo to give a slightly yellow solid which was triturated with 10% EtOAc in TBME (220 mL) from 50° C. to 0° C. to to give cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)− as a white solid (26.1 g, 75% yield). HPLC purity, 100%. ¹H NMR (DMSO-d₆, 300 MHz) δ 11.61 (s, 1H), 8.47 (s, 0.5H), 8.25 (s, 0.5H), 7.81-7.88 (m, 1H), 7.57-7.63 (m, 1H), 7.23-7.29 (m, 2H), 7.01-7.07 (m, 1H), 5.43 (d, J=15.0 Hz, 0.5H), 5.22 (d, J=15 Hz, 0.5H), 4.04 (dd, J=15.4 and 6.6 Hz, 0.5H), 3.83 (s, 3H), 3.75 (s, 1H), 3.08-3.47 (m, 0.5H), 3.29 (s, 3H), 2.73-2.92 (m, 8H), 1.11-1.99 (m, 10.5H), 0.20 (m, 0.5H); m/z 566 (M+H)⁺.

Intermediate 9

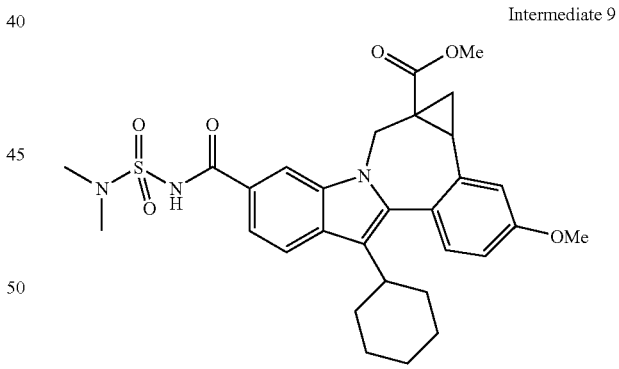

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)−. A sample of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-methyl ester was dissolved in EtOH/CH₃CN 1/1+0.5% DEA at a concentration of 50 mg/ml. [The addition of DEA ensures the compound remains in solution during the injection process]. This solution was then injected onto a Thar SFC-350 preparative SFC under the conditions shown below.

Preparative conditions on Thar SFC-350: Column: Chiralcel OJ-H 5×25 cm; mobile phase: 25% MeOH/CH3CN (1/1)

in CO2; pressure (bar): 100; flow rate (ml/min): 240; solution concentration (mg/ml): 50; injection amount (ml): 4.5-5; Cycle time (min/inj): 6.5-7; Temperature (° C.): 45; throughput (g/ hr): ~2; Detector wavelength (nm): 254.

From 371.4 g of racemic starting material, a total of 177.3 g of the desired second eluting (−) isomer was obtained, containing ~1 Meq of diethylamine. This material was purified using the following procedure. The mixture (24.7 g) dissolved in dichloromethane (800 mL)) was washed sequentially with; 0.5 N HCl (1×400 mL, 1×240 mL), H$_2$O (2×240 mL), and brine (2×240 mL). The organic layer was then dried (Anhy. Na$_2$SO$_4$), filtered and evaporated to give 22.33 g of (cycloprop[d]indolo[2,1-a][2]benzazepine-1a(2H)-carboxylic acid, 8-cyclohexyl-5-[[[(dimethylamino)sulfonyl]amino] carbonyl]-1,12b-dihydro-11-methoxy-, methyl ester, (−)− as a yellow solid (92% recovery). HPLC[1]>99% (Rt 2.38 min); LC/MS (ES$^+$) 566.51 (M+H, 100); $[\alpha]_D^{25\ C}$ −194.64° (c 1.03, MeOH). Anal. Calcd for C$_{30}$H$_{35}$N$_3$O$_6$S.0.33H$_2$O: C, 63.04; H, 6.29; N, 7.35; S, 5.61; H$_2$O, 1.04. Found: C, 63.07; H, 6.01; N, 7.24; S, 5.58; H$_2$O, 1.03. The NMR shows the absence of Et$_2$NH. The EE of this material was deteunined to be >99% using the following analytical HPLC procedure.

Analytical conditions of ee determination on Thar analytical SFC. Analytical Column: Chiralcel OJ (0.46×25cm, 10 μl); BPR pressure: 100 bars; Temperature: 35° C.; Flow rate: 3.0 ml/min; Mobile Phase: 15% MeOH/ CH$_3$CN (1/1) in CO$_2$; Detector Wavelength: 254 nm; Retention time (min): 4, 6.5.

Intermediate 10

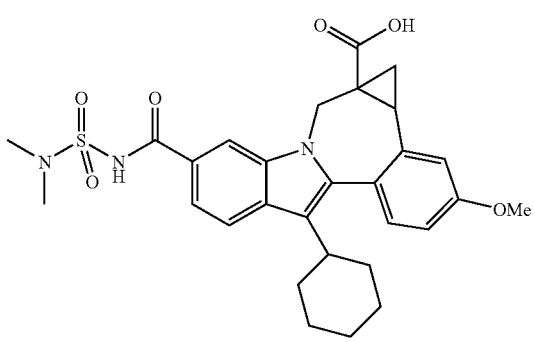

Cycloprop[d]indolo[2,1-a][2]benzazepine-1a(2H)-carboxylic acid, 8-cyclohaxyl-5-[[[(dimethylainino)sulfanyl] amino]carbonyl]-1,12b-dihydro-11-methoxy-, (−)-. To a solution of (−) cycloprop[d]indolo[2,1-a][2]benzazepine-1a (2H)-carboxylic acid, 8-cyclohexyl-5-[[[(dimethylamino) sulfonyl]amino]carbonyl]-1,12b-dihydro-11-methoxy-, methyl ester (22.33 g, 39.5 mmol) in MeOH (300 mL) was added 1 N NaOH (120 mL) slowly over 20 min., while maintaining the reaction temperature <30° C. The mixture was stirred at rt under N$_2$ for 18 h. The HPLC indicated the reaction was complete. To the reaction solution was added 1 N HCl (130 mL). After addition was complete, the pH of the reaction mixture was about 2. The methanol in the reaction mixture was evaporated. Water (300 mL) was added to the mixture which was then extracted with CH$_2$Cl$_2$ (1×600 mL, 1×200 mL). The combined extracts were washed with H$_2$O (2×300 mL), brine (2×300 mL), dried (Na$_2$SO$_4$) and evaporated to give 20.82 g (96% yield) of the title compound as a yellow solid. HPLC conditions column: Phenomenoex Synergi Polar-RP 4 um 4.6×50 mm; UV: 220 nm; gradient time: 4 min; flow rate: 4 mL/min, 75-100% B; solvent A: 10% MeOH/90% H$_2$O with 0.2% H$_3$PO$_4$, solvent B: 90% MeOH/ 10% H$_2$O with 0.2% H$_3$PO$_4$. HPLC >99% (Rt 1.80 min.) LC/MS (ES$^+$) 552.25 (M+H, 100); $[\alpha]_D^{25\ C}$ −166.99° (e 1.00, MeOH). GC analysis: CH$_2$Cl$_2$ 4.94%; Anal. Calcd for C$_{29}$H$_{33}$N$_3$O$_6$S.0.16H$_2$O. 0.35 CH$_2$Cl$_2$: C, 60.37; H, 5.87; N, 7.20; S, 5.49; H$_2$O, 0.49; CH$_2$Cl$_2$, 5.02. Found: C, 59.95; H, 5.89; N, 7.03; S, 5.38; H$_2$O, 0.47; CH$_2$Cl$_2$, 4.94.

Intermediate 11

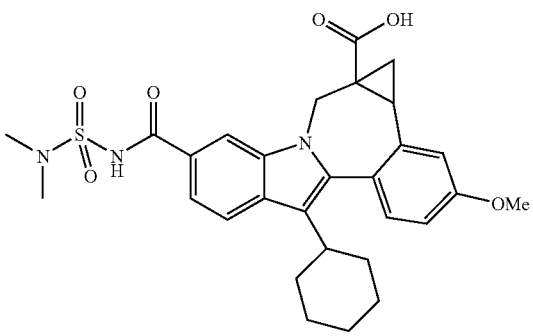

Cycloprop[d]indolo[2,1-a][2]benzazepine-1a(2H)-carboxylic acid, 8-cyclohexyl-5-[[[(dimethylamino)sulfonyl] amino]carbonyl]-1,12b-dihydra-11-methoxy-, (+/−)-. To a solution of (+/−) cycloprop[d]indolo[2,1-a][2]benzazepine-1a(2H)-carboxylic acid, 8-cyclohexyl-5-[[[(dimethylamino) sulfonyl]amino]carbonyl]-1,12b-dihydro-11-methoxy-, methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried (MgSO$_4$), filtered and concentrated. The residue was purified by preparative HPLC to afford the desired product as a light yellow solid, (59 mg, 60% yield). MS m/z 552(MH$^+$), Retention time: 3.850 min.1H NMR (300 MHz, MeOD) δ ppm 0.25 (m, 0.38 H) 1.14-2.22 (m, 11.62 H) 2.69-2.98 (m, 2 H) 3.02 (s, 2.28 H) 3.02 (s, 3.72 H) 3.41 (d, J=15.00 Hz, 0.62 H) 3.88 (s, 3 H) 4.01 (d, J=15.00 Hz, 0.38 H) 5.26 (d, J=15.00 Hz, 0.38 H) 5.45 (d, J=14.64 Hz, 0.62 H) 6.94-7.02 (m, 1 H) 7.13 (d, J=2.56 Hz, 0.38 H) 7.21 (d, J=2.20 Hz, 0.62 H) 7.26 (d, J=8.42 Hz, 0.62 H) 7.30 (d, J=8.78 Hz, 0.38 H) 7.53 (dd, J=8.42, 1.46 Hz, 0.62 H) 7.61 (dd, J=8.60, 1.65 Hz, 0.38 H) 7.85 (d, J=8.42 Hz, 0.62 H) 7.89 (d, J=8.42 Hz, 0.38 H) 8.10 (s, 0.38 H) 8.28 (d, J=1.46 Hz, 0.62 H).

Intermediate 12

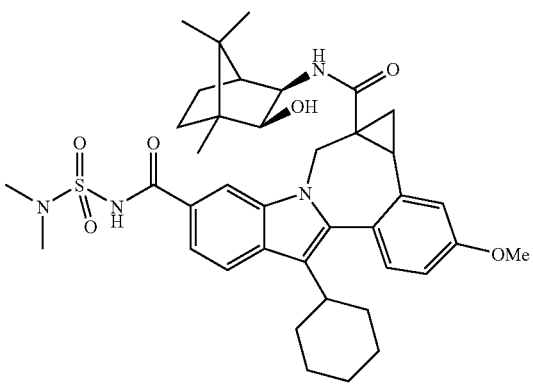

Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]-. TBTU (437 mg, 1.36 mmol) and DiPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (500 mg, 0.906 mmol) in DMSO (20.0 mL). The reaction mixture was stirred at rt for 15 min. (2S, 3R)-3-Amino-1,7,7-trimethylbicyclo[2.2.1]heptan-2-ol (280 mg, 1.36mmol) was then added and the reaction mixture was stirred at rt overnight. The reaction mixture was quenched with water and acidified with 1N HCl solution. A brown solid separated which was collected by filtration. This material was then fractionated by Preparative HPLC under the following conditions. Column: Waters Sunfire 19 mm×100 mm; Solvent A: 10% CH3CN-90% H₂O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]- elutes before Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aS)-[partial]- under the HPLC conditions described above. Product obtained as a light yellow solid, 230 mg, 36% yield). MS ml 703(MH⁺), Retention time: 3.936 min. 1H NMR (500 MHz, MeOD) δ ppm 0.14-0.24 (m, 2.64 H) 0.51 (s, 2.46 H) 0.72-2.21 (m, 20.9 H) 2.49 (m, 0.18 H) 2.62 (m, 0.82 H) 2.85 (m, 0.18 H) 2.96 (m, 0.82 H) 3.03 (s, 6 H) 3.39 (m, 0.82 H) 3.49-3.58 (m, 1.64 H) 3.71-3.80 (m, 0.36 H) 3.90 (s, 3 H) 4.17 (d, J=14.65 Hz, 0.18 H) 5.06 (d, J=14.65 Hz, 0.18 H) 5.37 (d, J=14.95 Hz, 0.82 H) 6.73 (d, J=5.49 Hz, 0.82 H) 6.98-7.05 (m, 1 H) 7.08 (d, J=4.58 Hz, 0.18 H) 7.10 (d, J=2.44 Hz, 0.18 H) 7.21 (d, J=2.44 Hz, 0.82 H) 7.31 (d, J=8.55 Hz, 0.82H) 7.34 (d, J=8.55 Hz, 0.18 H) 7.59-7.64 (m, 1 H) 7.87-7.93 (m, 1 H) 7.99 (s, 0.18 H) 8.09 (d, J=1.22 Hz, 0.82 H).

Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aS)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (500 mg, 0.906 mmol) in DMSO (20.0 mL). The reaction mixture was stirred at rt for 15 min. Then (2S,3R)-3-amino-1,7,7-trimethylbicyclo[2.2.1]heptan-2-ol (280 mg, 1.36mmol) was added, and the reaction mixture was stirred at rt overnight. The reaction mixture was quenched with water and then acidified with 1N HCl solution. A brown colored solid separated that was collected by filtration. This material was then fractionated by preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aS)-[partial] elutes after cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]- under the HPLC conditions described above. Product obtained as a light yellow solid, 215 mg, 34% yield). MS m/703(MH⁺), Retention time: 4.038 min. 1H NMR (500 MHz, MeOD) δ ppm 0.20 (m, 0.38 H) 0.75 (s, 1.86 H) 0.76 (s, 1.86 H) 0.84 (s, 1.86 H) 0.85 (s, 1.14 H) 0.89-2.18 (m, 18.9 H) 2.52 (m, 0.38 H) 2.70 (m, 0.62H) 2.85 (m, 0.38 H) 2.97 (m, 0.62 H) 3.03 (s, 2.28 H) 3.04 (s, 3.72 H) 3.33-3.39 (m, 0.62 H) 3.43-3.51 (m, 1.24 H) 3.73-3.77 (m, 0.38 H) 3.78-3.84 (m, 0.38 H) 3.90 (s, 1.86 H) 3.90 (s, 1.14H) 4.14 (d, J=14.65 Hz, 0.38 H) 5.11 (d, J=14.65 Hz, 0.38 H) 5.44 (d, J=15.26 Hz, 0.62 H) 6.68 (d, J=4.88 Hz, 0.62 H) 6.96-7.03 (m, 1 H) 7.07 (d, J=5.19 Hz, 0.38 H) 7.12 (d, J=2.44 Hz, 0.38 H) 7.23 (d, J=2.14 Hz, 0.62 H) 7.27 (d, J=8.54 Hz, 0.62 H) 7.33 (d, J=8.54 Hz, 0.38 H) 7.55 (dd, J=8.39, 1.68 Hz, 0.62 H) 7.62 (dd, J=8.55, 1.53 Hz, 0.38 H) 7.87 (d, J=8.54 Hz, 0.62 H) 7.91 (d, J=8.55 Hz, 0.38 H) 8.08 (d, J=1.22 Hz, 0.38 H) 8.10 (d, J=1.22 Hz, 0.62 H).

Intermediate 13

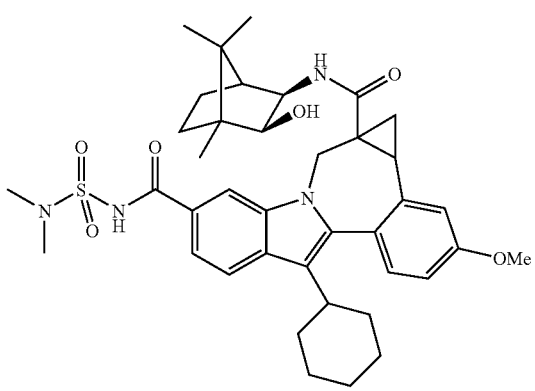

Intermediate 14

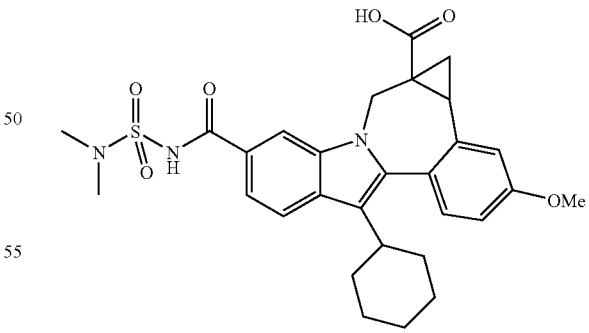

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. 10 N NaOH (2.0 mL, 20 mmol) solution and 4 mL of water were added to a solution of cycloprop[d]indolo[2,1-a][2]benzazepine-1a,5(2H)-dicarboxamide, 8-cyclohexyl-N⁵-[(dimethylamino)sulfonyl]-1,12b-dihydro-N¹ᵃ-[(2R,3S)-3-hydroxy-4,7,7-trimethylbicyclo[2.2.1]hept-2-yl]-11-methoxy-, (1aR)-[partial]- (160 mg, 0.228 mmol) in THF/MeOH (7 mL/7 mL). The reaction mixture was heated at 120° C. under microwave conditions for 1 hr. It was then concentrated, acidified with conc. HCl solution and extracted with ethyl acetate twice (2×30 mL). The organic layers were combined, dried (MgSO$_4$), filtered and concentrated in vacuo to an orange oil. The crude product was then purified by Prep. HPLC column to afford the product a light yellow solid, (80 mg, 64% yield). Average specific rotation −130.85°; Solvent MeOH; Wavelength 589 nm; 50 cm cell. MS m/552(MH$^+$), Retention time: 3.760 min. 1H NMR (500 MHz, MeOD) δ ppm 0.27 (m, 0.38 H) 1.14-2.22 (m, 11.62 H) 2.76 (m, 0.38 H) 2.80-2.92 (m, 1 H) 2.92-3.09 (m, 6.62 H) 3.45 (d, J=14.95 Hz, 0.62 H) 3.90 (s, 1.86 H) 3.91 (s, 1.14 H) 4.04 (d, J=15.26 Hz, 0.38 H) 5.28 (d, J=15.26 Hz, 0.38 H) 5.47 (d, J=15.26 Hz, 0.62 H) 6.95-7.05 (m, 1 H) 7.15 (d, J=2.75 Hz, 0.38 H) 7.23 (d, J=1.83 Hz, 0.62 H) 7.28 (d, J=8.55 Hz, 0.62 H) 7.33 (d, J=8.54 Hz, 0.38 H) 7.54 (dd, J=8.39, 1.68 Hz, 0.62 H) 7.63 (dd, J=8.55, 1.53 Hz, 0.38 H) 7.86 (d, J=8.55 Hz, 0.62 H) 7.91 (d, J=8.55 Hz, 0.38 H) 8.11 (d, J=1.22 Hz, 0.62 H) 8.29 (d, J=1.22 Hz, 0.38 H).

Intermediate 15

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+)-. 10 N NaOH (1.8 mL, 18 mmol) solution and 4 mL of water were added to a solution of cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]- (130 mg, 0.185 mmol) in bTHF/MeOH (7 mL/7 mL). The reaction mixture was heated at 120° C. under microwave conditions for 1 hr. It was concentrated, acidified with conc. HCl solution and extracted with ethyl acetate twice (2×30 mL). The organic layers were combined, dried (MgSO$_4$), filtered and concentrated in vacuo to give an orange oil. The crude product was then purified by Prep. HPLC column to afford the product as a light yellow solid, (68 mg, 67% yield). Average specific rotation+174.73°; Solvent MeOH; Wavelength 589 nm; 50 cm cell MS m/552(MH$^+$), Retention time: 3.773 min. 1 H NMR (500 MHz, MeOD) δ ppm 0.27 (m, 0.38 H) 1.14-2.22 (m, 11.62 H) 2.76 (m, 0.38 H) 2.80-2.92 (m, 1 H) 2.92-3.09 (m, 6.62 H) 3.45 (d, J=14.95 Hz, 0.62 H) 3.90 (s, 1.86 H) 3.91 (s, 1.14 H) 4.04 (d, J=15.26 Hz, 0.38 H) 5.28 (d, J=15.26 Hz, 0.38 H) 5.47 (d, J=15.26 Hz, 0.62 H) 6.95-7.05 (m, 1 H) 7.15 (d, J=2.75 Hz, 0.38 H) 7.23 (d, J=1.83 Hz, 0.62 H) 7.28 (d, J=8.55 Hz, 0.62 H) 7.33 (d, J=8.54 Hz, 0.38 H) 7.54 (dd, J=8.39, 1.68 Hz, 0.62 H) 7.63 (dd, J=8.55, 1.53 Hz, 0.38 H) 7.86 (d, J=8.55 Hz, 0.62 H) 7.91 (d, J=8.55 Hz, 0.38 H) 8.11 (d, J=1.22 Hz, 0.62 H) 8.29 (d, J=1.22 Hz, 0.38 H).

Intermediate 16

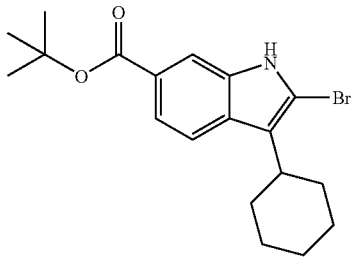

1H-bidole-6-carboxylic acid, 2-bromo-3-cyclohexyl-, 1,1-dimethylethyl ester

To a mechanically stirred solution of 2-bromo-3-cyclohexyl-1H-indole-6-carboxylic acid (80 g, 0.24 m) in dry methylene dichloride (1.2 L) and THF (100 mL) were added activated molecular sieves (4 A, 80 g) and silver carbonate (275 g, 0.99 m). The reaction mixture was cooled to 0° C. and t-Butyl bromide (142 g, 1.04 m) was added drop wise. The mixture was stirred overnight at rt and monitored by TLC (Hexane-Ethyl acetate 80:20, R$_f$(Product)=0.7). If any bromo acid was left unconverted a further 10% of silver carbonate was added and stirring was continued for an addition 2-4 h. On completion, the reaction mixture was filtered through a thin bed of celite. The filtrand was washed with methylene dichloride (500 mL). The combined filtrates were concentrated in-vacuo, and the crude product thus obtained was purified by silica gel chromatography: (230-400 mesh, eluted with a gradient of ethyl acetate in pet ether 0-2%). Homogeneous fractions were combined and evaporated under reduced pressure to give 80 g (85%) of the title compound. HPLC: 90.1% (RT=6.56 min), Column: C18 BDS, (50×4.6 mm), Mobile Phase: Gradient of 0.1% TFA in water: ACN (30→100→30), Flow rate 0.8 mL/min. LCMS: 99.8% (RT=4.44 min), Column: Geneis, C18 50×4.6 mm Mobile Phase: Gradient of 0.1% Formic acid in water: ACN (70→95→70), Flow rate: 0.8 mL/min; M−1=376.5; $^1$H NMR CDCl$_3$ (400 MHz) δ 1.37-1.40 (m, 3H, cyc.Hexyl), 1.62 (s, 9H, t-Bu), 1.80-1.94 (two sets of m, 3H, & 4H respectively, cyc.Hexyl part), 2.81 (m, 1H, CH of cyc.Hexyl benzylic), 7.70-7.75 (m, 2H, Indole-H$_{4\&5}$), 8.04 (s, 1H, Indole-H$_7$), 8.52 (s, 1H, Indole-NH).

Intermediate 17

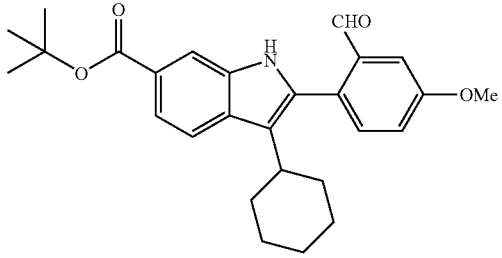

1H-Indole-6-carboxylic acid, 3-cyclohexyl-2-(2-formyl-4-methoxyphenyl)-, 1,1-dimethylethyl ester. tort-Butyl 2-bromo-3-cyclohexyl-1H-indole-6-carboxylate (72 g, 0.19 m) was dissolved in a 1:1 mixture of toluene and ethanol (720 mL) and degasified. LiCl (23.9 g, 0.51 m) was then added, followed by sodium carbonate (720 mL, 1.0 M solution degasified separately,) and Pd-tetrakis (13.1 g, 0.011 m). After stirring for 0.25 h, 2-formyl-4-methoxyphenylboronic acid (41.1 g, 0.22 m) was added and the reaction mixture was heated to 85° C. for 4 h. The reaction was then monitored by TLC, (Hexane-Ethyl acetate 80:20, $R_f$ (Product)=0.55). On completion, the reaction mixture was cooled to rt and water (1.0 L) was added followed by ethyl acetate (1.0 L). The organic layer was washed with brine, and dried and concentrated under vacuum to afford the title compound as a yellow solid. Yield 75 g (74%). HPLC: 99.7% (RT=6.30 min), Column: C18 BDS (4.6×50 mm), SC-307, Mobile Phase: Gradient of 0.1% TFA in water: ACN (30→100→30), Flow rate 0.8 mL/min. LCMS: 98.0% (RT=5.28 min), Column: Geneis, C18 (50×4.6 mm), Mobile Phase: Gradient of 0.1% Formic acid in water: ACN (70→95→70), Flow rate 0.8 mL/min; M−1=432.2; $^1$H NMR (DMSO-$d_6$) (400 MHz) δ 1.40-1.48 (m, 3H, cyc.Hexyl), 1.57 (s, 9H, t-Bu), 1.84-1.90 (m, 7H, cyc.Hexyl part), 3.09 (m, 1H, CH of cyc.Hexyl-benzylic), 3.84 (s, 3H, OCH$_3$), 6.55 (d, J=4 Hz, 1H, aryl H$_{2'}$), 7.06 (d, 1H, aryl H$_{3'}$), 7.08 (s, 1H, aryl H$_{6'}$), 7.23 (d, 1H, Indole-H$_5$), 7.53 (d, J=8 Hz, 1H, Indole-H$_4$), 7.70-7.75 (m, 2H, NH+Indole-H$_7$), 8.06 (s, 1H, CHO).

Intermediate 18

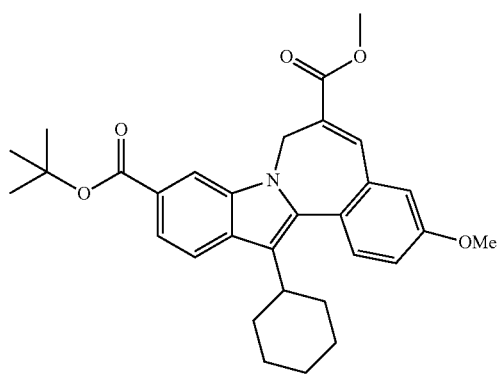

7H-Indolo[2,1-a][2]benzazepine-6,10-dicarboxylic acid, 13-cyclohexyl-, 10-(1,1-dimethylethyl) 6-methyl ester. tert-Butyl 3-cyclohexyl-2-(2-formyl-4-methoxyphenyl)-1H-indole-6-carboxylate (62.5 g, 0.144 m) was dissolved in dry DMF (1.2 L) and stirred mechanically. Cesium carbonate (84 g, 0.17 m) and methyl 2-(dimethoxyphosphoryl)acrylate (65-70% GC pure, 56.2 g, 0.18 m) were then added and the reaction mixture was heated to 65° C. for 4 h, and the reaction was monitored by TLC (Hexane-Ethyl acetate 80:20, $R_f$ (Product)=0.7). On completion, the mixture was cooled to rt, then quenched with water (1.0 L). A yellow solid precipitated, which was collected by filtration and air dried. This material was then slurried in methanol, filtered, and dried under vacuum to give the product as a yellow powder, (70 g, 90%). HPLC: 99.1% (RT=6.45 min), Column: C18 BDS (4.6×50 mm), Mobile Phase: Gradient of 0.1% TFA in water: ACN (30→100→30), Flow rate 0.8 mL/min. LCMS: 100% (RT=7.00 min), Column: Geneis, C18 (50→4.6 mm), Mobile Phase: Gradient of 0.1% Formic acid in water: ACN (70→95→70), Flow rate: 0.8 mL/min; M+1=502.2; $^1$H NMR (CDCl$_3$) (400 MHz) δ 1.10-1.30 (m, 3H, cyc.Hexyl), 1.64 (s, 9H, t-Bu), 1.77-2.07 (m, 7H, cyc.Hexyl part), 2.80 (m, 1H, CH of cyc.Hexyl-benzylic), 3.84 (s, 3H, OCH$_3$), 3.93 (s, 3H, COOCH$_3$), 4.15 & 5.65 (two br. peak., 1H each, allylic CH$_2$), 6.95 (s, 1H, aryl H$_{6'}$), 7.01 (d, 1H, aryl H$_{2'}$), 7.53 (d, J=8 Hz, 1H, aryl H$_{3'}$), ), 7.70 (d, J=4 Hz, 1H, Indole-H$_5$), 7.84 (s+d, 2H, olefinic H+Indole-H$_4$), 8.24 (s, 1H, indole=H$_7$); $^{13}$C NMR (CDCl$_3$) (100.0 MHz) δ 166.92, 165.71, 158.96, 142.28, 136.47, 13.50, 134.61, 132.43, 132.01, 129.73, 124.78, 124.68, 120.33, 119.39, 119.04, 115.62, 115.05, 111.27, 80.27, 55.49, 52.50, 39.09, 36.81, 33.40, 28.38, 27.15, 26.28.

Intermediate 19

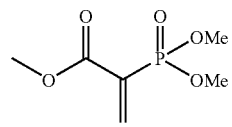

2-Propenoic acid, 2-(dimethoxyphosphinyl)-, methyl ester. To a 5 L four necked round bottom flask equipped with a mechanical stirrer, a condenser, a temperature controller and a N2 inlet, was charged paraformaldehyde (40.5 g, 1.35 mol), MeOH (2 L) and piperidine (2 mL). The reaction mixture was heated to reflux under N2 for 3 h. After cooling to 50° C., 2-(dimethoxyphosphoryl)acetate (150 g, 0.824 mol) was added in one portion. The reaction mixture was continued to reflux for 18 h. After cooling to rt, the reaction solution was concentrated in vacuo to give a clear colorless oil. The above oil was dissolved in dry toluene (1 L) in a 3 L four necked round bottom flask equipped a temperature controller, a N$_2$ inlet, a magnetic stirrer and a Dean-Stark apparatus. To the solution was added TsOH.H$_2$O (5.2 g). The reaction mixture was then refluxed azeotropically to remove methanol for 18 h. After cooling to rt, the solution was concentrated in vacuo to give a yellow oil which was vacuum distilled at 150-155° C./0.2 mmHg to afford the product as a colorless oil (135.0 g). Purity, 90% based on 1H NMR. $^1$H NMR (CDCl3, 300 MHz) δ 7.0 (dd, J=42.4 and 1.5 Hz, 1H), 6.73 (dd, J=20.5 and 1.8 Hz, 1H), 3.80 (s, 6H), 3.76 (s, 3H).

Intermediate 20

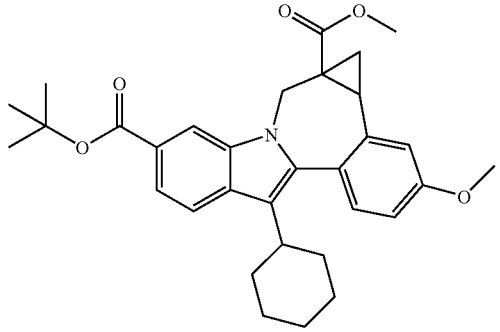

Cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−). Sodium hydride (96 mg, 4 mmol) was added to a stirred suspension of trimethylsulfoxonium chloride (567 mg, 4.4 mmol) in anhydrous DMSO (10 mL) under nitrogen. The resultant mixture was stirred at rt for 30-45 min and then neat 7H-indolo[2,1-a][2]benzazepine-6,10-dicarboxylic acid, 13-cyclohexyl-3-methoxy-, 10-(1,1-dimethylethyl) 6-methyl ester (1.0, 2 mmol) was added in small portions. The suspension was diluted with DMSO (5 mL) and heated at 50° C. for 3-4 h. The reaction mixture was allowed to cool to rt and water was added. A solid separated, which was collected by filtration and washed with water and then air dried overnight to afford 1.15 g of crude product. This material was purified by flash column chromatography (silica gel, 3% MeOH in DCM) to provide pure title compound (0.96 g): LC/MS: Retention time 3.816 min; m/e 516 (MH$^+$). $^1$H NMR (400 MHz, CDCl$_3$): The product was observed to exist as inter-converting rotamers, as evidenced from the compound's NMR spectrum.

The following procedure is an example of a method to effect the resolution of racemic cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−). A sample of cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−)- was dissolved in a mixture of isopropanol and acetonitrile (8:2) to give a final concentration of 20 mg/mL. This mixture was injected on a preparative chiral SFC chromatography system using the following conditions: Chiralcel OJ-H column, 4.6×250 mm, 5 μm; Mobile Phase: 8% MeOH in CO$_2$; Temp: 35° C.; Flow rate: 2 mL/min for 16 min; UV monitored @ 260 nm; Injection: 5 μL of ~20.0 mg/mL in IPA:ACN (8:2), Intermediate 21

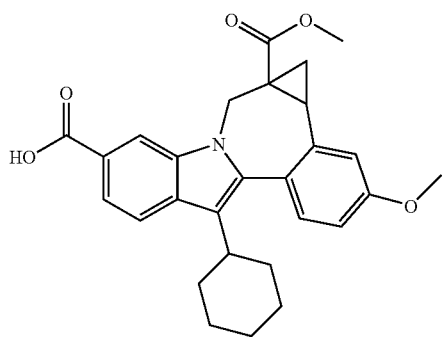

Cycloprop[d]indolo[2,1-a][2]benzazepine-1a,5(2H)-dicarboxylic acid, 8-cyclohexyl-1,12b-dihydro-11-methoxy-, 1a-methyl ester, (+/−)-. TFA (5 mL) was added to a solution of (+/−) 8-Cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester (515 mg, 1 mmol) in anhydrous DCM (10 mL). The resultant solution was stirred at rt for approximately 8 to 12 hr. The reaction was then evaporated to dryness to afford the title compound (0.47g, 100%). LC/MS: Retention time 2.245 min; m/e 460 (MH$^+$). $^1$H NMR (400 MHz, CDCl$_3$): From the compounds NMR spectrum, the product was observed to exist as a mixture of interconverting rotamers.

Intermediate 22

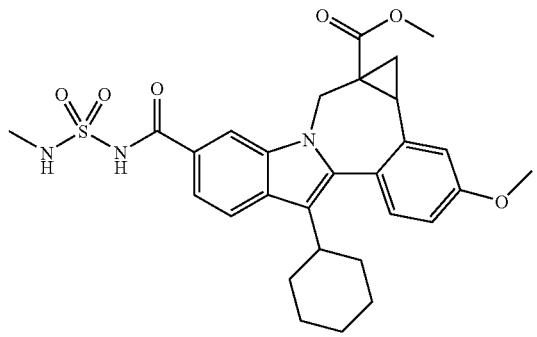

Cyclaprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-, methyl ester. A solution of 8-Cyclohexyl-1,1a,2,12b-tetrahydro-11-methoxy-1a-(methoxycarbonyl)-cycloprop[d]indolo[2,1-a][2]benzazepine-5-carboxylic acid (140 mg, 0.31 mmol) and CDI (64 mg, 0.40 mmol) in THF (3 mL) was stirred for 1 hr at 60° C. N-rnethylsulfamide (68 mg, 0.62 mmol) and DBU (71.6 mg, 0.47 mmol) were added and the mixture was stirred at 60° C. overnight. The reaction was then poured into cold water, acidified with dilute hydrochloric acid and extracted into ethyl acetate. The extracts were washed sequentially with dilute hydrochloric acid (0.1 N), and brine, and then dried (anhy. sodium sulfate), filtered and evaporated to provide the title compound as a brown solid. ESI-MS m/e 552 (MH$^+$). This material was used without further purification.

Intermediate 23

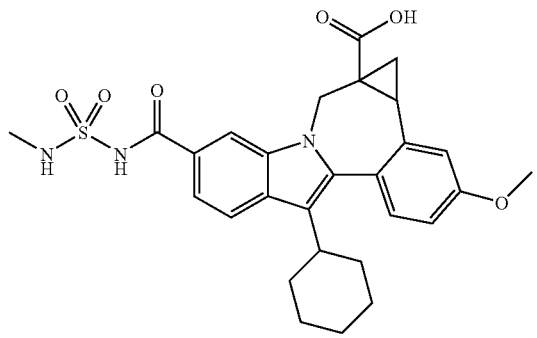

Cycloprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-. Cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-, methyl ester was dissolved in THF, MeOH mixture (2 mL,2 mL). 2.5 M NaOH (aq.) (1.2 mL, 3 mmol) was then added and the reaction was shaken at 22° C. for 2 hr. The solution was then neutralized with 1M HCl (aq.) (3 mL) and concentrated to remove the organic solvents. The residue was slurried with H$_2$O and the solids were collected by filtration, washed with H$_2$O and dried to yield compound the title compound (160 mg, 0.30 mmol). ESI-MS m/e 538 (MH$^+$). This material was used without further purification.

Intermediate 24

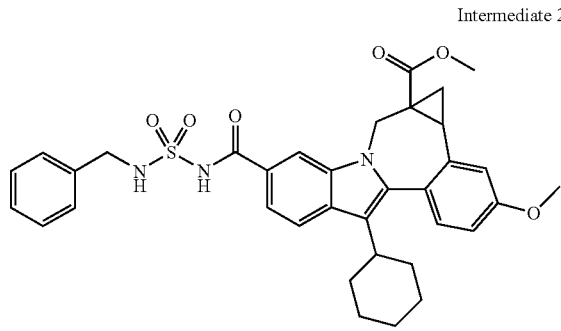

Cycloprop[d]indolo[2,1-a][2]benzazepine-1a(2H)-carboxylic acid, 8-cyclohexyl-5-[[[(benzylamino)sulfonyl]amino]carbonyl]-1,12b-dihydro-11-(methoxy)-12-(methoxy)-, methyl ester, (+/−)-. A soltion of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (200 mg, 0.44 mmol) and CDI (92 mg, 0.57 mmol) in THF (5 mL) was stirred for 1 hr at 60° C. N-benzylsulfamide (164 mg, 0.88 mmol) and DBU (100 mg, 0.66 mmol) were then added and the resultant mixture was stirred at 60° C. overnight. The reaction was then poured into cold water, acidified with dilute hydrochloric acid and extracted into ethyl acetate. The organic phase was washed hydrochloric acid (0.1 N), brine and dried (sodium sulfate) and evaporated in vacua to provide the title compound as a brown solid. ESI-MS m/e 628 (MH$^+$).

Intermediate 25

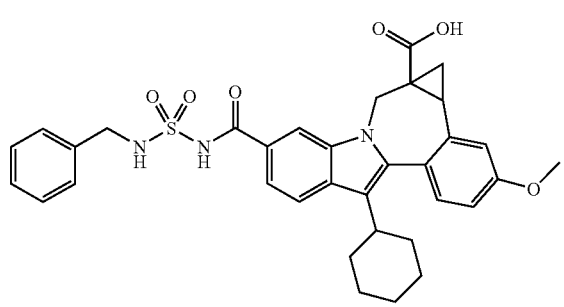

Cycloprop[d]indolo[2,1-a][2]benzazepine-1a(2H)-carbaxylic acid, 8-cyclahexyl-1,12b-dihydro-11-methoxy-5-[[[[(phenylmethyl)amino]sulfanyl]amino]carbonyl]-, (+/−)-. The title compound was prepared using a similar procedure to that described for cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-cycloprop[d]indolo[2,1-a][2]benzazepine-1a(2H)-carboxylic acid starting from (+/−) 8-cyclohexyl-1,1a,2,12b-tetrahydro-11-methoxy-1a-(methoxycarbonyl)-cycloprop[d]indolo[2,1-a][2]berizazepine-5-carboxylic acid. ESI-MS m/e 613 (MH+), 1H NMR (500 MHz, MeOD) δ ppm 1.22-2.20 (m, 13 H) 3.27-3.31 (m, 1H) 3.47 (d, J=14.95 Hz, 0.6 H) 3.92 (d, J=2.44 Hz, 3 H) 4.04 (d, 0.4 H) 4.31 (d, J=2.75 Hz, 2 H) 5.24 (d, 0.4 H) 5.48 (d, 0.6 H) 7.02 (d, 1 H) 7.17 (d, J=2.75 Hz, 1 H) 7.19-7.35 (m, 5 H) 7.39 (t, J=7.48 Hz, 2 H) 7.45-7.52 (m, 1 H) 7.80 (d, J=1.53 Hz, 0.4 H) 7.85 (dd, J=8.39, 6.87 Hz, 1 H) 8.22 (d, 3-1.53 Hz, 0.6 H).

Intermediate 26

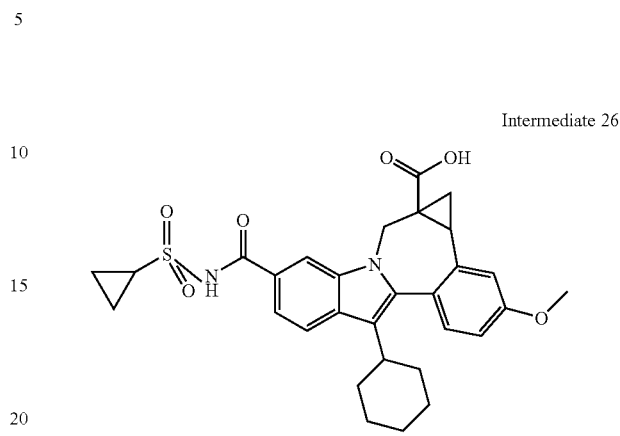

Cycloprop[d]indolo[2,1-a][2]benzazepine-1a(2H)-carboxylic acid, 8-cyclohexyl-5-[[[(cyclopropylsulfonyl)amino]carbonyl]-1,12b-dihydro-11-methoxy-, (+/−)-. A mixture of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (1 equiv), and carbonyldiimidazole (1.5 equiv) in anhydrous THF was heated at 50° C. for 30 min and allowed to cool to rt. Then 1 equiv of cyclopropanesulfonamide and 1,8-diazabicyclo[5.4.0]undec-7-ene (2 equiv) were added consecutively. The resultant mixture was stirred at rt overnight. After acidic aqueous workup, the isolated crude product was purified by prep. HPLC. The intermediate ester was then hydrolyzed using 1N NaOH in THF-MeOH to afford the title compound. LC/MS: Retention time: 2.030 min; m/e 549 (MH$^+$). $^1$H NMR (400 MHz, CDCl$_3$): The product was observed to exist as inter-converting rotarners, as evidenced from the compound's NMR spectrum.

Intermediate 31

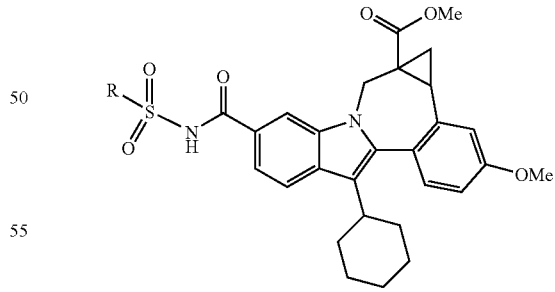

General procedure for making sulfonamides. A mixture of acid (1 equiv) and carbonyldiimidazole (1.5 equiv) in an. THF was heated at 50° C. for 30 min and allowed to cool to rt. Then 1 equiv of either sulfamide (R=NR$_2$) or sulfonamide (R=alkyl or aryl) and DBU (2 equiv) were added consecutively. The resultant mixture was stirred at rt overnight. After acidic aqueous workup, isolated crude product was purified by prep. HPLC to afford the title intermediates.

Intermediate 32

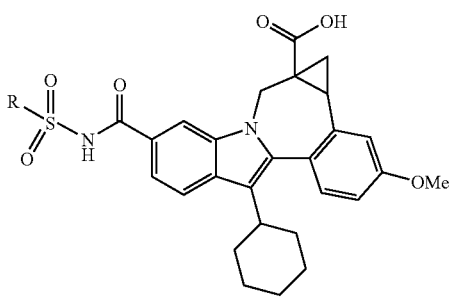

General procedure for making acids. Methyl esters hydrolyzed using 1N NaOH in THF-MeOH.

Intermediate 33

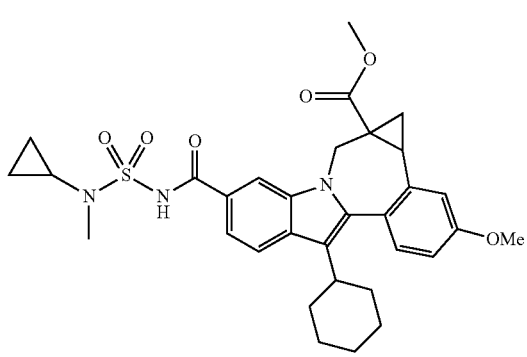

Neat CDI (0.049 g, 0.302 mmol) was added to stirred solution of the acid (0.092 g, 0.200 mmol) in THF (1 ml) and the mixture was heated at 50° C. for 30 min and then allowed to cool to rt. Then N-cyclopropyl-N-methylsulfamide (0.0451 g, 0.300 mmol) and DBU (0.060 ml, 0.400 mmol) were added consecutively. The mixture sonicated for 1-2 hand then stirred overnight at it Reaction was quenched with MeOH (0.5 ml) and then acidified with 1N HCl and extracted with EtOAc (2×25 mL), washed with water, brine and dried (Na2SO4). Crude product (0.123 g) was purified by silica gel flash chromatography (5% MeOH in DCM) to afford the expected product as an off-white solid (0.101 g 85%).

Intermediate 34

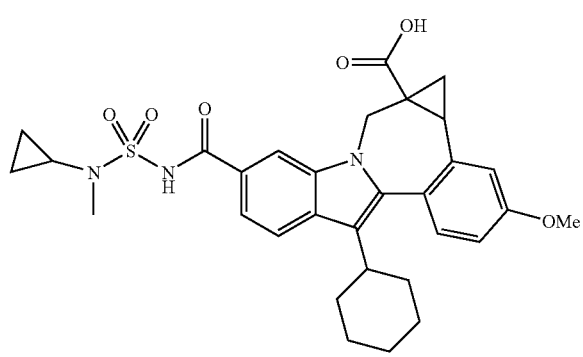

1N NaOH (2 mL, 2.000 mmol) was added to stirred solution of the methyl ester (0.098 g, 0.166 mmol) in THF-MeOH under nitrogen. The mixture was stirred at rt for 2 h and then acidified with 1N HCl (3 ml), extracted with EtOAc (2×25 ml), washed with water, brine and dried (MgSO4). Evaporation of solvents gave the acid as an off-white solid (0.0942 g, 98%). LC/MS: mle 578 (MH+). LC/MS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H$_2$O/90% MeOH/0.1% Trifluoroacetic Acid; Column: XBridge 4.6×50 mm S5.

Intermediate 35

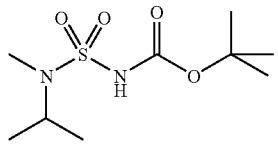

t-Butanol (1.35 mL, 14 mmol) was added dropwise to the solution of CSI (1.24 mL, 14 mmol) of CH$_2$Cl$_2$ (10 mL) at 0° C. The generated solution was stirred for 2 h at 0° C. A solution of N-methylpropan-2-amine (1.57 ml, 14.13 mmol) and TEA (2.167 ml, 15.54 mmol) in CH$_2$Cl$_2$ (3 ml) was added dropwise. The generated reaction mixture was stirred for 2 h at r.t. The reaction mixture was diluted with EtOAc and washed with cold 1N HCl, brine, dried (MgSO4), removed the solvent and the residue was purified by Biotage 40M column (EtOAc-MeOH (90-10)/hexane 5% to 100%) to afford the product as a colorless gel (2.3 g, 65%) 1H NMR (400 MHz, CHLOROFORM-d) δ ppm 1.19 (d, J=6.55 Hz, 6 H) 1.49 (s, 9H) 2.90 (s, 3 H) 4.05-4,26 (m, 1 H) 7.02 (br. s., 1 H).

Intermediate 36

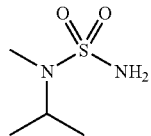

To tert-butyl N-isopropyl-N-methylsulfamoylcarbamate (2.3 g, 9.12 mmol) was added cold HCl (6 mL, 24.00 mmol) and stirred at room temperature for 2 h, removed the solvent to afford the product as a solid in light tan (1.38 g, 99%). 1 H NMR (400 MHz, CHLOROFORM-d) δ ppm 1.16 (d, J=6.80 Hz, 5 H) 2.72 (s, 3 H) 4.16 (dt, J=13.53, 6.70 Hz, 1 H) 4.43 (br. s., 1 H).

Intermediate 37

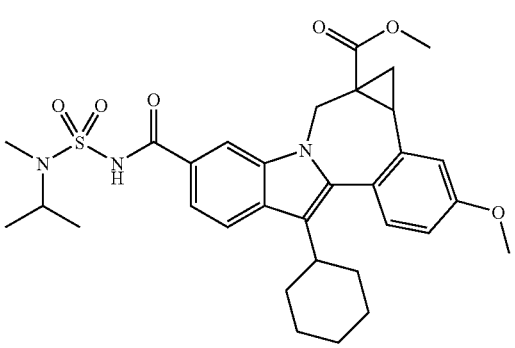

The product (0.261 g, 81%) was made from the acid (0.25 g, 0.54mmol) and amine using CDT and DBU. LC-MS retention time: 3.635 min; MS m/z (M+H) 594. H NMR showed compound existed as rotamers (~4/3). LC/MS method: Start % B: 0, Final % B: 100; Gradient time: 3 min; Stop time: 4 min; Flow rate: 4 ml/min; Wavelenth: 220; Solvent A: 10% MeOH/90% H₂O/0.1% Trifluoroacetic Acid; Solvent B: 10% H₂O/90% MeOH/0.1% Trifluoroacetic Acid; Column: XBridge 4.6×50 mm S5.

The compounds prepared in the following procedures were analyzed by the following LC/MS method until noted: Analysis Conditions: Column: PHENOMENNEX-LUNA 3.0×50 mm S10; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

Intermediate 38

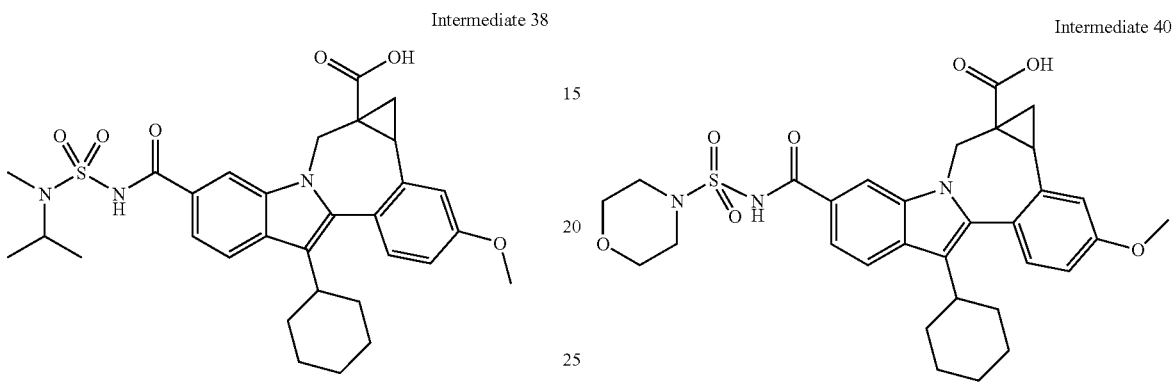

The acid (0.22g, 87%) was made from the ester (0.258 g, 0.435 mmol) using NaOH in THF/MeOH. The acid was isolated as a pale yellow solid. LC-MS retention time: 3.608 min; MS m/z (M+H) 580. LC/MS method: Start % B: 0, Final % B: 100; Gradient time: 3 min; Stop time: 4 min; Flow rate: 4 ml/min; Wavelenth: 220; Solvent A: 10% MeOH/90% H₂O/ 0.1% Trifluoroacetic Acid; Solvent B: 10% H₂O/90% MeOH/0.1% Trifluoroacetic Acid; Column: XBridge 4.6×50 mm S5. 1H NMR existed rotamers (~½). The major isomer: 1H NMR (400 MHz, CHLOROFORM-d) δ ppm 0.41 (t, J=6.30 Hz, 1 H) 1.08-2.15 (m, 17 H) 2.63-2.80 (m, 1 H) 2.84-2.96 (m, 1 H) 3.04 (s, 3 H) 3.84 (s, 3 H) 4.03 (d, J=14.86 Hz, 1 H) 4.22-4.41 (m, 1 H) 5.35 (d, J=15.11 Hz, 1 H) 6.86 (dd, J=8.44, 2.39 Hz, 1 H) 6.98 (d, J=2.27 Hz, 1 H) 7.20 (d, J=8.56 Hz, 1 H) 7.67 (d, J=8.31 Hz, 1 H) 7.81-7.89 (m, 1 H) 8.10 (s, 1 H).

(+/−)-8-Cyclohexyl-5-(morpholinosulfonylcarbamoyl)-1,1a,2,12b-tetrahydro-11-methoxy-cycloprop[d]indolo[2,1-a][2]benzazepine-1a-carboxylic acid. The product was purified by prep HPLC and isolated as a beige solid. LC/MS: Retention time: 1.968 min; m/e 460 (MH⁺). ¹H NMR (400 MHz, CDCl₃): The compound was observed to exist as inter-converting rotamers.

Intermediate 41

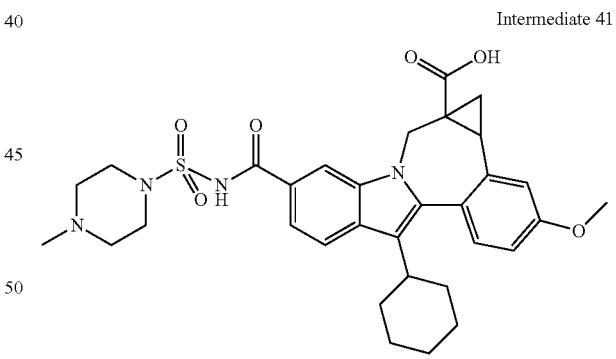

Intermediate 39

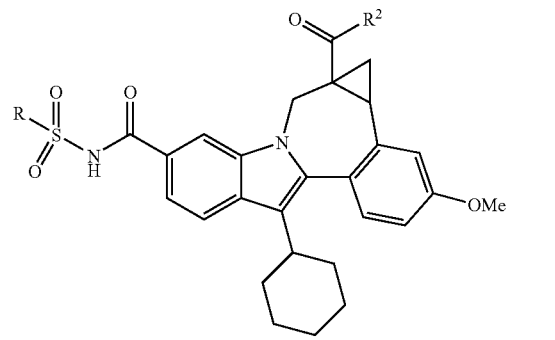

General procedure for making amides for some examples. Acid derivatives (1 equiv) were combined with corresponding amine (1.2 equiv), triethylamine (2-3 equiv) and TBTU (1.3 equiv) in anh. DMF and stirred at rt for 1-2 h until completion of the amide coupling. Isolated crude products were purified by prep. HPLC to provide the desired amides.

(+/−)-8-Cyclohexyl-5-(4-methylpiperazin-1-ylsulfonyl-carbamoyl)-1,1a,2,12b-tetrahydro-11-methoxy-cycloprop[d]indolo[2,1-a][2]benzazepine-1a-carboxylic acid. The product was purified by prep HPLC and isolated in mono TFA salt form as a beige solid. LC/MS: Retention time: 1.687 min; m/e 607 (MH⁺). ¹H NMR (400 MHz, CDCl₃): The compound was observed to exist as inter-converting rotamers.

All compounds labeled with an A are racemic mixtures and compounds labeled with a B are single enantiomers. Compounds with cyclopropyl rings fused to an azepine ring are cis-fused.

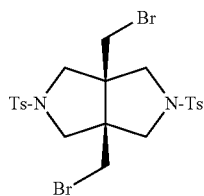

Intermediate 42

3a,6a-bis (bromomethyl)-2,5-bis((4-methylphenyl)sulfonyl)octahydropyrrolo[3,4-c]pyrrole. Prepared according to *J. Org. Chem.* 1996, 61, 8897-8903. MW 606.4.

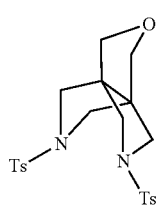

Intermediate 43

5,8-bis((4-methylphenyl)sulfonyl)dihydro-4H-3a,6a-(methanoiminomethano)furo[3,4-c]pyrrole. Prepared via the procedures outlined in *J. Org. Chem.* 1996, 61, 8897-8903.

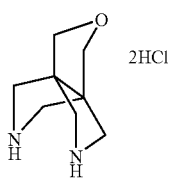

Intermediate 44 dihydro-4H-3a,6a-(methanoiminomethano)furo[3,4-c]pyrrole dihydrochloride. Lithium aluminum hydride (1.0 M in THF) (17.3 mL, 17.3 mmol) was added to a solution of crude 5,8-bis((4-methylphenyl)sulfonyl)dihydro-4H-3a,6a-(methanoiminomethano)furo[3,4-c]pyrrole (Intermediate 2) (800 mg, 1.73 mmol) in THF (10 mL) and the mixture was stirred at rt for 4 d. Et$_2$O (100 mL) was added to the reaction, followed by the dropwise addition of water (1.5 mL) and then 10 N NaOH (aq) (1.5 mL). After the gas evolution ceased, the mixture was filtered through celite. The filtrate was acidified with HCl (2.0 M in Et$_2$O, 2 mL), (white precipitate formed) and concentrated to a pink solid, which was triturated with Et$_2$O and then MeOH to yield dihydro-4H-3a,6a-(methanoiminomethano)furo[3,4-c]pyrrole dihydrochloride (254 mg, 1.65 mmol, 95% yield) as a white solid. LCMS: m/e 155 (M+H)$^+$. LCMS retention time: 0.26 min. (Column: SunFire C18 5u 4.6×50 mm. Solvent A=90% Water/10% Acetonitrile/0.1%TFA. Solvent B=10% Water/90% Acetonitrile/0.1% TFA. Start % B=0. Final % B=100. Gradient Time=2 min. Flow Rate=4 ml/min.). $^1$H NMR (500 MHz, DMSO-d$_6$) δ ppm 10.24-9.90 (4 H, m), 3.82 (4 H, s), 3.56 (4 H, d, J=12.21 Hz), 3.18 (4 H, d, J=12.21 Hz).

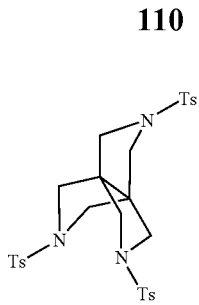

Intermediate 45

2,5,8-tris((4-methylphenyl)sulfonyl)tetrahydro-1H,4H-3a,6a-(nethanoiminomethano)pyrrolo[3,4-c]pyrrole. Prepared via the procedures outlined in *J. Org. Chem.* 1996, 61, 8897-8903.

Intermediate 46 tetrahydro-1H,4H-3a,6a-(methanoiminomethano)pyrrolo[3,4-c]pyrrole trihydrochloride. Lithium aluminum hydride (1.0 Min THF) (19.7 mL, 19.7 mmol) was added to a solution of 2,5,8-tris((4-methylphenyl)sulfonyl)tetrahydro-1H,4H-3a,6a-(methanoiminomethano)pyrrolo[3,4-c]pyrrole (Intermediate 4) (810 mg, 1.32 mmol) in THF (20 mL) and the mixture was stirred at rt for 2 d. Et$_2$O (100 mL) was added to the reaction, followed by the dropwise addition of water (2 mL) and then 10 N NaOH (aq) (2 mL). After the gas evolution ceased, the mixture was dried by Na$_2$SO$_4$ and filtered through celite. The filtrate was acidified with HCl (2.0 M in Et$_2$O, 2 mL), (white precipitate formed), concentrated to dryness and the residue was triturated with Et$_2$O and then MeOH to yield tetrahydro-1H,4H-3a,6a-(methanoiminomethano)pyrrolo[3,4-c]pyrrole trihydrochloride (80 mg, 0.52 mmol, 40% yield) as a white solid. LCMS: m/e=154 (M+H)$^+$. LCMS retention time: 0.25 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time =2 min. Flow Rate=4 mL/min.). $^1$H NMR (500 MHz, DMSO-d$_6$) δ ppm 10.21 (6H, br s), 3.59 (12H, br s).

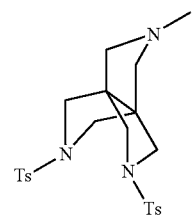

Intermediate 47 tetrahydro-2-methyl-5,8-bis[(4-methylphenyl)sulfonyl]-1H,4H-3a,6a-(methanoiminomethano)pyrrolo[3,4-c]pyrrole.
2.0 M Methylamine in THF (15 mL, 30 mmol) was added to a suspension of 3a,6a-bis(bromomethyl)-2,5-bis((4-methylphenyl)sulfonyl)octahydropyrrolo[3,4-c]pyrrole (Intermediate 1) (2 g, 3.3 mmol) in DMSO (30 mL) and the mixture was stirred at 120° C. in sealed tube for 1 d. The solvent was removed under vacuum and the residue was partitioned between CHCl₃ (100 mL) and brine (50 mL). The organic layer was washed with brine, dried (MgSO₄) and concentrated to a yellow solid, which was purified by flash silica chromatography (SiO₂, EtOAc/Hexanes, gradient from 33% to 100% EtOAc) to yield product tetrahydro-2-methyl-5,8-bis[(4-methylphenyl)sulfonyl]-1H,4H-3a,6a-(methanoiminomethano)pyrrolo[3,4-c]pyrrole (810 mg, 1.70 mmol, 52% yield) as a white solid. LCMS: m/e=476 (M+H)⁺. LCMS retention time: 1.10 min. (Column: SunFire C18 5u 4.6×50 mm. Solvent A=90% Water/10% Acetonitrile/0.1% TFA. Solvent B=10% Water/90% Acetonitrile/0.1%TFA. Start % B=0. Final % B=100. Gradient Time=2 min. Flow Rate=4 mL/min.)

Intermediate 48

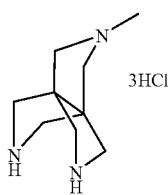

2-methyltetrahydro-1H,4H-3a,6a-(methanoiminoinethano)pyrrolo[3,4-c]pyrrole trihydrochloride. Lithium aluminum hydride (1.0 M in THF) (5.7 mL, 5.7 mmol) was added to a solution of tetrahydro-2-methyl-5,8-bis[(4-methylphenyl)sulfonyl]-1H,4H-3a,6a-(methanoiminomethano)pyrrolo[3,4-c]pyrrole (Intermediate 6) (270 mg, 0.57 mmol) in THF (6 mL) and the mixture was stirred at rt for 16 h. Et₂O (30 mL) and THF (20 mL) were added to the reaction, followed by the dropwise addition of water (0.6 mL) and then 10 N NaOH (act) (0.6 mL). After the gas evolution ceased, the mixture was filtered through celite. The filtrate was acidified with HCl (2.0 M in Et₂O, 0.9 mL) and concentrated to a pink solid, which was triturated with MeOH and EtOAc to yield 2-methyltetrahydro-1H,4H-3a,6a-(methanoiminomethano)pyrrolo[3,4-c]pyrrole trihydrochloride (100.6 mg, 0.364 mmol, 64% yield) as a white solid. LCMS: m/e=168 (M+H)⁺. LCMS retention time: 0.26 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). ¹H NMR (400 MHz, DMSO-d₆) □ ppm 12.28-9.36 (5H, m), 3.63 (12H, br s), 2.82 (3H, s).

Intermediate 49

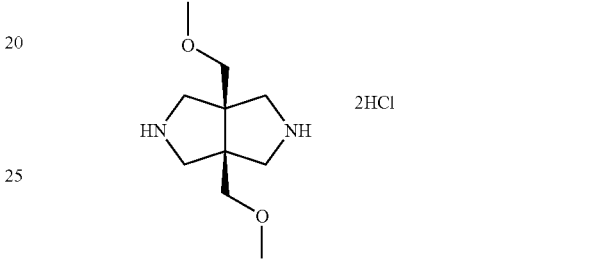

3a,6a-bis(methoxymethyl)-2,5-bis((4-methylphenyl)sulfonyl)octahydropyrrolo[3,4-c]pyrrole. 25 wt. % Sodium methoxide in MeOH (3.8 mL, 16 mmol) was added to a suspension of 3a,6a-bis(bromomethyl)-2,5-bis((4-methylphenyl)sulfonyl)octahydropyrrolo[3,4-c]pyrrole (Intermediate 1) (2 g, 3.30 mmol) in DMSO (10 mL) and the mixture was stirred at 120° C. under N₂ for 16 h. The solvent was evaporated under vacuum and the residue was partitioned between CHCl₃ and sat. NH₄Cl (aq). The organic layer was washed with brine, dried (MgSO₄) and concentrated to an orange solid, which was triturated with CH₂Cl₂ to yield the first crop of 3a,6a-bis(methoxymethyl)-2,5-bis((4-methylphenyl)sulfonyl)octahydropyrrolo[3,4-c]pyrrole (720 mg, 1.4 mmol, 43%) as a white solid. The mother liquor was purified by flash silica chromatography (SiO₂, eluted with EtOAc/Hexanes 1:2) to yield additional desired product (130 mg, 0.26 mmol, 8%) as awhite solid. LCMS: m/e=509 (M+H)⁺. LCMS retention time: 1.85 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=2 min. Flow Rate=4 mL/min.).

Intermediate 50

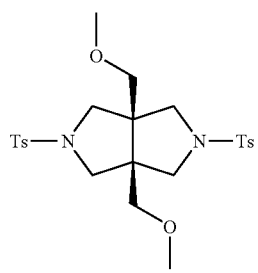

cis-3a,6a-bis(methoxymethyl)octahydropyrrolo[3,4-c]pyrrole dihydrochloride. Lithium aluminum hydride (1.0 M in THF) (14.2 mL, 14.2 mmol) was added to a solution of (3as,6as)-3a,6a-bis(methoxymethyl)-2,5-ditosyloctahychopyrrolo[3,4-c]pyrrole (Intermediate 8) (720 mg, 1.42 mmol) in THF (15 mL) and the mixture was stirred at rt for 3 d. Additional lithium aluminum hydride (1.0 M in THF) (10 mL, 10 mmol) was added and the reaction was continued for another day. The reaction was diluted with Et₂O (100 mL), followed by the dropwise addition of water (1.5 mL) and then 10 N NaOH (aq) (1.5 mL). After the gas evolution ceased, the mixture was filtered through celite. The filtrate was acidified with HCl (2.0 M in Et₂O, 2 mL), (white precipitate formed) and concentrated to an orange solid, which was triturated with Et₂O and then MeOH to yield cis-3a,6a-bis(methoxymethyl)octahydropyrrolo[3,4-c]pyrrole dihydrochloride (266 mg, 1.33 mmol, 94% yield) as a white solid. LCMS: m/e=201 (M+H)⁺. LCMS retention time: 0.26 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

Intermediate 51

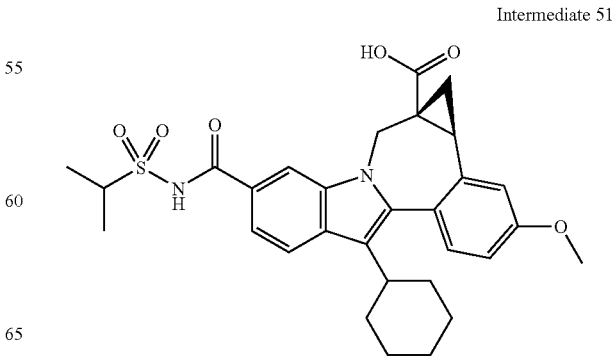

(1aR,12bS)-8-cyclohexyl-5-((isopropylsulfonyl)carbamoyl)-11-methoxy-1,12b-dihydrocyclopropa[d]indolo[2,1-a][2]benzazepine-1a(2H)-carboxylic acid. Prepared according to US 20080146537 and US 2007184024, Intermediate 52

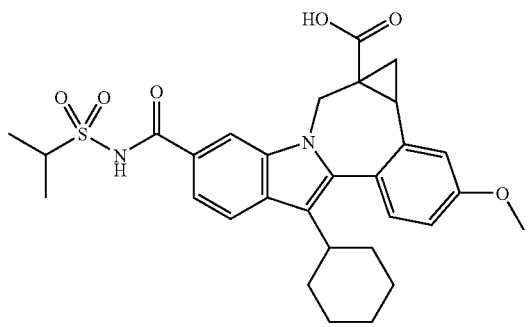

8-cyclohexyl-5-((isopropylsulfonyl)carbamoyl)-11-methoxy-1,12b-dihydrocyclopropa[d]indolo[2,1-a][2]benzazepine-1a(2H)-carboxylic acid. Prepared according US 20080146537 and US 2007184024.

Intermediate 53

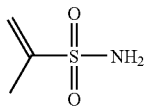

prop-1-ene-2-sulfonamide, A 0.5 M solution of prop-1-en-2-ylmagnesium bromide (20 mL 10.0 mmol) in Et$_2$O was added slowly to a stirring solution of sulfuryl dichloride (1.6 mL, 20 mmol) in hexanes (20 mL) at 0° C. The reaction was slowly allowed to warm to rt and stirred 16 h. The reaction was quenched with water (40 mL), the layers separated and the organic layer was concentrated to a clear liquid. The residue was dissolved into THF (30 mL), cooled to 0° C. and treated with ammonia (~10 mL) using a cold finger (−70° C.). The cooling bath was removed and the reaction was allowed to stir at rt for 1 h with the cold finger attached, and then stirred open to air at rt ON. The reaction was filtered, concentrated under vacuum and partially purified through a pad of silica (eluting with EtOAc/hexanes 1:1). Fractions containing product were combined, concentrated and then recrystallized from hexanes/EtOAc (3:1) to yield prop-1-ene-2-sulfonamide (161 mg, 1.33 mmol, 13%) as a white solid. $^1$H NMR (300 MHz, CDCl$_3$) δ ppm 6.06 (s, 1H), 5.55 (q, J=1.5 Hz, 1H), 4.57 (br s, 2H), 2.14 (, br s, 3H).

Intermediate 54

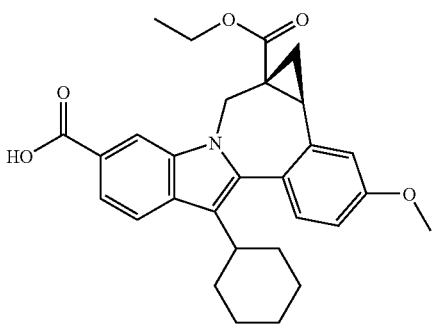

(1aR,12bS)-8-cyclohexyl-1a-(ethoxycarbonyl)-11-methoxy-1,1a,2,12b-tetrahydrocyclopropa[d]indolo[2,1-a][2]benzazepine-5-carboxylic acid. Prepared according US 2008146537.

Intermediate 55

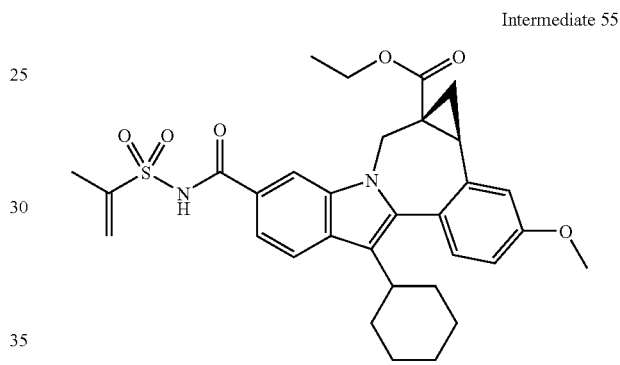

Ethyl (1aR,12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylate. CDI (243 mg, 1.501 mmol) was added to a solution of (1aR,12bS)-8-cyclohexyl-1a-(ethoxycarbonyl)-11-methoxy-1,1a,2,12b-tetrahydrocyclopropa[d]indolo[2,1-a][2]benzazepine-5-carboxylic acid (Intermediate 13) (474 mg, 1.00 mmol) in THF (5 mL) and the mixture was stirred at 60° C. for 1 h. Then prop-1-ene-2-sulfonamide (Intermediate 12) (182 mg, 1.50 mmol) and DBU (0.3 mL, 1.990 mmol) were added, the reaction was stirred at rt for 3 d. The reaction mixture was diluted with 0.5 N aq HCl (20 ml) and extracted with EtOAc (50 ml×2). The combined organics were washed with aq HCl and brine, dried (MgSO$_4$), filtered and concentrated to a yellow oil. The residue was purified by prep HPLC (H$_2$O—CH$_3$CN with 10 mM NH$_4$OAc buffer) to yield ethyl (1aR,12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylate (357 mg, 0.619 mmol, 62% yield) as a white solid. LCMS: m/e=577 (M+H)$^+$. LCMS retention time: 1.22 min. (Column: phenomenex 10u 4.6×50 mm C18. Solvent A=H$_2$O:ACN 95%:5% 10 mm Ammonium Acetate. Solvent B=H$_2$O:ACN 5%:95% 10 mm Ammonium Acetate. Start % B=30. Final % B=100. Gradient Time=2 min. Flow Rate=4 ml/min.). Presents as a 3:1 ratio of rotamers or atrope isomers. $^1$H NMR (300 MHz, MeOD) δ ppm 8.30 (s, 0.25H), 8.09 (s, 0.75H), 7.91 (d, J=8.8 Hz, 0.25H), 7.88 (d, J=8.4 Hz, 0.75H), 7.62 (dd, J=8.8, 1.5 Hz, 0.25H), 7.56 (dd, J=8.4, 1.5 Hz, 0.75H), 7.32 (d, J=8.4 Hz, 0.25H), 7.28 (d, J=8.8 Hz, 0.75H), 7.23 (d, J=2.2 Hz, 0.75H), 7.15 (d, J=2.6 Hz, 0.25H), 7.05-

6.97 (m, 1H), 6.31 (br s, 1H), 5.94 (br 5, 1H), 5.47 (d, J=15.0 Hz, 0.75H), 5.26 (d, J=15.0 Hz, 0.25H), 4.33-3.88 (m, 3H), 3.90 (s, 3H), 3.48 (d, J=15.0 Hz, 0.75H), 3.14-2.66 (m, 2.25H), 2.23-0.88 (m, 13.75H), 0.29-0.23 (m, 0.25H).

Intermediate 56

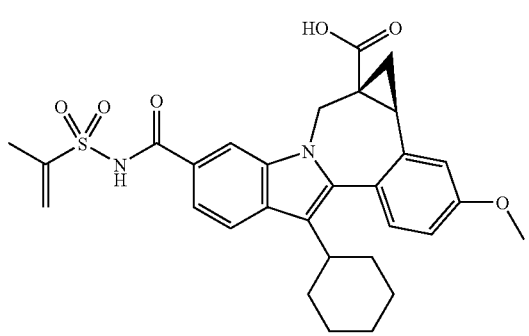

(1aR,12bS)-8-cyclohexyl-5-((isopropenylsulfonyl)carbamoyl)-11-methoxy-1,12b-dihydrocyclopropa[d]indolo [2,1-a][2]benzazepine-1a(2H)-carboxylic acid. Aqueous NaOH (1.8 mL, 1.8 mmol) was added to a solution of ethyl (1aR, 12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylate (Intermediate 14) (350 mg, 0.607 mmol) in MeOH (4 mL) and THF (4 mL) and the mixture was stirred at rt for 16 h. The reaction was quenched with 1N aq HCl (1.8 mL), concentrated and the residue was partitioned between EtOAc (50 mL) and H$_2$O (30 mL). The organic layer was washed with brine, dried (MgSO$_4$) and concentrated to yield crude (1aR,12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylic acid (333 mg, 0.577 mmol, 95% yield) as a yellow solid. LCMS: m/e=549 (M+H)$^+$. LCMS retention time: 1.55 min. (Column: phenomenex 10u 4.6×50 mm C18. Solvent A=H$_2$O:ACN 95%:5% 10 mm Ammonium Acetate. Solvent B=H$_2$O:ACN 5%:95% 10 mm Ammonium Acetate. Start % B=0. Final % B=100. Gradient Time=3 min. Flow Rate=4 ml/min.).

Intermediate 57

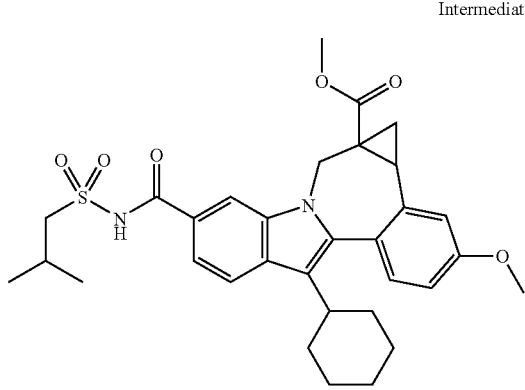

Methyl 8-cyclohexyl-5-((isobutylsulfonyl)carbamoyl)-11-methoxy-1,12b-dihydrocyclopropa[d]indolo[2,1-a][2]benzazepine-1a(2H)-carboxylate. Prepared according to US 20080146537.

Intermediate 58

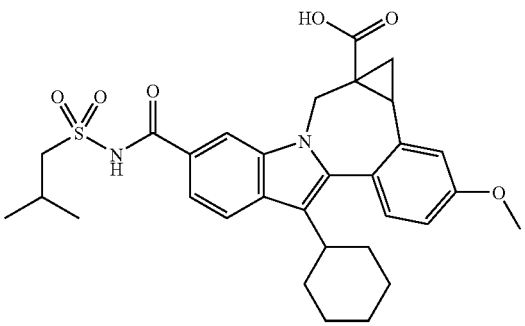

8-cyclohexyl-5-((isobutylsulfonyl)carbamoyl)-11-methoxy-1,12b-dihydrocyclopropa[d]indolo[2,1-a][2]benzazepine-1a (2H)-carboxylic acid. Prepared according to US 20080146537.

Intermediate 59

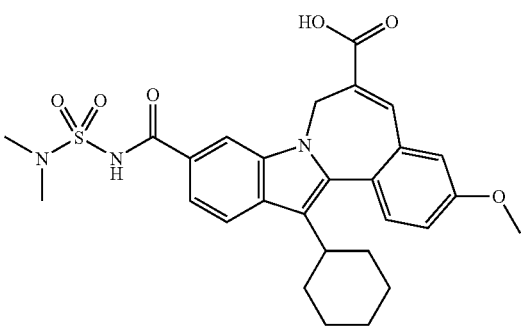

13-cyclohexyl-10-((dimethylsulfamoyl)carbamoyl)-3-methoxy-7H-indolo[2,1-a][2]benzazepine-6-carboxylic acid. Prepared according to WO 2008097796 and WO 2007033175.

Intermediate 60

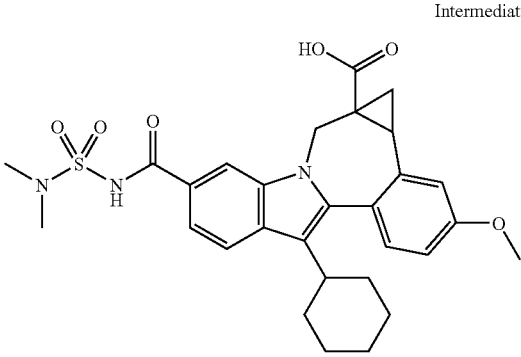

8-cyclohexyl-5-((dimethylsulfamoyl)carbamoyl)-11-methoxy-1,12b-dihydrocyclopropa[d]indolo[2,1-a][2]benzazepine-1a(2H)-carboxylic acid. Prepared according to US 20080146537, WO 2008097796 and WO 2007143521.

Intermediate 61

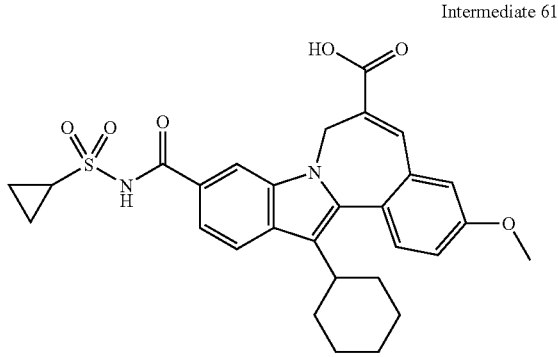

13-cyclohexyl-10-((cyclopropylsulfonyl)carbamoyl)-3-methoxy-7H-indolo[2,1-a][2]benzazepine-5-carboxylic acid. Prepared according to US 2007184024.

Intermediate 62

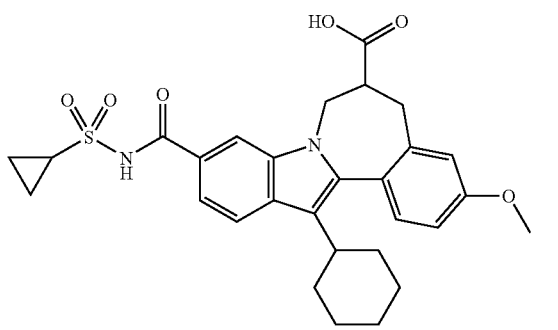

Methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate. A solution of 13-cyclohexyl-10-((cyclopropylsulfonyl)carbamoyl)-3-methoxy-7H-indolo[2,1-a][2]benzazepine-6-carboxylic acid (Intermediate 20) (80 mg, 0.15 mmol) in MeOH (20 mL) was passed through a 10% Pd—C cartridge with $H_2$ stream at 30 bar, rt in a ThalesNano H-cube reactor. The output was collected and concentrated to yield methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (61.6 mg, 0.115 mmol, 77% yield) as bright yellow solid. LCMS: m/e 537 (M+H)$^+$. LCMS retention time: 3.03 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min).

Intermediate 63

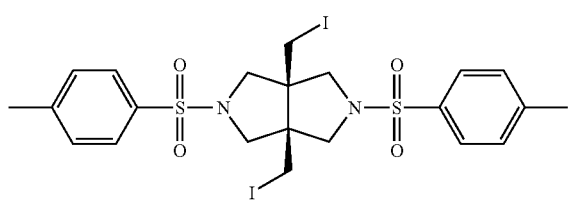

3a,6a-bis(Iodomethyl)-2,5-bis((4-methylphenyl)sulfonyl)octahydropyrrolo[3,4-c]pyrrole. A suspension of 3a,6a-bis(bromomethyl)-2,5-bis((4-methylphenyl)sulfonyl)octahydropyrrolo[3,4-c]pyrrole (0.606 g, 1.00 mmol) and potassium iodide (1.66 g, 10.0 mmol) in dry DMF (5 mL) was stirred under $N_2$ at 100° C. for 12 h. Upon heating to 100° C., the reaction turned from a white suspenson to a yellow suspension. After 12 h of stirring at 100° C., the reaction was cooled to r.t., diluted with $H_2O$ (30 mL) and concentrated to an aqueous mixture. The resulting mixture was extracted with $CH_2Cl_2$ (3×15 mL), the combined organic extracts were washed with sat. $NH_4Cl$ (aq.) (20 mL), dried over $Na_2SO_4$, filtered and concentrated to give diiodo-bis-pyrrolidine (0.65 g, 0.93 mmol, 93% yield). LCMS: m/e=701 (M+H)$^+$. LCMS retention time: 2.69 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). $^1$H NMR (400 MHz, CHLOROFORM-d) δ ppm 7.68 (4 H, d, J=8.28 Hz), 7.39 (4 H, d, J=7.78 Hz), 3.34 (4 H, d, J=10.54 Hz), 3.24 (4H, d, J=10.54 Hz), 3.00 (4 H, s), 2.49 (6 H, s).

Intermediate 64

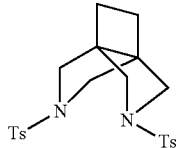

2,5-bis((4-methylphenyl)sulfonyl)tetrahydro-H1,4H-3a,6a-ethanopyrrolo[3,4-c]pyrrole. t-Butyl lithium (1.7 M pentane) (1.05 mL, 1.76 mmol) was added dropwise to a stirring solution of 3a,6a-bis(iodomethyl)-2,5-bis((4-methylphenyl)sulfonyl)octahydropyrrolo[3,4-c]pyrrole (0.50 g, 0.71 mmol) in THF (10 mL) at −78° C. The resulting orange mixture was stirred at −78° C. for 30 minutes. After this time, additional t-Butyl lithium 1.7 M in pentane (1.05 mL, 1.76 mmol) was added to the reaction mixture at −78° C. After 10 minutes of additional stirring at −78° C., the reaction was quenched with the addition of sat. $NH_4Cl$ (aq) (10 mL). The mixture was warmed to r.t., diluted with EtOAc (15 mL) and the layers were separated. The aq. layer was then extracted with EtOAc (3×20 mL) and once with $CH_2Cl_2$. The combined organic extracts were washed with brine (30 mL), dried over $Na_2SO_4$, filtered and concentrated to give 2,5-bis((4-methylphenyl)sulfonyl)tetrahydro-1H,4H-3a,6a-ethanopyrrolo[3,4-c]pyrrole (0.308 g, 0.690 mmol, 97% yield) as a white crystaline solid. LCMS: m/e=447 (M+H)$^+$. LCMS retention time: 2.39 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Structure was verified via single crystal X-ray diffraction. $^1$H NMR (400 MHz, CHLOROFORM-d) □ ppm 7.67 (4 H, d, J=8.28 Hz), 7.34 (4 H, d, J=8.03 Hz), 3.36 (4 H, d, J=9.79 Hz), 2.73 (4 H, d, J=9.79 Hz), 2.47 (6 H, s), 2.00 (4 H, s).

Intermediate 65

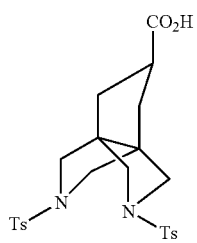

2,8-bis((4-methylphenyl)sulfonyl)tetrahydro-1H,4H-3a,6a-(methanoiminomethano)cyclopenta[c]pyrrole-5-carboxylic acid. A flame dried flask was charged with 3a,6a-bis(bromomethyl)-2,5-bis((4-methylphenyl)sulfonyl)octahydropyrrolo[3,4-c]pyrrole (1.00 g, 1.65 mmol) and cesium carbonate (5.37 g, 16.5 mmol). The flask was evacuated and backfilled with $N_2$. The solids were taken up in dry DMSO (10 mL). Finally, dry dimethyl malonate (0.377 mL, 3.30 mmol) was added and the mixture was heated to 100° C. The mixture was allowed to stir at this temperature under $N_2$ for 3 days. The reaction was cooled to r.t., diluted with $H_2O$ (30 mL) and $CH_2Cl_2$ (30 mL) and the layers were separated. The aqueous layer was extracted with $CH_2Cl_2$ (3×20 mL). The combined organic extracts were washed with brine (30 mL), dried over $Na_2SO_4$, filtered and concentrated to give an orange solid. This solid was purified on silica gel (Biotage, EtOAc/hexanes (20% EtOAc to 80% EtOAc over 10 CV, all fractions collected) to give a mixture of methyl 2,8-bis((4-methylphenyl)sulfonyl)tetrahydro-1H,4H-3a,6a-(methanoiminomethano)cyclopenta[c]pyrrole-5-carboxylate (0.30 g, 0.58 mmol, 46% yield) and 5,8-bis((4-methylphenyl)sulfonyl)dihydro-4H-3a,6a-(methanoiminomethano)furo[3,4-c]pyrrole (0.29 g, 0.63 mmol, 50% yield) as a white solid. This inseparable mixture was taken on to the hydrolysis where 2,8-bis((4-methylphenyl)sulfonyl)tetrahydro-1H,4H-3a,6a-(methanoiminomethano)cyclopenta[c]pyrrole-5-carboxylic acid and 5,8-bis((4-methylphenyl)sulfonyl)dihydro-4H-3a,6a-(methanoiminomethano)furo[3,4-c]pyrrole were separated. The mixture from the previous step was dissolved in THF (40 mL). The solution was cooled to 0° C. and 4M LiOH (aq) (10 mL, 20.0 mmol) was added. The yellow solution was allowed to warm to room temperature overnight. The solution was concentrated in vacuo. The resulting residue was diluted with 1M HCl (aq) (50 mL) and extracted with EtOAc (3×20 mL). The combined organic extracts were washed with brine, dried over $Na_2SO_4$, filtered and concentrated to give 0.9 g of a white solid consisting of the unreacted 5,8-bis((4-methylphenyl)sulfonyl)dihydro-4H-3a,6a-(methanoiminomethano)furo[3,4-c]pyrrole and the desire 2,8-bis((4-methylphenyl)sulfonyl)tetrahydro-1H,4H-3a,6a-(methanoiminomethano)cyclopenta[c]pyrrole-5-carboxylic acid. The solid was purified on silica gel (Biotage, EtOAc/hexanes (30% to 50% EtOAc over 5 CV) followed by a second gradient consisting of a 1:1 $CH_2Cl_2$: 10% MeOH in $CH_2Cl_2$ mixture for 3 CV ramping to only 10% MeOH in $CH_2Cl_2$ over 10 CV, all fractions collected) to give 2,8-bis((4-methylphenyl)sulfonyl)tetrahydro-1H,4H-3a,6a-(methanoiminomethano)cyclopenta[c]pyrrole-5-carboxylic acid (0.340 g, 0.674 mmol, 69.9% yield) as a white fluffy solid. LCMS: m/e=519 $(M+H)^+$. LCMS retention time: 2.28 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). 1H NMR (400 MHz, CHLOROFORM-d) δ ppm 7.65 (2 H, d, J=8.28 Hz), 7.58 (2 H, d, J=8.28 Hz), 7.36 (4 H, dd, J=16.06, 7.78 Hz), 3.48 (2 H, d, J=9.54 Hz), 3.33 (2 H, d, J=10.04 Hz), 2.60 (2 H, d, J=9.79 Hz), 2.55 (1 H, m), 2.49 (3 H, s), 2.46 (3 H, s), 2.38 (2 H, d, J=10.29 Hz), 2.04 (1 H, d, J=13.43 Hz), 2.02 (2 H, d, J=13.43 Hz), 1.91 (1 H, d, J=12.55 Hz), 1.87 (1 H, d, J=12.55 Hz).

Intermediate 66

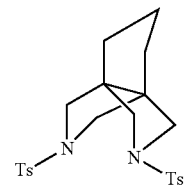

2,8-bis ((4-methylphenyl)sulfonyl)tetrahydro-1H,4H-3a,6a-(methanoiminomethano)cyclopenta[c]pyrrole. A mixture of 2,8-bis((4-methylphenyl)sulfonyl)tetrahydro-1H,4H-3a,6a-(methanoiminomethano)cyclopenta[c]pyrrole-5-carboxylic acid (200 mg, 0396 mmol), Iodobenzene diacetate (511 mg, 1.59 mmol) and iodine (402 mg, 1.59 mmol) in carbontetrachloride (8 mL) was irradiated with a 300 W tungsten filament lamp (to reflux temperature) for 8 h in a flask fitted with two sequential reflux condensers.

After this time, the reaction was diluted with $CH_2Cl_2$ and was washed with sat. $Na_2S_2O_3$ (aq) (25 mL). The aqueous layer was extracted with $CH_2Cl_2$ (3×10 mL). The combined organic extracts were washed with brine, dried over $Na_2SO_4$, filtered and concentrated to give an orange oil. This oil was purified on silica gel (Biotage, EtOAc/hexanes (ramp of 20% EtOAc to 90% EtOAc over 12 CV), all fractions collected) to give a mixture of 2,8-bis((4-methylphenyl)sulfonyl)-2,3-dihydro-1H,4H-3a,6a-(methanoiminomethano)cyclopenta[c]pyrrole and 5-iodo-2,8-bis((4-methylphenyl)sulfonyl)tetrahydro-1H,4H-3a,6a-(methanoiminomethano)cyclopenta[c]pyrrole (0.150 g). t-Butyl lithium 1.7 M in pentane (2.01 mL, 342 μmol) was added dropwise to a stirring solution of the mixture from the previous step in THF (4 mL) at −78° C. The orange tinted solution was stirred at −78° C. for 55 min. Next, the reaction was quenched with the addition of sat. $NH_4Cl$ (aq) (25 mL). The resulting mixture was diluted with $Et_2O$ and the layers were separated. The aqeous layer was extracted with $Et_2O$ (3×5 mL), and combined organic extracts were washed with brine, dried over $Na_2SO_4$, filtered and concentrated to give 160 mg of a mixture of 2,8-bis((4-methylphenyl)sulfonyl)-2,3-dihydro-1H,4H-3a,6a-(methanoiminomethano)cyclopenta[c]pyrrole and 2,8-bis((4-methylphenyl)sulfonyl)tetrahydro-1H,4H-3a,6a-(methanoiminomethano)cyclopenta[c]pyrrole. This mixture was taken on without further purification. The mixture from the previous step (160 mg, 0.348 mmol) was dissolved in a mixture of 10% MeOH in THF (1 mL). Palladium 10% on carbon (18.5 mg, 0.174 mmol) was added to the reaction solution and the mixture was degassed and the flask was backfilled with Ar (3×). Next, the Ar blanketed mixture was degassed and charged with $H_2$ (3×). The $H_2$ blanketed mixture was allowed to stir at r.t. under a balloon of $H_2$ overnight. The mixture was then filtered through a pad of Celite rinsing with THF. The filtrate was concentrated, diluted with $CH_2Cl_2$ and purified on silica gel (Biotage, EtOAc/hexanes (ramp of 20% EtOAc to 90% EtOAc over 12 CV), all fractions collected) to give 2,8-bis((4-methylphenyl)sulfonyl)tetrahydro-1H,4H-3a,6a-(methanoiminomethano)cyclopenta[c]pyrrole (102 mg, 0.221 mmol, 64% yield) (56% yield from the carboxylic acid). LCMS: m/e=461 $(M+H)^+$. LCMS retention time: 2.46 min. (Column: SunFire C18 5u 4.6×50 mm. Solvent A =90%

Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). $^1$H NMR (400 MHz, CHLOROFORM-d) δ ppm 7.62 (4H, d, J=8.28 Hz), 7.35 (4H, d, J=8.03 Hz), 2.81-3.03 (8H, m), 2.47 (6H, s), 1.64 (4H, t, J=6.53 Hz), 1.34-1.46 (2H, m).

Intermediate 67

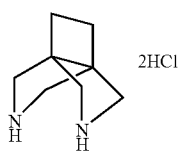

tetrahydro-1H,4H-3a,6a-ethanopyrrolo[3,4-c]pyrrole dihydrochloride. A solution of lithium aluminum hydride 2M THF (26.2 mL, 52.4 mmol) was added to a stirring solution of 2,5-bis((4-methylphenyl)sulfonyl)tetrahydro-1H,4H-3a,6a-ethanopyrrolo[3,4-c]pyrrole (1.17 mg, 2.62 mmol) in THF (10 mL) at r.t. The mixture was then allowed to stir at r.t. for 48 h. The reaction was then diluted with Et$_2$O and then quenched with the addition of H$_2$O (1.0 mL) followed by 1M NaOH (aq) (1.0 mL). The resulting mixture was allowed to stir at room temperature overnight. The mixture was then filtered through a pad of Celite rinsing with THF. The filtrate was then acidified with the addition of 2M HCl in Et$_2$O, affording a white ppt. This mixture was concentrated to give a sticky tan solid. This sticky solid was triturated with Et$_2$O and dried in vacuo to give tetrahydro-1H,4H-3a,6a-ethanopyrrolo[3,4-c]pyrrole dihydrochloride (518 mg, 2.45 mmol, 94% yield) as a tan solid containing less than 5% of the mono-protected amine. This compound does not exhibit a detectable LCMS signal. $^1$H NMR (400 MHz, MeOD) δ ppm 3.64 (4H, d, J=12.30 Hz), 3.47 (4H, d, J=12.30 Hz), 2.27 (4H, s).

EXAMPLE 1A and 1B

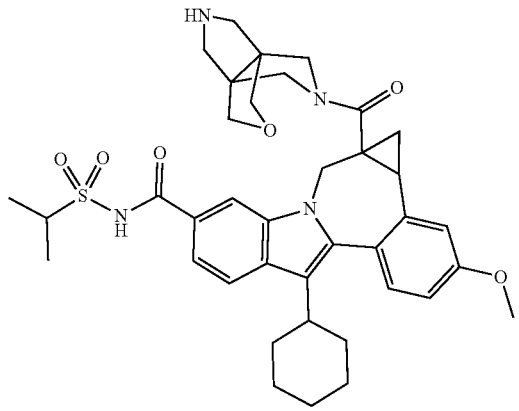

1A Racemate: 8-cyclohexyl-N-(isopropylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide and 1B Homochiral: (1aR,12bS)-8-cyclohexyl-N-(isopropylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide. BOP-Cl (69 mg, 0.27 mmol) was added to a stirring solution of (1aR,12bS)-8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (Intermediate 10) (100 mg, 0.182 mmol) and dihydro-4H-3a,6a-(methanoiminomethano)furo[3,4-c]pyrrole dihydrochloride (Intermediate 3) (62 mg, 0.27 mmol) in CH$_2$Cl$_2$ (5 mL) and TEA (0.50 mL, 3.6 mmol), and the mixture was stirred at rt for 16 h. The reaction was diluted with MeOH and purified by preparative HPLC (H$_2$O-MeOH with 0.1% TFA buffer) to yield (1aR,12bS)-8-cyclohexyl-N-(isopropylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (72 mg, 0.085 mmol, 47% yield) as a bright yellow solid. LCMS: m/e 687 (M+H)$^+$. LCMS retention time: 2.43 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min.). Presents as a 2:1 ratio of rotamers or atrope isomers. $^1$H NMR (400 MHz, MeOD) δ ppm 8.09 (br s, 0.33H), 7.97 (br s, 0.67H), 7.88 (d, J=8.5 Hz, 1H), 7.61-7.55 (m, 1H), 7.31-7.26 (m, 1H), 7.16 (d, J=2.8 Hz, 0.67H), 7.14 (d, J=2.5 Hz, 0.33H), 7.02-6.94 (m, 1H), 5.10 (d, J=15.1 Hz, 0.67H), 4.80 (d, J=15.1 Hz, 0.33H), 4.16-3.43 (m, 9H), 3.88 (s, 1H), 3.86 (s, 2H), 3.38-3.09 (m, 4H), 3.00-2.89 (m, 0.66H), 2.84-2.74 (m, 0.33H), 2.65 (dd, J=9.0, 5.8 Hz, 0.67H), 2.52 (dd, J=10.0, 6.3 Hz, 0.33H), 2.15-1.01 (m, 12.67H), 1.42 (d, J=7.0 Hz, 4H), 1.41 (d, J=7.0 Hz, 2H), 0.20-0.12 (m, 0.33H).

EXAMPLE 2A and 2B

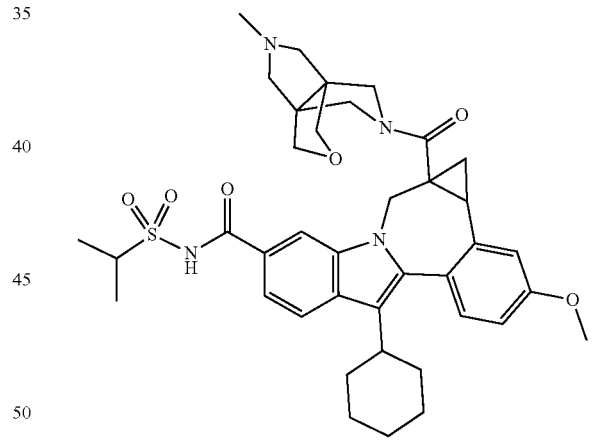

2A Racemate: 8-cyclohexyl-N-(isopropylsulfonyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide and 2B Homochiral: (1aR,12bS)-8-cyclohexyl-N-(isopropylsulfonyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide. A 1M solution of sodium cyanoborohydride in THF (0.51 mL, 0.51 mmol) was added to a solution of (1aR,12bS)-8-cyclohexyl-N-(isopropylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (Example 1A) (35 mg, 0.051 mmol) and formaldehyde (37 wt. % in water) (0.038 mL, 0.51 mmol) in MeOH (1 mL) and the reaction mixture was stirred at rt for 16 h. The reaction was concentrated, dissolved into MeOH, filtered and purified by preparative HPLC (H$_2$O-MeOH with 0.1% TFA buffer) to yield (1aR,12bS)-8-cyclohexyl-N-(isopropylsulfonyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide (28 mg, 0.033 mmol, 64% yield) as an off-white solid. LCMS: m/e 701 (M+H)$^+$. LCMS retention time: 1.86 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:1 ratio of rotamers or atrope isomers. $^1$H NMR (400 MHz, MeOD) δ ppm 8.12 (br s, 0.33H), 7.99 (br s, 0.67H), 7.92-7.86 (m, 1H), 7.62-7.56 (m, 1H), 7.30 (d, J=8.5 Hz, 0.67H), 7.28 (d, J=8.5 Hz, 0.33H), 7.16 (d, J=2.5 Hz, 0.67H), 7.15 (d, J=2.8 Hz, 0.33H), 7.00 (dd, J=8.5, 2.5 Hz, 0.67H), 6.97 (dd, J=8.5, 2.8 Hz, 0.33H), 5.11 (d, J=15.6 Hz, 0.67H), 4.92-4.80 (m, 0.33H), 4.19-3.53 (m, 8H), 3.88 (s, 1H), 3.86 (s, 2H), 3.12-2.48 (m, 8H), 2.14-1.02 (m, 14.67H), 1.42 (d, J=6.8 Hz, 4H), 1.42 (d, J=7.0 Hz, 2H), 0.21-0.15 (in, 0.33H).

EXAMPLE 3A

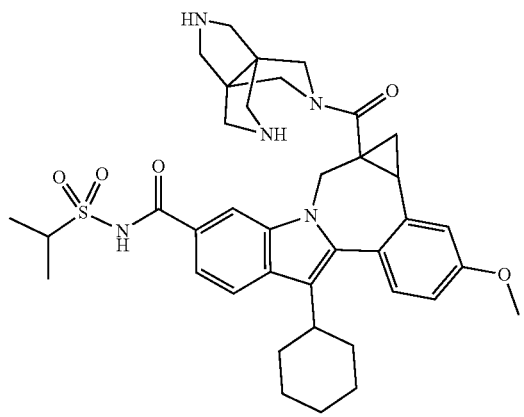

(Racemate) 8-cyclohexyl-N-(isopropylsulfonyl)-11-methoxy-1a-(3,7,10-triazatricyclo[3,3,3.0$^{1,5}$]undec-3-ylcarbonyl)-1,1a,2,12b-tetrahydrocyclopropa[d]indolo[2]benzazepine-5-carboxamide. BOP-Cl (36 mg, 0.14 mmol) was added to a solution of 8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (Intermediate 11) (60 mg, 0.11 mmol) and tetrahydro-1H,4H-3a,6a-(methanoiminomethano)pyrrolo[3,4-c]pyrrole trihydrochloride (Intermediate 5) (43 mg, 0.16 mmol) in CH$_2$Cl$_2$ (1 mL) and DIPEA (0.2 mL, 1.1 mmol) and the reaction mixture was stirred at rt for 16 h. The reaction was diluted with MeOH and purified by preparative HPLC (H$_2$O-MeOH with 0.1% TFA buffer) to yield 8-cyclohexyl-N-(isopropylsulfonyl)-11-methoxy-1a-(3,7,10-triazatricyclo[3.3.3.0$^{1,5}$]undec-3-ylcarbonyl)-1,1a,2,12b-tetrahydrocyclopropa[d]indolo[2,1-a][2]benzazepine-5-carboxamide (17 mg, 0.017 mmol, 15% yield) as a yellow solid. LCMS: m/e 686 (M+H)$^+$. LCMS retention time: 2.93 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min).

EXAMPLE 4A and 4B

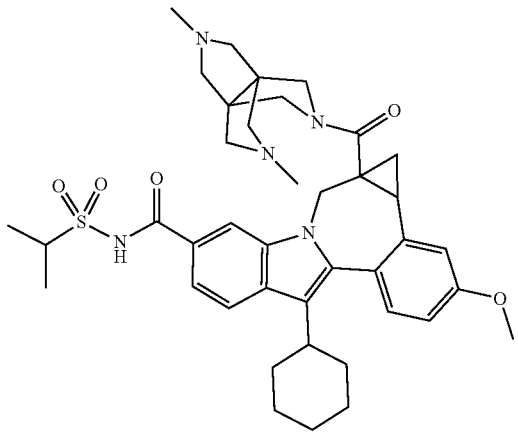

4A Racemate: 8-cyclohexyl-1a-((7,10-dimethyl-3,7,10-triazatricyclo[3.3.3.0$^{1,5}$]undec-3-yl)carbonyl)-N-(isopropylsulfonyl)-11-methoxy-1,1a,2,12b-tetrahydrocyclopropa[d]indolo[2,1-a][2]benzazepine-5-carboxamide and 4B Homochiral: (1aR,12bS)-8-cyclohexyl-1a-((7,10-dimethyl-3,7,10-triazatricyclo[3.3.3.0$^{1,5}$]undec-3-yl)carbonyl)-N-(isopropylsulfonyl)-11-methoxy-1,1a,2,12b-tetrahydrocyclopropa[d]indolo[2,1-a][2]benzazepine-5-carboxamide. A 1M solution of sodium cyanoborohydride in THF (0.24 mL, 0.24 mmol) was added to a solution of 8-cyclohexyl-N-(isopropylsulfonyl)-11-methoxy-1a-(3,7,10-triazatricyclo[3.3.3.0$^{1,5}$]undec-3-ylcarbonyl)-1,1a,2,12b-tetrahydrocyclopropa[d]indolo[2,1-a][2]benzazepine-5-carboxamide (Example 3A) (12 mg, 0.017 mmol) and formaldehyde (37 wt. % in water) (0.013 mL, 0.18 mmol) in MeOH (1 mL) and the mixture was stirred at rt for 16 h. The reaction was diluted with MeOH and purified by preparative HPLC (H$_2$O-MeOH with 0.1% TFA buffer) to yield 8-cyclohexyl-1a-((7,10-dimethyl-3,7,10-triazatricyclo[3.3.3.0$^{1,5}$]undec-3-yl)carbonyl)-N-(isopropylsulfonyl)-11-methoxy-1,1a,2,12b-tetrahydrocyclopropa[d]indolo[2,1-a][2]benzazepine-5-carboxamide (12 mg, 0.012 mmol, 70% yield) as a bright yellow solid. LCMS: m/e 714 (M+H)$^+$. LCMS retention time: 2.10 min. (Column: LUNA 4.6×50 MM S10. Solvent A=H$_2$O:CH$_3$CN 95%:5% 10 mm Ammonium Acetate. Solvent B=H$_2$O: CH$_3$CN 5%:95% 10 mm Ammonium Acetate. Start % B=0. Final % B=100. Gradient Time=3 min. Flow Rate=4 mL/min.). Presents as a 2:3 ratio of rotamers or atrope isomers. $^1$H NMR (400 MHz, MeOD) δ ppm 8.22 (br s, 0.4H), 8.05 (d, J=1.5 Hz, 0.6H), 7.91 (d, J=8.5 Hz, 0.6H), 7.89 (d, J=8.5 Hz, 0.4H), 7.62 (dd, J=8.5, 1.5 Hz, 0.4H), 7.61 (dd, J=8.5, 1.5 Hz, 0.6H), 7.31 (d, J=8.5 Hz, 0.6H), 7.29 (d, J=8.5 Hz, 0.4H), 7.17-7.13 (m, 1H), 7.00 (dd, J=8.5, 2.5 Hz, 0.6H), 6.97 (dd, J=8.5, 2.8 Hz, 0.4H), 5.10 (d, J=15.3 Hz, 0.6H), 4.97-4.82 (m, 0.4H), 4.14 (d, J=15.1 Hz, 0.4H), 4.08-3.82 (m, 4H), 3.88 (s, 1.2H), 3.86 (s, 1.8H), 3.78-3.22 (m, 8.61-1), 3.12-2.74 (m, 7H), 2.64-2.58 (m, 0.6H), 2.55-2.50 (m, 0.4H), 2.15-1.05 (m, 12.6H), 1.42 (d, J=7.0 Hz, 3.6H), 1.42 (d, J=7.0 Hz, 2.4H), 0.23-0.18 (m, 0.4H).

EXAMPLE 5B

EXAMPLE 6B

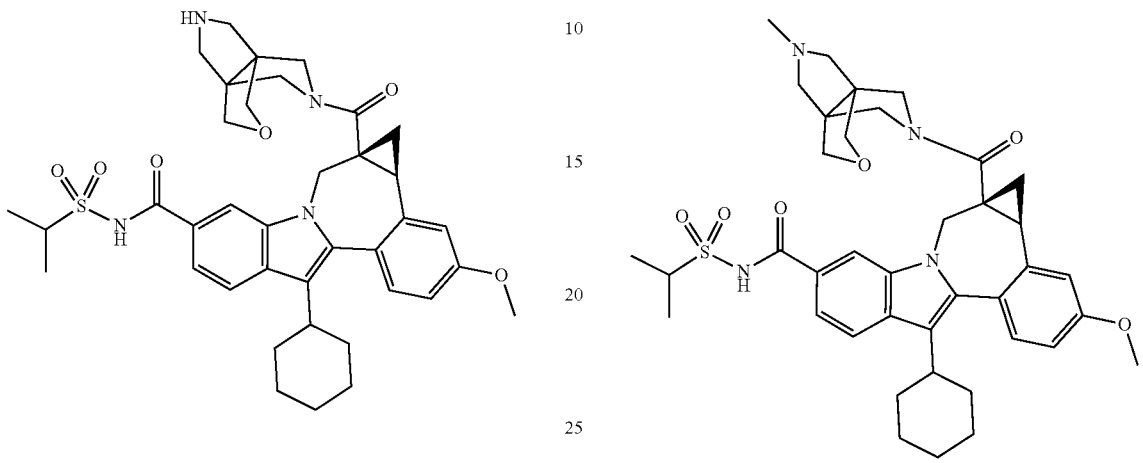

(homochiral) (1aR,12bS)-8-cyclohexyl-N-(isopropenylsulfonyl)-1a-(4H-3a,6a-(methanoiminomethano)furo[3,4-c]pyrrol-5(1H,3H,6H)-ylcarbonyl)-11-methoxy-1,1a,2,12b-tetrahydrocyclopropa[d]indolo[2,1-a][2]benzazepine-5-carboxamide. BOP-Cl (30 mg, 0.12 mmol) was added to a solution of (1aR,12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylic acid (Intermediate 15) (50 mg, 0.091 mmol) and dihydro-4H-3a,6a-(methanoiminomethano)furo[3,4-c]pyrrole dihydrochloride (31 mg, 0.14 mmol) in $CH_2Cl_2$ (1 mL) and DIPEA (0.10 mL, 0.57 mmol) and the mixture was stirred at rt for 16 h. The reaction was diluted with MeOH and purified by preparative HPLC ($H_2O$-MeOH with 0.1% TFA buffer) to yield (1aR, 12bS)-8-cyclohexyl-N-(isopropenylsulfonyl)-1a-(4H-3a,6a-(methanoiminomethano)furo[3,4-c]pyrrol-5(1H,3H,6H)-ylcarbonyl)-11-methoxy-1,1a,2,12b-tetrahydrocyclopropa[d]indolo[2,1-a][2]benzazepine-5-carboxamide (45 mg, 0.054 mmol, 59% yield) as a light yellow solid. LCMS: m/e 685 $(M+H)^+$. LCMS retention time: 1.14 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=2 min. Flow Rate=4 mL/min). Presents as a 7:3 ratio of rotamers or atrope isomers. $^1$H NMR (400 MHz, MeOD) δ ppm 8.08 (br s, 0.3H), 7.94 (br s, 0.7H), 7.89 (d, J=8.5 Hz, 1H), 7.59-7.54 (m, 1H), 7.29 (d, J=8.5 Hz, 1H), 7.16 (d, J=2.3 Hz, 0.7H), 7.14 (d, J=2.5 Hz, 0.3H), 7.00 (dd, J=8.5, 2.3 Hz, 0.7H), 6.97 (dd, J=8.5, 2.5 Hz, 0.3H), 6.27-6.24 (m, 1H), 5.93-5.89 (m, 1H), 5.11 (d, J=15.3 Hz, 0.7H), 4.92-4.81 (m, 0.3H), 4.15 (d, J=15.0 Hz, 0.3H), 4.10-3.08 (m, 11.7H), 3.87 (s, 0.9H), 3.86 (s, 2.1H), 3.00-2.90 (m, 0.7H), 2.84-2.74 (m, 0.3H), 2.65 (dd, J=9.0, 5.8 Hz, 0.7H), 2.52 (dd, J=10.0, 6.3 Hz, 0.3H), 2.15 (s, 3H), 2.12-1.02 (m, 12.7H), 0.19-0.13 (in, 0.3H).

(homochiral) (1aR, 12bS)-8-cyclohexyl-N-(isopropenylsulfonyl)-11-methoxy-1a-((8-methyl-4H-3a,6a-(methanoiminomethano)furo[3,4-c]pyrrol-5 (1H,3H,6H)-yl)carbonyl)-1,1a,2,12b-tetrahydrocyclopropa[d]indolo[2,1-a][2]benzazepine-5-carboxamide. A 1M solution of sodium cyanoborohydride in THF (0.17 mL, 0.17 mmol) was added to a solution of (1aR,12bS)-8-cyclohexyl-N-(isopropenylsulfonyl)-1a-(4H-3a,6a-(methanoiminomethano)furo[3,4-c]pyrrol-5(1H,3H,6H)-ylcarbonyl)-11-methoxy-1,1a,2,12b-tetrahydrocyclopropa[d]indolo[2,1-a][2]benzazepine-5-carboxamide (Example 5B) (20 mg, 0.029 mmol) and formaldehyde (37 wt. % in water) (0.013 mL, 0.18 mmol) in MeOH (1 mL) and the mixture was stirred at rt for 2 h. The reaction was diluted with MeOH and purified by preparative HPLC ($H_2O$—$CH_3CN$ with 10 mM $NH_4OAc$ buffer) to yield (1aR,12bS)-8-cyclohexyl-N-(isopropenylsulfonyl)-11-methoxy-1a-((8-methyl-4H-3a,6a-(methanoiminomethano)furo[3,4-c]pyrrol-5(1H,3H,6H)-yl)carbonyl)-1,1a,2,12b-tetrahydrocyclopropa[d]indolo[2,1-a][2]benzazepine-5-carboxamide (11 mg, 0.014 mmol, 49% yield) as a white solid. LCMS: m/e 699 $(M+H)^+$. LCMS retention time: 1.87 min. (Column: LUNA 4.6×50 MM S10. Solvent A=$H_2O$: $CH_3CN$ 95%:5% 10 mm Ammonium Acetate. Solvent B=$H_2O$:$CH_3CN$ 5%:95% 10 mm Ammonium Acetate. Start % B=0. Final % B=100. Gradient Time=3 min. Flow Rate=4 mL/min.). Presents as a 2:3 ratio of rotamers or atrope isomers. $^1$H NMR (500 MHz, MeOD) δ ppm 8.23 (br s, 0.4H), 8.12 (br s, 0.6H), 7.84-7.73 (m, 2H), 7.36-7.27 (m, 1H), 7.20 (br s, 0.6H), 7.17 (br s, 0.4H), 7.02 (br d, J=8.5 Hz, 0.6H), 6.98 (br d, J=8.5 Hz, 0.4H), 6.04 (s, 1H), 5.57 (s, 1H), 5.24-5.10 (m, 1H), 4.16-3.52 (m, 6H), 3.92 (s, 1.2H), 3.90 (s, 1.8H), 3.32-2.40 (m, 9H), 2.15 (s, 3H), 2.12-0.97 (m, 14.6H), 0.28-0.23 (m, 0.4H).

EXAMPLE 7A

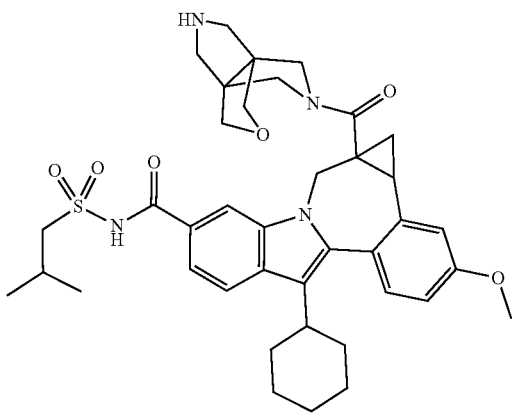

(racemate) 8-cyclohexyl-N-(isobutylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide. BOP-Cl (29 mg, 0.12 mmol) was added to a solution of 8-cyclohexyl-5-((isobutylsulfonyl)carbamoyl)-11-methoxy-1,12b-dihydrocyclopropa[d]indolo[2,1-a][2]benzazepine-1a(2H)-carboxylic acid (Intermediate 17) (50 mg, 0.089 mmol) and dihydro-4H-3a,6a-(methanoiminomethano)furo[3,4-c]pyrrole dihydrochloride (30 mg, 0.13 mmol) in CH$_2$Cl$_2$ (1 mL) and DIPEA (0.1 mL, 0.6 mmol) and the mixture was stirred at rt for 16 h. The reaction was diluted with MeOH and purified by preparative HPLC (H$_2$O—CH$_3$CN with 10 mM NH$_4$OAc buffer) to yield 8-cyclohexyl-N-(isobutylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (34 mg, 0.047 mmol, 53% yield) as a white solid. LCMS: m/e 701 (M+H)$^+$. LCMS retention time: 1.45 min. (Column: LUNA 4.6×50 MM S10. Solvent A=H$_2$O: CH$_3$CN 95%:5% 10 mm Ammonium Acetate. Solvent B=H$_2$O:CH$_3$CN 5%:95% 10 mm Ammonium Acetate. Start % B=0. Final % B=100. Gradient Time=2 min. Flow Rate=5 mL/min.).

EXAMPLE 8A

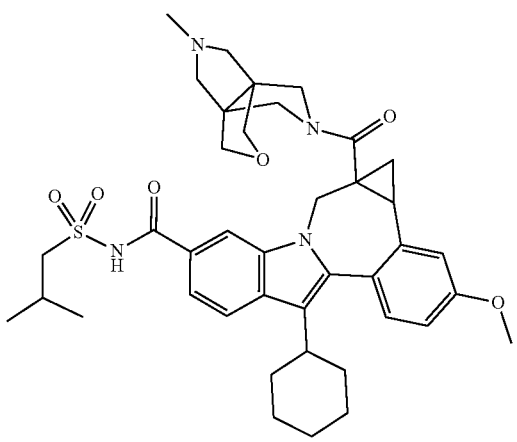

(racemate) 8-cyclohexyl-N-(isobutylsulfonyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide. A 1M solution of sodium cyanoborohydride in THF (0.17 mL, 0.17 mmol) was added to a solution of 8-cyclohexyl-N-(isobutylsulfonyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (Example 7A) (20 mg, 0.029 mmol) and formaldehyde (37 wt. % in water) (0.013 mL, 0.17 mmol) in MeOH (1 mL) and the mixture was stirred at rt for 2 h. The reaction was diluted with MeOH and purified by preparative HPLC (H$_2$O—CH$_3$CN with 10 mM NH$_4$OAc buffer) to yield 8-cyclohexyl-N-(isobutylsulfonyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide (15.2 mg, 0.020 mmol, 71% yield) as a white solid. LCMS: m/e 715 (M+H)$^+$. LCMS retention time: 2.06 min. (Column: LUNA 4.6×50 MM S10. Solvent A=H$_2$O:CH$_3$CN 95%:5% 10 mm Ammonium Acetate. Solvent B=H$_2$O:CH$_3$CN 5%:95% 10 mm Ammonium Acetate. Start % B=0. Final % B=100. Gradient Time=3 min. Flow Rate=4 mL/min.). Presents as a 2:1 ratio of rotamers or atrope isomers. $^1$H NMR (400 MHz, MeOD) δ ppm 8.20 (br s, 0.33H), 8.10 (br s, 0.67H), 7.87-7.79 (m, 1H), 7.76-7.70 (m, 1H), 7.32-7.24 (m, 0.33H), 7.30 (d, J=8.6 Hz, 0.67H), 7.20 (d, J=2.5 Hz, 0.67H), 7.15 (br s, 0.33H), 7.01 (dd, J=8.6, 2.5 Hz, 0.67H), 6.97 (br d, J=8.2 Hz, 0.33H), 5.20-5.05 (m, 0.67H), 4.94-4.81 (m, 0.33H), 4.08-3.69 (m, 4H), 3.91 (s, 1H), 3.90 (s, 2H), 3.62-1.72 (m, 25H), 1.97 (s, 3H), 1.17-1.13 (m, 6H), 1.08-0.76 (m, 0.67H), 0.24-0.15 (m, 0.33H).

EXAMPLE 9A and B

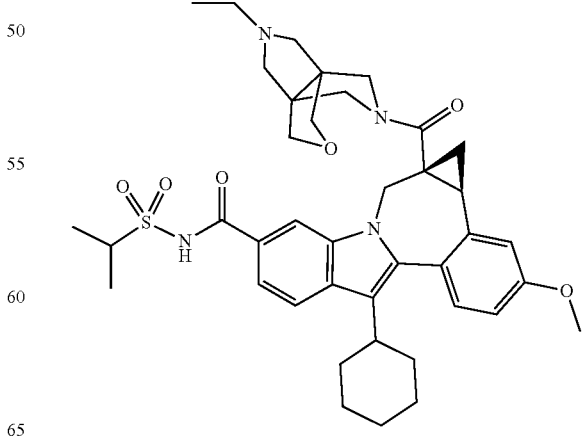

9A (racemate) 8-cyclohexyl-1a-((10-ethyl-3-oxa-7,10-diazatricyclo[3.3.3.0$^{1,5}$]undec-7-yl)carbonyl)-N-(isopropylsulfonyl)-11-methoxy-1,1a,2,12b-tetrahydrocyclopropa[d]indolo[2,1-a][2]benzazepine-5-carboxamide and 9B (homochiral) (1aR,12bS)-8-cyclohexyl-1a-((10-ethyl-3-oxa-7,10-diazatricyclo[3.3.3.0$^{1,5}$]undec-7-yl)carbonyl)-N-(isopropylsulfonyl)-11-methoxy-1,1a,2,12b-tetrahydrocyclopropa[d]indolo[2,1-a][2]benzazepine-5-carboxamide. A 1M solution of sodium cyanoborohydride in THF (0.82 mL, 0.82 mmol) was added to a solution of (1aR,12bS)-8-cyclohexyl-N-(isopropylsulfonyl)-11-methoxy-1a-(3-oxa-7,10-diazatricyclo [3.3.3.0$^{1,5}$]undec-7-ylcarbonyl)-1,1a,2,12b-tetrahydrocyclopropa[d]indolo[2,1-a][2]benzazepine-5-carboxamide (Example 1B) (94 mg, 0.14 mmol) and acetaldehyde (0.046 mL, 0.82 mmol) in MeOH (2 mL) and the mixture was stirred at rt for 2 h. The reaction was concentrated, dissolved into MeOH, filtered and purified by preparative HPLC (H$_2$O-MeOH with 0.1% TFA buffer) to yield (1aR,12bS)-8-cyclohexyl-1a-((10-ethyl-3-oxa-7,10-diazatricyclo[3.3.3.0$^{1,5}$]undec-7-yl)carbonyl)-N-(isopropylsulfonyl)-11-methoxy-1,1a,2,12b-tetrahydrocyclopropa[d]indolo[2,1-a][2]benzazepine-5-carboxamide (51 mg, 0.058 mmol, 43% yield) as a light yellow solid. LCMS: m/e 715 (M+H)$^+$. LCMS retention time: 2.88 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). Presents as a 7:3 ratio of rotamers or atrope isomers. $^1$H NMR (500 MHz, MeOD) δ ppm 8.20 (br s, 0.3H), 8.12 (br s, 0.7H), 7.86-7.71 (m, 2H), 7.35-7.26 (m, 1H), 7.20 (d, J=2.8 Hz, 0.7H), 7.18-7.15 (m, 0.3H), 7.01 (dd, J=8.6, 2.8 Hz, 0.7H), 7.00-6.95 (m, 0.3H), 5.22-5.08 (m, 0.7H), 4.93-4.73 (m, 0.3H), 4.18-0.95 (m, 38.7H), 3.92 (s, 0.9H), 3.90 (s, 2.1H), 0.26-0.20 (m, 0.3H).

EXAMPLE 10A

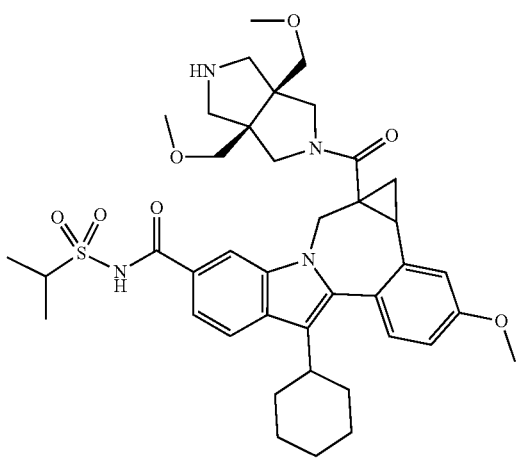

(racemate) 1a-(((3aR,6aS)-3a,6a-bis(methoxymethyl) hexahydropyrrolo[3,4-c]pyrrol-2(1H)-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide. BOP-Cl (36 mg, 0.14 mmol) was added to a solution of 8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (Intermediate 11) (60 mg, 0.109 mmol) and cis-3a,6a-bis(methoxymethyl)octahydropyrrolo[3,4-c]pyrrole dihydrochloride (Intermediate 9) (32.7 mg, 0.163 mmol) in CH$_2$Cl$_2$ (1 mL) and DIPEA (0.1 mL, 0.57 mmol) and the mixture was stirred at rt for 16 h. The reaction was diluted with MeOH and purified by preparative HPLC (H$_2$O—CH$_3$CN with 10 mM NH$_4$OAc buffer) to yield product 1a-(((3aR,6aS)-3a,6a-bis(methoxymethyl)hexahydropyrrolo[3,4-c]pyrrol-2(1H)-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide (28.6 mg, 0.036 mmol, 33% yield) as a white solid. LCMS: m/e 733 (M+H)$^+$. LCMS retention time: 2.02 min. (Column: LUNA 4.6×50 MM S10. Solvent A=H$_2$O:CH$_3$CN 95%:5% 10 mm Ammonium Acetate. Solvent B=H$_2$O:CH$_3$CN 5%:95% 10 mm Ammonium Acetate. Start % B=0. Final % B=100. Gradient Time=3 min. Flow Rate=4 mL/min.). Presents as a 2:3 ratio of rotamers or atrope isomers. $^1$H NMR (400 MHz, DMSO-d$_6$) δ ppm 8.44 (br s, 0.4H), 8.12 (br s, 0.6H), 7.76-7.61 (m, 2H), 7.26 (d, J=8.2 Hz, 1H), 7.16 (br s, 0.4H), 7.11 (br s, 0.6H), 7.03 (d, J=8.2 Hz, 0.6H), 7.00 (d, J=8.2 Hz, 0.4H), 5.21 (d, J=15.3 Hz, 0.6H), 5.10 (d, J=15.3 Hz, 0.4H), 4.18 (d, J=11.6 Hz, 0.6H), 3.86 (s, 1.2H), 3.85 (s, 1.8H), 3.98-2.35 (in, 23.4H), 2.12-0.89 (m, 19.6H), 0.15-0.08 (m, 0.4H),

EXAMPLE 11A

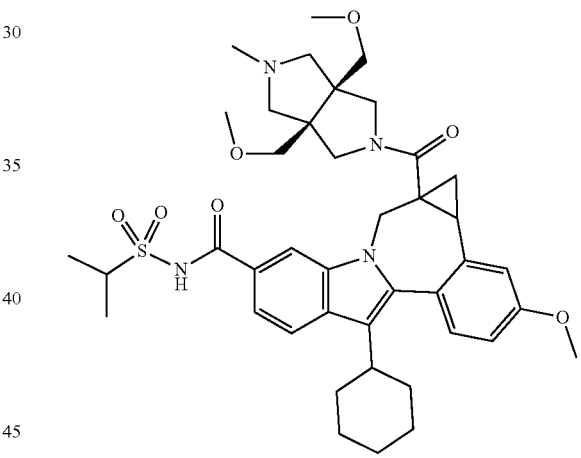

(racemate) 1a-(((3aR,6aS)-3a,6a-bis (methoxymethyl)-5-methylhexahydropyrrolo[3,4-c]pyrrol-2(1H)-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide. A 1M solution of sodium cyanoborohydride in THF (0.16 mL, 0.16 mmol) was added to a solution of 1a-(((3aR,6aS)-3a,6a-bis(methoxymethyl)hexahydropyrrolo[3,4-c]pyrrol-2(1H)-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide (Example 10A) (19.6 mg, 0.027 mmol) and formaldehyde (37 wt. % in water) (0.012 mL, 0.16 mmol) in MeOH (1 mL) and the mixture was stirred at rt for 16 h. The reaction was diluted with MeOH and purified by preparative HPLC (H$_2$O—CH$_3$CN with 10 mM NH$_4$OAc buffer) to yield 1a-(((3aR,6aS)-3a,6a-bis(methoxymethyl)-5-methylhexahydropyrrolo[3,4-c]pyrrol-2(1H)-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide (11.7 mg, 0.015 mmol, 57% yield) as a white solid. LCMS: m/e 747 (M+H)+. LCMS retention time: 1.72 min. (Column: Luna 4.6×50 mm S10. Solvent A=H₂O:CH₃CN 95%:5% 10 mm Ammonium Acetate. Solvent B H₂O:CH₃CN 5%:95% 10 mm Ammonium Acetate. Start % B=0. Final % B=100. Gradient Time=3 min. Flow Rate=4 mL/min.). Presents as a 2:1:1 ratio of rotamers or atrope isomers. ¹H NMR (500 MHz, MeOD) δ ppm 8.44 (br s, 0.25H), 8.14 (br s, 0.25H), 8.06 (br s, 0.5H), 7.88-7.11 (m, 2H), 7.88-7.71 (m, 1H), 7.35-7.26 (n, 1H), 7,22-7.12 (m, 1H), 7.04-6.95 (m, 1H), 5.22-5.08(m, 0.75H), 4.97-4.69 (m, 0.25H), 4.16-0.89 (m, 44.75H), 0.30-0.21 (m, 0.25H).

EXAMPLE 12B

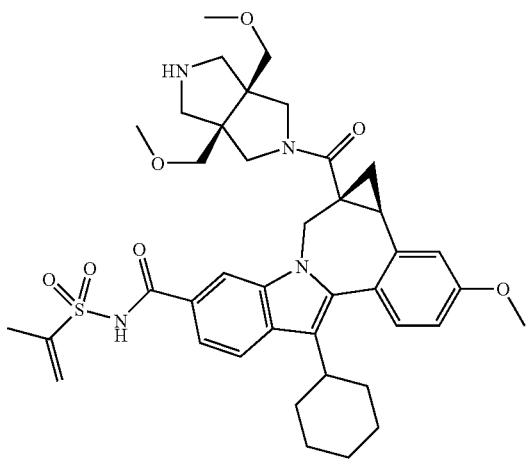

(homochiral) (1aR,12bS)-1a-(((3aR,6aS)-3a,6a-bis(methoxymethyl)hexahydropyrrolo[3,4-c]pyrrol-2(1H)-yl)carbonyl)-8-cyclohexyl-N-(isopropenylsulfonyl)-11-methoxy-1,1a,2,12b-tetrahydrocyclopropa[d]indolo[2,1-a][2]benzazepine-5-carboxamide. BOP-Cl (36.2 mg, 0.142 mmol) was added to a solution of (1aR,12bS)-8-cyclohexyl-5-((isopropenylsulfonyl)carbamoyl)-11-methoxy-1,12b-dihydrocyclopropa[d]indolo[2,1-a][2]benzazepine-1a(2H)-carboxylic acid (Intermediate 15) (60 mg, 0.109 mmol) and cis-3a,6a-bis(methoxymethyl)octahydropyrrolo[3,4-c]pyrrole dihydrochloride (Intermediate 9) (32.9 mg, 0.164 mmol) in CH₂Cl₂ (1 mL) and DIPEA (0.1 mL, 0.6 mmol) and the mixture was stirred at rt for 16 h. The reaction was diluted with MeOH, and purified by preparative HPLC (H₂O—CH₃CN with 10 mM NH4OAc buffer) to yield (1aR,12bS)-1a-(((3aR,6aS)-3a,6a-bis(methoxymethyl)hexahydropyrrolo[3,4-c]pyrrol-2(1H)-yl)carbonyl)-8-cyclohexyl-N-(isopropenylsulfonyl)-11-methoxy-1,1a,2,12b-tetrahydrocyclopropa[d]indolo[2,1-a][2]benzazepine-5-carboxamide (31.9 mg, 0.041 mmol, 38% yield) as a white solid. LCMS: m/e 731 (M+H)+. LCMS retention time: 1.99 min. (Column: LUNA 4.6×50 MM S10. Solvent A=H₂O:CH₃CN 95%:5% 10 mm Ammonium Acetate. Solvent B=H₂O:CH₃CN 5%:95% 10 mm Ammonium Acetate. Start % B=0. Final % B=100. Gradient Time=3 min. Flow Rate=4 mL/min.).

EXAMPLE 13B

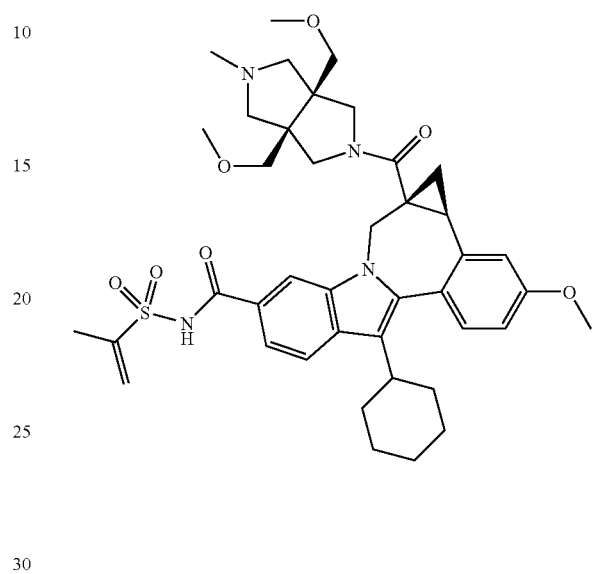

(homochiral) (1aR,2bS)-1a-(0aR,6aS)-3a,6a-bis(methoxymethyl)-5-methylhexahydropyrrolo[3,4-c]pyrrol-2(1H)-yl)carbonyl)-8-cyclohexyl-N-(isopropenylsulfonyl)-11-methoxy-1,1a,2,12b-tetrahydrocyclopropa[d]indolo[2,1-a][2]benzazepine-5-carboxamide. A 1M solution of sodium cyanoborohydride in THF (0.22 mL, 0.22 mmol) was added to a solution of (1aR,12bS)-1a-(((3aR,6aS)-3a,6a-bis(methoxymethyl)hexahydropyrrolo[3,4-c]pyrrol-2(1H)-yl)carbonyl)-8-cyclohexyl-N-(isopropenylsulfonyl)-11-methoxy-1,1a,2,12b-tetrahydrocyclopropa[d]indolo[2,1-a][2]benzazepine-5-carboxamide (Example 12B) (27.2 mg, 0.037 mmol) and formaldehyde (37 wt. % in water) (0.017 mL, 0.22 mmol) in MeOH (1 mL) and the mixture was stirred at rt for 16 h. The reaction was diluted with MeOH and purified by preparative HPLC (H₂O—CH₃CN with 10 mM NH₄OAc buffer) to yield product (1aR,12bS)-1a-(((3aR,6aS)-3a,6a-bis(methoxymethyl)-5-methylhexahydropyrrolo[3,4-c]pyrrol-2(1H)-yl)carbonyl)-8-cyclohexyl-N-(isopropenylsulfonyl)-11-methoxy-1,1a,2,12b-tetrahydrocyclopropa[d]indolo[2,1-a][2]benzazepine-5-carboxamide (16.5 mg, 0.021 mmol, 58% yield) as a white solid. LCMS: m/e 745 (M+H)+. LCMS retention time: 1.69 min. (Column: Luna 4.6×50 mm S10. Solvent A=H₂O:CH₃CN 95%:5% 10 mm Ammonium Acetate. Solvent B=H₂O:CH₃CN 5%:95% 10 mm Ammonium Acetate. Start % B=0. Final % B=100. Gradient Time=3 min. Flow Rate=4 mL/min.). Presents as a 1:1:1 ratio of rotarners or atrope isomers. ¹H NMR (500 MHz, MeOD) δ ppm 8.24 (br s, 0.33H), 8.12 (br s, 0.33H), 8.09 (br s, 0.33H), 7.86-7.73 (m, 2H), 7.35-7.27 (m, 1H), 7.04-6.95 (m, 1H), 6.01 (s, 1H), 5.54 (s, 1H), 5.22-5.11 (m, 0.67H), 4.96-4.76 (m, 0.33H), 4.17-0.95 (m, 38.67H), 3.92 (s, 1H), 3.90 (s, 2H), 0.33-0.22 (m, 0.33H).

EXAMPLE 14B

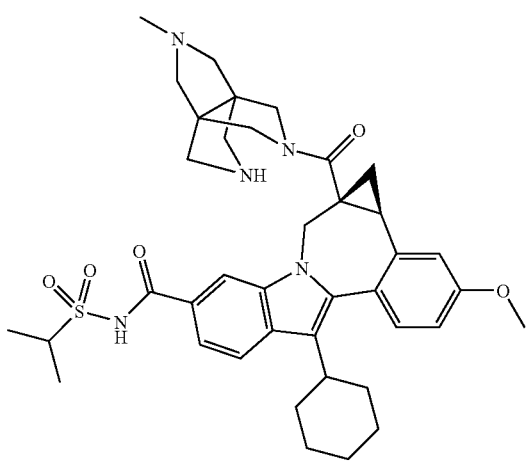

(homochiral) (1aR,12bS)-8-cyclohexyl-N-(isopropylsulfonyl)-11-methoxy-1a-((7-methyl-3,7,10-triazatricyclo[3.3.3.0$^{1,5}$]undec-3-yl)carbonyl)-1,1a,2,12b-tetrahydrocyclopropa[d]indolo[2,1-a][2]benzazepine-5-carboxamide. BOP-Cl (35 mg, 0.14 mmol) was added to a solution of 2-methyltetrahydro-1H,4H-3a,6a-(methanoiminomethano)pyrrolo[3,4-c]pyrrole trihydrochloride (Intermediate 7) (37.7 mg, 0.136 mmol) and (1aR,12bS)-8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (Intermediate 10) (50 mg, 0.091 mmol) in CH$_2$Cl$_2$ (3 mL) and TEA (0.3 mL, 2 mmol) and the mixture was stirred at it for 16 h. The reaction was concentrated, dissolved into MeOH, filtered and purified by preparative HPLC (H$_2$O-MeCN with 0.1% TFA buffer) to yield (1aR,12bS)-8-cyclohexyl-N-(isopropylsulfonyl)-11-methoxy-1a-((7-methyl-3,7,10-triazatricyclo[3.3.3.0$^{1,5}$]undec-3-yl)carbonyl)-1,1a,2,12b-tetrahydrocyclopropa[d]indolo[2,1-a][2]benzazepine-5-carboxamide (24 mg, 0.034 mmol, 38% yield) as light yellow solid. LCMS: m/e 700 (M+H)$^+$. LCMS retention time: 1.67 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:1 ratio of rotamers or atrope isomers. $^1$H NMR (400 MHz, MeOD) δ ppm 8.19 (br s, 0.33H), 8.03 (d, J=1.3 Hz, 0.67H), 7.90 (d, J=8.5 Hz, 0.33H), 7.90 (d, J=8.5 Hz, 0.67H), 7.63-7.57 (m, 1H), 7.31 (d, J=8.5 Hz, 0.67H), 7.31 (d, J=8.5 Hz, 0.33H), 7.17-7.14 (m, 1H), 7.01 (dd, J-8.5, 2.3 Hz, 0.67H), 6.98 (dd, J=8.5, 2.8 Hz, 0.33H), 5.13 (d, J=15.1 Hz, 0.67H), 4.96-4.93 (m, 0.33H), 4.15 (d, J=15.1 Hz, 0.67H), 3.98-3.89 (m, 2.33H), 3.88 (s, 1H), 3.86 (s, 2H), 3.75-3.21 (m, 11H), 3.01-2.79 (m, 4H), 2.63-2.51 (m, 1H), 2.14-1.61 (m, 7H), 1.52-1.06 (m, 11.67H), 0.24-0.19 (m, 0.33H).

EXAMPLE 15

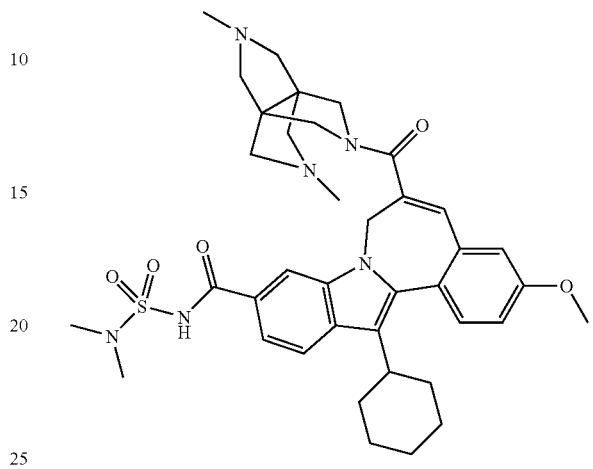

(achiral) 13-cyclohexyl-N-(dimethylsulfamoyl)-6-((7,10-dimethyl-3,7,10-triazatricyclo[3.3.3.0$^{1,5}$]undec-3-yl)carbonyl)-3-methoxy-7H-indolo[2,1-a][2]benzazepine-10-carboxamide. BOP-Cl (28 mg, 0.11 mmol) was added to a solution of 2-methyltetrahydro-1H,4H-3a,6a-(methanoiminomethano)pyrrolo[3,4-c]pyrrole trihydrochloride (Intermediate 5) (31 mg, 0.11 mmol) and 13-cyclohexyl-10-((dimethylsulfamoyl)carbamoyl)-3-methoxy-7H-indolo[2,1-a][2]benzazepine-6-carboxylic acid (Intermediate 18) (40 mg, 0.074 mmol) in CH$_2$Cl$_2$ (2 mL) and TEA (0.2 mL, 1.4 mmol), and the mixture was stirred at rt for 16 h. The solvent was removed under vacuum and the residue was partitioned between EtOAc (5 mL)/sat. aq NaHCO$_3$ (2 mL). The organic layer was washed with sat, aq NH$_4$Cl, brine, dried (MgSO$_4$), filtered and concentrated to yield a crude intermediate as a yellow solid. This material was dissolved into MeOH (1 mL) and to it was added formaldehyde (37 wt. % in water) (0.016 mL, 0.22 mmol) and then a 1M solution of sodium cyanoborohydride in THF (0.22 mL, 0.22 mmol). The mixture was stirred at rt for 3 d. The reaction was filtered and purified by preparative HPLC (H$_2$O-MeOH with 0.1% TFA buffer) to yield product 13-cyclohexyl-N-(dimethylsulfamoyl)-6-((7,10-dimethyl-3,7,10-triazatricyclo[3.3.3.0$^{1,5}$]undec-3-yl)carbonyl)-3-methoxy-7H-indolo[2,1-a][2]benzazepine-10-carboxamide (9.3 mg, 9.5 μmol, 44% yield) as a bright yellow solid. LCMS: m/e 701 (M+H)$^+$. LCMS retention time: 2.29 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). $^1$H NMR (400 MHz, MeOD) δ ppm 8.13 (d, J=1.5 Hz, 1H), 7.92 (d, J=8.5 Hz, 1H), 7.59-7.55 (m, 2H), 7.18 (dd, J=8.5, 2.5 Hz, 1H), 7.13-7.01 (m. 2H), 5.43-5.13 (m, 2H), 4.39-4.27 (m, 1H), 3.92 (s, 3H), 3.86-3.45 (m, 4H), 3.43-3.29 (m, 2H), 3.14-3.10 (m, 1H), 3.00 (s, 6H), 2.92-2.67 (m, 8H), 2.23-1.69 (m, 7H), 1.56-1.10 (m, 6H).

EXAMPLE 16A

EXAMPLE 17A

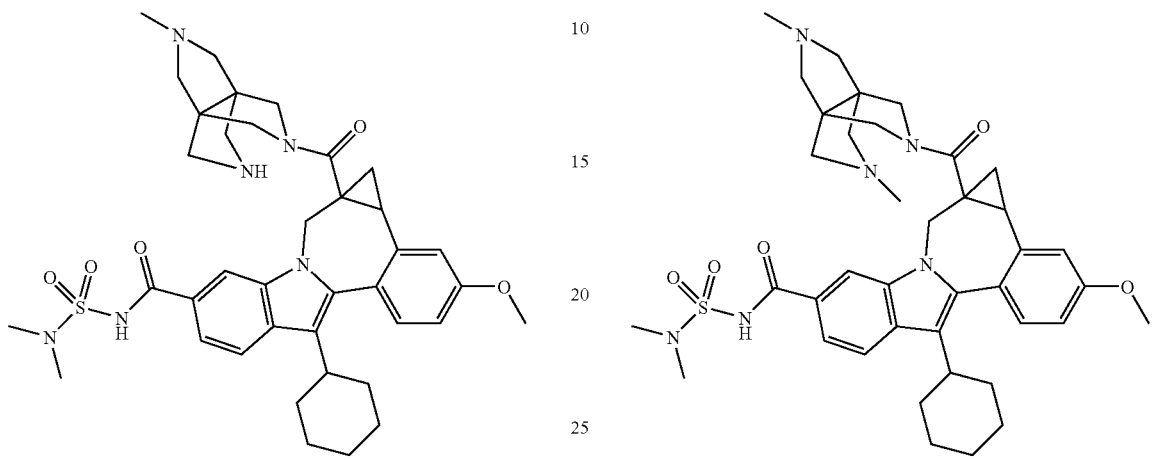

(racemic) 8-cyclohexyl-N-(dimethylsulfamoyl)-11-methoxy-1a-((7-methyl-3,7,10-triazatricyclo[3.3.3.0$^{1,5}$]undec-3-yl)carbonyl)-1,1a,2,12b-tetrahydrocyclopropa[d]indolo[2,1-a][2]benzazepine-5-carboxamide. BOP-Cl (27.7 mg, 0.109 mmol) was added to a solution of 2-methyltetrahydro-1H,4H-3a,6a-(methanoiminomethano)pyrrolo[3,4-c]pyrrole trihydrochloride (Intermediate 5) (30.1 mg, 0.109 mmol) and 8-cyclohexyl-5-((dimethylsulfamoyl)carbamoyl)-11-methoxy-1,12b-dihydrocyclopropa[d]indolo[2,1-a][2]benzazepine-1a(2H)-carboxylic acid (Intermediate 19) (40 mg, 0.073 mmol) in CH$_2$Cl$_2$ (2 mL) and TEA (0.20 mL, 1.4 mmol) and the mixture was stirred at rt for 16 h. The reaction was concentrated, dissolved into MeOH, filtered and purified by preparative HPLC (H$_2$O-MeCN with 0.1% TFA buffer) to yield 8-cyclohexyl-N-(dimethylsulfamoyl)-11-methoxy-1a-((7-methyl-3,7,10-triazatricyclo[3.3.3.0$^{1,5}$]undec-3-yl)carbonyl)-1,1a,2,12b-tetrahydrocyclopropa[d]indolo[2,1-a][2]benzazepine-5-carboxamide (13.6 mg, 0.014 mmol, 19% yield) as yellow solid. LCMS: m/e 701 (M+H)$^+$. LCMS retention time: 1.66 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:3 ratio of rotamers or atrope isomers. $^1$H NMR (400 MHz, MeOD) δ ppm 8.17 (br s, 0.4H), 8.00 (d, J=1.3 Hz, 0.6H), 7.89 (d, J=8.5 Hz, 1H), 7.60 (dd, J=8.5, 1.3 Hz, 0.4H), 7.58 (dd, J-8.5, 1.3 Hz, 0.6H), 7.31 (d, J=8.5 Hz, 1H), 7.17-7.13 (m, 1H), 7.00 (dd, J=8.5, 2.5 Hz, 0.6H), 6.97 (dd, J=8.5, 2.5 Hz, 0.4H), 5.11 (d, J=15.3 Hz, 0.6H), 4.97-4.90 (m, 0.4H), 4.15 (d, J=14.8 Hz, 0.4H), 4.15-3.84 (m, 2.6H), 3.88 (s, 1.2H), 3.86 (s, 1.8H), 3.82-3.21 (m, 10.4H), 3.06-2.74 (m, 4.6H), 2.98 (s, 6H), 2.64-2.50 (m, 1H), 2.15-1.59 (m, 7H), 1.52-1.07 (m, 4.6H), 0.24-0.19 (m, 0.4H).

(racemic) 8-cyclohexyl-N-(dimethylsulfamoyl)-1a-((7,10-dimethyl-3,7,10-triazatricyclo[3.3.3.0$^{1,5}$]undec-3-yl)carbonyl)-11-methoxy-1,1a,2,12b-tetrahydrocyclopropa[d]indolo[2,1-a][2]benzazepine-5-carboxamide. A 1M solution of sodium cyanoborohydride in THF (0.20 mL, 0.20 mmol) was added to a solution of 8-cyclohexyl-N-(dimethylsulfamoyl)-11-methoxy-1a-((7-methyl-3,7,10-triazatricyclo[3.3.3.0$^{1,5}$]undec-3-yl)carbonyl)-1,1a,2,12b-tetrahydrocyclopropa[d]indolo[2,1-a][2]benzazepine-5-carboxamide (Example 16A) (14 mg, 0.020 mmol) and formaldehyde (37 wt. % in water) (0.015 mL, 0.20 mmol) in MeOH (1 mL) and the mixture was stirred at rt for 16 h. The reaction was filtered and purified by preparative HPLC (H$_2$O-MeOH with 0.1% TFA buffer) to yield product 8-cyclohexyl-N-(dimethylsulfamoyl)-1a-((7,10-dimethyl-3,7,10-triazatricyclo[3.3.3.0$^{1,5}$]undec-3-yl)carbonyl)-11-methoxy-1,1a,2,12b-tetrahydrocyclopropa[d]indolo[2,1-a][2]benzazepine-5-carboxamide (8.2 mg, 8.3 μmol, 41% yield) as a bright yellow solid. LCMS: m/e 715 (M+H)$^+$. LCMS retention time: 1.71 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:3 ratio of rotamers or atrope isomers. $^1$H NMR (400 MHz, MeOD) δ ppm 8.19 (br s, 0.4H), 8.04 (br s, 0.6H), 7.90 (d, J=8.5 Hz, 0.6H), 7.88 (d, J=8.5 Hz, 0.4H), 7.59 (dd, J=8.5, 1.5 Hz, 0.611), 7.58 (dd, J=8.5, 1.5 Hz, 0.4H), 7.30 (d, J=8.5 Hz, 0.6H), 7.29 (d, J=8.5 Hz, 0.4H), 7.15 (d, J=2.5 Hz, 0.6H), 7.15 (d, J=2.8 Hz, 0.4H), 7.00 (dd, J=8.5, 2.5 Hz, 0.6H), 6.97 (dd, J=8.5, 2.8 Hz, 0.4H), 5.12 (d, J=15.3 Hz, 0.6H), 4.96 (d, J=15.1 Hz, 0.4H), 4.14 (d, J=15.1 Hz, 0.4H), 4.12-3.24 (m, 11.6H), 3.88 (s, 1.2H), 3.86 (s, 1.8H), 3.07-2.74 (m, 7H), 2.99 (s, 2.4H), 2.98 (s, 3.6H), 2.62 (dd, J=9.0, 5.8 Hz, 0.6H), 2.53 (dd, J=10.0, 6.3 Hz, 0.4H), 2.16-1.05 (m, 11.6H), 0.23-0.17 (m, 0.4H).

EXAMPLE 18A

EXAMPLE 19A

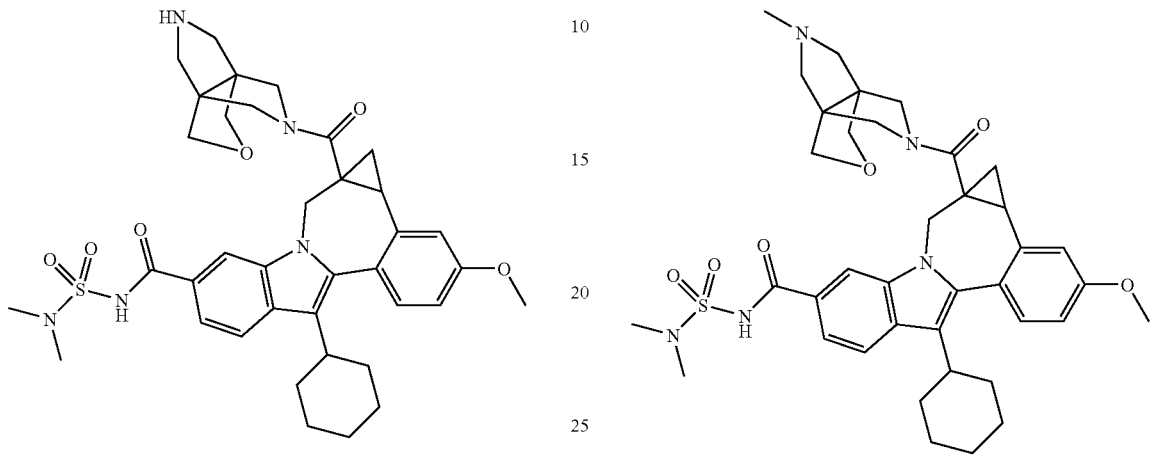

(racemic) 8-cyclohexyl-N-(dimethylsulfamoyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide. BOP-Cl (14 mg, 0.054 mmol) was added to a solution of dihydro-4H-3a,6a-(methanoiminomethano)furo[3,4-c]pyrrole dihydrochloride (Intermediate 3) (12.4 mg, 0.054 mmol) and 8-cyclohexyl-5-((dimethylsulfamoyl)carbamoyl)-11-methoxy-1,12b-dihydrocyclopropa[d]indolo[2,1-a][2]benzazepine-1a(2H)-carboxylic acid (Intermediate 19) (20 mg, 0.036 mmol) in CH$_2$Cl$_2$ (1 mL) and TEA (0.1 mL, 0.7 mmol) and the mixture was stirred at rt for 16 h. The reaction was concentrated, dissolved into MeOH, filtered and purified by preparative HPLC (H$_2$O-MeOH with 0.1% TFA buffer) to yield product 8-cyclohexyl-N-(dimethylsulfamoyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (12 mg, 0.013 mmol, 37% yield) as a bright yellow solid. LCMS: m/e 688 (M+H)$^+$. LCMS retention time: 2.41 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). Presents as a 7:3 ratio of rotamers or atrope isomers. $^1$H NMR (400 MHz, MeOD) δ ppm 8.09 (br s, 0.3H), 7.95 (br s, 0.7H), 7.88 (d, J=8.5 Hz, 1H), 7.59-7.53 (m, 1H), 7.29 (d, J=8.5 Hz, 1H), 7.16 (d, J=2.5 Hz, 0.7H), 7.15 (d, J=2.5 Hz, 0.3H), 6.99 (dd, J=8.5, 2.5 Hz, 0.7H), 6.97 (dd, J=8.5, 2.5 Hz, 0.3H), 5.11 (d, J=15.3 Hz, 0.7H), 4.93-4.79 (m, 0.3H), 4.15 (d, J=14.8 Hz, 0.3H), 4.11-3.44 (m, 8H), 3.88 (s, 0.9H), 3.86 (s, 2.1H), 3.60 (d, J=15.3 Hz, 0.7H), 3.41-3.14 (m, 3H), 2.98 (s, 6H), 3.04-2.89 (m, 1.7H), 2.85-2.75 (m, 0.3H), 2.66 (dd, J=8.8, 5.8 Hz, 0.7H), 2.52 (dd, J=10.0, 6.3 Hz, 0.3H), 2.16-1.04 (m, 12.7H), 0.20-0.14 (m, 0.3H).

(racemic) 8-cyclohexyl-N-(dimethylsulfamoyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide. A 1M solution of sodium cyanoborohydride in THF (0.13 mL, 0.13 mmol) was added to a solution of 8-cyclohexyl-N-(dimethylsulfamoyl)-11-methoxy-1a-(3-oxa-7,10-diazatricyclo[3.3.3.0$^{1,5}$]undec-7-ylcarbonyl)-1,1a,2,12b-tetrahydrocyclopropa[d]indolo[2,1-a][2]benzazepine-5-carboxamide (Example 18A) (9.0 mg, 0.013 mmol) and formaldehyde (37wt. % in water) (0.010 mL, 0.10 mmol) in MeOH (1 mL) and the mixture was stirred at rt for 16 h. The reaction was concentrated, dissolved into MeOH, filtered and purified by preparative HPLC (H$_2$O-MeOH with 0.1% TFA buffer) to yield 8-cyclohexyl-N-(dimethylsulfamoyl)-11-methoxy-1a-((10-methyl-3-oxa-7,10-diazatricyclo[3.3.3.0$^{1,5}$]undec-7-yl)carbonyl)-1,1a,2,12b-tetrahydrocyclopropa[d]indolo[2,1-a][2]benzazepine-5-carboxamide (7.5 mg, 8.7 μmol, 67% yield) as a white solid. LCMS: m/e 702 (M+H)$^+$. LCMS retention time: 1.84 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:1 ratio of rotamers or atrope isomers. $^1$H NMR (400 MHz, MeOD) δ ppm 8.11 (br s, 0.33H), 7.97 (br s, 0.67H), 7.89 (d, J=8.5 Hz, 0.33H), 7.88 (d, J=8.5 Hz, 0.67H), 7.60-7.54 (m, 11-1), 7.29 (d, J=8.5 Hz, 0.67H), 7.29 (d, J=8.5 Hz, 0.33H), 7.16 (d, J=2.5 Hz, 0.67H), 7.15 (d, J-2.8 Hz, 0.33H), 7.00 (dd, J=8.5, 2.5 Hz, 0.67H), 6.97 (dd, J=8.5, 2.8 Hz, 0.33H), 5.11 (d, J=15.1 Hz, 0.67H), 4.92-4.80 (m, 0.33H), 4.21-3.44 (m, 9H), 3.87 (s, 1H), 3.86 (s, 2H), 3.16-2.49 (m, 8H), 2.99 (s, 2H), 2.98 (s, 4h), 2.16-1.04 (m, 12.67H), 0.21-0.15 (m, 0.33H).

EXAMPLE 20

EXAMPLE 21

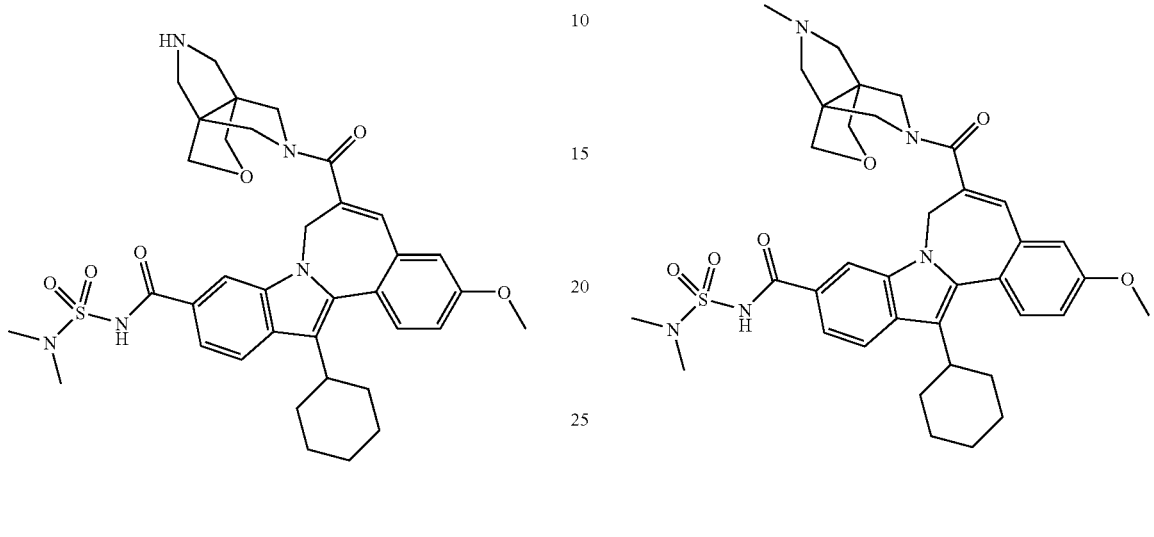

(achiral) 13-cyclohexyl-N-(dimethylsulfamoyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide. BOP-Cl (14 mg, 0.056 mmol) was added to a solution of dihydro-4H-3a,6a-(methanoiminomethano)furo[3,4-c]pyrrole dihydrochloride (Intermediate 3) (12.7 mg, 0.056 mmol) and 13-cyclohexyl-10-((dimethylsulfamoyl)carbamoyl)-3-methoxy-7H-indolo[2,1-a][2]benzazepine-6-carboxylic acid (Intermediate 18) (20 mg, 0.037 mmol) in CH$_2$Cl$_2$ (1 mL) and TEA (0.1 mL, 0.7 mmol) and the mixture was stirred at rt for 16 h. The reaction was concentrated, diluted with MeOH, filtered and purified by preparative HPLC (H$_2$O-MeOH with 0.1% TFA buffer) to yield 13-cyclohexyl-N-(dimethylsulfamoyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide (12.5 mg, 0.014 mmol, 38% yield) as a yellow solid. LCMS: m/e 674 (M+H)$^+$. LCMS retention time: 2.44 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). $^1$H NMR (400 MHz, MeOD) δ ppm 8.06 (d, J=1.3 Hz, 1H), 7.86 (d, J=8.5 Hz, 1H), 7.55-7.51 (m, 2H), 7.15 (dd, J=8.5, 2.8 Hz, 1H), 7.09 (br d, J=2.8 Hz, 1H), 7.06 (br s, 1H), 5.26-5.16 (m, 1H), 4.93-4.82 (m, 1H), 4.30-4.18 (m, 1H), 4.12-4.01 (m, 1H), 3.96-3.89 (m, 1H), 3.89 (s, 3H), 3.62-3.39 (m, 5H), 3.32-3.09 (m, 3H), 2.98 (s, 6H), 2.86-2.77 (m, 1H), 2.14-1.11 (m, 11H).

(achiral) 13-cyclohexyl-N-(dimethylsulfamoyl)-3-methoxy-6-((10-methyl-3-oxa-7,10-diazatricyclo[3.3.3.0$^{1,5}$]undec-7-yl)carbonyl)-7H-indolo [2,1-a][2]benzazepine-10-carboxamide. A 1M solution of sodium cyanoborohydride in THF (0.15 mL, 0.15 mmol) was added to a solution of 13-cyclohexyl-N-(dimethylsulfamoyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide (Example 20) (10 mg, 0.015 mmol) and formaldehyde (37 wt. % in water) (0.01 mL, 0.1 mmol) in MeOH (1 mL) and the mixture was stirred at rt for 16 h. The reaction was filtered and purified by preparative HPLC (H$_2$O-MeOH with 0.1% TFA buffer) to yield product 13-cyclohexyl-N-(dimethylsulfamoyl)-3-methoxy-6-((10-methyl-3-oxa-7,10-diazatricyclo[3.3.3.0$^{1,5}$]undec-7-yl)carbonyl)-7H-indolo[2,1-a][2]benzazepine-10-carboxamide (8.5 mg, 10 µmol, 68% yield) as a bright yellow solid. LCMS: m/e 688 (M+H)$^+$. LCMS retention time: 1.91 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.) $^1$H NMR (400 MHz, MeOD) δ ppm 8.07 (br s, 1H), 7.87 (d, J=8.5 Hz, 1H), 7.54 (br d, J=8.5 Hz, 1H), 7.53 (d, J=8.5 Hz, 1H), 7.14 (dd, J=8.5, 2.5 Hz, 1H), 7.09 (d, J=2.5 Hz, 1H), 7.06 (s, 1H), 5.23 (br d, J=14.8 Hz, 1H), 4.37-3.06 (in, 10H), 4.25 (br d, J=14.8 Hz, 1H), 3.89 (s, 3H), 2.98 (s, 6H), 2.94-2.76 (m, 4H), 2.15-1.69 (m, 6H), 1.52-1.10 (m, 4H).

EXAMPLE 22

EXAMPLE 23

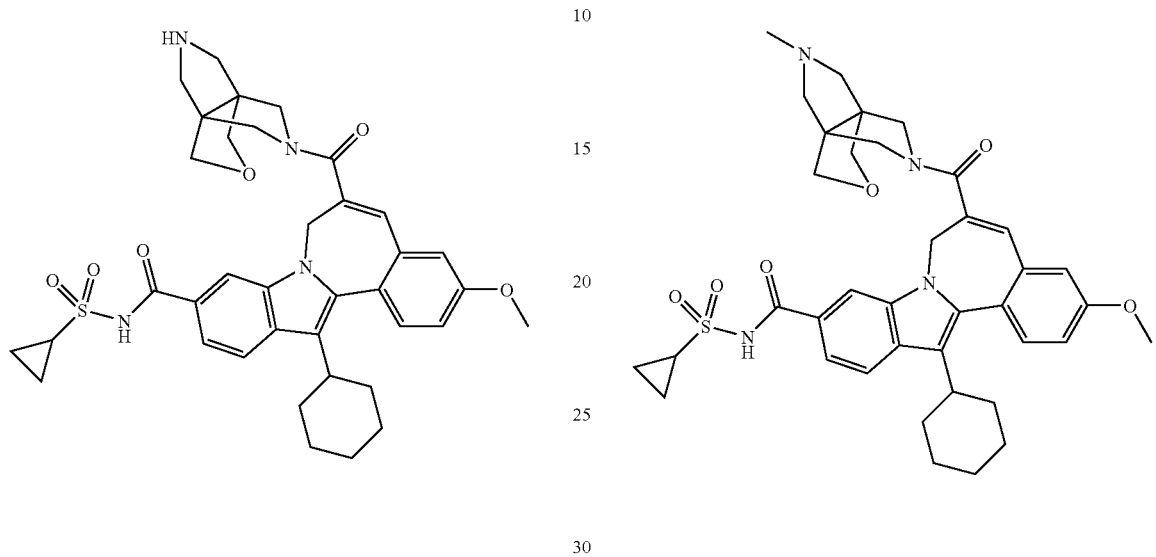

(achiral) 13-cyclohexyl-N-(cyclopropylsulfonyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide. BOP-Cl (14.3 mg, 0.056 mmol) was added to a solution of dihydro-4H-3a,6a-(methanoiminomethano)furo[3,4-c]pyrrole dihydrochloride (Intermediate 3) (12.7 mg, 0.056 mmol) and 13-cyclohexyl-10-((cyclopropylsulfonyl)carbamoyl)-3-methoxy-7H-indolo[2,1-a][2]benzazepine-6-carboxylic acid (Intermediate 20) (20 mg, 0.037 mmol) in CH$_2$Cl$_2$ (1 mL) and TEA (0.1 mL, 0.7 mmol) and the mixture was stirred at rt for 16 h. The reaction was concentrated, diluted with MeOH, filtered and purified by preparative HPLC (H$_2$O-MeOH with 0.1% TFA buffer) to yield product 13-cyclohexyl-N-(cyclopropylsulfonyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide (12 mg, 0.014 mmol, 37% yield) as a yellow solid. LCMS: m/e 671 (M+H)$^+$. LCMS retention time: 2.41 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). $^1$H NMR (400 MHz, MeOD) δ ppm 8.07 (d, J=1.3 Hz, 1H), 7.87 (d, J=8.5 Hz, 1H), 7.54 (d, J=8.8 Hz, 2H), 7.15 (dd, J=8.8, 2.8 Hz, 1H), 7.09 (d, J=2.8 Hz, 1H), 7.07 (br s, 1H), 5.26-5.16 (in, 1H), 4.93-4.81 (m, 1H), 4.29-4.18 (m, 1H), 4.07-3.88 (m, 2H), 3.90 (s, 3H), 3.64-3.39 (m, 6H), 3.28-3.09 (m, 4H), 2.87-2.77 (m, 1H), 2.18-1.09 (m, 14H).

(achiral) 13-cyclohexyl-N-(cyclopropylsulfonyl)-3-methoxy-6-((10-methyl-3-oxa-7,10-diazatricyclo[3.3.3.0$^{1,5}$]undec-7-yl)carbonyl)-7H-indolo[2,1-a][2]benzazepine-10-carboxamide. A 1M solution of sodium cyanoborohydride in THF (0.15 mL, 0.15 mmol) was added to a solution of 13-cyclohexyl-N-(cyclopropylsulfonyl)-3-methoxy-6-(3-oxa-7,10-diazatricyclo[3.3.3.0$^{1,5}$]undec-7-ylcarbonyl)-7H-indolo[2,1-a][2]benzazepine-10-carboxamide (Example 22) (10 mg, 0.015 mmol) and formaldehyde (37 wt. % in water) (0.01 mL, 0.1 mmol) in MeOH (1 mL) and the mixture was stirred at rt for 16 h. The reaction was concentrated, dissolved into MeOH, filtered and purified by preparative HPLC (H$_2$O-MeOH with 0.1% TFA buffer) to yield 13-cyclohexyl-N-(cyclopropylsulfonyl)-3-methoxy-6-((10-methyl-3-oxa-7,10-diazatricyclo[3.3.3.0$^{1,5}$]undec-7-yl)carbonyl)-7H-indolo[2,1-a][2]benzazepine-10-carboxamide (7.9 mg, 9.4 µmol, 63% yield) as a bright yellow solid. LCMS: m/e 685 (M+H)$^+$. LCMS retention time: 1.92 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.) $^1$H NMR (400 MHz, MeOD) δ ppm 8.09 (br s, 1H), 7.87 (d, J=8.5 Hz, 1H), 7.54 (br d, J=8.5 Hz, 1H), 7.53 (d, J=8.5 Hz, 1H), 7.14 (dd, J=8.5, 2.5 Hz, 1H), 7.10 (d, J=2.5 Hz, 1H), 7.07 (s, 1H), 5.22 (br d, J=14.8 Hz, 1H), 4.13-3.12 (m, 10H), 4.23 (br d, J=14.8 Hz, 1H), 3.90 (s, 3H), 2.97-2.76 (m, 5H), 2.15-1.67 (m, 6H), 1.52-1.07 (m, 8H).

EXAMPLE 24A

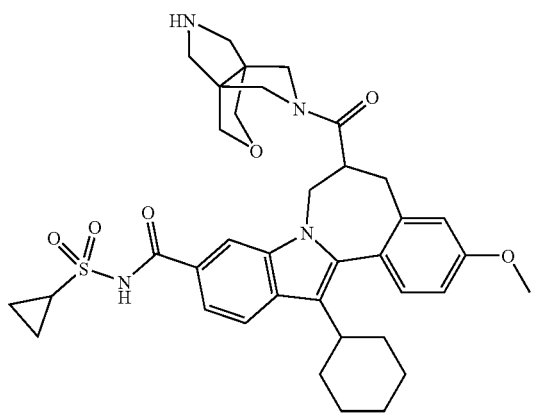

(racemate) 13-cyclohexyl-N-(cyclopropylsulfonyl)-3-methoxy-6-(3-oxa-7,10-diazatricyclo[0.3.3.0$^{1,5}$]undec-7-ylcarbonyl)-6,7-dihydro-5H-indolo[2,1-a][2]benzazepine-10-carboxamide. BOP-Cl (21.5 mg, 0.084 mmol) was added to a solution of dihydro-4H-3a,6a-(methanoiminomethano)furo[3,4-c]pyrrole dihydrochloride (Intermediate 3) (19 mg, 0.084 mmol) and methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (Intermediate 21) (30 mg, 0.056 mmol) in CH$_2$Cl$_2$ (1 mL) and TEA (0.16 mL, 1.1 mmol) and the mixture was stirred at rt for 4 d. The reaction was concentrated, dissolved into MeOH, filtered and purified by preparative HPLC (H$_2$O-MeOH with 0.1% TFA buffer) to yield 13-cyclohexyl-N-(cyclopropylsulfonyl)-3-methoxy-6-(3-oxa-7,10-diazatricyclo[3.3.3.0$^{1,5}$]undec-7-ylcarbonyl)-6,7-dihydro-5H-indolo[2,1-a][2]benzazepine-10-carboxamide (17.9 mg, 0.020 mmol, 37% yield) as a yellow solid. LCMS: m/e 673 (M+H)$^+$. LCMS retention time: 2.83 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). Presents as a 2:1 ratio of rotamers or atrope isomers. $^1$H NMR (400 MHz, MeOD) δ ppm 8.04-7.94 (m, 1H), 7.89-7.76 (m, 1H), 7.59-7.48 (m, 1H), 7.38-7.28 (m, 1H), 7.08-6.72 (m, 2H), 4.57-4.37 (m, 1H), 4.12-3.29 (m, 17H), 3.23-3.15 (m, 1H), 2.96-1.08 (m, 17H).

EXAMPLE 25A

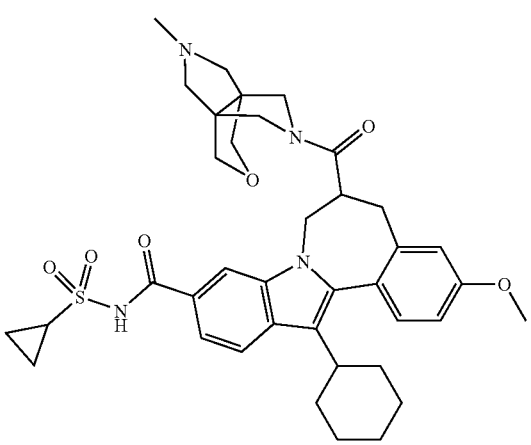

(racemate) 13-cyclohexyl-N-(cyclopropylsulfonyl)-3-methoxy-6-((10-methyl-3-oxa-7,10-diazatricyclo[3.3.3.0$^{1,5}$]undec-7-yl)carbonyl)-6,7-dihydro-5H-indolo[2,1-a][2]benzazepine-10-carboxamide. A 1M solution of sodium cyanoborohydride in THF (0.16 mL, 0.16 mmol) was added to a solution of 13-cyclohexyl-N-(cyclopropylsulfonyl)-3-methoxy-6-(3-oxa-7,10-diazatricyclo[3.3.3.0$^{1,5}$]undec-7-ylcarbonyl)-6,7-dihydro-5H-indolo[2,1-a][2]benzazepine-10-carboxamide (Example 24A) (11 mg, 0.016 mmol) and formaldehyde (37 wt. % in water) (0.01 mL, 0.1 mmol) in MeOH (1 mL) and the mixture was stirred at rt for 16 h. The reaction was concentrated, dissolved into MeOH, filtered and purified by preparative HPLC (H$_2$O-MeOH with 0.1% TFA buffer) to yield 13-cyclohexyl-N-(cyclopropylsulfonyl)-3-methoxy-6-((10-methyl-3-oxa-7,10-diazatricyclo[3.3.3.0$^{1,5}$]undec-7-yl)carbonyl)-6,7-dihydro-5H-indolo[2,1-a][2]benzazepine-10-carboxamide (12 mg, 0.013 mmol, 82% yield) as a yellow solid. LCMS: m/e 687 (M+H)$^+$. LCMS retention time: 2.47 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min).

EXAMPLE 26A

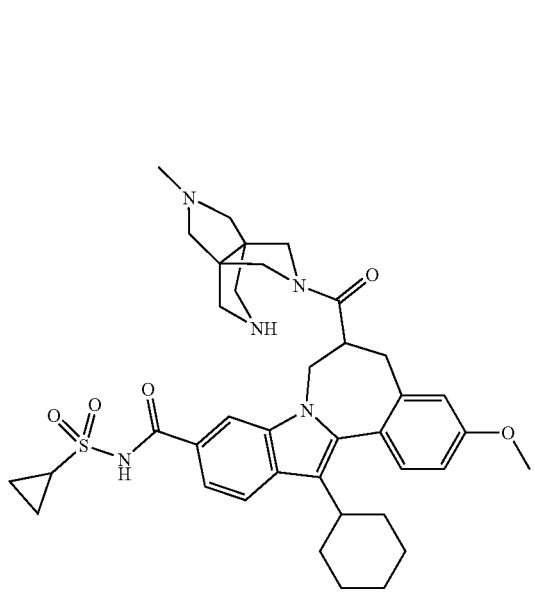

(racemate) 13-cyclohexyl-N-(cyclopropylsulfonyl)-3-methoxy-6-((7-methyl-3,7,10-triazatricyclo[3.3.3.0$^{1,5}$]undec-3-yl)carbonyl)-6,7-dihydro-5H-indolo[2,1-a][2]benzazepine-10-carboxamide. BOP-Cl (21.3 mg, 0.084 mmol) was added to a solution of 2-methyltetrahydro-1H,4H-3a,6a-(methanoiminomethano)pyrrolo[3,4-c]pyrrole trihydrochloride (Intermediate 5) (23.2 mg, 0.084 mmol) and methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (Intermediate 21) (30 mg, 0.056 mmol) in CH$_2$Cl$_2$ (1 mL) and TEA (0.16 mL, 1.1 mmol) and the mixture was stirred at rt for 3 d. The reaction was concentrated, dissolved into MeOH, filtered and purified by preparative HPLC (H$_2$O-MeCN with 0.1% TFA buffer) and repurified by preparative HPLC (H$_2$O-MeOH with 0.1% TFA buffer) to yield product 13-cyclohexyl-N-(cyclopropylsulfonyl)-3-methoxy-6-((7-methyl-3,7,10-triazatricyclo[3.3.3.0$^{1,5}$]undec-3-yl)carbonyl)-6,7-dihydro-5H-indolo[2,1-a][2]benzazepine-10-carboxamide (3.7 mg, 3.8 µmol, 6.9% yield) as a yellow solid. LCMS: m/e 686 (M+H)$^+$. LCMS retention time: 2.37 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). $^1$H NMR (500 MHz, MeOD) δ ppm 8.08-7.98 (m, 1H), 7.94-7.86 (m, 1H), 7.65-7.57 (m, 1H), 7.45-7.36 (m, 1H), 7.09-7.01 (m, 1.75H), 6.90-6.84 (in, 0,25H), 4.62-2.91 (m, 23H), 2.85-2.64 (m, 2H), 2.15-1.92 (in, 4H), 1.86-1.77 (in, 2H), 1.68-1.24 (m, 6H), 1.22-1.12 (m, 2H).

EXAMPLE 27A

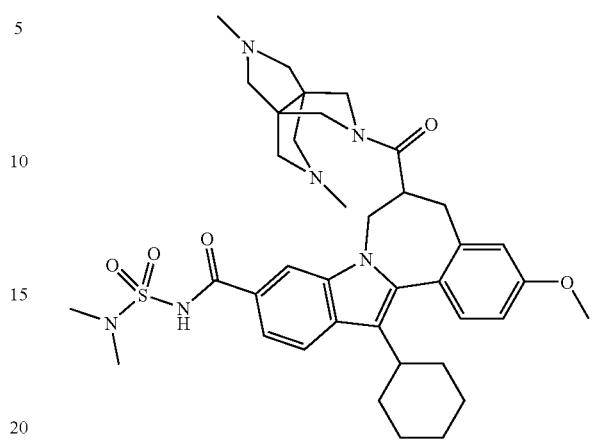

(racemate) 13-cyclohexyl-N-(dimethylsulfamoyl)-6-((7,10-dimethyl-3,7,10-triazatricyclo[3.3.3.0$^{1,5}$]undec-3-yl)carbonyl)-3-methoxy-6,7-dihydro-5H-indolo[2,1-a][2]benzazepine-10-carboxamide. 10% Pd/C (4 mg, 4 µmol) was added to a suspension of 13-cyclohexyl-N-(dimethylsulfamoyl)-6-((7,10-dimethyl-3,7,10-triazatricyclo[3.3.3.0$^{1,5}$]undec-3-yl)carbonyl)-3-methoxy-7H-indolo[2,1-a][2]benzazepine-10-carboxamide (Example 15) (6.0 mg, 8.6 µmol) in MeOH (2 mL). The reaction mixture was vacuum flushed with N$_2$, and then with H$_2$ and stirred under a H$_2$ balloon at rt for 16 h. The reaction mixture was filtered through celite, and concentrated to yield 13-cyclohexyl-N-(dimethylsulfamoyl)-6-((7,10-dimethyl-3,7,10-triazatricyclo[3.3.3.0$^{1,5}$]undec-3-yl)carbonyl)-3-methoxy-6,7-dihydro-5H-indolo[2,1-a][2]benzazepine-10-carboxamide (3.1 mg, 4.2 µmol, 49% yield) as an off white solid. LCMS: m/e 703 (M+H)$^+$. LCMS retention time: 2.35 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min).

EXAMPLE 28A

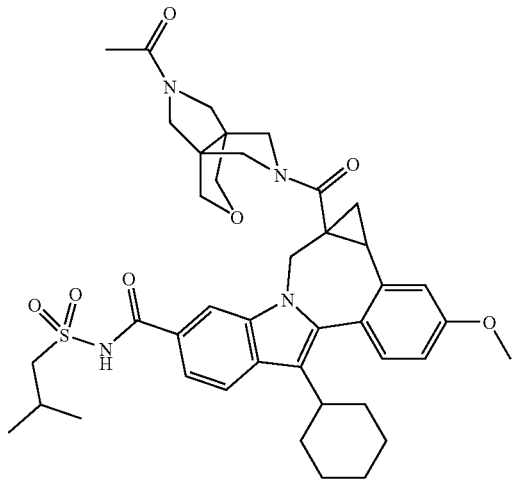

(racemate) 1a-((10-acetyl-3-oxa-7,10-diazatricyclo[3.3.3.0[1,5]]undec-7-yl)carbonyl)-8-cyclohexyl-N-(isobutylsulfonyl)-11-methoxy-1,1a,2,12b-tetrahydrocyclopropa[d]indolo[2,1-a][2]benzazepine-5-carboxamide. HATU (7.6 mg, 0.020 mmol) was added to a solution of 8-cyclohexyl-N-(isobutylsulfonyl)-11-methoxy-1a-(3-oxa-7,10-diazatricyclo[3.3.3.0[1,5]]undec-7-ylcarbonyl)-1,1a,2,12b-tetrahydrocyclopropa[d]indolo[2,1-a][2]benzazepine-5-carboxamide (Example 7A) (9.4 mg, 0.013 mmol) and acetic acid (0.01 mL, 0.2 mmol) in DMF (1 mL) and TEA (0.05 mL, 0.4 mmol) and the mixture was stirred at rt for 16 h. The reaction was diluted with MeOH, filtered and purified by preparative HPLC ($H_2O$-MeOH with 0.1% TFA buffer) to yield product 1a-((10-acetyl-3-oxa-7,10-diazatricyclo[3.3.3.0[1,5]]undec-7-yl)carbonyl)-8-cyclohexyl-N-(isobutylsulfonyl)-11-methoxy-1,1a,2,12b-tetrahydrocyclopropa[d]indolo[2,1-a][2]benzazepine-5-carboxamide (9.4 mg, 0.011 mmol, 85% yield) as a tan solid. LCMS: m/e 743 (M+H)+. LCMS retention time: 2.74 min. (Column: Phenomenex-Luna 3.0×50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min). Presents as a 3:1 ratio of rotamers or atrope isomers. $^1$H NMR (400 MHz, MeOD) δ ppm 8.08 (s, 0.25H), 7.94 (br s, 0.75H), 7.91-7.84 (m, 1H), 7.60-7.50 (in, 1H), 7.31-7.25 (m, 1H), 7.19-7.14 (m, 1H), 7.01-6.93 (m, 1H), 5.10 (br d, J=15.1 Hz, 0.75H), 4.95-4.86 (m, 0.25H), 4)23-1.16 (m, 22.75H), 3.87 (s, 0.75H), 3.85 (s, 2.25H), 1.14-1.08 (m, 6H), 0.19-0.09 (m, 0.25H).

EXAMPLE 29B

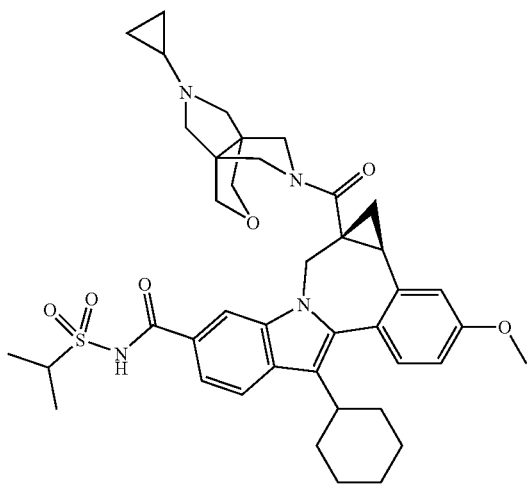

(homochiral) (1aR,12bS)-8-cyclohexyl-1a-((10-cyclopropyl-3-oxa-7,10-diazatricyclo[3.3.3.0[1,5]]undec-7-yl)carbonyl)-N-(isopropylsulfonyl)-11-methoxy-1,1a,2,12b-tetrahydrocyclopropa[d]indolo[2,1-a][2]benzazepine-5-carboxamide. A 1M solution of sodium cyanoborohydride in THF (0.16 mL, 0.16 mmol) was added to a solution of (1aR,12bS)-8-cyclohexyl-N-(isopropylsulfonyl)-11-methoxy-1a-(3-oxa-7,10-diazatricyclo[3.3.3.0[1,5]]undec-7-ylcarbonyl)-1,1a,2,12b-tetrahydrocyclopropa[d]indolo[2,1-a][2]benzazepine-5-carboxamide (Example 1B) (22 mg, 0.032 mmol) and (cyclopropyl(ethoxy)methoxy)trimethylsilane (0.04 mL, 0.2 mmol) in acetic acid (0.02 mL, 0.3 mmol) and MeOH (1 mL) and the mixture was heated by microwave at 90° C. for 2 h. The reaction was concentrated, dissolved into MeOH, filtered and purified by preparative HPLC ($H_2O$-MeOH with 0.1% TFA buffer) to yield (1aR,12bS)-8-cyclohexyl-1a-((10-cyclopropyl-3-oxa-7,10-diazatricyclo[3.3.3.0[1,5]]undec-7-yl)carbonyl)-N-(isopropylsulfonyl)-11-methoxy-1,1a,2,12b-tetrahydrocyclopropa[c]indolo[2,1-a][2]benzazepine-5-carboxamide (14.2 mg, 0.016 mmol, 50% yield) as a bright yellow solid. LCMS: m/e 727 (M+H)+. LCMS retention time: 2.39 min. (Column: Luna 4.6×50 mm S10. Solvent A=$H_2O$:$CH_3CN$ 95%:5% 10 mm Ammonium Acetate. Solvent B=$H_2O$:$CH_3CN$ 5%:95% 10 mm Ammonium Acetate. Start % B=0. Final % B=100. Gradient Time=4 min. Flow Rate=4 mL/min.). Presents as a 2:1 ratio of rotamers or atrope isomers. $^1$H NMR (500 MHz, MeOD) δ ppm 8.20 (br s, 0.33H), 8.03 (s, 0.67H), 7.96 (d, J=8.6 Hz, 0.67H), 7.93 (d, J=8.6 Hz, 0.33H), 7.66-7.60 (m, 1H), 7.34 (d, J=8.6 Hz, 0.67H), 7.33 (d, J=8.6 Hz, 0.33H), 7.21 (d, J=2.5 Hz, 0.67H), 7.20 (d, J=2.5 Hz, 0.33H), 7.04 (dd, J=8.6, 2.5 Hz, 0.67H), 7.01 (dd, J=8.5, 2.5 Hz, 0.33H), 5.17 (d, J=15.6 Hz, 0.67H), 4.99-4.92 (m, 0.33H), 4.27-3.44 (m, 11H), 3.93 (s, 1H), 3.91 (s, 2H), 3.30-2.80 (m, 4H), 2.77-2.70 (m, 0.67H), 2.60-2.57 (m, 0.33H), 2.22-0.88 (m, 22.67H), 0.25-0.19 (m, 0.33H).

EXAMPLE 30

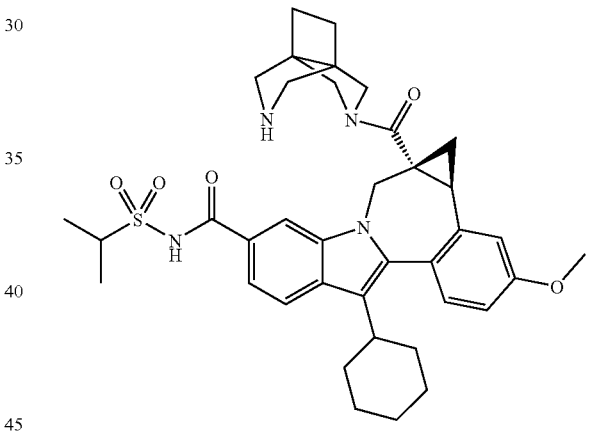

(1aR,12B)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide. BOP-Cl (0.090 g, 0.353 mmol) was added to a stirring solution of (1aR,12bS)-8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (0.049 g, 0.088 mmol) and tetrahydro-1H,4H-3a,6a-ethanopyrrolo[3,4-c]pyrrole dihydrochloride (20 mg, 0.14 mmol) in $CH_2Cl_2$ (2 mL) and triethyl amine (0.074 mL, 0.53 mmol), and the mixture was stirred at r.t. for 1 h. The reaction was concentrated, diluted with MeOH and purified by preparative HPLC ($H_2O$—$CH_3CN$ with 0.1% TFA buffer) to yield (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide (13 mg, 0.019 mmol, 13% yield) as a yellow solid. LCMS: m/e 671 (M+H)+ LCMS retention time: 1.84 min. (Column: Phenomenex-Luna 3.0× 50 mm S10. Solvent A=90% Water: 10% Methanol: 0.1%

TFA. Solvent B=10% Water: 90% Methanol: 0.1% TFA. Start % B=0. Final % B=100. Gradient Time=3 min. Flow Rate=4 mL/min.).

EXAMPLE 31

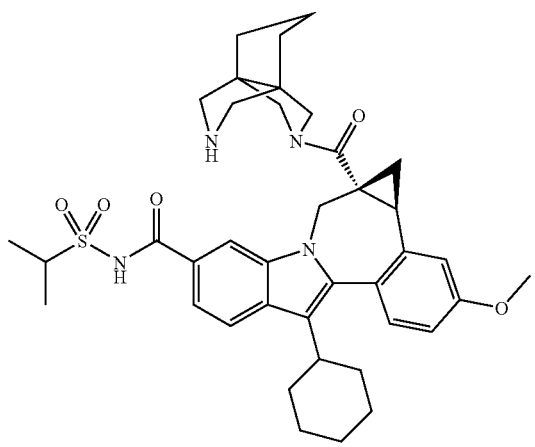

(1aR,12bS)-8-cyclohexyl-N-(isopropylsulfonyl)-11-methoxy-1a-(tetrahydro-1H,4H-3a,6a-(methanoiminomethano)pentalen-2-ylcarbonyl)-1,1a,2,12b-tetrahydrocyclopropa[d]indolo[2,1-a][2]benzazepine-5-carboxamide. BOP-Cl (38.2 mg, 0.150 mmol) was added to a solution of (1aR,12bS)-8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (41 mg, 0.075 mmol) and tetrahydro-1H,4H-3a,6a-(methanoiminomethano)cyclopenta[c]pyrrole dihydrochloride (25.3 mg, 0.113 mmol) in CH$_2$Cl$_2$ (1 mL) and triethyl amine (0.031 mL, 0.23 mmol) and the reaction mixture was stirred at r.t. for 1 h. The reaction was concentrated, diluted with MeOH and purified by preparative HPLC (H$_2$O—CH$_3$CN with 0.1% TFA buffer) to yield 8-cyclohexyl-N-(isopropylsulfonyl)-11-methoxy-1a-(3,7,10-triazatricyclo[3.3.3.0$^{1,5}$]undec-3-ylcarbonyl)-1,1a,2,12b-tetrahydrocyclopropa[d]indolo[2,1-a][2]benzazepine-5-carboxamide (19 mg, 0.028 mmol, 37% yield) as a yellow solid. LCMS: m/e 685 (M+H)$^+$. LCMS retention time: 1.87 min. (Column: Phenomenex-Luna 3.0× 50 mm S10. Solvent A=90% Water: 10% Methanol: 0.1% TFA. Solvent B=10% Water: 90% Methanol: 0.1% TFA. Start % B=0. Final % B=100. Gradient Time=3 min. Flow Rate=4 mL/min).

EXAMPLE 32

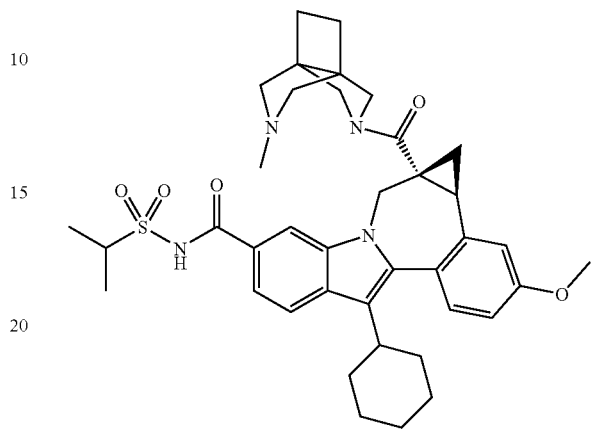

(1aR,12bS)-8-cyclohexyl-N-(isopropylsulfonyl)-11-methoxy-1a-((2-methyltetrahydro-1H,4H-3a,6a-ethanocyclopenta[c]pyrrol-5-yl)carbonyl)-1,1a,2,12b-tetrahydro-eyelopropa[d]indolo[2,1-a][2]benzazepine-5-carboxamide. A 1M solution of sodium cyanoborohydride in THF (0.45 mL, 0.45 mmol) was added to a solution of (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2] benzazepine-5-carboxamide (30 mg, 0.045 mmol) and formaldehyde (37 wt. % in water) (0.034 mL, 0.45 mmol) in MeOH (1 mL) and the reaction mixture was stirred at rt for 2 h. The reaction was concentrated, dissolved into MeOH, filtered and purified by preparative HPLC (H$_2$O—CH$_3$CN with 0.1% TFA buffer) to give (1aR,12bS)-8-cyclohexyl-N-(isopropylsulfonyl)-11-methoxy-1a-((2-methyltetrahydro-1H, 4H-3a,6a-ethanocyclopenta[c]pyrrol-5-yl)carbonyl)-1,1a,2, 12b-tetrahydrocyclopropa[d]indolo[2,1-a][2]benzazepine-5-carboxamide (13 mg, 0.019 mmol, 42% yield) as white solid. LCMS: m/e 685 (M+H)$^+$. LCMS retention time: 1.86 min. (Column: SunFire C18 5u 4.6×50 mm. Solvent A=90% Water/10% Acetonitrile/0.1% TFA. Solvent B=10% Water/ 90% Acetonitrile/0.1% TFA. Start % B=0. Final % B=100. Gradient Time=3 min. Flow Rate=4 mL/min.). Presents as a 2:1 ratio of rotamers or atrope isomers. $^1$H NMR (400 MHz, CHLOROFORM-d) δ ppm 8.64 (1H, s), 8.11 (0.33H, s), 7.85-7.95 (2.67H, m), 7.33 (0.33H, d, J=8.53 Hz), 7.25-7.27 (0.67H, m), 7.08-7.17 (1H, m), 6.94-6.99 (0.33H, m), 6.91 (0.67H, dd, J=8.53, 2.51 Hz), 4.97-5.05 (0.33 H, m), 4.81-4.89 (0.33H, m), 4.70-4.78 (1.33H, m), 3.97-4.44 (5H, m), 3.86-3.95 (3H, m), 3.54-3.62 (0.33H, m), 3.47 (0.67H, d, J=13.05 Hz), 3.29-3.36 (0.33H, m), 3.13-3.19 (1H, m), 3.06-3.13 (2H, m), 3.05-3.20 (3H, m), 2.67-2.99 (4H, 1.88-2.25 (6H, m), 1.79 (2H, br. s.), 1.53-1.61 (0.33H, m), 1.45-1.53 (2.66H, m), 1.34-1.44 (3H, m), 1.19-1.33 (3.67H, m), 1.14 (0.67H, br. s), 1.07 (0.33H, s), 0.95 (0.67H, d, J=4.27 Hz), 0.56 (0.33H, s).

EXAMPLE 33

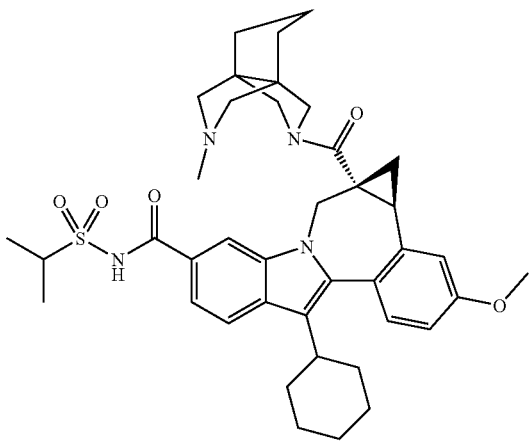

(1aR,12bS)-8-cyclohexyl-N-(isopropylsulfonyl)-11-methoxy-1a-((8-methyltetrahydro-1H,4H-3a,6a-(methanoiminomethano)pentalen-2-yl)carbonyl)-1,1a,2,12b-tetrahydrocyclopropa[d]indolo[2,1-a][2]benzazepine-5-carboxamide. A 1M solution of sodium cyanoborohydride in THF (0.28 mL, 0.28 mmol) was added to a solution of (1aR,12bS)-8-cyclohexyl-N-(isopropylsulfonyl)-11-methoxy-1a-(tetrahydro-1H,4H-3a,6a-(methanoiminomethano)pentalen-2-ylcarbonyl)-1,1a,2,12b-tetrahydrocyclopropa[d]indolo[2,1-a][2]benzazepine-5-carboxamide (19 mg, 0.028 mmol) and formaldehyde (37 wt. % in water) (0.021 mL, 0.28 mmol) in MeOH (1 mL) and the reaction mixture was stirred at rt for 2 h. The reaction mixture was then concentrated, dissolved into MeOH, filtered and purified by preparative HPLC ($H_2O$—$CH_3CN$ with 0.1% TFA buffer) to give (1aR,12bS)-8-cyclohexyl-N-(isopropylsulfonyl)-11-methoxy-1a-((8-methyltetrahydro-1H,4H-3a,6a-(methanoiminomethano)pentalen-2-yl)carbonyl)-1,1a,2,12b-tetrahydrocyclopropa[d]indolo[2,1-a][2]benzazepine-5-carboxamide (18 mg, 0.026 mmol, 93% yield) as white solid. LCMS: m/e 699 (M+H)$^+$. LCMS retention time: 1.89 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.). Presents as a 2:1 ratio of rotamers or atrope isomers. $^1$H NMR (400 MHz, CHLOROFORM-d) δ ppm 8.66 (1H, s), 8.09 (0.033H, s), 7.94 (1.67H, s), 7.88 (1H, br. s.), 7.33 (0.33 H, d, J=8.53 Hz), 7.23-7.27 (0.67H, m), 7.07-7.15 (1H, m), 6.93-6.98 (0.33 H, m), 6.90 (0.67H, dd, J=8.53, 2.51 Hz), 4.85 (1H, d, J=11.04 Hz), 4.72 (1H, d, J=15.06 Hz), 4.04-4.33 (4H, m), 3.95 (1H, d, J=11.54 Hz), 3.90 (3H, s), 3.52-3.60 (0.33 H, m), 3.49 (0.67H, d, J=12.55 Hz), 3.28-3.39 (0.33H, m), 3.07 (1H, br. s.), 3.05(2H, br. s.), 2.67 (2H, dd, J=9.79, 6.27 Hz), 2.52-2.64 (2H, m), 1.86-2.11 (7H, m), 1.79 (2H, br. s.), 1.52-1.66 (2H, m), 1.45-1.53 (3H, m), 1.36-1.45 (3H, m), 1.22-1.33 (5H, m), 0.89 (1.67H, d, J=6.78 Hz), 0.85 (0.33H, d, J=5.52 Hz), 0.55 (0.67H, s).

The following examples (34-38) were prepared using a previously described methodology.

EXAMPLE 34

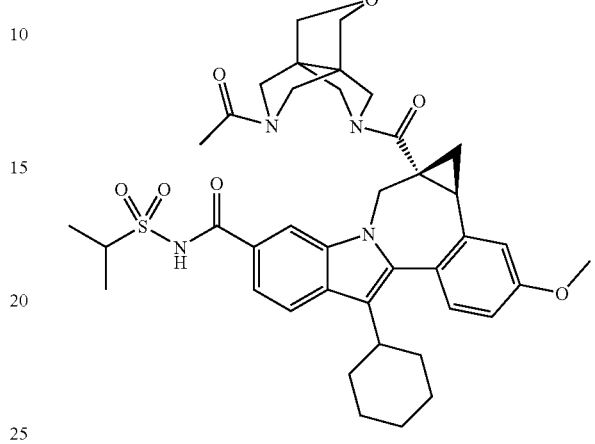

(1aR, 12bS)-1a-((10-acetyl-3-oxa-7,10-diazatricyclo[3.3.3.0-1,5]undec-7-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide, White solid. LCMS: m/e =729 (M+H)$^+$. LCMS retention time: 2.25 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 35

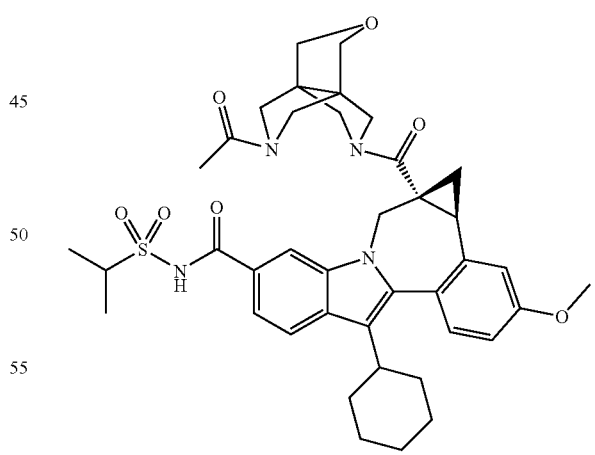

(1aR,2bS)-1a-((10-acetyl-3-oxa-7,10-diazatricyclo[3.3.3.0~1,5~]undee-7-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. White solid. LCMS: m/e =730 (M+H)$^+$. LCMS retention time: 2.25 min. (Column: SunFire C18 5u 4.6~50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 36

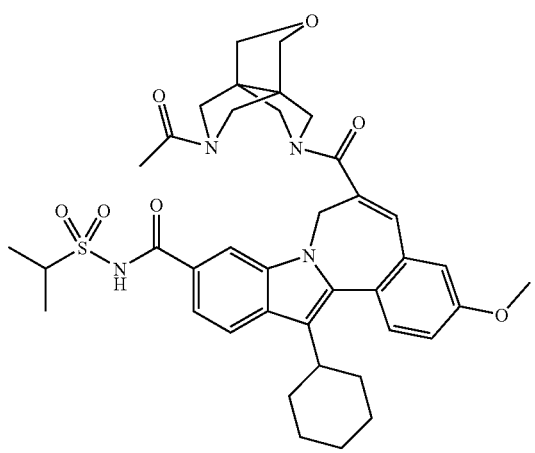

6-((10-acetyl-3-oxa-7,10-diazatricyclo[3.3.3.0~1,5~]undec-7-yl)carbonyl)-13-cyclohexyl-N-(isopropylsulfonyl)-3-methoxy-7H-indolo[2,1-a][2]benzazepine-10-carboxamide. Yellow solid. LCMS: m/e=715 (M+H)⁺. LCMS retention time: 2.45 min. (Column: SunFire C18 5u 4.6~50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 37

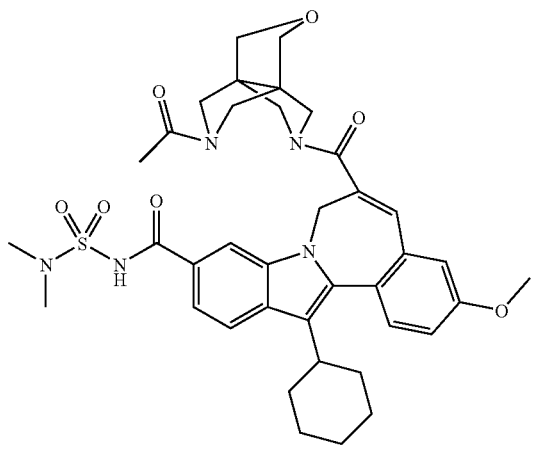

6-((10-acetyl-3-oxa-7,10-diazatricyclo[3.3.3.0~1,5~]undec-7-yl)carbonyl)-13-cyclohexyl-N-(dimethylsulfamoyl)-3-methoxy-7H-indolo[2,1-a][2]benzazepine-10-carboxamide. Yellow solid. LCMS: m/e =716 (M+H)⁺. LCMS retention time: 2.42 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 38

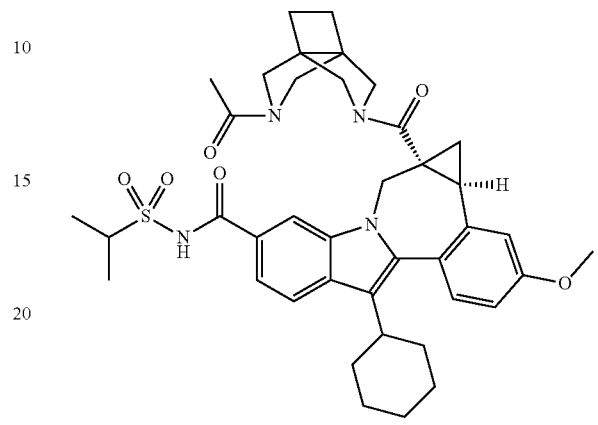

(1aR,12bS)-1a-(((7-acetyl-3,7-diazatricyclo[3.3.2.0~1,5~]dec-3-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide. White solid. LCMS: m/e = 713 (M+H)⁺. LCMS retention time: 2.42 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 39

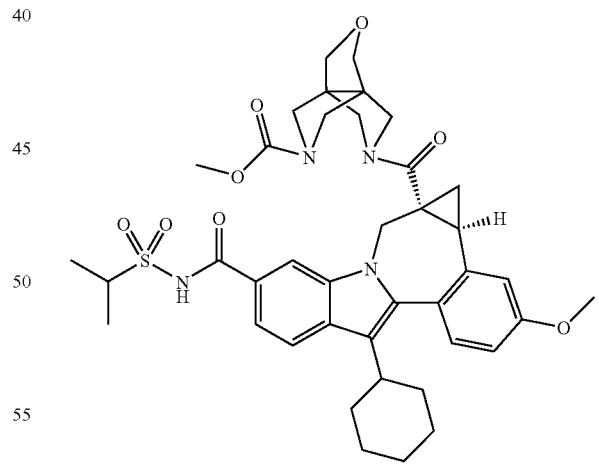

Methyl 10-(((1aR,12bS)-8-cyclohexyl-5-((isopropylsulfonyl)carbamoyl)-11-methoxy-1,12b-dihydrocyclopropa[d]indolo[2,1-a][2]benzazepin-1a(2H)-yl)carbonyl)-3-oxa-7,10-diazatricyclo[3.3.3.0~1,5~]undecane-7-carboxylate. (1aR,12bS)-8-cyclohexyl-N-(isopropylsulfonyl)-11-methoxy-1a-(3-oxa-7,10-diazatricyclo[3.3.3.0~1,5~]undec-7-yl-carbonyl)-1,1a,2,12b-tetrahydrocyclopropa[d]indolo[2,1-a][2]benzazepine-5-carboxamide (example 1B) (45 mg, 0.066 mmol), diisopropyl ethyl amine (0.057 mL, 0.33 mmol), and methyl chloroformate (0.025 mL, 0.33 mmol) were combined in $CH_2Cl_2$ (1 mL) and stirred at r.t. for 1 h. The reaction mixture was then concentrated, dissolved into MeOH, filtered and purified by preparative HPLC ($H_2O$—$CH_3CN$ with 0.1% TFA buffer) to give methyl 10-(((1aR,12bS)-8-cyclohexyl-5-((isopropylsulfonyl)carbamoyl)-11-methoxy-1,12b-dihydrocyclopropa[d]indolo[2,1-a][2]benzazepin-1a(2H)-yl)carbonyl)-3-oxa-7,10-diazatricyclo[3.3.3.0~1,5~]undecane-7-carboxylate (16.2 mg, 0.022 mmol, 33% yield) as a yellow solid. LCMS: m/e=745 (M+H)+. LCMS retention time: 2.53 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate4 mL/min.).

EXAMPLE 40

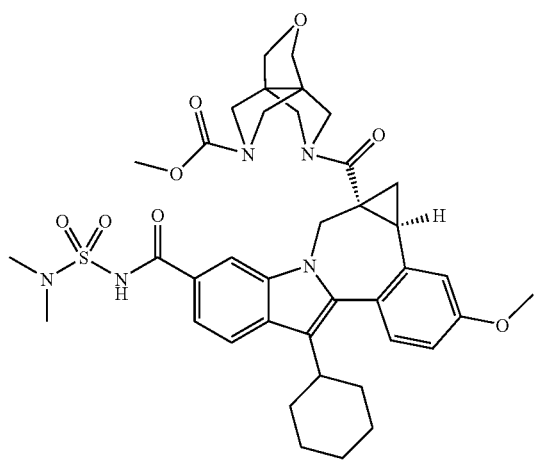

Methyl 10-(((1aR,12bS)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbonyl)-3-oxa-7,10-diazatricyclo[3.3.3.0~1,5~]undecane-7-carboxylate. Prepared as previously described (example 39). White solid. LCMS: m/e=768 (M+Na)+. LCMS retention time: 2.49 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 41

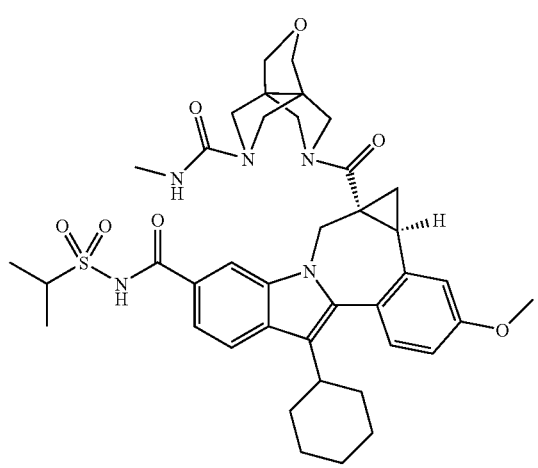

(1aR,12bS)-8-cyclohexyl-N-(isopropylsulfonyl)-11-methoxy-1a-((10-(methylcarbamoyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide. (1aR,12bS)-8-cyclohexyl-N-(isopropylsulfonyl)-11-methoxy-1a-(3-oxa-7,10-diazatricyclo[3.3.3.01,5]undec-7-ylcarbonyl)-1,1a,2,12b-tetrahydrocyclopropa[d]indolo[2,1-a][2]benzazepine-5-carboxamide (example 1B) (35 mg, 0.051 mmol), diisopropyl ethyl amine (0.089 mL, 0.51 mmol), and methylisocyanate (0.030 mL, 0.51 mmol) were combined in $CH_2Cl_2$ (1 mL) and stirred at r.t. for 1 h. The reaction mixture was then concentrated, dissolved into MeOH, filtered and purified by preparative HPLC ($H_2O$—$CH_3CN$ with 0.1% TFA buffer) to give (1aR,12bS)-8-cyclohexyl-N-(isopropylsulfonyl)-11-methoxy-1a-((10-(methylcarbamoyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide (30 mg, 0.040 mmol, 79% yield) as a white solid. LCMS: m/e=744 (M+H)+. LCMS retention time: 2.26 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 42

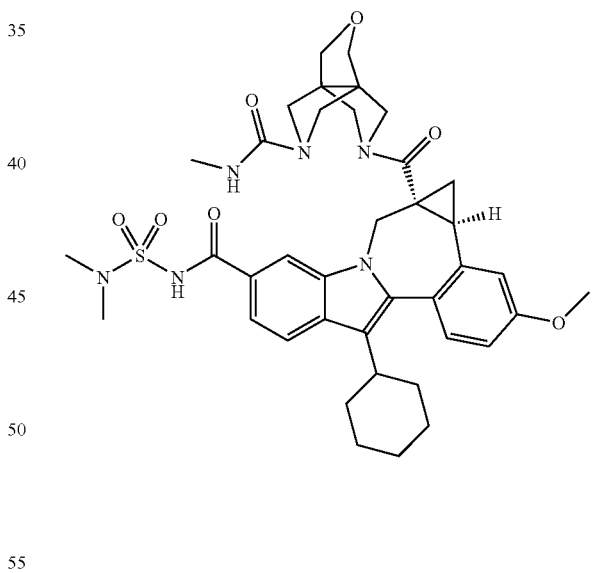

(1aR,12bS)-8-cyclohexyl-N-(dimethylsulfamoyl)-11-methoxy-1a-((10-(methylcarbarnoyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide. Prepared as previously described (example 41). White solid. LCMS: m/e=745 (M+H)+. LCMS retention time: 2.24 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 43

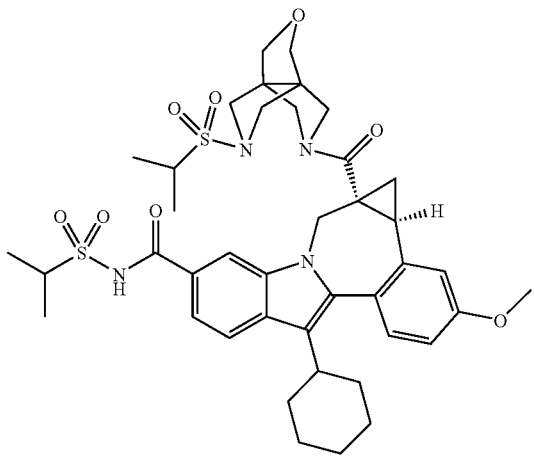

(1aR,12bS)-8-cyclohexyl-N-(isopropylsulfonyl)-1a-((10-(isopropylsulfonyl)-3-oxa-7,10-diazatricyclo[3.3.3.0~1,5~]undec-7-yl)carbonyl)-11-methoxy-1,1a,2,12b-tetrahydrocyclopropa[d]indolo[2,1-a][2]benzazepine-5-carboxamide. (1aR,12bS)-8-cyclohexyl-N-(isopropylsulfonyl)-11-methoxy-1a-(3-oxa-7,10-diazatricyclo[3.3.3.01,5]undec-7-ylcarbonyl)-1,1a,2,12b-tetrahydrocyclopropa[d]indolo[2,1-a][2]benzazepine-5-carboxamide (example 1B) (35 mg, 0.051 mmol), diisopropyl ethyl amine (0.089 mL, 0.51 mmol), and isopropylsulfonyl chloride (0.057 mL, 0.51 mmol) were combined in CH$_2$Cl$_2$ (1 mL) and stirred at r.t. for 1 h. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-N-(isopropylsulfonyl)-1a-((10-(isopropylsulfonyl)-3-oxa-7,10-diazatricyclo[3.3.3.0~1,5~]undec-7-yl)carbonyl)-11-methoxy-1,1a,2,12b-tetrahydrocyclopropa[d]indolo[2,1-a][2]benzazepine-5-carboxamide (23 mg, 0.028 mmol, 56% yield) as a white solid. LCMS: m/e=816 (M+Na)$^+$. LCMS retention time: 2.68 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 44

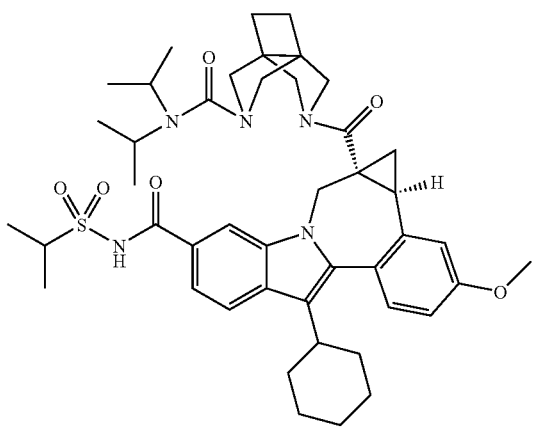

(1aR,12bS)-8-cyclohexyl-1a-((7-(diisopropylcarbamoyl)-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2,1-a][2]benzazepine-5-carboxamide. (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide (example 30) (35 mg, 0.052 mmol), diisopropylcarbamic chloride (34 mg, 0.21 mmol), and diisopropyl ethyl amine (0.046 mL, 0.26 mmol) were combined in CH$_2$Cl$_2$ (1 mL) and allowed to stir at r.t. for 1 h. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-1a-((7-(diisopropylcarbamoyl)-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2,1-a][2]benzazepine-5-carboxamide (19 mg, 0.024 mmol, 46% as a white solid. LCMS: m/e=798(M+H)$^+$. LCMS retention time: 2.13 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 45

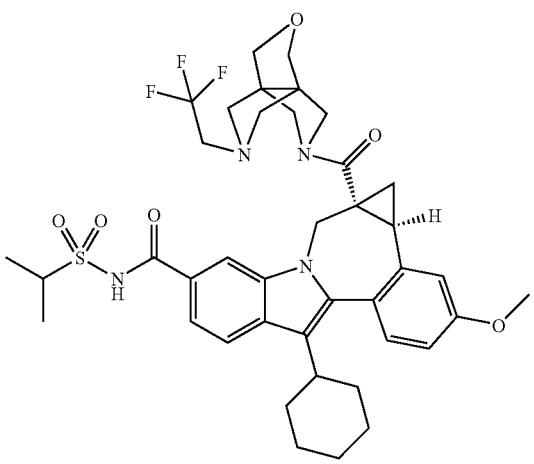

(1aR,12bS)-8-cyclohexyl-N-(isopropylsulfonyl)-11-methoxy-1a-((10-(2,2,2-trifluoroethyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide. (1aR,12bS)-8-cyclohexyl-N-(isopropylsulfonyl)-11-methoxy-1a-(3-oxa-7,10-diazatricyclo[3.3.3.01,5]undec-7-ylcarbonyl)-1,1a,2,12b-tetrahydrocyclopropa[d]indolo[2,1-a][2]benzazepine-5-carboxamide (example 1B) (35 mg, 0.051 mmol), 2-Iodo-1,1,1-trifluoroethane (0.10 mL, 1.0 mmol), and potassium carbonate (35 mg, 0.26 mmol) were combined in acetonitrile (1 mL) and stirred at 100° C. for twelve days. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-N-(isopropylsulfonyl)-11-methoxy-1a-((10-(2,2,2-trifluoroethyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide (23 mg, 0.030 mmol, 59% yield) as a white solid. LCMS: m/e=769 (M+H)$^+$. LCMS retention time: 2.90 min. (Column: SunFire C18 5u 4.6×50 mm. Solvent A=90% Water/10% Acetonitrile/0.1% TFA, Solvent B=10% Water/

EXAMPLE 46

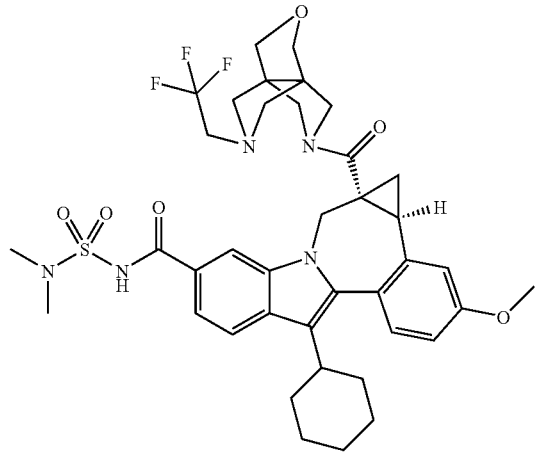

(1aR,12bS)-8-cyclohexyl-N-(dimethylsulfamoyl)-11-methoxy-1a-((10-(2,2,2-trifluoroethyl)-3-oxa-7,10-diazatricyclo[3.3.3.0~1,5~]undec-7-yl)carbonyl)-1,1a,2,12b-tetrahydrocyclopropa[d]indolo[2,1-a][2]benzazepine-5-carboxamide. Prepared as previously described (example 45). White solid. LCMS: m/e=770 (M+H)$^+$. LCMS retention time: 2.90 min, (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 47

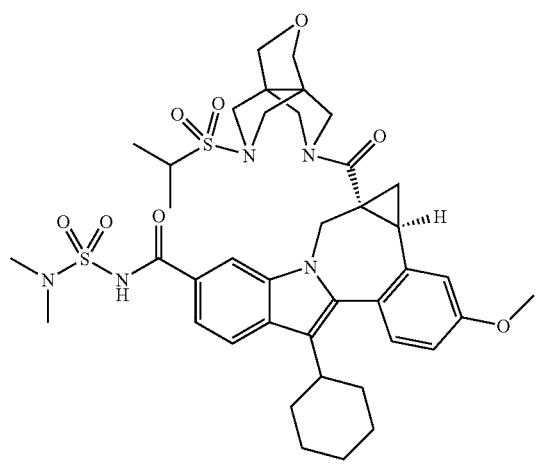

(1aR,12bS)-8-cyclohexyl-N-(dimethylsulfamoyl)-1a-((10-(isopropylsulfonyl)-3-oxa-7,10-diazatricyclo[3.3.3.0~1,5~]undec-7-yl)carbonyl)-11-methoxy-1,1a,2,12b-tetrahydrocyclopropa[d]indolo[2,1-a][2]benzazepine-5-carboxamide. Prepared as previously described (example 43). Tan solid. LCMS: m/e=794 (M+H)$^+$. LCMS retention time: 2.65 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 48

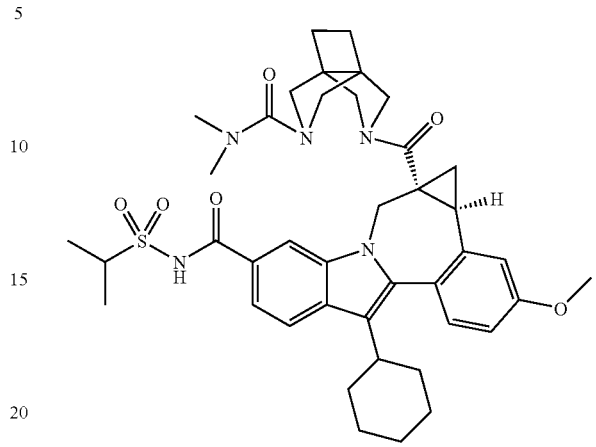

(1aR,12bS)-8-cyclohexyl-1a-((7-(dimethylcarbamoyl)-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2]benzazepine-5-carboxamide. (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide (example 30) (35 mg, 0.052 mmol), dimethylcarbamic chloride (22 mg, 0.21 mmol), and diisopropyl ethyl amine (0.046 mL, 0.26 mmol) were combined in CH$_2$Cl$_2$ (1 mL) and allowed to stir at r.t. for 1 h. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-1a-((7-(dimethylcarbamoyl)-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2,1-a][2]benzazepine-5-carboxamide (25 mg, 0.032 mmol, 62% yield) as a white solid. LCMS: m/e=742 (M+H)$^+$. LCMS retention time: 2.92 min. (Column: SunFire C18 5u 4.6~50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 49

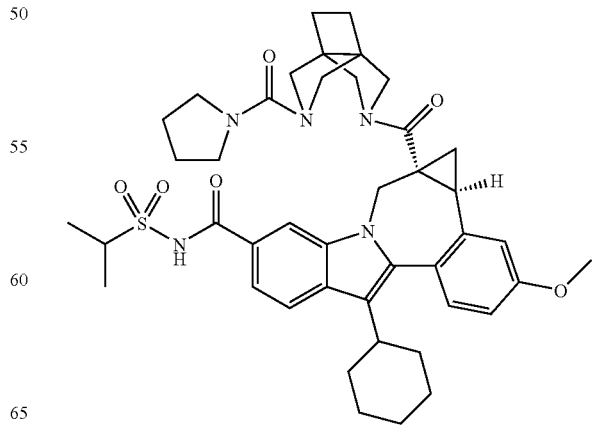

(1aR,12bS)-8-cyclohexyl-N-(isopropylsulfonyl)-11-methoxy-1a-((7-(1-pyrrolidinylcarbonyl)-3,7-diazatricyclo[3.3.2.0~1,5~]dec-3-yl)carbonyl)-1,1a,2,12b-tetrahydrocyclopropa[d]indolo[2]benzazepine-5-carboxamide. (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide (example 30) (35 mg, 0.052 mmol), pyrrolidine-1-carbonyl chloride (7.0 mg, 0.052 mmol), and diisopropyl ethyl amine (0.046 mL, 0.26 mmol) were combined in CH$_2$Cl$_2$ (1 mL) and allowed to stir at r.t. for 1 h. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-N-(isopropylsulfonyl)-11-methoxy-1a-((7-(1-pyrrolidinylcarbonyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide (22 mg, 0.028 mmol, 54% yield) as a white solid. LCMS: m/e=768 (M+H)$^+$. LCMS retention time: 2.20 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 50

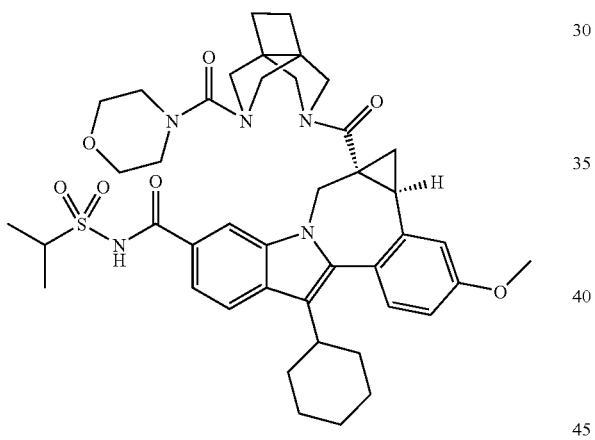

(1aR,12bS)-8-cyclohexyl-N-(isopropylsulfonyl)-11-methoxy-1a-((7-(4-morpholinylcarbonyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide. (1aR,12bS)-8-cyclohexyl-N-(isopropylsulfonyl)-11-methoxy-1a-(tetrahydro-1H,4H-3a,6a-ethanocyclopenta[c]pyrrol-5-ylcarbonyl)-1,1a,2,12b-tetrahydrocyclopropa[d]indolo[2,1-a][2]benzazepine-5-carboxamide (example 30) (35 mg, 0.052 mmol), morpholine-4-carbonyl chloride (31 mg, 0.21 mmol), and diisopropyl ethyl amine (0.046 mL, 0.26 mmol) were combined in CH$_2$Cl$_2$ (1 mL) and allowed to stir at r.t. for 1 h. The reaction mixture was then concentrated, dissolved into MeOH, filtered and purified by preparative HPLC (H$_2$O—CH$_3$CN with 0.1% TFA buffer) to give (1aR,12bS)-8-cyclohexyl-N-(isopropylsulfonyl)-11-methoxy-1a-((7-(4-morpholinylcarbonyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide (36.5 mg, 0.047 mmol, 89% yield) as a white solid. LCMS: m/e=784 (M+H)$^+$. LCMS retention time: 2.89 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 51

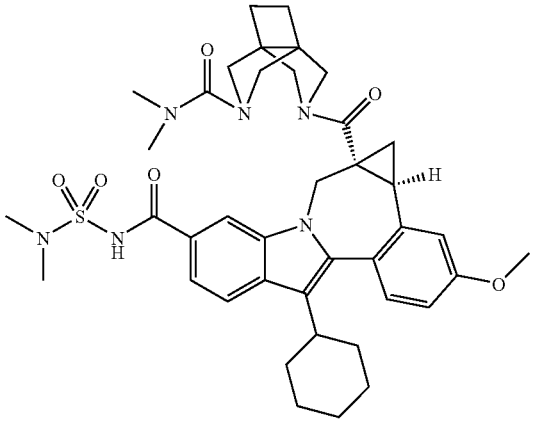

(1aR,12bS)-8-cyclohexyl-1a-((7-(dimethylcarbamoyl)-3,7-diazatricyclo[3.3.2.0~1,5~]dec-3-yl)carbonyl)-N-(dimethylsulfamoyl)-11-methoxy-1,1a,2,12b-tetrahydrocyclopropa[d]indolo[2,1-a][2]benzazepine-5-carboxamide. Prepared as previously described (example 48). White solid. LCMS: m/e=743 (M+H)$^+$. LCMS retention time: 2.20 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 52

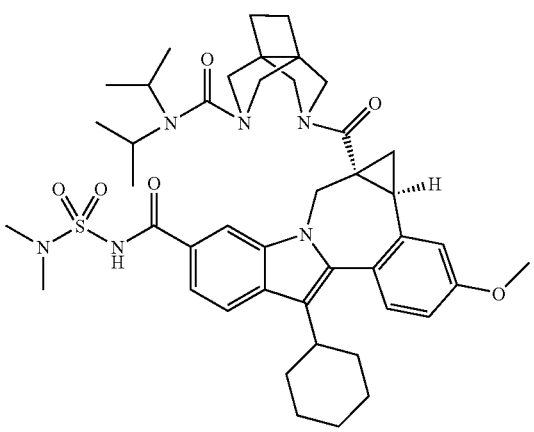

(1aR,12bS)-8-cyclohexyl-1a-((7-(diisopropylcarbamoyl)-3,7-diazatricyclo[3.3.2.0~1,5~]dec-3-yl)carbonyl)-N-(dimethylsulfamoyl)-11-methoxy-1,1a,2,12b-tetrahydrocyclopropa[d]indolo[2,1-a][2]benzazepine-5-carboxamide. Prepared as previously described (example 44). White solid. LCMS: m/e=799 (M+H)$^+$. LCMS retention time: 3.24 min. (Column: SunFire C18 5u 4.6×50 mm. Solvent A=90% Water/10% Acetonitrile/0.1% TFA. Solvent B=10% Water/

90% Acetonitrile/0.1% TFA. Start % B=0. Final % B=100. Gradient Time=3 min. Flow Rate=4 mL/min.).

EXAMPLE 53

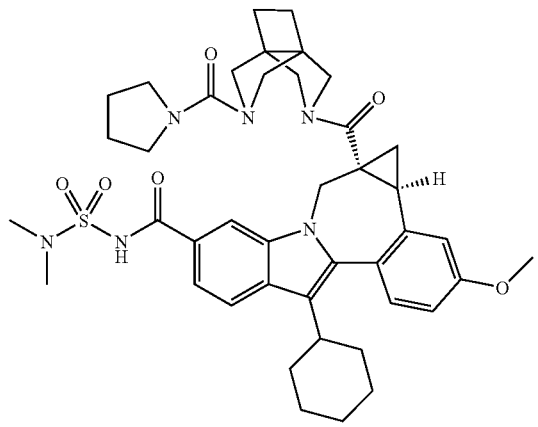

(1aR, 12B)-8-cyclohexyl-N-(dimethylsulfamoyl)-11-methoxy-1a-((7-(1-pyrrolidinylcarbonyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxanzide. Prepared as previously described (example 48). White solid. LCMS: m/e=769 (M+H)+. LCMS retention time: 2.80 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 54

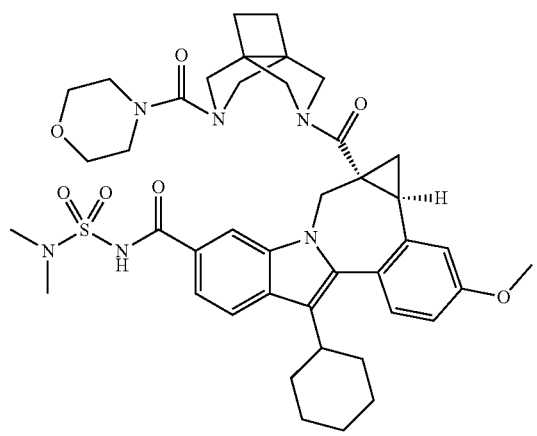

(1aR,12bS)-8-cyclohexyl-N-(dimethylsulfamoyl)-11-methoxy-1a-((7-(4-morpholinylcarbonyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide. Prepared as previously described (example 49). White solid. LCMS: m/e=785 (M+H)+. LCMS retention time: 2.60 min. (Column: SunFire C18 5u 4.6×50 mm. Solvent A=90% Water/10% Acetonitrile/0.1% TFA. Solvent B=10% Water/

90% Acetonitrile/0.1% TFA. Start % B=0. Final % B=100. Gradient Time=3 min. Flow Rate=4 mL/min.).

EXAMPLE 55

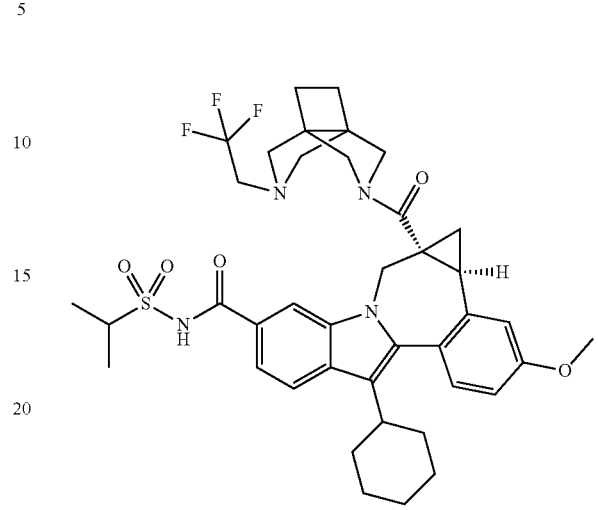

(1aR,12bS)-8-cyclohexyl-N-(isopropylsulfonyl)-11-methoxy-1a-((7-(2,2,2-trifluoroethyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide. Prepared as previously described (example 45). White solid. LCMS: m/e=753 (M+H)+. LCMS retention time: 2.89 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 56

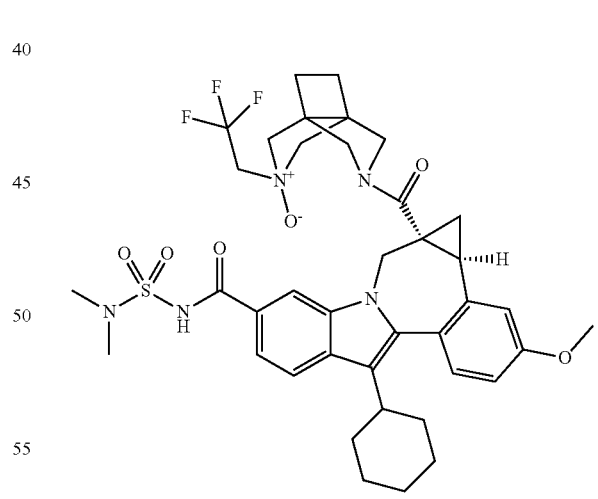

(1aR,12bS)-8-cyclohexyl-N-(dimethylsulfamoyl)-11-methoxy-1a-((7-oxido-7-(2,2,2-trifluoroethyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide. Prepared as previously described (example 45) (oxidation note: concomitant oxidation to N-oxide). Off-white solid. LCMS: m/e=770 (M+H)+. LCMS retention time: 2.05 min. (Column: SunFire C18 5u 4.6×50 mm. Solvent A=90% Water/10% Acetonitrile/0.1% TFA. Solvent B=10% Water/

90% Acetonitrile/0.1% TFA. Start % B=0. Final % B=100. Gradient Time=3 min. Flow Rate=4 mL/min.).

EXAMPLE 57

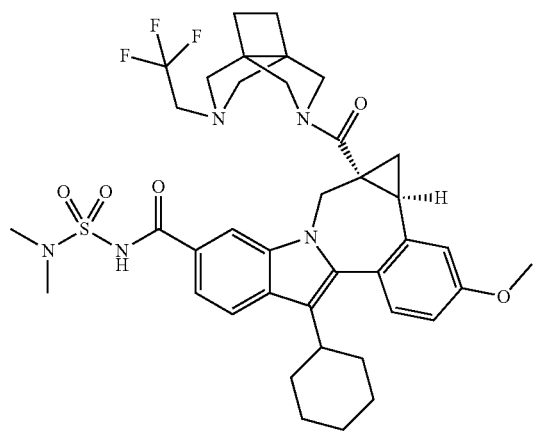

(1aR,12bS)-8-cyclohexyl-N-(dimethylsulfamoyl)-11-methoxy-1a-((7-(2,2,2-trifluoroethyl)-3,7-diazatricyclo[3.3.2.0~1,5~]dec-3-yl)carbonyl)-1,1a,2,12b-tetrahydrocyclopropa[d]indolo[2,1-a]benzazepine-5-carboxamide. Prepared as previously described (example 45). Off-white solid. LCMS: m/e=776 (M+Na)+. LCMS retention time: 2.79 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 58

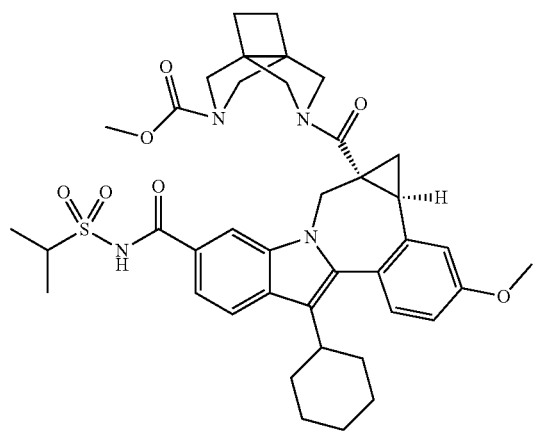

Methyl 7-(((1aR,12bS)-8-cyclohexyl-5-((isopropylsulfonyl)carbamoyl)-11-methoxy-1,12b-dihydrocyclopropa[d]indolo[2,1-a][2]benzazepin-1a(2H)-yl)carbonyl)-3,7-diazatricyclo[3.3.2.0~1,5~]decane-3-carboxylate. Prepared as previously described (example 39). Yellow solid. LCMS: m/e=729 (M+H)+. LCMS retention time: 2.66 min. (Column: SunFire C18 5u 4.6×50 mm. Solvent A=90% Water/10% Acetonitrile/

0.1% TFA. Solvent B=10% Water/90% Acetonitrile/0.1% TFA. Start % B=0. Final % B=100. Gradient Time=3 min. Flow Rate=4 mL/min.).

EXAMPLE 59

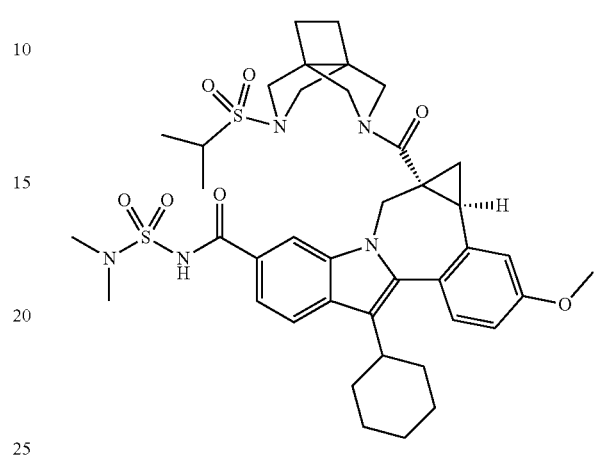

(1aR,12bS)-8-cyclohexyl-N-(dimethylsulfamoyl)-1a-((7-(isopropylsulfonyl)-3,7-diazatrieyelo[3.3.2.0~1,5~]dec-3-yl)carbonyl)-11-methoxy-1,1a,2,12b-tetrahydrocyclopropa[d]indolo[2,1-a][2]benzazepine-5-carboxamide. Prepared as previously described (example 43). White solid. LCMS: m/e=778 (M+H)+. LCMS retention time: 2.79 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 60

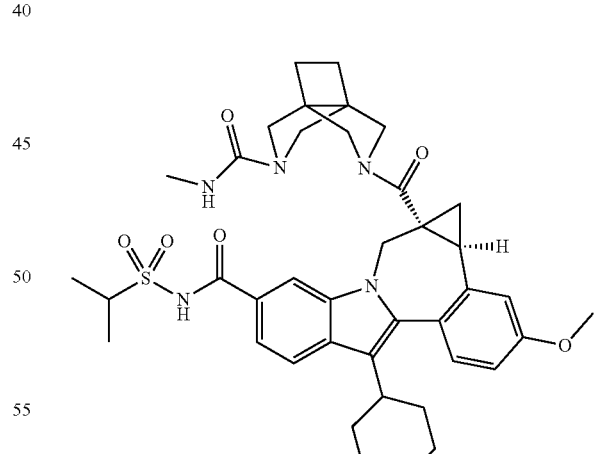

(1aR,12bS)-8-cyclohexyl-N-(isopropylsulfonyl)-11-methoxy-1a-((7-(methylcarbamoyl)-3,7-diazatricyclo[3.3.2.0~1,5~]dec-3-yl)carbonyl)-1,1a,2,12b-tetrahydrocyclopropa[d]indolo[2,1-a][2]benzazepine-5-carboxamide. Prepared as previously described (example 41). White solid. LCMS: m/e=728 (M+H)+. LCMS retention time: 2.14 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 61

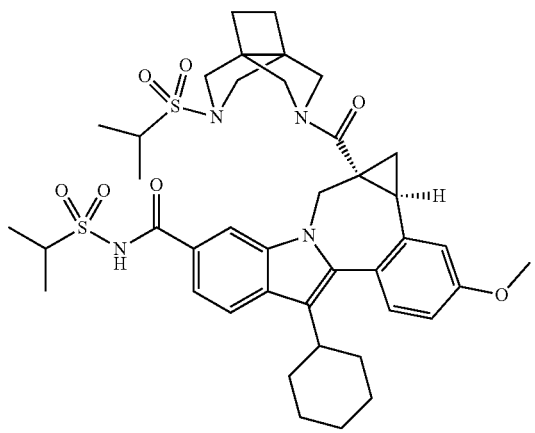

(1aR,12bS)-8-cyclohexyl-N-(isopropylsulfonyl)-1a-((7-(isopropylsulfonyl)-3,7-diazatricyclo[3.3.2.0~1,5~]dec-3-yl)carbonyl)-11-methoxy-1,1a,2,12b-tetrahydrocyclopropa[d]indolo[2,1-a][2]benzazepine-5-carboxamide. Prepared as previously described (example 43). Yellow solid. LCMS: m/e=779 (M+H)⁺. LCMS retention time: 2.84 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 62

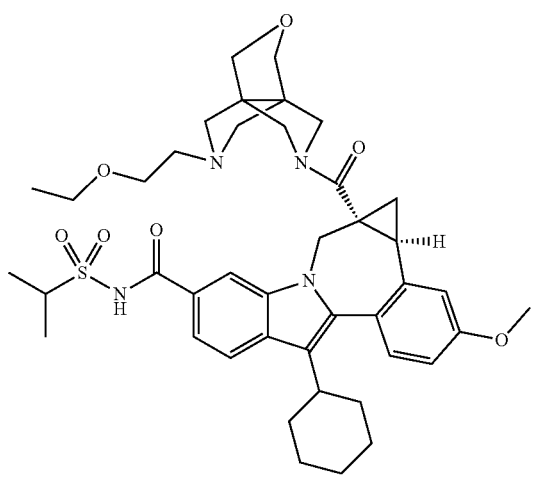

(1aR,12bS)-8-cyclohexyl-1a-((10-(2-ethoxyethyl)-3-oxa-7,10-diazatricyclo[3.3.3.0~1,5~]undec-7-yl)carbonyl)-N-(isopropylsulfonyl)-11-methoxy-1,1a,2,12b-tetrahydrocyclopropa[d]indolo[2,1-a][2]benzazepine-5-carboxamide. K₂CO₃ (10 mg, 0.073 mmol) was added to a solution of (1aR,12bS)-8-cyclohexyl-N-(isopropylsulfonyl)-11-meth-oxy-1a-(3-oxa-7,10-diazatricyclo[3.3.3.01,5]undec-7-ylcarbonyl)-1,1a,2,12b-tetrahydrocyclopropa[d]indolo[2,1-a][2]enzazepine-5-carboxamide (example 1B) (10 mg, 0.015 mmol) and 1-chloro-2-ethoxyethane (158 mg, 1.46 mmol) in DMF (1 mL). The resulting mixture was allowed to stir at r.t for 12 hours. LCMS showed no remaining starting material. The reaction mixture was then diluted with MeOH, filtered and purified by preparative HPLC (H₂O—CH₃CN with 0.1% TFA buffer) to give (1aR,12bS)-8-cyclohexyl-1a-((10-(2-ethoxyethyl)-3-oxa-7,10-diazatricyclo[3.3.3.0~1,5~]undec-7-yl)carbonyl)-N-(isopropylsulfonyl)-11-methoxy-1,1a,2,12b-tetrahydrocyclopropa[d]indolo[2,1-a][2]benzazepine-5-carboxamide (9.0 mg, 0.012 mmol, 81% yield).as a white solid. LCMS: m/e=759(M+H)⁺. LCMS retention time: 2.27 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.) Presents as a 2:1 ratio of rotamers or atrope isomers—reporting partial data (aromatic reagion)—aliphatic reagion presents as a multiple multiplets. ¹H NMR (400 MHz, CHLOROFORM-d) δ ppm 7.98 (1H, s), 7.88 (1H, m), 7.53 (0.67H, m), 7.26-7.35 (1.67H, m), 7.13 (1H, s), 7.05-7.11 (0.33H, m), 6.94-7.01 (1H, m), 6.89-6.94 (0.33H, m), 1.13-5.27 (44H), 3.91 (3H, s).

EXAMPLE 63

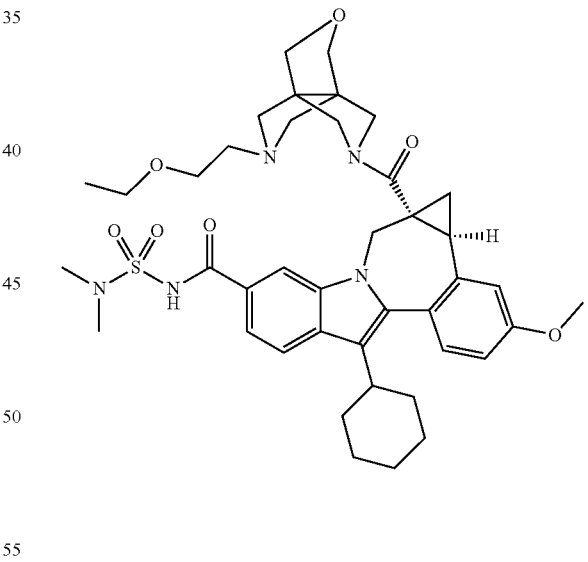

(1aR,12bS)-8-cyclohexyl-N-(dimethylsulfamoyl)-1a-((10-(2-ethoxyethyl)-3-oxa-7,10-diazatricyclo[3.3.3.0~1,5~]undec-7-yl)carbonyl)-11-methoxy-1,1a,2,12b-tetrahydrocyclopropa[d]indolo[2,1-a][2]benzazepine-5-carboxamide. Prepared as previously described (example 62). White solid. LCMS: m/e=760 (M+H)⁺. LCMS retention time: 2.22 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 64

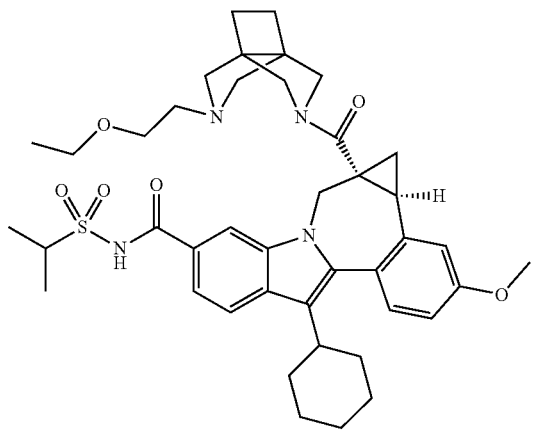

(1aR,12bS)-8-cyclohexyl-1a-((7-(2-ethoxyethyl)-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2,1-a][2]benzazepine-5-carboxamide. Prepared as previously described (example 62). White solid. LCMS: m/e=743 (M+H)$^+$. LCMS retention time: 2.03 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 66

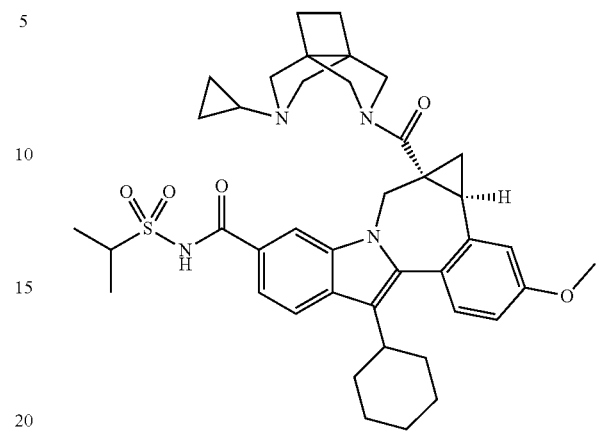

(1aR,12bS)-8-cyclahexyl-1a-((7-cyclopropyl-3,7-diazatricyclo[3.3.2.0~1,5~]dec-3-yl)carbonyl)-N-(dimethylsulfamoyl)-11-methoxy-1,1a,2,12b-tetrahydrocyclopropa[d]indolo[2]benzazepine-5-carboxamide. Prepared as previously described (example 29B). White solid. LCMS: m/e=711 (M+H)$^+$. LCMS retention time: 2.00 min. (Column: SunFire C18 5u 4.6×50 mm. Solvent A=90% Water/10% Acetonitrile/ 0.1% TFA. Solvent B=10% Water/90% Acetonitrile/0.1% TFA. Start % B=0. Final % B=100. Gradient Time=3 min. Flow Rate=4 mL/min.).

EXAMPLE 65

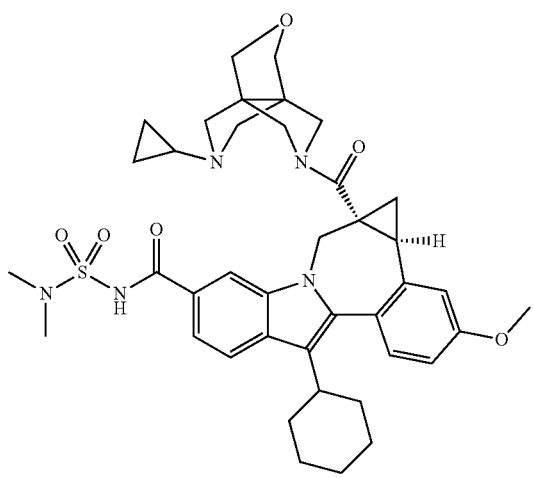

(1aR,12bS)-8-cyclohexyl-1a-((10-cyclopropyl-3-oxa-7,10-diazatricyclo[3.3.3.0~1,5~]undee-7-yl)carbonyl)-N-(dimethylsulfamoyl)-11-methoxy-1,1a,2,12b-tetrahydrocyclopropa[d]indolo[2,1-a][2]benzazepine-5-carboxamide. Prepared as previously described (example 29B). White solid. LCMS: m/e=728 (M+H)$^+$. LCMS retention time:2.97 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

EXAMPLE 67

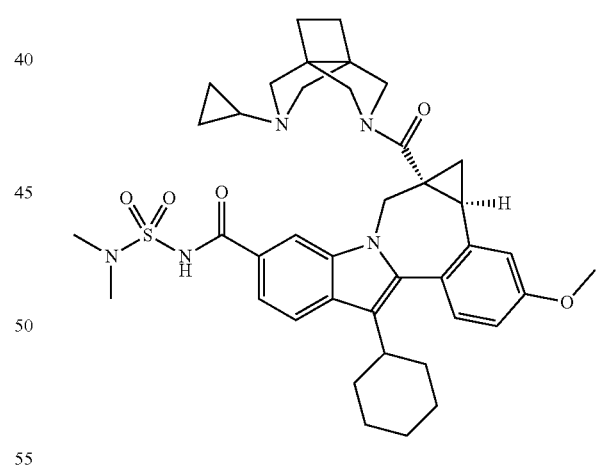

(1aR,12bS)-8-cyclohexyl-1a-((7-cyclopropyl-3,7-diazatricyclo[3.3.2.0~1,5~]dec-3-yl)carbonyl)-N-(isopropylsulfonyl)-11-methoxy-1,1a,2,12b-tetrahydrocyclopropa[d]indolo[2,1-a][2]benzazepine-5-carboxamide, Prepared as previously described (example 29B). White solid. LCMS: m/e=712 (M+H)$^+$. LCMS retention time: 1.99 min. (Column: SunFire C18 5u 4.6×50 mm. Solvent A=90% Water/10% Acetonitrile/0.1% TFA. Solvent B=10% Water/90% Acetonitrile/0.1% TFA. Start % B=0. Final % B=100. Gradient Time=3 min. Flow Rate=4 mL/min.).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

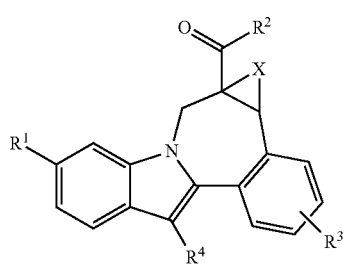

where:
$R^1$ is $CO_2R^5$ or $CONR^6R^7$;
$R^2$ is

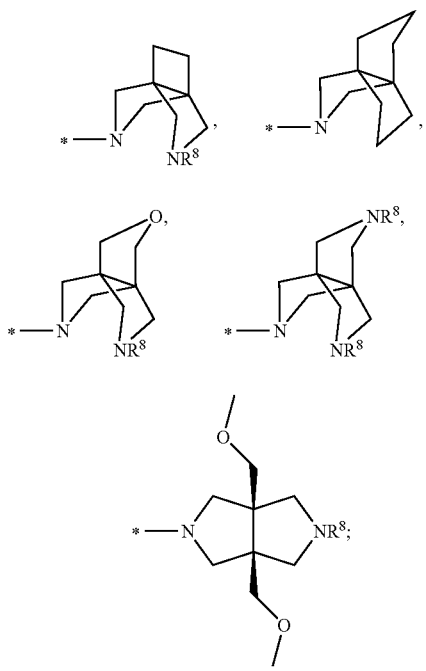

$R^3$ is hydrogen, halo, alkyl, alkenyl, hydroxy, benzyloxy, alkoxy, or haloalkoxy;
$R^4$ is cycloalkyl;
$R^5$ is hydrogen or alkyl;
$R^6$ is hydrogen, alkyl, alkylSO$_2$, alkenylSO$_2$, cycloalkylSO$_2$, haloalkylSO$_2$, $(R^9)_2NSO_2$, or $(R^{10})SO_2$;
$R^7$ is hydrogen or alkyl;
$R^8$ is hydrogen, alkyl, cycloalkyl, (cycloalkyl)alkyl, haloalkyl, alkoxyalkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, $(R^{11})CO$, benzyl, benzyloxycarbonyl, or pyridinyl;
$R^9$ is hydrogen, alkyl, or cycloalkyl;
$R^{10}$ is azetidinyl, pyrrolidinyl, piperidinyl, piperazinyl, morpholinyl, thiomorpholinyl, homopiperidinyl, or homomorpholinyl and is substituted with 0-3 alkyl substituents;
$R^{11}$ is azetidinyl, pyrrolidinyl, piperidinyl, piperazinyl, morpholinyl, thiomorpholinyl, homopiperidinyl, or homomorpholinyl and is substituted with 0-3 alkyl substituents; and
X is absent, a bond, or methylene;
or a pharmaceutically acceptable salt thereof.

2. A compound of claim 1 where
$R^1$ is $CONR^6R^7$;
$R^2$ is

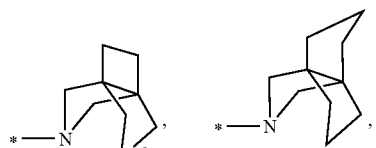

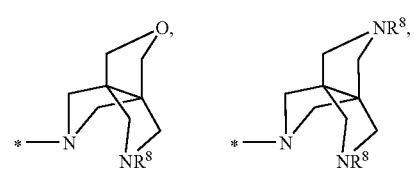

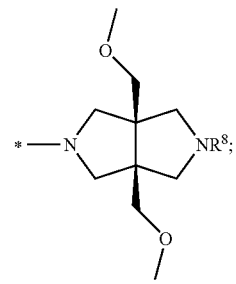

$R^3$ is alkoxy;
$R^4$ is cycloalkyl;
$R^6$ is alkylSO$_2$, alkenylSO$_2$, cycloalkylSO$_2$, or $(R^9)_2NSO_2$;
$R^7$ is hydrogen;
$R^8$ is hydrogen, alkyl, cycloalkyl, haloalkyl, alkoxyalkyl, alkylcarbonyl, alkoxycarbonyl, alkylSO$_2$, aminocarbonyl, (alkylamino)carbonyl, (dialkylamino)carbonyl, or $(R^{11})CO$;
$R^9$ is alkyl; and
X is absent, a bond, or methylene;
or a pharmaceutically acceptable salt thereof.

3. A compound of claim 2 where
$R^1$ is $CONR^6R^7$;

$R^2$ is

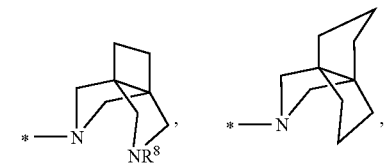

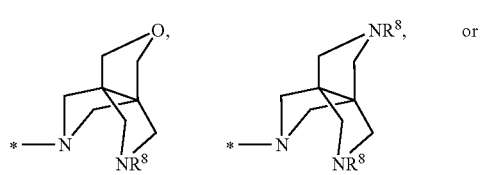

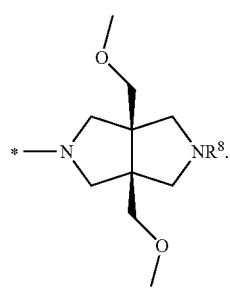

$R^3$ is methoxy;

$R^4$ is cyclohexyl;

$R^6$ is isopropylSO$_2$, isobutylSO$_2$, isopropenylSO$_2$, cyclopropylSO$_2$, or (Me)$_2$NSO$_2$;

$R^7$ is hydrogen; and $R^8$ is hydrogen, methyl, ethyl, cyclopropyl, trifluoroethyl, ethoxyethyl, acetyl, methoxycarbonyl, isopropylSO$_2$, (methylamino)carbonyl, (dimethylamino)carbonyl, (diisopropylamino)carbonyl, (pyrrolidinyl)CO, or (morpholinyl)CO; and X is absent, a bond, or methylene;

or a pharmaceutically acceptable salt thereof.

4. A compound of claim 1 where $R^1$ is CONR$^6$R$^7$.

5. A compound of claim 1 where $R^3$ is hydrogen, halo, or alkoxy.

6. A compound of claim 1 where $R^6$ is alkylSO$_2$, alkenylSO$_2$, cycloalkylSO$_2$, haloalkylSO$_2$, (R$^9$)$_2$NSO$_2$, or(R$^{10}$)SO$_2$ and $R^7$ is hydrogen or alkyl.

7. A compound of claim 1 where $R^8$ is hydrogen, alkyl, cycloalkyl, (cycloalkyl)alkyl, haloalkyl, alkoxyalkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, (R$^{11}$)CO, benzyl, benzyloxycarbonyl, or pyridinyl.

8. A compound of claim 1 where X is absent.

9. A compound of claim 1 where X is a bond.

10. A compound of claim 1 where X is methylene.

11. A compound of claim 1 selected from the group consisting of

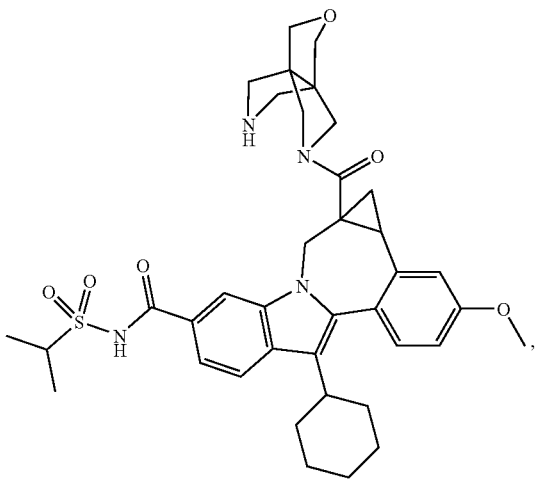

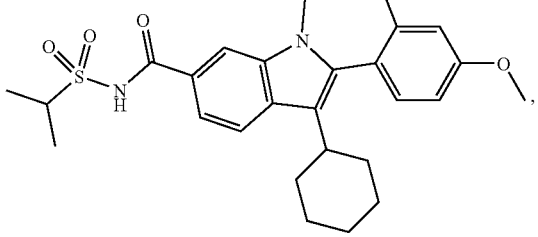

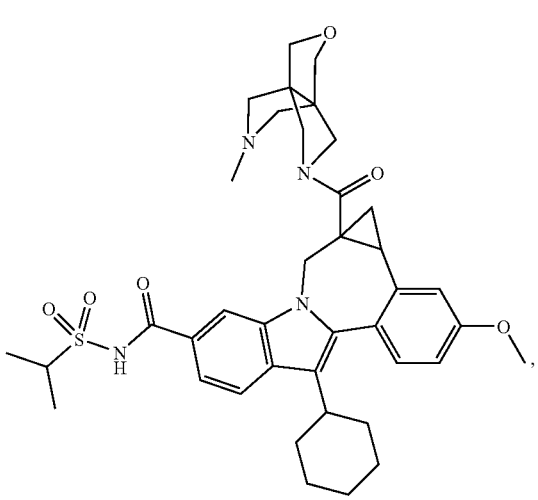

175
-continued
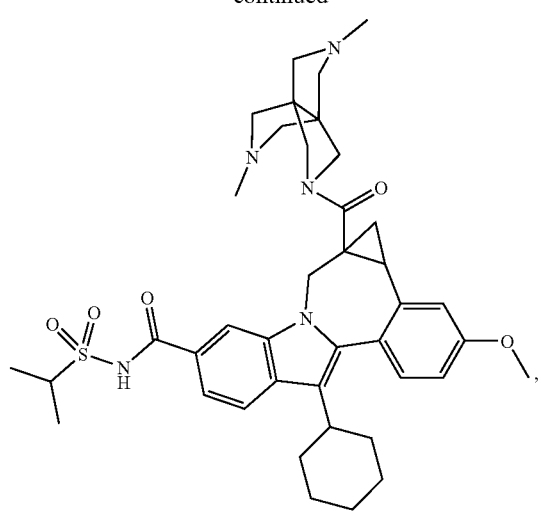
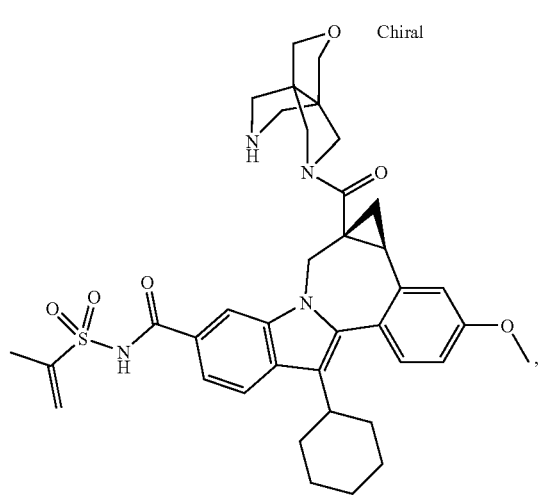
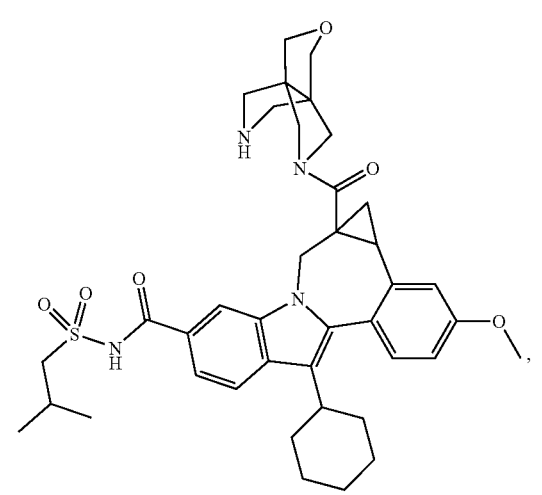
176
-continued
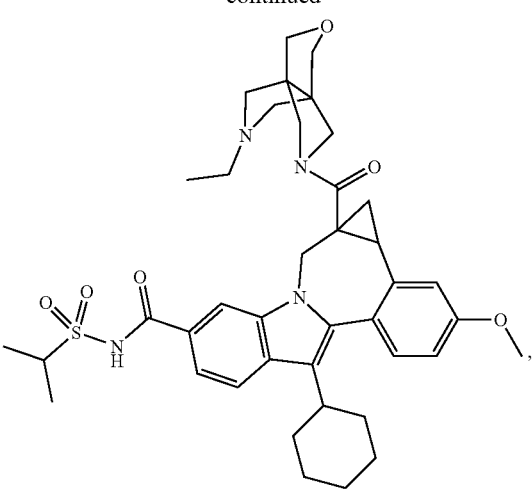
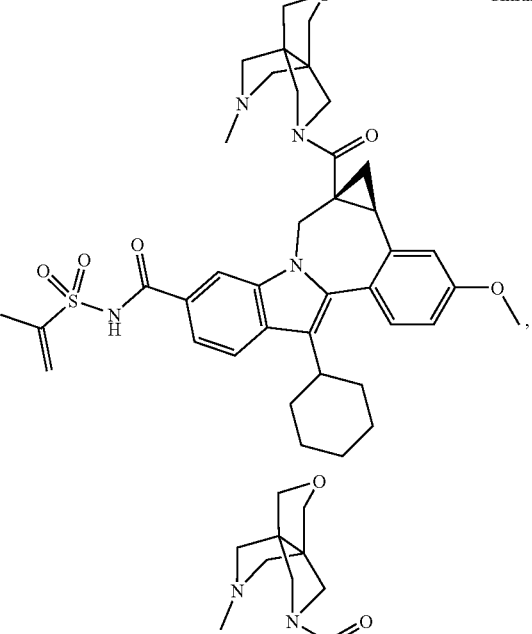
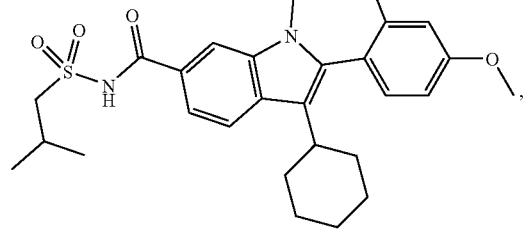

177
-continued
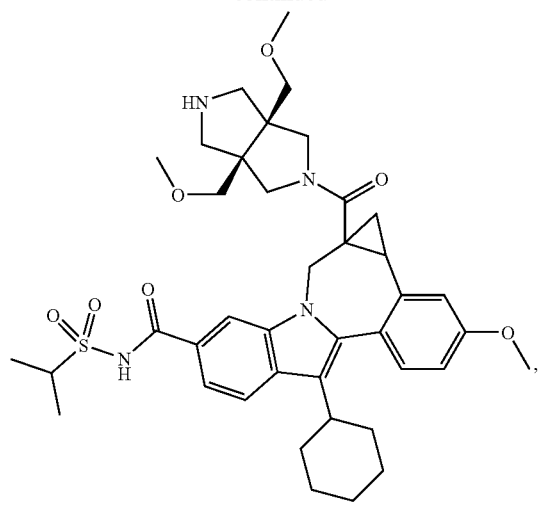
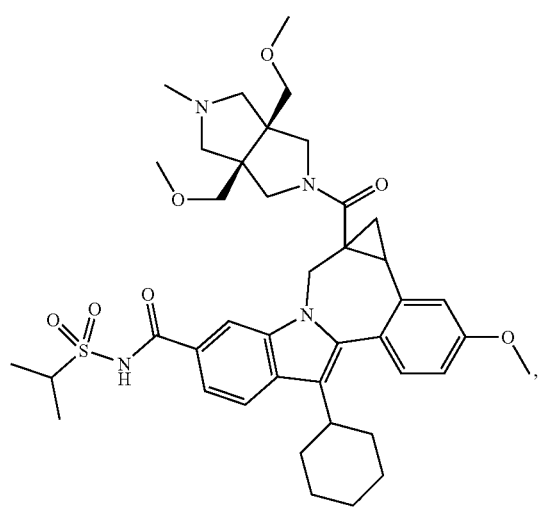
178
-continued
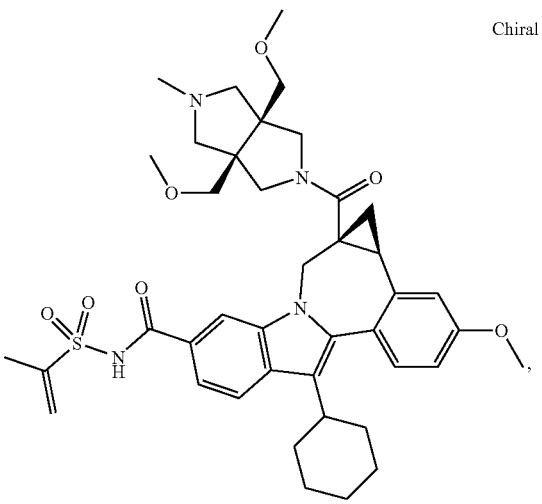
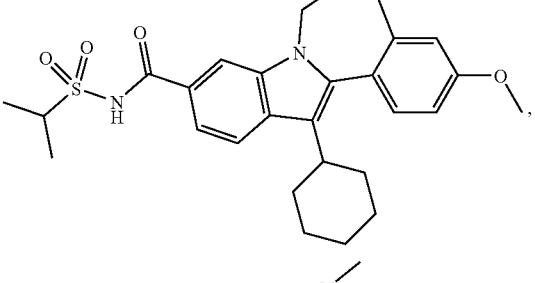
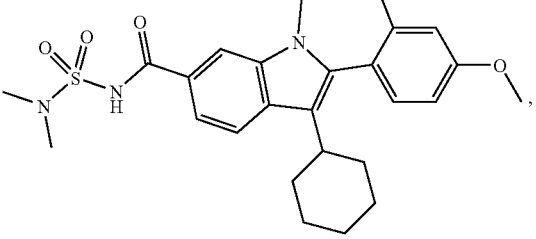

| 179 | 180 |
|---|---|
| -continued | -continued |
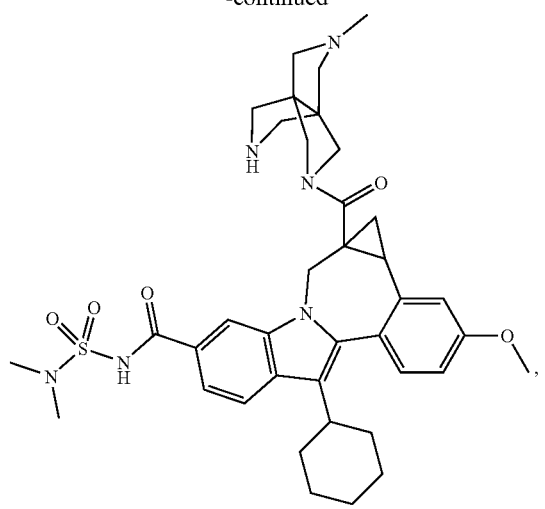
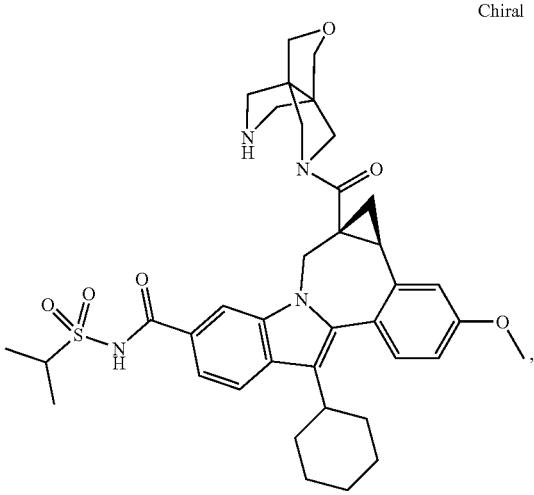
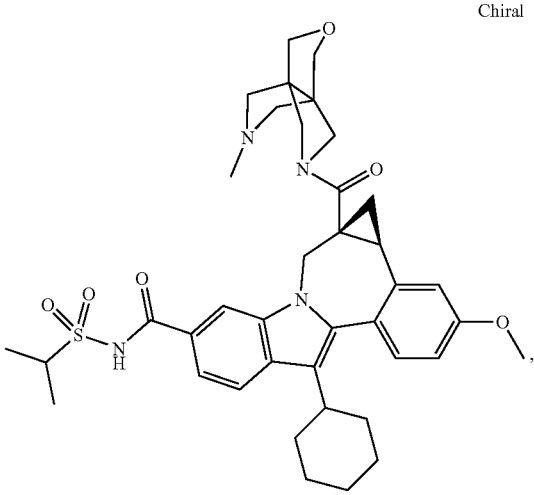
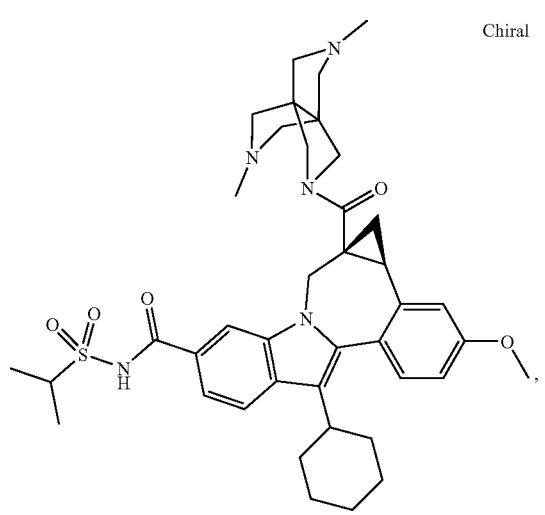
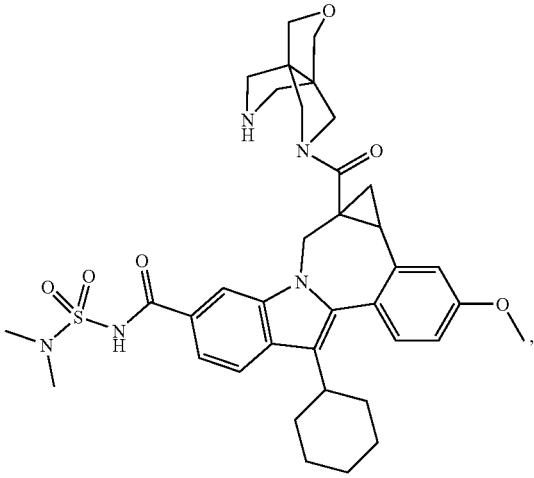

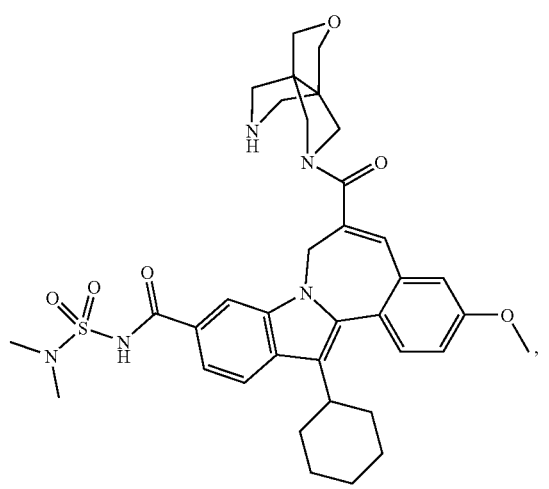
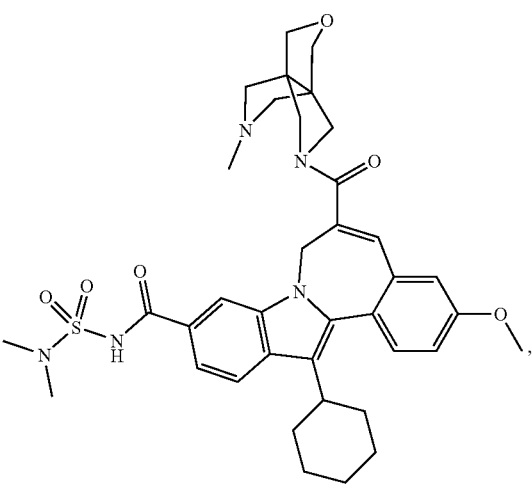

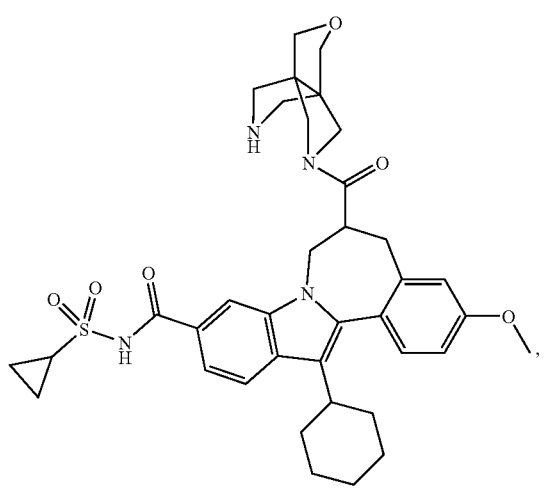
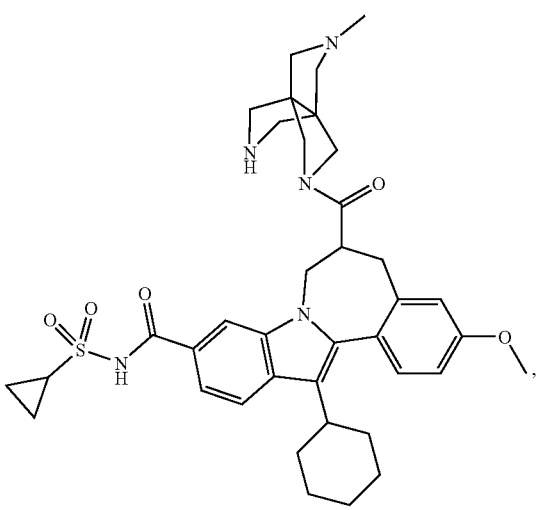
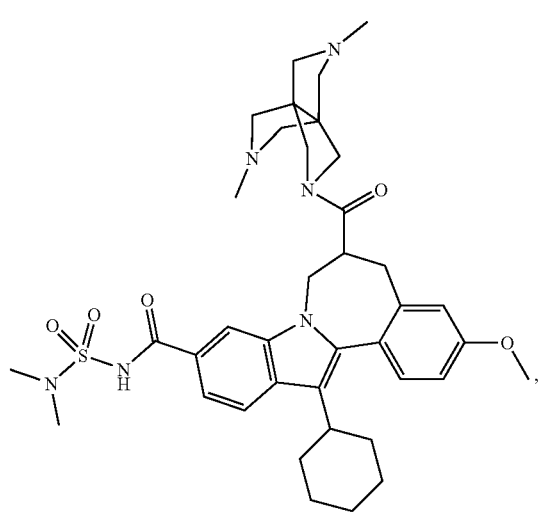
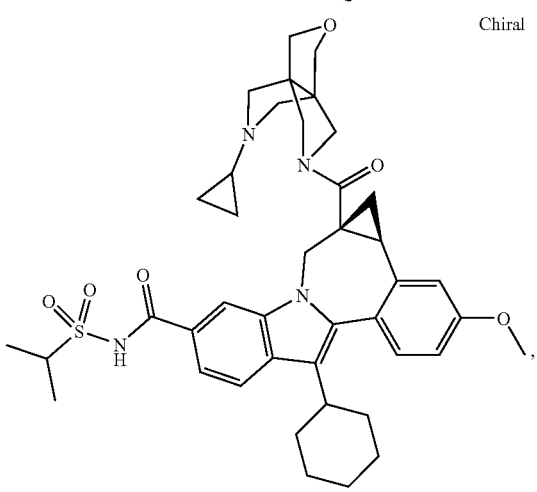
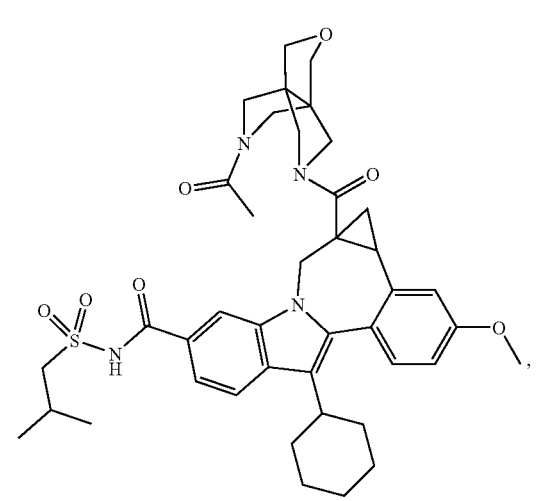

-continued
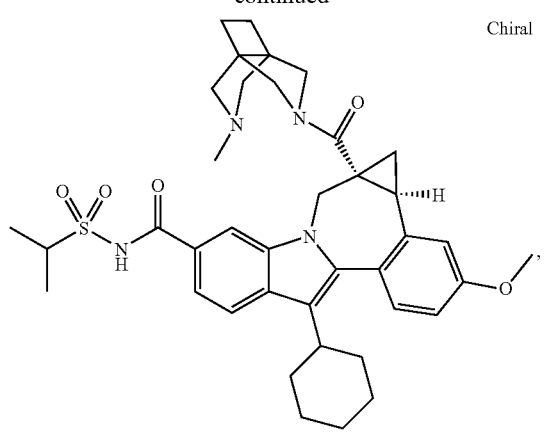
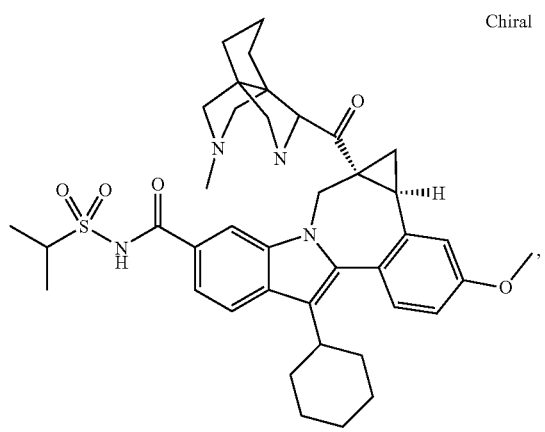
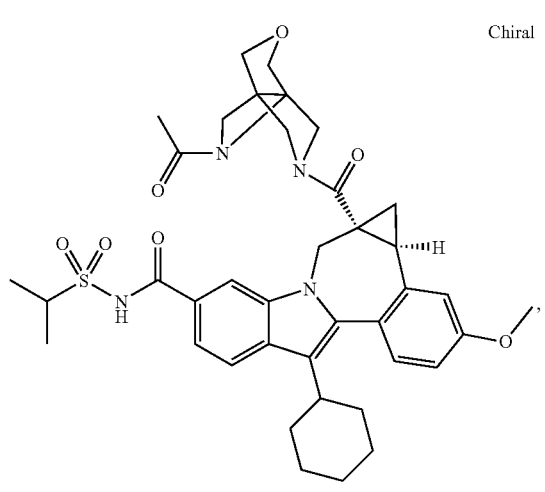
-continued
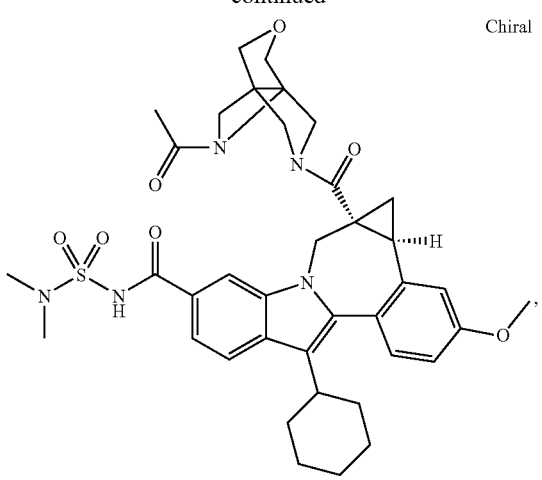
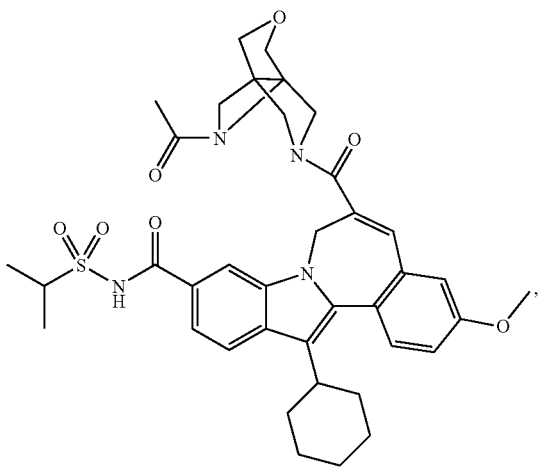
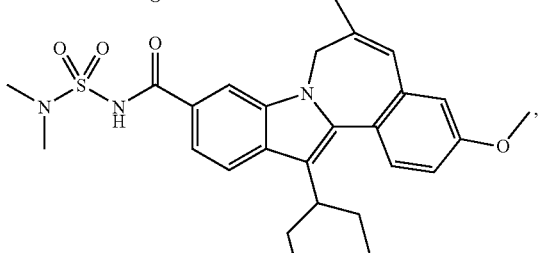

187
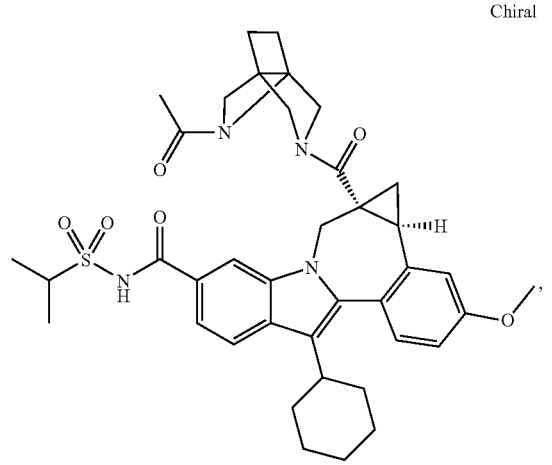
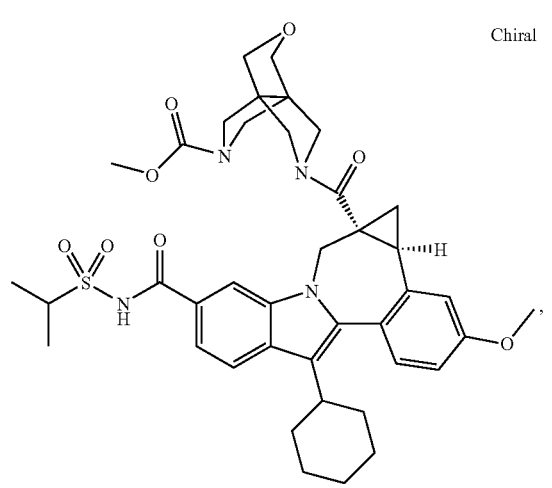
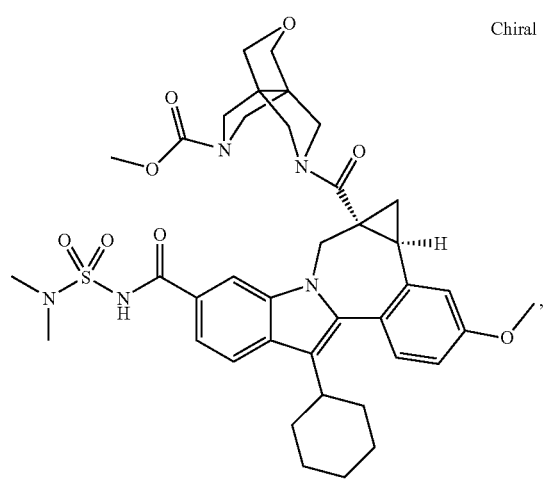
188
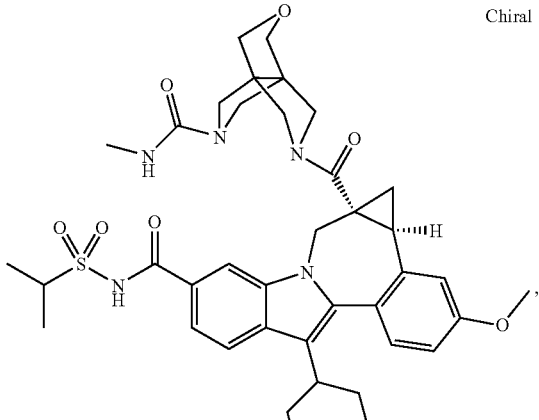
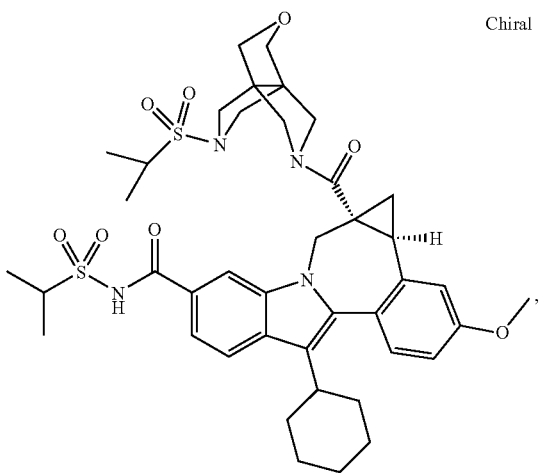

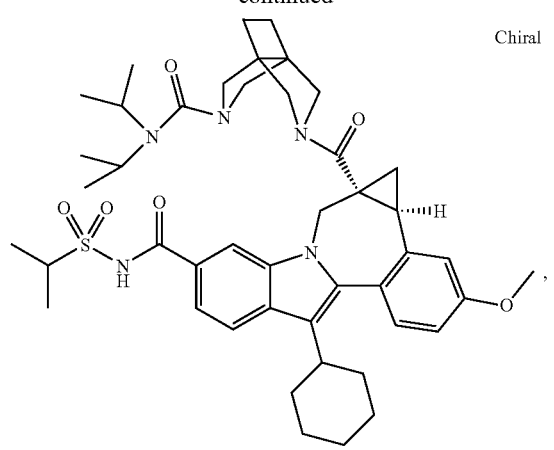
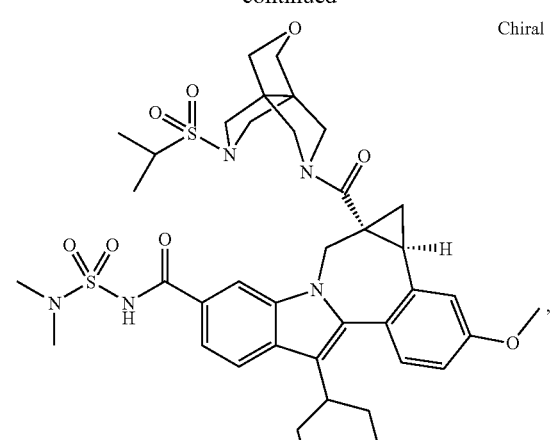
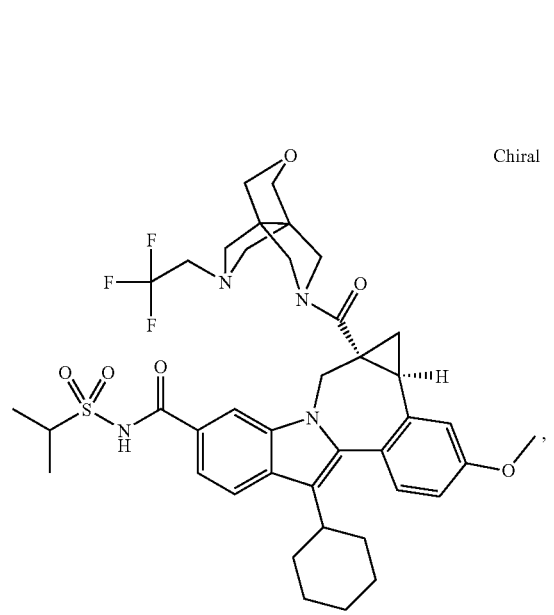
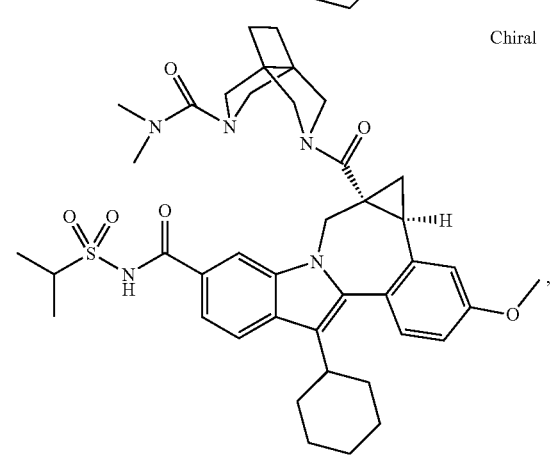
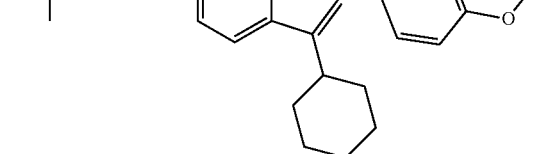
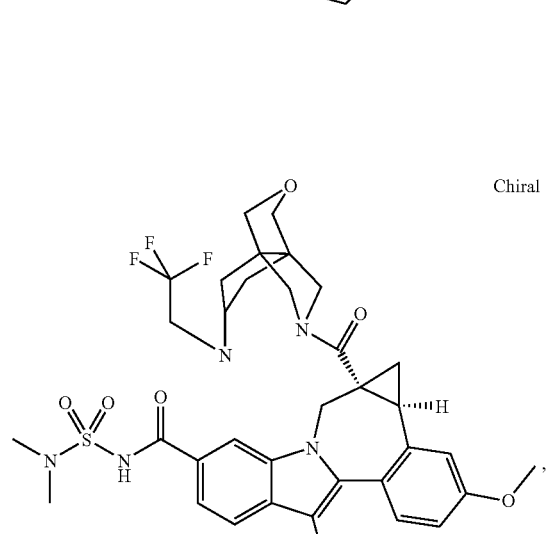

191
-continued
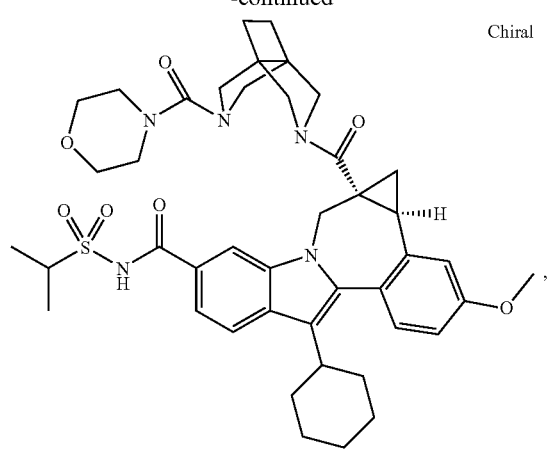
Chiral
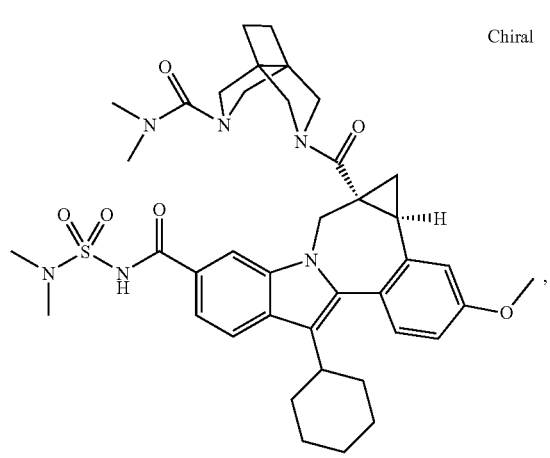
Chiral
192
-continued
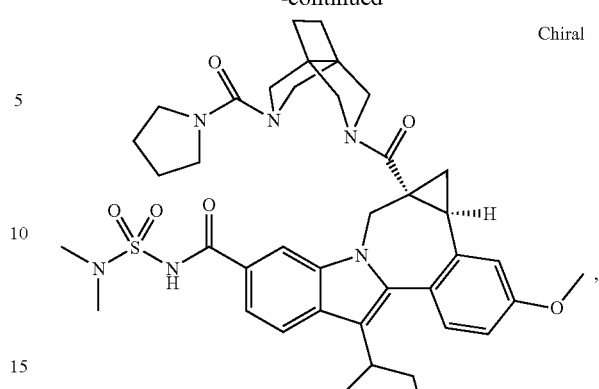
Chiral
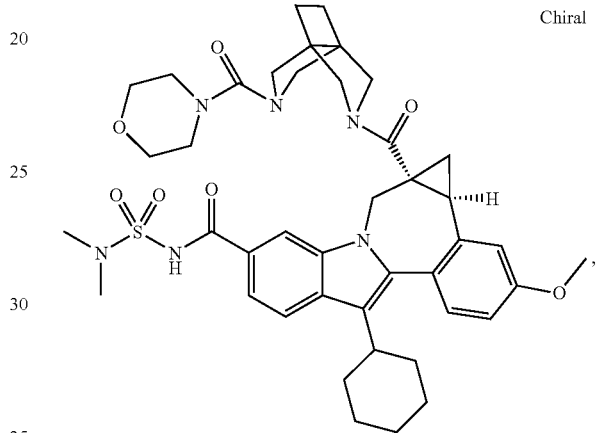
Chiral
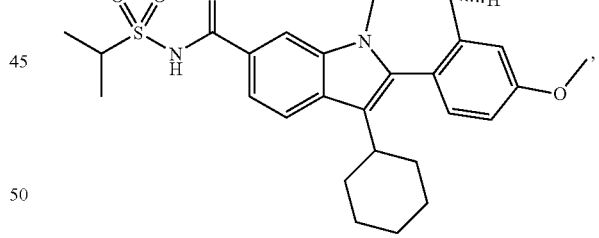
Chiral 193
-continued
194
-continued
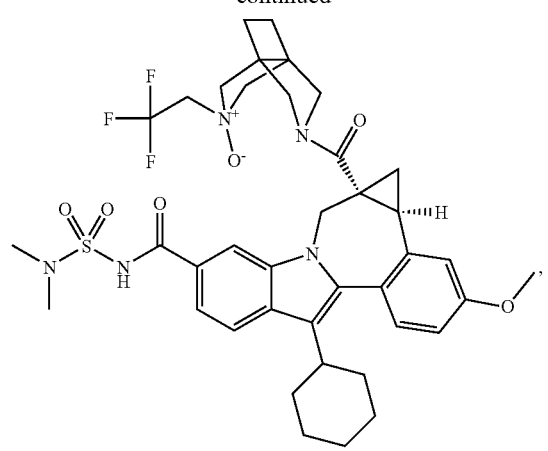
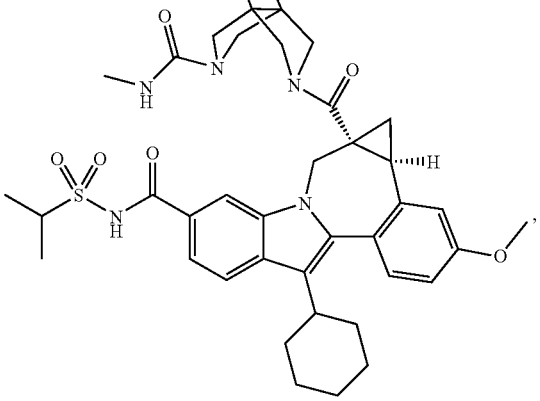
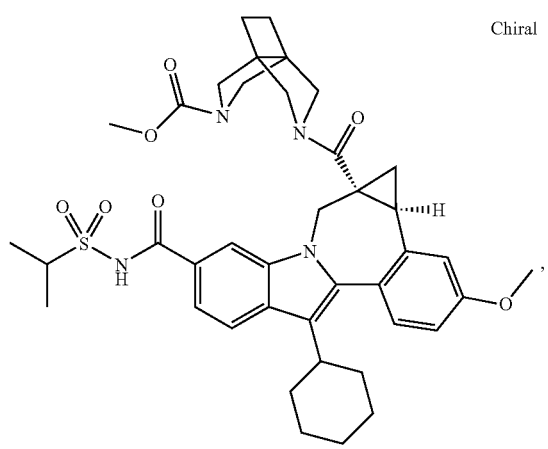
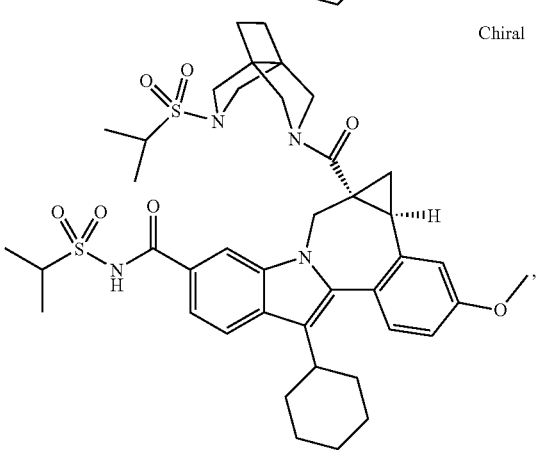
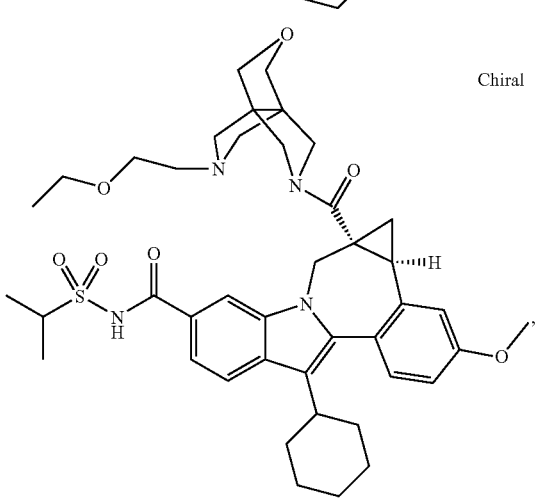
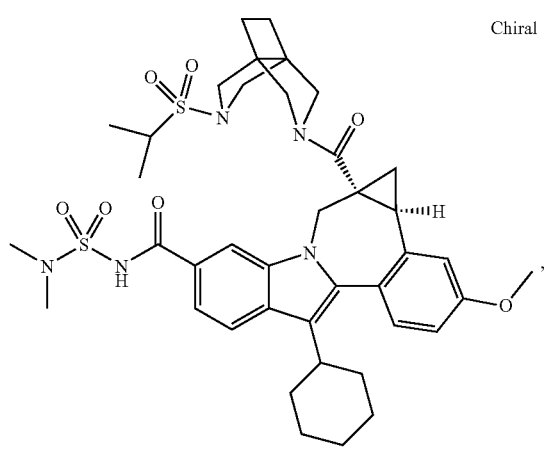

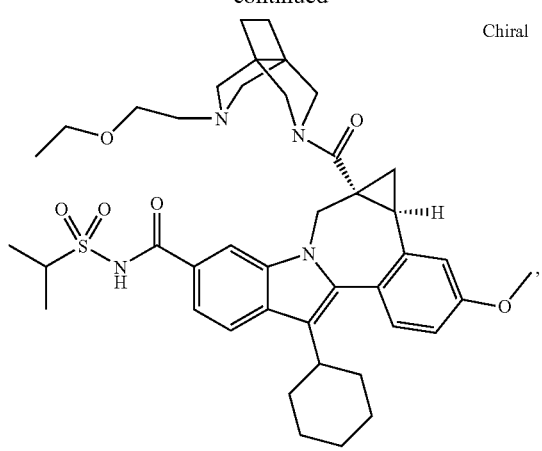
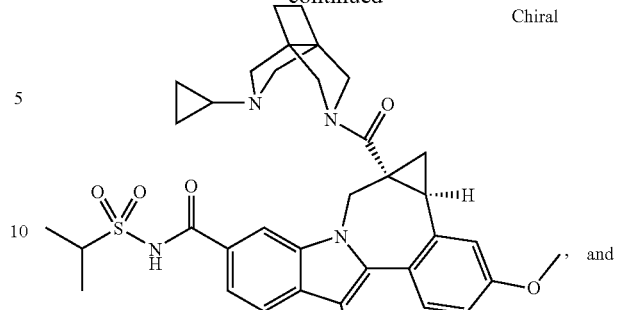
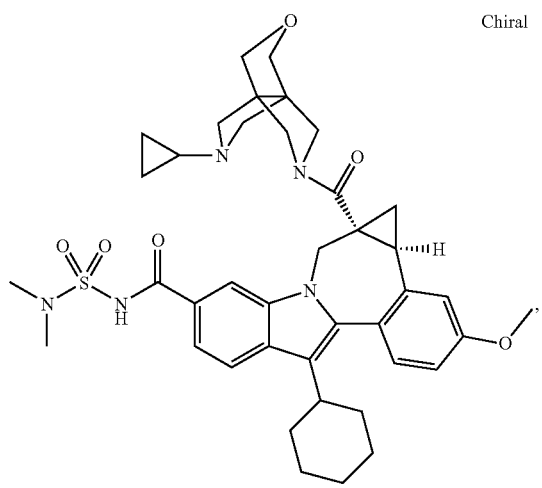
or a pharmaceutically acceptable salt thereof.
12. A composition comprising a compound of claim 1, or a pharmaceutically acceptable salt thereof, and a pharmaceutically acceptable carrier.
13. A method of treating hepatitis C infection comprising administering a therapeutically effective amount of a compound of claim 1 to a patient.
* * * * *

UNITED STATES PATENT AND TRADEMARK OFFICE
CERTIFICATE OF CORRECTION

PATENT NO.        : 8,143,244 B2                            Page 1 of 1
APPLICATION NO.   : 12/710527
DATED             : March 27, 2012
INVENTOR(S)       : John A. Bender et al.

It is certified that error appears in the above-identified patent and that said Letters Patent is hereby corrected as shown below:

In the Claims:

Claim 3:
  Column 173, lines 22 to 32, change " 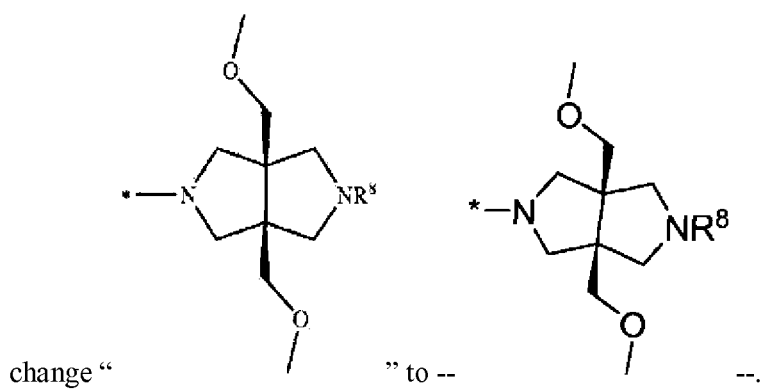 " to -- --.

Claim 6:
  Column 173, line 55, change "or($R^{10}$)" to -- or ($R^{10}$) --.

Signed and Sealed this
Fourth Day of March, 2014

Michelle K. Lee
*Deputy Director of the United States Patent and Trademark Office*